United States Patent
Chen et al.

(10) Patent No.: US 12,187,681 B2
(45) Date of Patent: Jan. 7, 2025

(54) ION CHANNEL ANTAGONISTS/BLOCKERS AND USES THEREOF

(71) Applicant: Shanghai East Hospital, Shanghai (CN)

(72) Inventors: Yihan Chen, Shanghai (CN); Dandan Liang, Shanghai (CN); Yi Liu, Shanghai (CN); Subas Man Sakya, Shanghai (CN); Jinhua Yang, Shanghai (CN); Li Li, Shanghai (CN); Duanyang Xie, Shanghai (CN); Dan Shi, Shanghai (CN); Ke Xiong, Shanghai (CN)

(73) Assignee: Shanghai East Hospital, Shanghai (CN)

( * ) Notice: Subject to any disclaimer, the term of this patent is extended or adjusted under 35 U.S.C. 154(b) by 6 days.

(21) Appl. No.: 17/755,398

(22) PCT Filed: Dec. 14, 2019

(86) PCT No.: PCT/CN2019/125453
§ 371 (c)(1),
(2) Date: Apr. 28, 2022

(87) PCT Pub. No.: WO2021/114313
PCT Pub. Date: Jun. 17, 2021

(65) Prior Publication Data
US 2023/0015875 A1    Jan. 19, 2023

(51) Int. Cl.
| | |
|---|---|
| C07D 217/24 | (2006.01) |
| C07C 39/14 | (2006.01) |
| C07C 39/15 | (2006.01) |
| C07C 43/20 | (2006.01) |
| C07C 43/23 | (2006.01) |
| C07C 49/83 | (2006.01) |
| C07C 63/38 | (2006.01) |
| C07C 211/58 | (2006.01) |
| C07C 215/86 | (2006.01) |
| C07C 233/65 | (2006.01) |
| C07C 235/66 | (2006.01) |
| C07C 311/08 | (2006.01) |
| C07C 311/24 | (2006.01) |
| C07C 311/29 | (2006.01) |
| C07C 317/22 | (2006.01) |
| C07D 209/34 | (2006.01) |
| C07D 211/22 | (2006.01) |
| C07D 213/30 | (2006.01) |
| C07D 217/02 | (2006.01) |
| C07D 231/20 | (2006.01) |
| C07D 235/26 | (2006.01) |
| C07D 241/42 | (2006.01) |

(Continued)

(52) U.S. Cl.
CPC ............ *C07D 217/24* (2013.01); *C07C 39/14* (2013.01); *C07C 39/15* (2013.01); *C07C 43/202* (2013.01); *C07C 43/23* (2013.01); *C07C 49/83* (2013.01); *C07C 63/38* (2013.01); *C07C 211/58* (2013.01); *C07C 215/86* (2013.01); *C07C 233/65* (2013.01); *C07C 235/66* (2013.01); *C07C 311/08* (2013.01); *C07C 311/24* (2013.01); *C07C 311/29* (2013.01); *C07C 317/22* (2013.01); *C07D 209/34* (2013.01); *C07D 211/22* (2013.01); *C07D 213/30* (2013.01); *C07D 217/02* (2013.01); *C07D 231/20* (2013.01); *C07D 235/26* (2013.01); *C07D 241/42* (2013.01); *C07D 295/084* (2013.01); *G01N 33/502* (2013.01)

(58) Field of Classification Search
CPC .................................................. C07C 43/202
See application file for complete search history.

(56) References Cited

U.S. PATENT DOCUMENTS 2,703,324 A     3/1995    Binkley et al.
6,632,836 B1   10/2003   Baker et al.
(Continued)

FOREIGN PATENT DOCUMENTS

JP     2008500337 A    1/2008
WO   2002000603 A1   1/2002
(Continued)

OTHER PUBLICATIONS

American Chemical Society. Chemical Abstract Service. RN 384841-87-6. Entered into STN: Jan. 20, 2002. (Year: 2002).*
(Continued)

*Primary Examiner* — John S Kenyon
(74) *Attorney, Agent, or Firm* — Ice Miller LLP

(57) ABSTRACT

Provided are ion channel antagonists/blockers and uses thereof. Specifically, it provides the compounds of formula (I) or pharmaceutically acceptable salts, stereoisomers, solvates or prodrugs, preparation method therefor and application thereof. Definition of each group in the formula can be found in the specification for details. Provided is also pharmaceutical composition useful for treatment of heart disease and other ion channel related diseases.

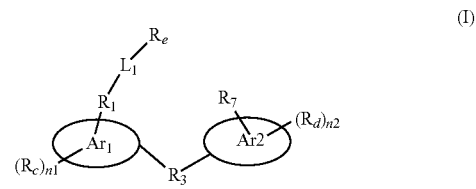

18 Claims, No Drawings

(51) Int. Cl.
*C07D 295/084* (2006.01)
*G01N 33/50* (2006.01)

(56) References Cited

U.S. PATENT DOCUMENTS

| 2001/0041814 A1 | 11/2001 | Toiinishi |
| 2009/0018116 A1 | 1/2009 | Jin et al. |

FOREIGN PATENT DOCUMENTS

| WO | 2003103656 A1 | 12/2003 | |
| WO | 2007009661 A2 | 1/2007 | |
| WO | WO-2007146136 A2 * | 12/2007 | ........... C07C 235/78 |
| WO | 2015130957 A1 | 9/2015 | |

OTHER PUBLICATIONS

Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
International Search Report issued Sep. 16, 2020 in PCT/CN2019/125453.
Written Opinion issued Sep. 16, 2020 in PCT/CN2019/125453.
Gonec, T., et al., "Photosynthesis-Inhibiting Activity of 1-[(2-Chlorphenyl)carbamoyl]-and 1-[(2-Nitrophenyl)cabamoyl] naphthalen-2-yl Alkylcarbamates," Molecules, vol. 22, No. 7, Jul. 17, 2017.
Davies, K.S., et al., "Extended rhodamine photosensitizers for photodynamic therapy of cancer cells," Bioorganic & Medicinal Chemistry, vol. 24, pp. 3908-3917, May 20, 2016.
Kryman, M.W., et al., "Longer-Wavelength-Absorbing, Extended Chalcogenorhodamine Dyes," Organometallics, vol. 35, pp. 1944-1955, May 19, 2016.
Colombo, L., et al., "ST1859 reduces prion infectivity and increase survival in experimental scrapie," Arch Virol, vol. 154, pp. 1539-1544, Aug. 15, 2009.
Kiselyov, A.S., et al., "2-((1H-Azol-1-yl)methyl)-N-arylbenzamides: Novel dual inhibitors of VEGFR-1/2 kinases," Bioorganice & Medicinal Chemistry Letters, vol. 16, pp. 1726-1730, Dec. 20, 2005.
Wheatley, W.B., et al., "2-Benzylphenol Derivatives, III, Basic Ethers," Journal of the American Chemical Society, vol. 71, pp. 3795-3797, Nov. 30, 1949.
Bagal, Sharan K., et al., "Ion Channels as Therapeutic Targets: A Drug Discovery Perspective," Journal of Medical Chemistry, vol. 56, pp. 593-624 (2013).
Saulnier, Mark G., et al., "An Efficient Method for the Synthesis of Guanidino Prodrugs," Bioorganic & medicinal Chemistry Letters, vol. 4, No. 16, pp. 1985-1990 (1994).
Greenwald, Richard B., et al., "Drug Delivery Systems Based on Trimethyl Lock Lactonization: Poly(ethylene glycol) Prodrugs of Amino-Containing Compounds," Journal of Medical Chemistry, vol. 43, No. 3, pp. 475-487 (2000).
Azuma, Eriko, et al., "Alternative simple and effective synthesis of (di)benzoxanthones and their functions toward fluorescent dyes," Tetrahedron, vol. 69, No. 6, pp. 1694-1699 (2013).
Kasturi, Tirumalai R., et al., "Reaction of Spironaphthalenones with Hydroxylamine Hydrochloride: Part IV," Tetrahedron, vol. 51, No. 10, pp. 3051-3060 (1995).
Xu, Cong, et al., "Hydrobromic acid-catalyzed Friedel-Crafts type reactions of naphthols," RSC Advances, vol. 4, No. 4, pp. 1559-1562 (2014).
Liang, Deqiang, et al., "Novel and potent Lewis acid catalyst: Br2-catalyzed Friedel-Crafts reactions of naphthols with aldehydes," Synthetic Communications, vol. 46, No. 4, pp. 379-385 (2016).
Ito, Kazuaki, et al., "Study on Host-Guest Complexation of Anions Based on 2,2'-Dihydroxyl-1,1'-Binaphtalene Derivatives," Letters in Organic Chemistry, vol. 3, pp. 735-740 (2006).
Field, Jason E., et al., "Bridged Triarylamines: A New Class of Heterohelicenes," Journal of Organic Chemistry, vol. 68, No. 16, pp. 6071-6078, Aug. 8, 2003.
Lombardi, Christopher, et al., "Selective Cross-Coupling of (Hetero)aryl Halides with Ammonia to Produce Primary Arylamines using Pd-NHC Complexes," Organometallics, vol. 36, No. 2, pp. 251-254 (2017).
DiSanto, Roberto, et al., "Design, Synthesis, and Structure-Activity Relationship of N-Arylnaphthylamine Derivatives as Amyloid Aggregation Inhibitors," Journal of Medicinal Chemistry, vol. 55, No. 19, pp. 8538-8548 (2012).
Arvind Singh Negi, et al, "Benzophenones, Naphthophenones and Related Compounds as Spermicidal Agents," Indian Journal of Pharmaceutical Sciences, vol. 56 (3), pp. 105-108, 1994.

* cited by examiner

ION CHANNEL ANTAGONISTS/BLOCKERS AND USES THEREOF

CROSS-REFERENCE TO RELATED APPLICATION

This application is a Section 371 of International Application No. PCT/CN2019/125453, filed on Dec. 14, 2019, that published in the English language on Jun. 17, 2021, under International Publication No. WO 2021/114313 A1, the disclosure of which is incorporated herein by reference in its entirety.

FIELD OF INVENTION

The present invention belongs to the field of medical technology and pharmaceuticals, and specifically, relates to ion channel antagonists/blockers and uses thereof, especially for treatment of arryhythmias and other ion channel mediated diseases.

BACKGROUND

Ion channels are important for well functioning cells in human body, especially in controlling nerve and muscle relaxation, cognition, regulation of blood pressure, etc. Changes in functions of ion channels can lead to many diseases, especially for heart and neuronal diseases. Thus, ion channel blockers and activators (agonists and antagonists) of ion channels play an important role in alleviating such diseases that can be modulated by ion channel function. (Ref Ion Channels as Therapeutic Targets: A Drug Discovery Perspective J. Med. Chem. 2013, 56, 593-624) Heart arrhythmia is a heart disease associated with dysfuction of the heart resulting from either irregular, rapid or slowing down of heartbeat. A heart rate above 100 beats per minute is called tachycardia and heart rate below 60 beats per minute is called bradycardia, both of which can be deadly if not treated promptly. Most of these arrhythmias are due to problems with the electrical conduction system of the heart.

Four main types of arrhythmia are extra beats, supraventricular tachycardias, ventricular arrhytmias and brady arrhytmias. Premature atrial contractions, premature ventricular contractions and premature junctional contractions are all considered as extra beats. Atrial fibrillation, atrial flutter and paroxysmal supraventricular tarchycardia are all considered as supraventricular tachycardias. Ventricular arrhythmia then covers ventricular fibrillation and ventricular tachycardia. Most of these dysfuctions can be detected and diagnosed using electrocardiogram (ECG) and Holter monitor, a portable cardiac ECG monitoring device.

Most arrhythmias are treated with anti-arrhythmic drugs depending on the type of arrhythmia. Current approved Drugs are generally classified according to Vaughan Williams classification based on mechanism of actions. Class I agents refer to compounds acting of sodium channel. This class has subclasses based on their functional outcome. Drugs in this class are Class Ia: quinidine, ajmaline, procainamide, disopyramide; Class Ib: lidocaine, phenytoin, mexiletine, tocainide; Class Ic: encainide (withdrawn); flecainide (withdrawn); propafenone; morizine (withdrawn). Class II agents are beta-blockers and are anti-sympathetic nervous system agents. Current Class II agents: carvediol, propranolol, esmolol, timolol, metoprolol, atenolol, bisoprolol, nebivolol; Class III agents work by modulating potassium channel. Current Class III agents: amiodarone, sotalol, ibutilide, dofetalide, dronedarone, vernakalant; Class IV agents affect calcium channel and the AV node. Current Class IV agents: verapamil, diltiazem; and the Class V agents work via other mechanisms and current Class V agents include Adenosine, digoxin.

Many of the drugs mentioned above have activity against multiple channels or other target. Thus, use of these agents against various forms of arrhythmia is dictated based on pharmacological affects seen in vivo. Some of the drugs have recently been withdrawn due to pro-arrhymia because of the treatment during several large clinical studies to see the benefits of treatment versus placebo. Since these studies were published, further analysis of the clinical data showed that several drugs such as amiodarone and verapamil with multiple ion channel inhibition had no pro-arrythmic potential. Most recently, studies using CIPA guidelines showed that comparison of drugs with IKr (Herg) and CaV1.2 (Calcium) channel blockade ratio was a good indicator of safer drugs from pro-arrhythmic potential.

It is an urgent need in the art to develop effective and safe ion channel antagonist which is useful for treatment of heart disease and other ion channel related diseases.

SUMMARY OF INVENTION

The object of the present invention is to provide an effective and safe ion channel antagonist which is useful for treatment in heart disease and other ion channel related diseases.

In the first aspect of the present invention, it provides a compound of formula (I), or a pharmaceutically acceptable salt, a solvate, a stereoisomer or a prodrug thereof:

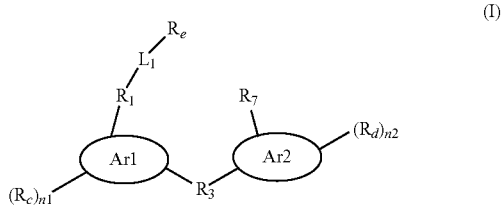

wherein
each of ring $Ar_1$ and ring $Ar_2$ is independently selected from the group consisting of substituted or unsubstituted phenyl ring, substituted or unsubstituted naphthyl, substituted or unsubstituted biphenyl; with the proviso that ring $Ar_1$ and ring $Ar_2$ are not phenyl at the same time;
$R_1$ is selected from the group: —O—, —S—, —N($R_a$)—, —C($R_b$)$_2$—, —C(O)—, —C(S)—, —S(O)$_2$—, —S(O)—; preferably, $R_1$ is selected from the group: —O—, —S—;
$R_3$ is selected from the group: —O—, —S—, —N($R_a$)—, —C($R_b$)$_2$—, —C(O)—, —S(O)$_2$—, —S(O)—, —C(O)N$R_f$, —N$R_f$C(O)—;
$L_1$ is selected from null, substituted or unsubstituted C3-C8 cycloalkyl or a substituted or unsubstituted C1-C6 alkylene group, substituted or unsubstituted C6-C14 aryl, unsubstituted 4 to 10 membered heterocyclic group, or substituted or unsubstituted 5- to 10-membered heteroaryl; wherein when $L_1$ is C1-C6 alkylene, the carbon atom on the middle chain of $L_1$ is optionally substituted with 0, 1 or 2 divalent groups selected from the group: —O—, —S—, —N($R_a$)—, —C(O)—;

R₇ is selected from the group consisting of: H, —OH, halogen, R_f—, R_f—O—, R_f—S—, R_f—C(O)O—, R_f—S(O)₂—, R_f—S(O)—, R_f—C(O)—, NHR_f, NH(SO₂)R_f, and —R₁-L₁-R_d; wherein R_f is selected from the group consisting of: H, substituted or unsubstituted C1-C6 alkyl, substituted or unsubstituted C3-C6 cycloalkyl; R₁ and L₁ is as defined above;

R_e is selected from the group: —N(R₂)₂, —N⁺(R₂)₃

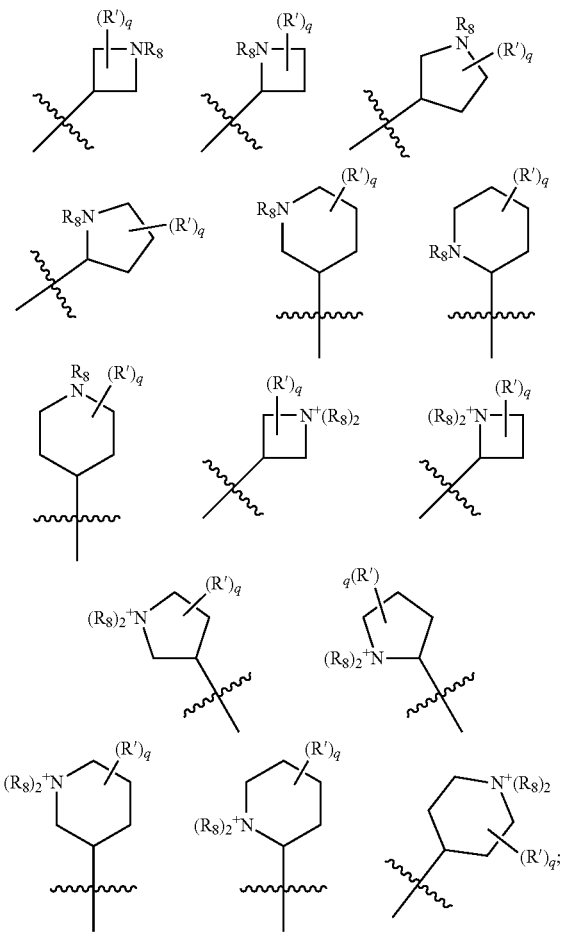

q=0, 1 or 2;

each R₈ is independently selected from the group consisting of: H, substituted or unsubstituted C1-C6 alkyl, substituted or unsubstituted C3-C6 cycloalkyl, substituted or unsubstituted 5- to 7-membered heteroaryl; substituted or unsubstituted 4 To 7-membered heterocycloalkyl;

each R₂ is independently selected from the group consisting of: H, substituted or unsubstituted C1-C6 alkyl, —C(O)-substituted or unsubstituted C1-C6 alkyl; or two R₂ and the nitrogen atom to which they are attached form a substituted or unsubstituted 4 to 10 membered heterocyclic group or 5 to 10-membered heteroaryl, and the heterocyclyl or heteroaryl contains 1-2 N atoms and 0, 1, 2 O or S heteroatoms;

R_a is selected from the group consisting of: H, substituted or unsubstituted C1-C4 alkyl;

R_b are each independently selected from the group consisting of H, —OH, cyano(—CN), substituted or unsubstituted C1-C6 alkyl, substituted or unsubstituted C1-C6 alkenyl, substituted or unsubstituted C2-C6 alkynyl, substituted or unsubstituted C3-C8 cycloalkyl, substituted or unsubstituted C1-C6 alkoxy, and substituted or unsubstituted —S—C1-C4 alkyl;

R_c and R_d are independently selected from the group consisting of halogen (preferably, F, Cl, Br, I), —OH, nitro, cyano, sulfonyl, R", —N(R")₂—, R"—O—, R"—S—, R"—S(O)₂—, R"—S(O)—, R"—C(O), R"—C(O)O—, R"—OC(O)—;

n1 and n2 are independently 0, 1, 2, 3, 4 or 5;

unless otherwise specified, the term "substituted" refers to one or more (preferably 1, 2, 3, 4 or 5) hydrogens in the group is replaced with an R 'group;

each R' is independently selected from the group consisting of D, halogen (preferably F, Cl, Br, I), —OH, nitro, cyano, sulfonyl, R", —N(R"), R"—O—, R"—S—, R"—S(O)₂—, R"—S(O)—, R"—C(O), R"—C(O)O—, R"—OC(O)—, oxo (O=); or when two R' attached to the same carbon atom, the two R' and the carbon atom to which they are attached form substituted or unsubstituted C3-C8 cycloalkyl, substituted or unsubstituted C6-C10 aryl, substituted or unsubstituted 4 to 7 membered heterocyclic group or 5 to 7-membered heteroaryl where R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, -C1-C4 alkylene-C6-C10 aryl, -C1-C4 alkylene-(4 to 7-membered heterocycloalkyl), -C1-C4 alkylene-(5 to 7-membered heteroaryl);

and in R", the alkyl, alkenyl, alkynyl, cycloalkyl, aryl, heterocycloalkyl and heteroaryl, as a whole group or a partial group, can be optionally substituted by a substituent selected from the group consisting of: halogen (preferably F, Cl, Br, I), C1-C4 alkyl, C1-C4 alkoxy, C1-C4 haloalkyl, —OH, nitro, cyano, sulfonyl, and amino.

In another preferred embodiment, L₁ is C1-C6 alkylene; more preferably, L₁ is selected from:—(CH₂)—, —(CH₂)₂—, —(CH₂)₃—, —(CH₂)₄—.

In another preferred embodiment, the compound has a structure of formula Ia:

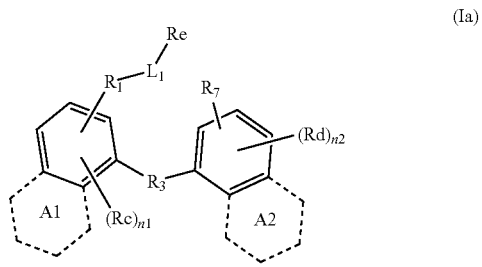

wherein

R₁, R₃, R₇, R_c, R_d, R_e, L₁, n1 and n2 are as defined above;

Rings A1 and A2 are each independently selected from the group consisting of: none, and substituted or unsubstituted benzene rings, with the proviso that rings A1 and A2 are not none at the same time;

wherein, the term "substituted" means that one or more (preferably 1, 2, 3, 4 or 5) hydrogens in the group are replaced by an R' group; and R' is as defined above.

In another preferred embodiment, $R_b$ is selected from the group consisted of —(CH$_2$)—, —CH(OH)—, —NH—, —N(CH$_3$)—, —O—, and —S—.

In another preferred embodiment, the compound has a structure of formula II:

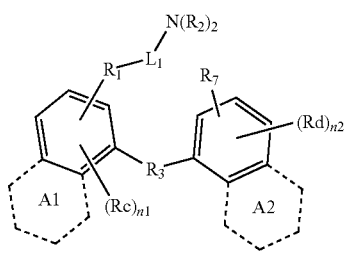

(II)

wherein, $R_1$, $R_3$, $R_7$, $R_c$, $R_d$, $R_2$, $L_1$, n1, n2, ring A1 and ring A2 are as defined above.

In another preferred embodiment, unless otherwise specified, the heteroaryl group refers to an aromatic ring group containing 1, 2, or 3 heteroatoms selected from: O, N, and S.

In another preferred embodiment, unless otherwise specified, the heterocycloalkyl group refers to a cycloalkyl group containing 1, 2, or 3 heteroatoms selected from: O, N, and S.

In another preferred embodiment, A1 is a substituted or unsubstituted benzene ring.

In another preferred embodiment, the compound of formula II is represented by formula IIa or IIb:

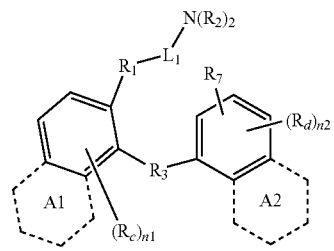

(IIa)

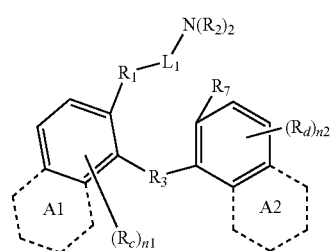

(IIb)

wherein, $R_1$, $R_2$, R3, $R_7$, $R_c$, $R_d$, $L_1$, n1, n2, ring A1 and ring A2 are as defined above.

In another preferred embodiment, the compound of formula II is represented by formula IIa or IIb:

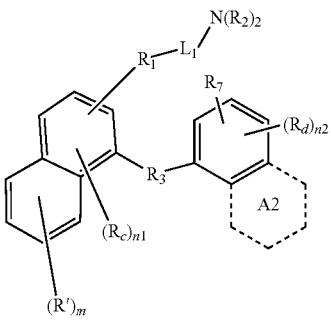

(IIc)

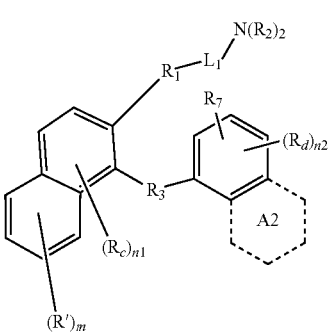

(IId)

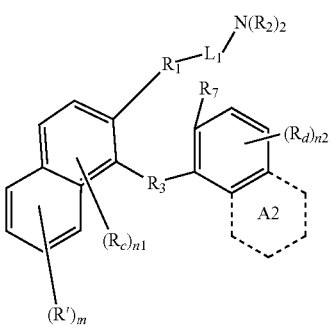

(IIf)

wherein, $R_1$, $R_2$, $R_3$, $R_7$, $R_c$, $R_d$, $L_1$, and ring A2 are as define above;

each of R' are independently defined as in formula I;

n1 and n2 are independently 0, 1 or 2; and m=0, 1, 2, or 3.

In another preferred embodiment, the compound has a structure of formula IIg, IIh or IIi

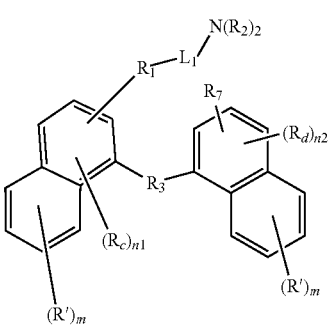

(IIg)

-continued

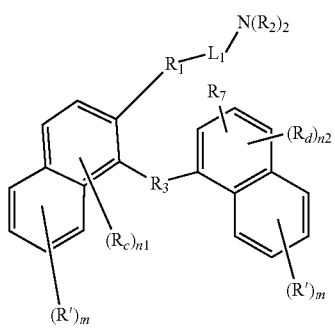
(IIh)

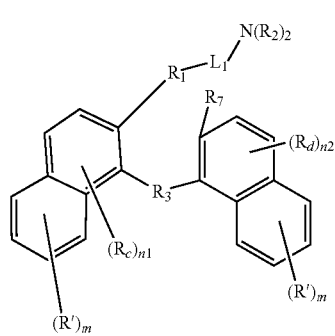
(IIi)

wherein, $R_1$, $R_2$, $R_3$, $R_7$, $R_c$, $R_d$, $L_1$, and R' are as define above;

n1 and n2 are independently 0, 1 or 2; and each of m is independently 0, 1, 2 or 3.

In another preferred embodiment, the compound has a structure of formula IIIa, IIIb or IIIc:

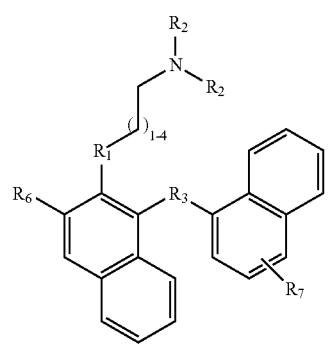
(IIIa)

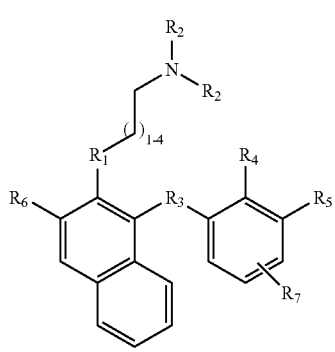
(IIIb)

-continued

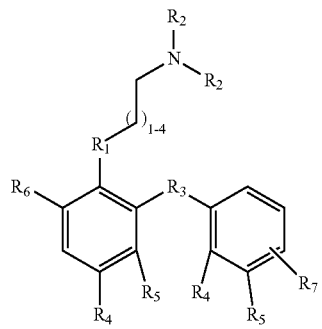
(IIIc)

wherein, $R_1$ is O, NH, CH$_2$, S, S(O) and S(O)$_2$.

$R_2$ is substituted or unsubstituted C1-C3 alkyl;

$R_3$ is —NH—, —N(R$_a$)—, —CH$_2$—, —C(O)—, —CHOH—, —S—, —SO—, or —SO$_2$—;

$R_7$ is selected from the group consisting of H, F, Cl, Br, —OH, NHR$_f$, NH(SO$_2$)R$_f$, R$_f$, R$_f$—O—, R$_f$—C(O)O—, R$_f$—S(O)$_2$—, R$_f$—S(O)—, R$_f$—C(O)—, and —R$_1$-L$_1$-R$_d$; wherein R$_f$ is selected from the group consisting of H, substituted or unsubstituted C1-C6 alkyl, substituted or unsubstituted C3-C6 cycloalkyl; $R_1$ and $L_1$ is as defined above;

$R_4$, $R_5$, and $R_6$ is independently selected from the group consisting of H, Cl, F, OR$_f$, N(R$_f$)$_2$, C(O)ORf, C(O)N (R$_f$)$_2$—R$_f$ where R$_f$ is as described above.

In another preferred embodiment, the compound has a structure of formula IIIa-1, IIIb-1 or IIIc-1:

(IIIa-1)

(IIIb-1)

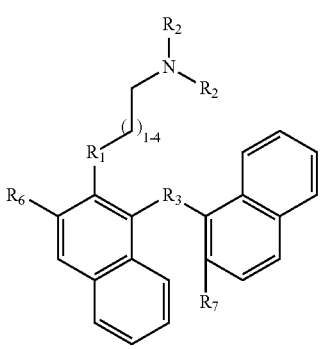

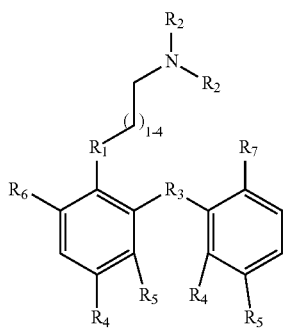

(IIIc-1)

wherein,
R₁, R₂, R₃, R₄, R₅, R₆, and R₇ are as defined above.

In another preferred embodiment, in any of formula IIIa, IIIb, IIIc, IIIa-1, IIIb-1 or IIIc-1, R₁ is O, NH, CH₂, or S;
R₂ is substituted or unsubstituted C1-C3 alkyl (including halogenated or deuterated C1-C3 alkyl);
R₃ is —NH—, —N(R_a)—, —CH₂—, —C(O)—, —CHOH—, —S—, —SO—, or —SO₂—.

In another preferred embodiment, each of R₁, R₂, R₃, R₄, R₅, R₆, R₇, R_c, R_e, R_d, L₁, n1, n2, ring A1 and ring A2 are the corresponding groups in the compounds as prepared in the Examples.

In another preferred embodiment, the compound of formula (I) is any of compounds as prepared in Examples 1 to 166.

In another preferred embodiment, the compound is any selected from Table A, Table 1 or Table 2.

In another preferred embodiment, the compound of formula (I) is selected from Table A

TABLE A 1,1'-methylenebis(naphthalen-2-ol)
1,1'-(methylazanediyl)bis(naphthalen-2-ol)
1,1'-sulfonylbis(naphthalen-2-ol)
1,1'-sulfinylbis(naphthalen-2-ol)
bis(2-methoxynaphthalen-1-yl)methanol
bis(2-hydroxynaphthalen-1-yl)methanone
1,1'-(ethane-1,1-diyl)bis(naphthalen-2-ol)
1-((2-methoxynaphthalen-1-yl)methyl)naphthalen-2-ol
bis(2-methoxynaphthalen-1-yl)methane
2,2'-methylenediphenol
2,2'-methylenebis(3,4-dimethylphenol)
1-((2-aminonaphthalen-1-yl)methyl)naphthalen-2-ol
1,1'-methylenebis(naphthalen-2-amine)
4-((2-aminonaphthalen-1-yl)methyl)naphthalen-2-amine
N-(3-((2-(methylsulfonamido)naphthalen-1-yl)methyl)naphthalen-2-yl)methanesulfonamide
N,N'-(methylenebis(naphthalene-1,2-diyl))dimethanesulfonamide
N-(1-((3-(methylsulfonamido)naphthalen-1-yl)methyl)naphthalen-2-yl)methanesulfonamide
N-(1-((2-hydroxynaphthalen-1-yl)methyl)naphthalen-2-yl)methanesulfonamide
N-(1-((2-hydroxynaphthalen-1-yl)methyl)naphthalen-2-yl)benzenesulfonamide
4-((2-hydroxynaphthalen-1-yl)methyl)isoquinolin-3-ol
1-((2-hydroxynaphthalen-1-yl)methyl)-3-methylnaphthalen-2-ol
1,1'-methylenebis(3-methylnaphthalen-2-ol)
2,2''-methylenebis(([1,1-biphenyl]-3-ol))
2,2'-methylenebis(3-methylnaphthalen-1-ol)
2-hydroxy-N-(2-hydroxynaphthalen-1-yl)-1-naphthamide
1,1'-methylenebis(3-chloronaphthalen-2-ol)
1,1'-methylenebis(3-(2-hydroxypropan-2-yl)naphthalen-2-ol)
1,1'-methylenebis(3-fluoronaphthalen-2-ol)
1,1'-methylenebis(3-methoxynaphthalen-2-ol)
1-(naphthalen-1-ylmethyl)naphthalen-2-ol TABLE A-continued 1-((2-hydroxynaphthalen-1-yl)methyl)-1H-benzo[d]imidazol-2-ol
1-((2-hydroxynaphthalen-1-yl)methyl)indolin-2-one
1-((2-hydroxynaphthalen-1-yl)methyl)-4-phenyl-1H-pyrazol-5-ol
N,N-bis(2-hydroxynaphthalen-1-yl)acetamide
8-(ethoxymethoxy)-3,4-dihydronaphthalen-1(2H)-one
1',2',3',4'-tetrahydro-[1,1'-binaphthalene]-2,8'-diol
1',2',3',4',5,6,7,8-octahydro-[1,1'-binaphthalene]-2,8'-diol
1-(4-hydroxy-1H-inden-3-yl)naphthalen-2-ol
1-(7-hydroxy-2,3-dihydro-1H-inden-1-yl)naphthalen-2-ol
bis(2-(((4-methoxybenzyl)oxy)methyl)naphthalen-1-yl)methanol
1,1'-methylenebis(3-isopropylnaphthalen-2-ol)
1-((2-(2-(diethylamino)ethoxy)naphthalen-1-yl)methyl)naphthalen-2-ol formate
1-((2-(2-(diethylamino)ethoxy)naphthalen-1-yl)methyl)-3-methylnaphthalen-2-ol
1,1'-methylenebis(2-naphthoic acid)
1,1'-methylenebis(2-naphthamide)
1-((2-(2-(diethylamino)ethoxy)-3-isopropylnaphthalen-1-yl)methyl)-3-isopropylnaphthalen-2-ol hydrochloride salt
2,2'-((methylenebis(naphthalene-1,2-diyl))bis(oxy))bis(N,N-diethylethan-1-amine) formic acid
1,1'-methylenebis(2-naphthoic acid)
1-((2-hydroxynaphthalen-1-yl)methyl)-2-naphthoic acid
1-((2-(2-(diethylamino)ethoxy)-3-methylnaphthalen-1-yl)methyl)-3-methylnaphthalen-2-ol
8-((2-hydroxynaphthalen-1-yl)methyl)isoquinolin-7-ol
2-(2-(diethylamino)ethoxy)-N-(2-methoxynaphthalen-1-yl)naphthalen-1-amine
2-(2-(diethylamino)ethoxy)-N-(2-methoxynaphthalen-1-yl)-N-methylnaphthalen-1-amine 2,2,2-trifluoroacetate
6-hydroxy-5-((2-hydroxynaphthalen-1-yl)methyl)-2-naphthoic acid
2,2'-methylenebis(3-(pyridin-3-yl)phenol)
2-(2-methoxy-6-(pyridin-3-yl)benzyl)-3-(pyridin-3-yl)phenol
2-(2-methoxy-6-(pyridin-4-yl)benzyl)-3-(pyridin-4-yl)phenol
6-hydroxy-5-((2-hydroxynaphthalen-1-yl)methyl)-2-naphthamide
5,5'-methylenebis(6-hydroxy-2-naphthamide)
5-((6-carboxy-2-(2-(diethylamino)ethoxy)naphthalen-1-yl)methyl)-6-hydroxy-2-naphthoic acid
5,5'-methylenebis(6-(2-(diethylamino)ethoxy)-2-naphthoic acid)
1-((2-(2-(pyrrolidin-1-yl)ethoxy)naphthalen-1-yl)methyl)naphthalen-2-ol
1-(2-((1-((2-methoxynaphthalen-1-yl)methyl)naphthalen-2-yl)oxy)ethyl)-1-methylpyrrolidin-1-ium formate
1-((2-(2-morpholinoethoxy)naphthalen-1-yl)methyl)naphthalen-2-ol
4-(2-((1-((2-methoxynaphthalen-1-yl)methyl)naphthalen-2-yl)oxy)ethyl)-4-methylmorpholin-4-ium formate
1-((2-(2-(dimethylamino)ethoxy)naphthalen-1-yl)methyl)naphthalen-2-ol
1-((2-(3-(diethylamino)propoxy)naphthalen-1-yl)methyl)naphthalen-2-ol
1-((2-(2-(piperidin-1-yl)ethoxy)naphthalen-1-yl)methyl)naphthalen-2-ol
2-((1-((2-methoxynaphthalen-1-yl)methyl)naphthalen-2-yl)oxy)ethan-1-ol
8-((2-hydroxynaphthalen-1-yl)methyl)-1,2,3,4-tetrahydroisoquinolin-7-ol
8-((2-hydroxy-5,6,7,8-tetrahydronaphthalen-1-yl)methyl)-1,2,3,4-tetrahydroisoquinolin-7-ol
1-((2-(2-(diethylamino)ethoxy)naphthalen-1-yl)thio)naphthalen-2-ol
N,N-diethyl-2-((1-((2-methoxynaphthalen-1-yl)thio)naphthalen-2-yl)oxy)ethan-1-amine
1-((6-(2-(diethylamino)ethoxy)quinoxalin-5-yl)methyl)naphthalen-2-ol
diethyl(2-((1-((2-methoxynaphthalen-1-yl)thio)naphthalen-2-yl)oxy)ethyl)(methyl)-14-azane,
1-((2-(diethylamino)ethyl)(3,4-dimethoxyphenyl)amino)naphthalen-2-ol
2,2'-((2-((1-((2-methoxynaphthalen-1-yl)methyl)naphthalen-2-yl)oxy)ethyl)azanediyl)bis(ethan-1-ol)
2-methoxy-N-(2-nitronaphthalen-1-yl)naphthalen-1-amine
1-((2-methoxynaphthalen-1-yl)methyl)naphthalen-2-yl diethylglycinate
(2-hydroxynaphthalen-1-yl)(2-(2-(pyrrolidin-1-yl)ethoxy)naphthalen-1-yl)methanone TABLE A-continued N-(2-(diethylamino)ethyl)-1-((2-methoxynaphthalen-1-yl)methyl)-2-naphthamide
2-((1-((2-(ethoxymethoxy)naphthalen-1-yl)methyl)naphthalen-2-yl)oxy)ethan-1-amine
2-((1-((2-isopropoxynaphthalen-1-yl)methyl)naphthalen-2-yl)oxy)ethan-1-amine
1-(2-((1-((2-(ethoxymethoxy)naphthalen-1-yl)methyl)naphthalen-2-yl)oxy)ethyl)pyrrolidine
1-(2-((1-((2-ethoxynaphthalen-1-yl)methyl)naphthalen-2-yl)oxy)ethyl)pyrrolidine
1-(2-((1-((2-isopropoxynaphthalen-1-yl)methyl)naphthalen-2-yl)oxy)ethyl)pyrrolidine
4-(((1-((2-methoxynaphthalen-1-yl)methyl)naphthalen-2-yl)oxy)methyl)piperidine
4-(((1-((2-(ethoxymethoxy)naphthalen-1-yl)methyl)naphthalen-2-yl)oxy)methyl)piperidine
2-(diethylamino)-N-(1-((2-methoxynaphthalen-1-yl)methyl)naphthalen-2-yl)acetamide
1-[(isoquinolin-1-yl)methyl]naphthalen-2-ol hydrochloride
1-[(2-hydroxynaphthalen-1-yl)(4-methoxyphenyl)methyl]naphthalen-2-ol
1-({2-[2-(piperidin-4-yl)ethoxy]naphthalen-1-yl}methyl)naphthalen-2-ol hydrochloride
{2-[(1-{[2-(benzyloxy)naphthalen-1-yl]methyl}naphthalen-2-yl)oxy]ethyl}diethylamine
1-{2-[(1-{[2-(benzyloxy)naphthalen-1-yl]methyl}naphthalen-2-yl)oxy]ethyl}pyrrolidine
1-[2-({1-[(2-methoxynaphthalen-1-yl)methyl]naphthalen-2-yl}methoxy)ethyl]pyrrolidine
[2-(diethylamino)ethyl]({1-[(2-methoxynaphthalen-1-yl)methyl]naphthalen-2-yl}methyl)amine
1-{2-[(1-{[2-(hexyloxy)naphthalen-1-yl]methyl}naphthalen-2-yl)oxy]ethyl}pyrrolidine
1-{2-[(1-{[2-(2-methoxyethoxy)naphthalen-1-yl]methyl}naphthalen-2-yl)oxy]ethyl}pyrrolidine
1-({2-[(1-methylpyrrolidin-3-yl)methoxy]naphthalen-1-yl}methyl)naphthalen-2-ol
2-[(1-{[2-(hexyloxy)naphthalen-1-yl]methyl}naphthalen-2-yl)oxy]ethan-1-amine
1-({2-[2-(azetidin-1-yl)ethoxy]naphthalen-1-yl}methyl)naphthalen-2-ol
1-(2-{2-[bis(2-hydroxyethyl)amino]ethoxy}naphthalen-1-yl)methyl]naphthalen-2-ol
8-[(2-hydroxynaphthalen-1-yl)methyl]quinolin-7-ol
1-({2-[2-(diethylamino)ethoxy]naphthalen-1-yl}sulfonyl)naphthalen-2-ol
diethyl[2-({1-[(2-methoxynaphthalen-1-yl)sulfonyl]naphthalen-2-yl}oxy)ethyl]amine
2-methoxy-N-methyl-N-(2-nitronaphthalen-1-yl)naphthalen-1-amine
1-({2-[2-(diethylamino)ethoxy]naphthalen-1-yl}methyl)naphthalen-2-amine
N-[1-({2-2-(diethylamino)ethoxy]naphthalen-1-yl}methyl)naphthalen-2-yl]methanesulfonamide
N-[1-({2-2-(pyrrolidin-1-yl)ethoxy]naphthalen-1-yl}methyl)naphthalen-2-yl]methanesulfonamide
1-[(2-hydroxynaphthalen-1-yl)methyl]naphthalen-2-yl 2-(diethylamino)acetate
1-{2-[2-(diethylamino)ethoxy]naphthalene-1-carbonyl}naphthalen-2-ol
2-(diethylamino)ethyl 1-[(2-methoxynaphthalen-1-yl)methyl]naphthalene-2-carboxylate
1-(2-{[1-(2-methoxynaphthalene-1-carbonyl)naphthalen-2-yl]oxy}ethyl)pyrrolidine
N-[2-(diethylamino)ethyl]-1-[(2-hydroxynaphthalen-1-yl)methyl]naphthalene-2-carboxamide
2-((1-[(2-ethoxynaphthalen-1-yl)methyl]naphthalen-2-yl)oxy)ethan-1-amine
2-[(1-{[2-(2-methoxyethoxy)naphthalen-1-yl]methyl}naphthalen-2-yl)oxy]ethan-1-amine
1-({2-[(azetidin-3-yl)methoxy]naphthalen-1-yl}methyl)naphthalen-2-ol bis(formic acid)
1-({2-[(1-methylazetidin-3-yl)methoxy]naphthalen-1-yl}methyl)naphthalen-2-ol
1-({2-(piperidin-4-yl)methoxy]naphthalen-1-yl}methyl)naphthalen-2-ol hydrochloride
1-({2-[(1-methylpiperidin-4-yl)methoxy]naphthalen-1-yl}methyl)naphthalen-2-ol
3-[({1-[(2-methoxynaphthalen-1-yl)methyl]naphthalen-2-yl}oxy)methyl]azetidine
4-[({1-[(2-methoxynaphthalen-1-yl)methyl]naphthalen-2-yl}oxy)methyl]-1-methylpiperidine
3-{[(1-{[2-(ethoxymethoxy)naphthalen-1-yl]methyl}naphthalen-2-yl)oxy]methyl}-1-methylazetidine
3-{[(1-{[2-(ethoxymethoxy)naphthalen-1-yl]methyl}naphthalen-2-yl)oxy]methyl}-1-methylpyrrolidine
4-{[(1-{[2-(ethoxymethoxy)naphthalen-1-yl]methyl}naphthalen-2-yl)oxy]methyl}-1-methylpiperidine
4-{2-[(1-{[2-(ethoxymethoxy)naphthalen-1-yl]methyl}naphthalen-2-yl)oxy] ethyl}piperidine
1-{2-[(1-{[2-(benzyloxy)naphthalen-1-yl]methyl}naphthalen-2-yl)oxy]ethyl}pyrrolidine
1-({2-[2-(azetidin-3-yl)ethoxy]naphthalen-1-yl}methyl)naphthalen-2-ol
diethyl[2-({1-[(2-methoxynaphthalen-1-yl)methyl]naphthalen-2-yl}methoxy)ethyl]amine
diethyl(2-{[1-(2-methoxynaphthalene-1-carbonyl)naphthalen-2-yl]oxy}ethyl)amine
diethyl[2-({1-[(naphthalen-1-yl)methyl]naphthalen-2-yl}oxy)ethyl]amine
1-[2-({1-[(naphthalen-1-yl)methyl]naphthalen-2-yl}oxy)ethyl]pyrrolidine
3-{2-[(1-{[2-(ethoxymethoxy)naphthalen-1-yl]methyl}naphthalen-2-yl)oxy]ethyl}azetidine hydrogen hydride
1-{[2-({[2-(diethylamino)ethyl]amino}methyl)naphthalen-1-yl]methyl}naphthalen-2-ol
({1-[(2-methoxynaphthalen-1-yl)methyl]naphthalen-2-yl}methyl)[2-(pyrrolidin-1-yl)ethyl]amine
formic acid;
{2-[(1-{[2-(benzyloxy)naphthalen-1-yl]methyl}naphthalen-2-yl)methoxy]ethyl}diethylamine
1-(2-{[2-(diethylamino)ethoxy]methyl}naphthalen-1-yl)methyl]naphthalen-2-ol
1-{2-[(1-{[2-(benzyloxy)naphthalen-1-yl]methyl}naphthalen-2-yl)methoxy]ethyl}pyrrolidine
[(1-{[2-(benzyloxy)naphthalen-1-yl]methyl}naphthalen-2-yl)methyl][2-(diethylamino)ethyl]amine
diethyl[2-({1-[(2-methoxynaphthalen-1-yl)(phenyl)methyl]naphthalen-2-yl}oxy)ethyl]amine
[(1-{[2-(benzyloxy)naphthalen-1-yl]methyl}naphthalen-2-yl)methyl][2-(pyrrolidin-1-yl)ethyl]amine
1-{[2-({[2-(pyrrolidin-1-yl)ethyl]amino}methyl)naphthalen-1-yl]methyl}naphthalen-2-ol
[2-({1-[(3,4-dimethoxyphenyl)methyl]naphthalen-2-yl}oxy)ethyl]diethylamine
1-[2-({1-[(3,4-dimethoxyphenyl)methyl]naphthalen-2-yl}oxy)ethyl]pyrrolidine
N-[2-({1-[(2-ethoxynaphthalen-1-yl)methyl]naphthalen-2-yl}oxy)ethyl]acetamide
N-{2-[(1-{[2-(hexyloxy)naphthalen-1-yl]methyl}naphthalen-2-yl)oxy]ethyl}acetamide
N-{2-[(1-{[2-(2-methoxyethoxy)naphthalen-1-yl] methyl}naphthalen-2-yl)oxy]ethyl}acetamide
1-(2-{[1-(3,4-dimethoxybenzoyl)naphthalen-2-yl]oxy}ethyl)pyrrolidine
(2-{[1-(3,4-dimethoxybenzoyl)naphthalen-2-yl]oxy}ethyl)diethylamine
4-{[(1-{[2-(ethoxymethoxy)naphthalen-1-yl]sulfanyl}naphthalen-2-yl)oxy]methyl}piperidine
2-[(1-{[2-(ethoxymethoxy)naphthalen-1-yl]sulfanyl}naphthalen-2-yl)oxy]ethan-1-amine
1-(4-{[(1-{[2-(ethoxymethoxy)naphthalen-1-yl]methyl}naphthalen-2-yl)oxy]methyl}piperidin-1-yl)ethan-1-one
4-{[(1-{[2-(2-methoxyethoxy)naphthalen-1-yl]methyl}naphthalen-2-yl)oxy]methyl}piperidine hydrochloride
3-({1-[(2-methoxynaphthalen-1-yl)methyl]naphthalen-2-yl}oxy)cyclobutan-1-amine
N-{2-[(1-{2-(ethoxymethoxy)naphthalen-1-yl]methyl}naphthalen-2-yl)oxy]ethyl}acetamide
1-{[2-(2-aminoethoxy)naphthalen-1-yl]methyl}naphthalen-2-ol hydrochloride
1-{[2-(2-aminophenoxy)naphthalen-1-yl]methyl}naphthalen-2-ol
2-({1-[(2-methoxynaphthalen-1-yl)methyl]naphthalen-2-yl}oxy)aniline
1-{[2-(2-aminoethoxy)naphthalen-1-yl]sulfanyl}naphthalen-2-ol
1-({2-[(piperidin-4-yl)methoxy]naphthalen-1-yl}sulfanyl)naphthalen-2-ol
2-({1-[(2-methoxynaphthalen-1-yl)methyl]naphthalen-2-yl}oxy)ethan-1-amine
1-({2-[2-(ethylamino)ethoxy]naphthalen-1-yl}methyl)naphthalen-2-ol hydrochloride
{2-[(1-{[2-(methoxynaphthalen-1-yl]methyl}naphthalen-2-yl)oxy}ethyl](ethyl)amine
4-({1-[(2-methoxynaphthalen-1-yl)methyl]naphthalen-2-yl}oxy)aniline
1-[(2-hydroxynaphthalen-1-yl)sulfanyl}naphthalen-2-ol TABLE A-continued (1-{[2-(hydroxymethyl)naphthalen-1-yl]methyl}naphthalen-2-yl)methanol In the second aspect of the present invention, it provides a pharmaceutical composition, which comprises the compound of the first aspect of the present invention, or a pharmaceutically acceptable salt, solvate, stereoisomer, or prodrug thereof, and a pharmaceutically acceptable carrier.

In the third aspect of the present invention, it provides a use of the compound of the first aspect of the present invention, or a pharmaceutically acceptable salt, solvate, stereoisomer or prodrug thereof for the manufacture of a medicament for treating or preventing ion channel related disease.

In another preferred embodiment, the ion channel is selected from the group consisting of Herg K channel, Ca channel, and combinations thereof.

In another preferred example, the ion channel related disease is selected from the group consisting of cardiovascular disease, Parkinsons, seizures, and combinations thereof.

In another preferred example, the ion channel related disease is selected from the group consisting of arterial arryhthmia (AF), ventricular arryhthmia (VF) disease, and combinations thereof.

In the fourth aspect of the present invention, it provides a method for treating an ion channel related disease comprising a step of administering the compound of the first aspect of the present invention, or a pharmaceutically acceptable salt, solvate, stereoisomer, or prodrug thereof (preferably in a safe and/or therapeutically effective amount).

In another preferred embodiment, the subjects comprises human and non-human mammal.

In the fifth aspect of the present invention, it provides a method for promoting growth of cardiomyocytes in vitro, which comprises a step of culturing cardiomyocyte in the present of a compound of the first aspect of the present invention, or a pharmaceutically acceptable salt, a solvate, a stereoisomer or a prodrug.

In the sixth aspect of the present invention, it provides a method for inhibiting ion channel in vitro, which comprises a step of contacting cardiomyocyte with a compound of the first aspect of the present invention, or a pharmaceutically acceptable salt, a solvate, a stereoisomer or a prodrug, thereby inhibiting ion channel.

It should be understood that each of the above technical features of the invention and each technical feature specifically described below (such as in Examples) can be combined with each other within the scope of the present invention so as to constitute new or preferred technical solutions.

DETAILED DESCRIPTION OF INVENTION

After extensive and intensive research, the inventors have unexpectedly developed a novel compound of formula I that effectively inhibits ion channel. The experiments show that the compounds of formula I are potent inhibitors of IKr (Herg K channel) and CaV1.2 (Ca channel) along with other sodium and potassion channels. The compound of invention is effective and safe ion channel antagonist which is useful for treatment in heart diseases and other ion channel related diseases. The present invention is completed on this basis.

Definition of Terms

As used herein, term "C1-C6 alkyl" refers to a straight or branched saturated aliphatic hydrocarbon group having 1 to 6 carbon atoms, for example, methyl, ethyl, propyl, iso-propyl, n-butyl, iso-butyl, tert-butyl, pentyl, hexyl and the like, and more preferably alkyl having 1 to 4 carbon atoms. Likely, "C1-C6 alkyl" refers to a straight or branched saturated aliphatic hydrocarbon group having 1 to 6 carbon atoms.

As used herein, term "C2-C6$_1$ alkenyl" refers to a straight or branched unsaturated aliphatic hydrocarbon group having 2 to 6) carbon atoms and carbon-carbon double bond (C=C), for example ethenyl, propenyl, iso-propenyl, n-butenyl, iso-butenyl, pentenyl, hexenyl and the like.

As used herein, term "C2-C6 alkynyl" refers to a straight or branched unsaturated aliphatic hydrocarbon group having 2 to 6 carbon atoms and carbon-carbon triple bond, for example ethynyl, propynyl, n-butynyl, iso-butynyl, pentynyl, hexynyl and the like.

As used herein, term "C3-C8cycloalkyl" refers to cycloalkyl having 3 to 8 carbon atoms, for example cyclopropyl, cyclobutyl, cyclopentyl, cyclohexyl and the like.

As used herein, term "C1-C6 alkoxy" refers to C1-C6 alkyl-O—, for example methoxy, ethoxy, propoxy, butoxy and the like.

As used herein, term "C6-C10 aryl" refers to aromatic hydrocarbon group having 6 to 10 carbon atoms, for example phenyl, naphthyl and the like.

As used herein, term "Halogen" refers to fluorine, chlorine, bromine or iodine.

As used herein, term "Divalent $C_{1-6}$ hydrocarbyl" refers to a straight or branched alkylidene(or "alkylene group"), alkenylidene or alkynylidene, wherein, "alkylidene" or "alkylene group" refers to divalent alkyl, for example, methylidene, ethylidene and the like; and "alkenylidene" refers to divalent alkenyl. "Alkylidene is replaced" refers to the methylidene in the divalent straight or branched $C_{1-3}$ hydrocarbyl may be replaced with the groups as defined herein, for example, it is —CH$_2$—S(O)—CH$_2$—, —CH$_2$—O—CH$_2$—, —CH$_2$—C(O)NR$^y$—CH$_2$—, —C(O)—CH$_2$—CH$_2$—, —CH$_2$—C(R$^y$R$^x$)—CH$_2$—, —N(R$^y$)—CH$_2$—CH$_2$—, —C(R$^y$R$^x$)—C(R$^y$R$^x$)—CH$_2$— and the like after replacement.

As used herein, terms "heteroaryl ring" and "heteroaryl" may be used changeably, and refer to a group having 5 to 10 ring atoms (preferably 5, 6, 9 or 10 ring atoms), wherein 1 to 5 of ring atoms are heteroatoms and others are carbon atoms and the ring shares 6, 10 or 14 π electron. As used herein, term "heteroatom" refers to nitrogen, oxygen or sulfur. Preferably, term "heteroaryl ring" or "heteroaryl" refer to either of monocyclic heteroaryl (ring) and bicyclic heteroaryl (ring). Preferably when the "heteroaryl ring" or "heteroaryl" is monocyclic heteroaryl (ring), the group preferably has 5 or 6 ring atoms, i.e 5 to 6 membered monocyclic heteroaryl (ring); and when the "heteroaryl ring" or "heteroaryl" is bicyclic heteroaryl (ring), the group preferably has 8, 9 or 10 ring atoms, i.e 8 to 10 membered bicyclic heteroaryl (ring).

As used herein, term "5 to 6 membered monocyclic heteroaryl ring" refers to a monocyclic heteroaryl ring having 5 to 6 ring atoms, for example, including (but not limited to): thiophene ring, furan ring, thiazole ring, imidazole ring, oxazole ring, pyrrole ring, imidazole ring, triazole ring, tetrazole ring, isoxazole ring, oxadiazole ring, thiadiazole ring, pyridine ring, pyridazine ring, pyrimidine ring, pyrazine ring and the like.

As used herein, term "8 to 10 membered bicyclic heteroaryl ring" refers to bicyclic hetero aryl ring having 8 to 10 ring atoms, for example, including (but not limited to): benzofuran ring, benzothiophene ring, indole ring, isoindole ring, quinoline ring, isoquinoline ring, indazole ring, benzothiazole ring, benzimidazole ring, quinazoline ring, quinoxaline ring, cinnoline ring, phthalazine ring.

As used herein, the 5 to 6 membered monocyclic heteroaryl ring or 8 to 10 membered bicyclic heteroaryl ring may be selected from the group consisting of

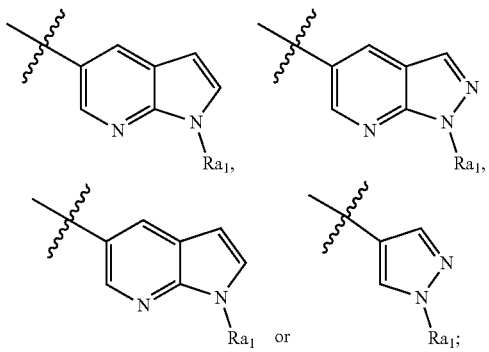

wherein, $R_{a1}$ is a hydrogen, methyl or ethyl.

As used herein, term "cycloalkyl" and "heterocycloalkyl" (or "heterocyclyl") include satured ring and partially unsaturated ring. term "partially unsaturated" refers to those having one or more unsaturated bonds while do not have fully conjugated 7l electron system.

Perferly, "cycloalkyl" refers to either of "monocyclic ring" and "bicyclic ring".

As used herein, term "monocyclic ring", saturated or partially unsaturated, refers to a saturated all-carbon monocyclic ring or partially unsaturated all-carbon monocyclic ring. Preferably the "monocyclic ring" having 3 to 7 ring atoms, i.e. 3 to 7 membered monocyclic ring. The examples of 3 to 7 membered monocyclic ring including (but not limited to): cyclopropane, cyclobutane, cyclopentane, cyclohexane, cyclohexadiene ring, cycloheptane, cycloheptanetriene ring and the like.

As used herein, term "bicyclic ring", saturated or partially unsaturated, refers to a saturated all-carbon bicyclic ring or partially unsaturated all-carbon bicyclic ring. Preferably the "bicyclic ring" having 8 to 10 ring atoms, i.e. 8 to 10 membered bicyclic ring.

Perferly, term "heterocyclic group" (or "heterocyclyl") refers to either of "heterocyclic monoring" and "heterocyclic biring".

As used herein, term "heterocyclic monoring", saturated or partially unsaturated, refers to saturated monocyclic ring or partially unsaturated monocyclic ring. Preferably the "heterocyclic monoring" having 3 to 7 ring atoms(i.e. 3 to 7 membered heterocyclic monoring) wherein 1 to 3 carbon atoms are substituted by heteroatom(s) selected from nitrogen, oxygen or sulfur. An example of heterocyclic monoring includes (but not limited to): tetrahydrofuran ring, thiophane ring, pyrrolidinyl ring, piperidine ring, pyrroline ring, oxazolidine ring, piperazine ring, dioxalame, morpholine ring.

As used herein, term "heterocyclic biring", saturated or partially unsaturated, refers to saturated bicyclic ring or partially unsaturated bicyclic ring. Preferably the "heterocyclic biring" having 8 to 10 ring atoms(i.e. 8 to 10 membered heterocyclic monoring) wherein 1 to 5 carbon atoms are substituted by heteroatom(s) selected from nitrogen, oxygen or sulfur. An example of heterocyclic biring includes (but not limited to): tetrahydroquinoline ring, tetrahydroisoquinoline ring, decahydroquinoline ring and the like.

As used herein, term "the heterocyclyl or heteroaryl contains 1-2 N atoms and 0, 1, 2 O or S heteroatoms" refers to a heterocyclic group or heteroaryl wherein 1 or 2 carbon ring atom are replaced by nitrogen and 0, 1, 2 or 3 carbon ring atoms are replaced by oxygen or sulfur.

Pharmaceutical Composition

Generally, the compound of the present invention or a pharmaceutically acceptable salt solvate, stereoisomer, or prodrug thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present invention contained in these formulations may be solid powders or granules; solutions or suspensions in aqueous or non-aqueous liquid; water-in-oil or oil-in-water emulsions etc.. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylidene glycol, polyethylidene glycol and the like. The active compounds may form a solution or suspension with the above-mentioned carriers.

The compositions of the present invention are formulated, quantified and administrated in a manner consistent with the practice of medicine. The "effective amount" of the administrated compound depends on the factors such as the specific disease to be treated, the individual being treated, the cause of diseases, the drug targets and the mode of administration, etc.

As used herein, term "the active material of the invention" or "the active compound of the invention" refers to the compound of formula (I) of the invention, or a pharmaceutically acceptable salt, solvate, stereoisomer, or prodrug thereof.

As used herein, "pharmaceutically acceptable salt(s)" includes pharmaceutically acceptable acid addition salt(s) and base addition salt(s).

As used herein, term "Pharmaceutically acceptable acid addition salts" refer to salts that are able to retain the biological effectiveness of the free base without other side effects and are formed with inorganic or organic acids. Inorganic acid salts include, but not limited to, hydrochloride, hydrobromide, sulfate, phosphate and the like; organic acid salts include, but not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

As used herein, term "Pharmaceutically acceptable base addition salts" include, but not limited to the salts of inorganic bases such as sodium, potassium, calcium and magnesium salts, and include but not limited to the salts of organic bases, such as ammonium salt, triethylamine salt, lysine salt, arginine salt and the like. These salts can be prepared by the methods known in the art.

As used herein, the compounds of formula (I) may exit in one or more crystalline forms. The active compounds of the present invention include various polymorphs and mixtures thereof.

The "solvate" mentioned in the present invention refers to a complex formed with the compound of the present invention and a solvent. The solvate can be formed either through a reaction in a solvent or precipitated or crystallized from the solvent. For example, a complex formed with water is referred to as "hydrate". The solvates of the compounds of formula (I) are within the scope of the present invention.

The compounds of formula (I) of the invention may contain one or more chiral centers, and may exist in different optically active forms. When the compound contains one chiral center, the compound includes enantiomers. The present invention includes both of two isomers and a mixture thereof, such as racemic mixtures. Enantiomers can be resolved using methods known in the art, such as crystallization and chiral chromatography and the like. When the compound of formula (I) contain more than one chiral centers, the compounds may include diastereomers. The present invention includes specific isomers resolved into optically pure isomers as well as the mixtures of diastereomeric isomers. Diastereomeric isomers can be resolved using methods known in the art, such as crystallization and preparative chromatography.

The present invention includes prodrugs of the above-mentioned compounds. Prodrugs include known amino protecting groups and carboxyl protecting groups which are hydrolyzed under physiologic conditions or released by enzyme reaction to obtain the parent compounds. Specific preparation methods of prodrugs can refer to (Saulnier, M G; Frennesson, D B; Deshpande, M S; Hansel, S B and Vysa, DMBioorg.Med.Chem Lett.1994, 4, 1985-1990; and Greenwald, R B; Choe, Y H; Conover, C D; Shum, K.; Wu, D.; Royzen, M.J.Med.Chem.2000, 43, 475).

As used herein, term "therapeutically effective amount" refers to an amount that yields a function or activity to humans and/or animals and may be tolerated by humans and/or animals.

The pharmaceutical composition provided by the present invention preferably contains the active ingredient in a weight ratio of 1 to 99%. Preferably, the compound of the general formula I accounts for 65 wt % to 99 wt % of the total weight as the active ingredient, and the rest are pharmaceutically acceptable carriers, diluents, solutions or salt solutions.

The compounds and pharmaceutical compositions provided by the present invention may be in various forms, such as tablets, capsules, powders, syrups, solutions, suspensions, aerosols, etc., and may be present in suitable solid or liquid carriers or diluents, and in disinfectors suitable for injection or instillation.

Various dosage forms of the pharmaceutical compositions of the present invention can be prepared according to the conventional preparation methods in the pharmaceutical field. The unit dosage of its formulation formula comprises 0.05-200 mg of the compound of formula I, preferably, the unit dosage of the formulation formula contains 0.1 mg-100 mg of the compound of formula I.

The compounds of the present invention may be administered alone or in combination with other pharmaceutically acceptable compounds (such as other ion channel inhibitors).

The compounds and pharmaceutical compositions of the present invention can be used clinically in mammals, including humans and animals, and can be administered via mouth, nose, skin, lung or gastrointestinal tract. Most preferred is oral. The most preferred daily dose is 0.01-200 mg/kg body weight in one dose, or 0.01-100 mg/kg body weight in divided doses. Regardless of the administering method, the individual's optimal dose should be based on the specific treatment. Usually, it starts with a small dose, which is gradually increased until the most suitable dose is found.

Preparation Method

The present invention provides preparation methods of compounds of formula (I). The compounds of the present invention can be easily prepared by a variety of synthetic operations, and these operations are familiar to those skilled in the art. An exemplary preparation of these compounds may include (but not limited to) the processes described below.

Generally, in the preparation process, each reaction is generally conducted in an inert solvent, under room temperature to reflux temperature (such as 0 –150° C., preferably from 0-100° C.). The reaction time is usually 0.1 hours-60 hours, preferably 0.5 to 48 hours.

Preferably, compounds of formula (I) of the present invention can be prepared referring to any of the following schemes. The procedures of method can be extended or combined as desired in practice.

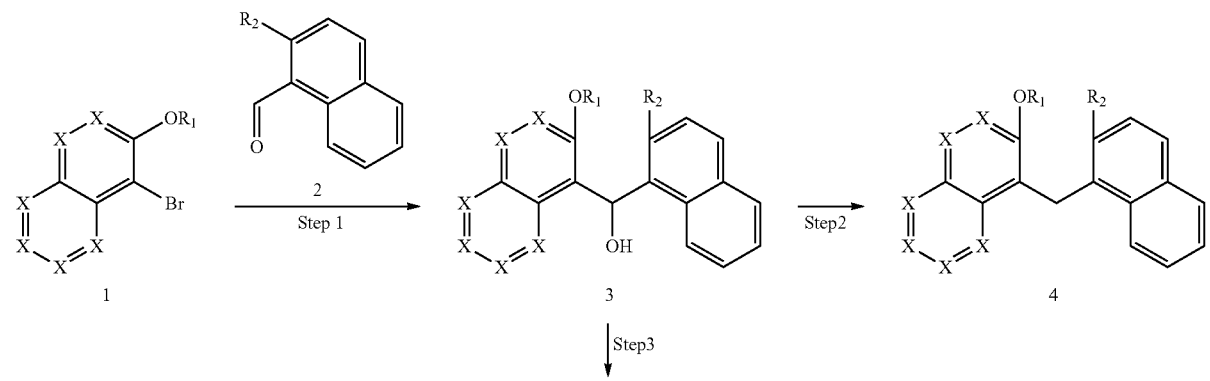

Scheme 1

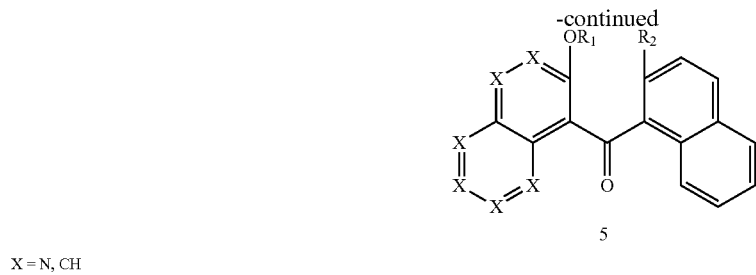

5

X = N, CH

Scheme 1 shows one route where the appropriately protected bromo or iodo napthol ether, where R₁ can be alkyl, Mom, Benzyl, etc. that can be removed easily to reveal the alcohol for further functionalization after reaction with the substituted naphaldehyde 2. Metal halogen exchange with appropriate base such as nBuLi is a widely known principle in organic chemistry and should be performed readily by those skilled in the art. This method of reaction specifically for napthyl bromide has been described in *Tetrahedron* 2013, 69(6), 1694-1699. Alternatively, a Grignard reagent can be generated with Mg metal or alkylmagnesium bromide or chloride. After reaction, the intermediate alcohol 3 can be oxidized with oxidation reagents such as MnO₂, DMP, etc. to intermediate ketone 5. Alternatively, the alcohol can be reduced to make intermediate 4 using acid, such at TFA, acetic acid, etc. and reducing agents such as NaBH₄, Et₃SiH, etc. Such reduction to make alkyl intermediate 4 have been described in *Tetrahedron* 1995, 51(10), 3051-3060.

Scheme 2.

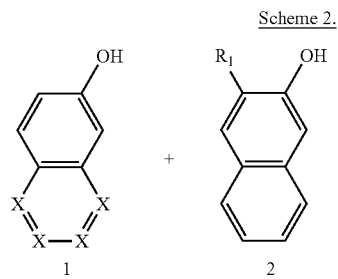

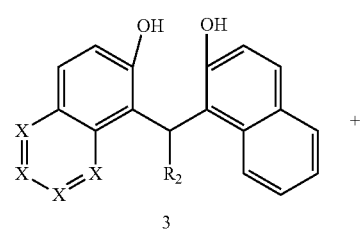

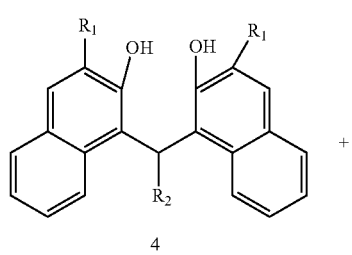

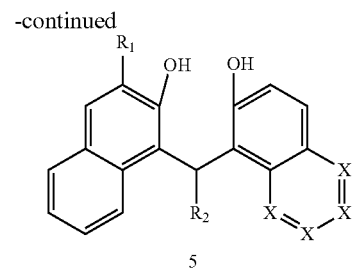

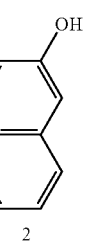

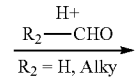

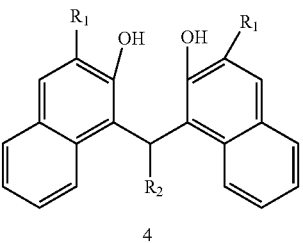

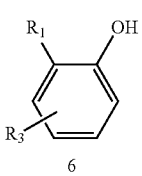

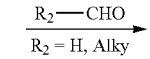

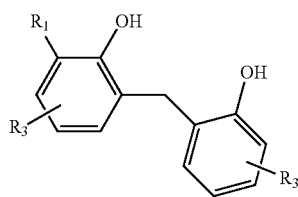

Scheme 2 shows an alternate route to access di-napthol methane intermediates 3 and 4. Reaction of unsubstituted napthol, substituted napthol and formaldehyde or alkylaldehyde in the presence of acid gave a mixture of two intermediates 3 and 4. If you only reacted unsubstituted or substituted napthols such as 5 with aldehydes (formaldehyde or alkyl aldehydes), then only symmetrical intermediate diol 4 was isolated.

Acids such as p-toluene sulfonic acid, HBr, etc can be used in appropriate solvents as described in several references: RSC Advances 2014, 4(4), 1559-1562; Synthetic Communications 2016, 46(4), 379-385; Letters in Organic Chemistry 2006, 3(10), 735-740. Di-napthol methane 3 ($R_3$=H, Me, select Alkyl, select Aryl) have been disclosed in the references mentioned above.

Other substituted phenols were also used in similar reactions to get di-phenol methanes 7 as shown in scheme 2.

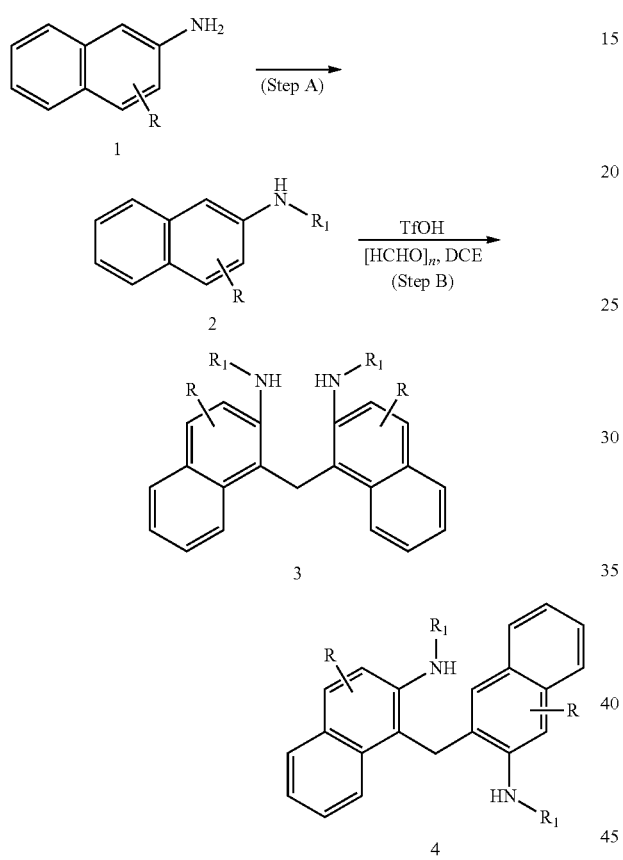

Scheme 3.

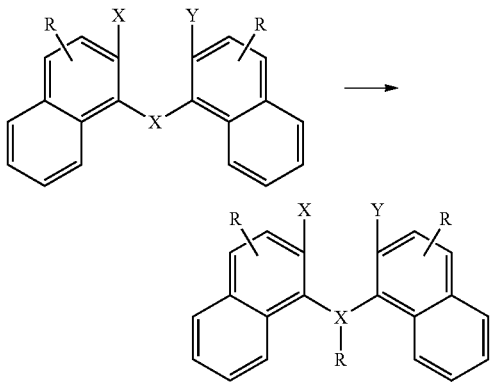

X = $NH_2$, SH
X = N, R = Alkyl, aryl
X = S, R = O, $O_2$

Scheme 4 shows the preparation of di-napthol amine and thioether derivatives or intermediates. Buchwald reaction conditions using palladium catalysts and base combinations. Normally, Pd2(dba)3 and Ph3P additive along with strong base such as NaOtBu, Cs2CO3, etc are used in the reaction. Several examples of this type of reactions have been described in literature, such as J. Org. Chem., 2003, 68(16), 6071-6078; Organometallics, 2017, 36(2), 251-254. The parent compound (R═H, Y═OMe and OH) are known and have been reported in J. Med. Chem, 2012, 55(19), 8538-8548. The amino group can be further functionalized to give alkyl and aryl amines. In the case of thioether, it can be oxidized to give sulforide (R ═O) or sulforne (R═)$_2$) using oxidants such as hyderogen peroxide, Oxone, mCPBA, etc. For alkyl amines, the amines are reacted with appropriate alkyl groups with either halide and other leaving groups or reacted with alkyl and aryl aldehydes under reductive conditions.

Appropriately protected and functionalized amino napthalenes can also be coupled to formaldeyde or substituted aldehyde to prepare the amino napthalene methane intermediates 3 and 4 as shown in Scheme 3. This procedure is similar to the one used for the napthol derivatives as shown on Scheme 2.

Scheme 4

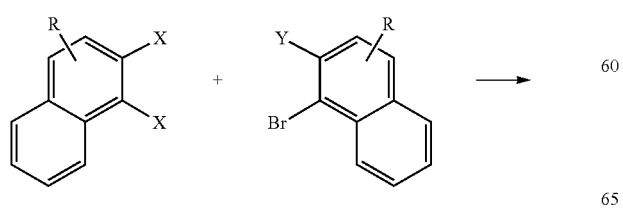

Scheme 5

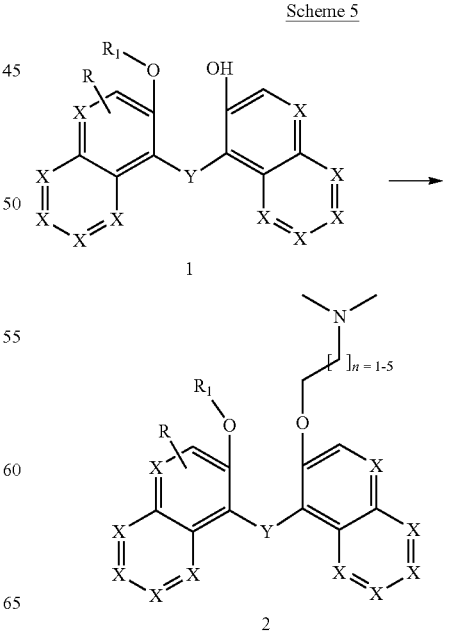

-continued

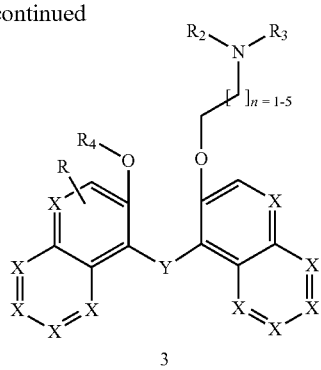

X = C, N
$R_2 = R_3$ = Alkyl, cycloalkyl
R4 = alkyl, substituted alkyletc
Y = N-PG, N-alkyl, S, SO, $SO_2$ One method for preparation of alkyl amino ethers 3 is shown on Scheme 5. Intermediate where $R_1$ is hydrogen can be selectively reacted with appropriate amino alkyl reagents via several known methods to give intermediate 2. For example, use of amino alkyl alcohol can with reaction with the phenol in 1 using Mitsubobu conditions. Another way would be to reaction amino alkyl halides or sulfonates with phenol 1 using mild base such as $K_2CO_3$, etc. Another way would be to prepare an alkyl ether first by reacting alkoxy alkyl alcohol, sulfonates or halides to make the alkyl napthol ethers. After deprotection of the terminal alcohol, it can be oxidized to aldehyde or converted to an appropriate leaving group. Then reaction with appropriate amines can furnish intermediate 2. Finally, the second phenol can be reacted with various alkyl groups with appropriate leaving groups, such as halides or mesylate, tosylate, etc, to provide targets 3.

Scheme 6

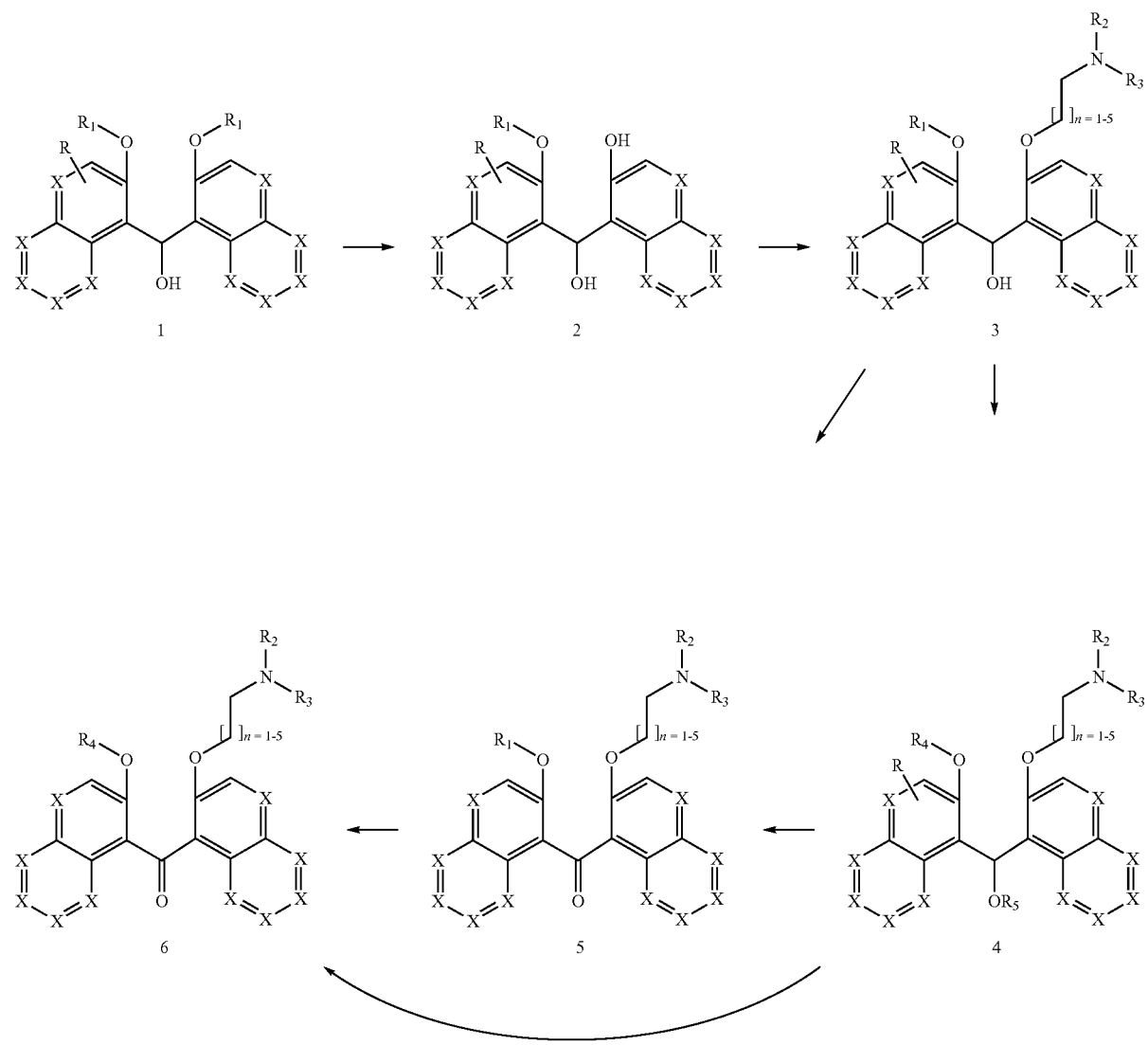

Scheme 6 shows one of the methods used to make the dinapthol methanol and ketone derivatives 4, 5 and 6. The intermediate made in scheme 2 where $R_1$ is alkyl (e.g. $R_1$=Me), one of the alkyl groups can be selectively deprotected using dealkylating reagents, such as $BBr_3$, $BCl_3$, TMSI, etc. Then the freed phenol can be reacted as described in scheme 5 to give 3. Once the side chain is attached to give the ether 3, then the second group can be deprotected again followed by addition of other alkyl groups to give 4 ($R_4$=alkyl) or kept a phenol ($R_4$=H) for testing. The ketone can also be made from alcohol 3 or 4 via oxidation of the secondary alcohol to give 5. If made from 3, then the protecting group needs to be removed and an alkyl side chain added as previously described.

tution by making a leaving group, such as triflate by reacting with trifluoroacetic anhydride in the presence of base such as pyridine or other trialkyl amines. The triflate can then be substituted with appropriately functionalized amine ($R_2$=alkyl, sulfonyl, carbonyl, etc) or ammonia ($R_2$=H) under Buchwald conditions to give 2. The ether in 2 ($R_1$=alkyl such as methyl) can be deprotected and then functionalized to give target 3 as described before.

Alternatively, the intermediate 2 ($R_2$=H) can be selectively functionalized to give 5 ($R_3$=H) where the amine is capped with amino alkyl chain via reductive amination of amino alkyl aldehydes or reacted with amino alkyl halides and sulfonates. The intermediate 2 can also be capped to make alkyl amine, amides and sulfonamides ($R_3$=alkyl, Alkyl-CO, Alkyl-SO2) before capping with the amino alkyl side chain in target 5.

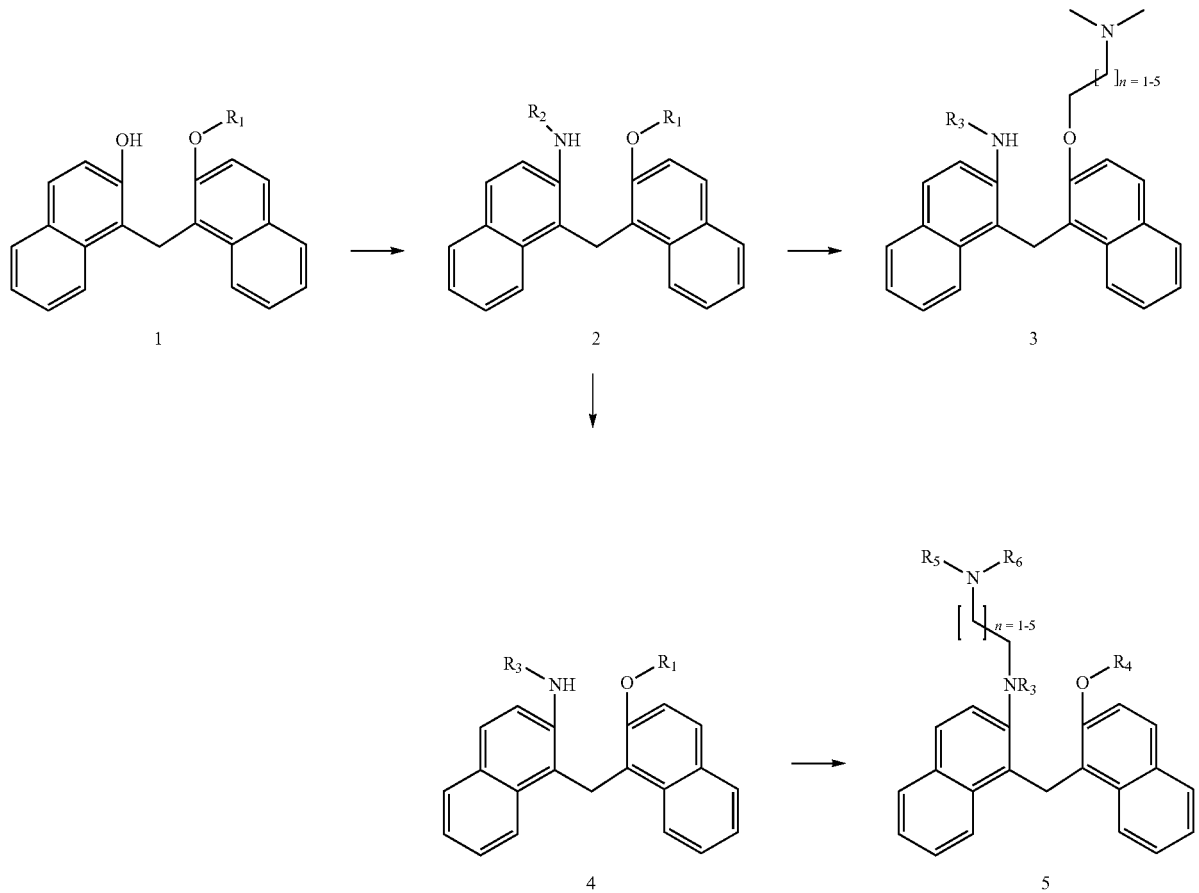

Scheme 7

$R_5 = R_6$ = Alkyl, cycloalkyl, H
R5 = Alkyl; $R_6$ = Boc, COAlkyl, H, etc
$R_4$ = alkyl, substituted alkyl, etc Scheme 7 shows methods to make unsymmetrical amino naphthalene napthol methane starting from singly protected napthol methane 1. The phenol can be activated for substi- Scheme 8
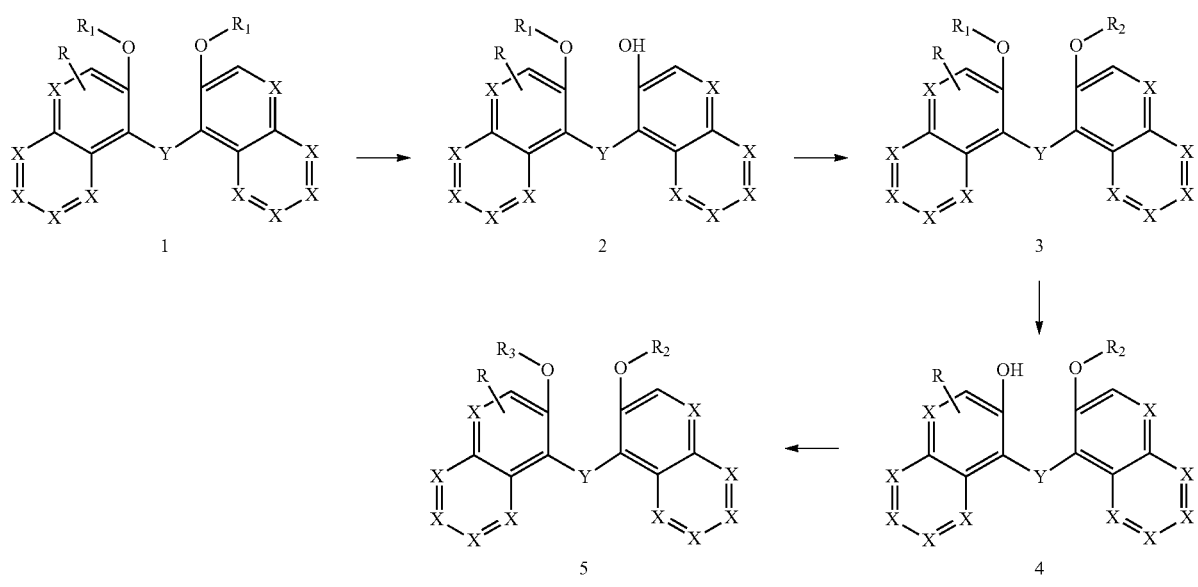
X = C, N
Y = CH$_2$, CHOR$_4$, CO, NR$_4$
R$_4$ = H, Me, Alkyl, COR$_5$, SO$_2$R$_5$
Scheme 8 shows methods for preparing alkyl ether chain where R$_2$ is amino alkyl group when the linear chain is substituted with cycloalkyl and other substitutions, some examples are shown below.
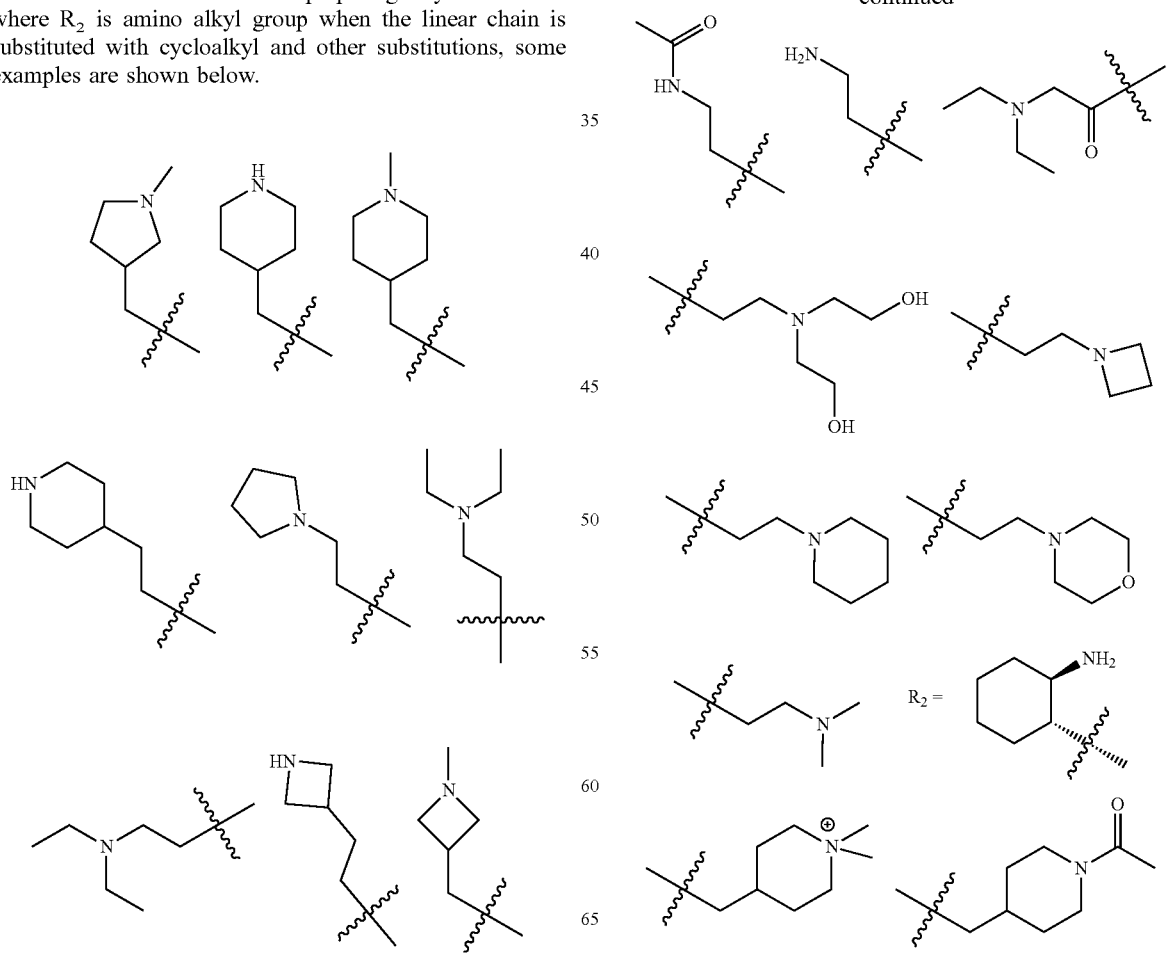

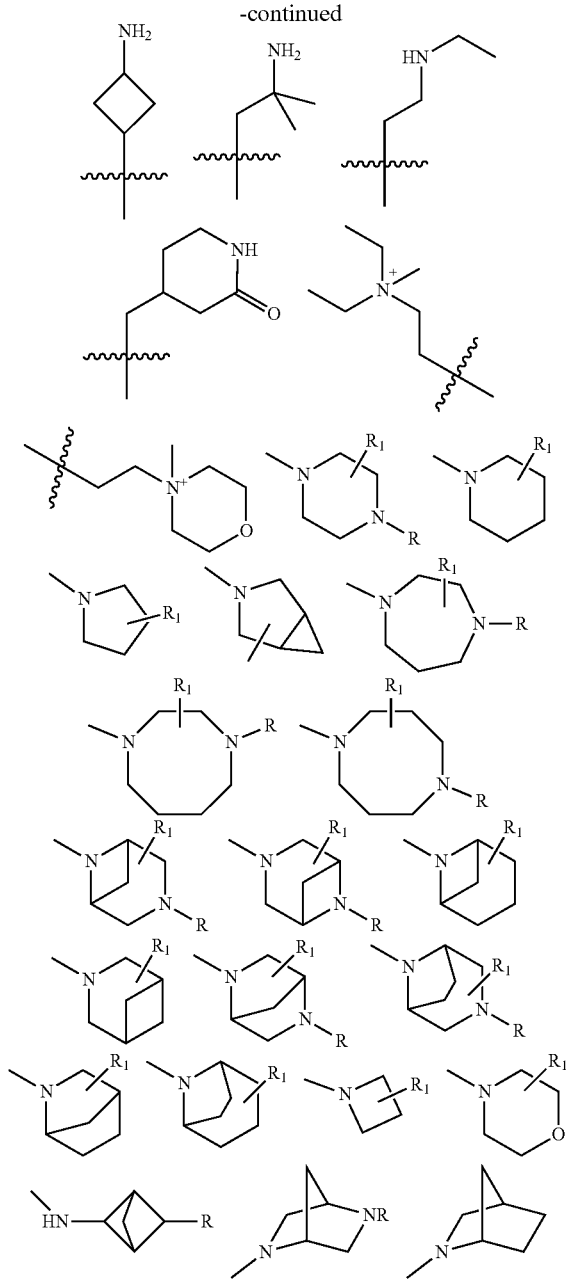

Then deprotection of the protecting alkyl group $R_1$ provides the target 4 whose phenol group can then be further capped via known reaction methods to make target 5.

All of the reactions in the above schemes are conventional reactions known to the skilled in the art. Starting compounds in the schemes are available commercially or prepared through methods known to the skilled in the art.

Compounds of formula (I), preparation methods thereof, pharmaceutical compositions and treatment protocols disclosed in the present invention can be achieved by the person skilled in the art through appropriate improvements of process parameters referring to this disclosure of invention. It should be particularly noted that all such alterations and changes are obvious to the skilled artisan, and they are deemed to be included in the present invention. Preferred embodiments of products, methods and applications of the present invention have been described, and relevant personnel can obviously alter or change and combine the methods and uses of the present invention without departing from the content, spirit and scope of the present invention for implementation and application of the present technology.

Compared with the prior art, the main advantages of the present invention include:

(1) The compounds of the present invention show a high inhibitory activity against Herg channels as well as Calcium channels.
(2) The compounds of the present invention also exhibit broad activity against Iks channel while keeping potency against Herg and Calcium channel (e.g., CaV1.2).
(3) The compounds of the present invention have shown good safety and efficacy in vivo in Arrhythmia models.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions.

Unless indicated otherwise, parts and percentage are calculated by weight.

Unless defined otherwise, terms used herein are the same as those familiar to the skilled in the art.

Moreover, any method or material similar or equivalent to those recorded in the present invention can be used in the present invention.

Reagents and Instruments

Experimental procedures: All reactions were conducted under an atmosphere of dry nitrogen unless specified otherwise. TLC plates were visualized with u.v. light. Flash chromatography refers to column chromatography over silica gel (40-60 μm) using glass columns. Alternatively, automated chromatography was performed using ISCO, Biotage SP1 or Biotage Isolera systems with u.v. detection at 220 or 254 nm and employing Biotage normal phase or reverse phase silica cartridges. Details can be found under the relevant experimental procedure.

The following methods were used for Agilent LCMS: Agilent 1260 HPLC(binary pump) with single-quadrupole Mass detector, ESI for ionization. Waters analytical column CORTECS C18, 2.7 μm, 4.6×30 mm, 45° C., 1 μL injection volume, 1.8 mL/min, with a gradient of mobile phase according to the following timings:

| Time (min) | Acetonitrile (0.05% FA/0.05% TFA)(%) | $H_2O$ (0.05% FA/0.05% TFA)(%) |
| --- | --- | --- |
| 0.00 | 5 | 95 |
| 0.80 | 95 | 5 |
| 1.60 | 95 | 5 |
| 1.61 | 5 | 95 |
| 2.00 | 5 | 95 |

| Time (min) | Acetonitrile (0.05% FA/0.05% TFA)(%) | $H_2O$ (0.05% FA/0.05% TFA)(%) |
| --- | --- | --- |
| 0.00 | 5 | 95 |
| 1.00 | 95 | 5 |
| 2.00 | 95 | 5 |
| 2.10 | 5 | 95 |
| 2.50 | 5 | 95 |

| Time (min) | Acetonitrile (0.05% FA/0.05% TFA)(%) | H₂O (0.05% FA/0.05% TFA)(%) |
|---|---|---|
| 0.00 | 50 | 50 |
| 0.80 | 95 | 5 |
| 1.60 | 95 | 5 |
| 1.61 | 50 | 50 |
| 2.00 | 50 | 50 |

| Time (min) | Acetonitrile (0.05% FA/0.05% TFA)(%) | H₂O (0.05% FA/0.05% TFA)(%) |
|---|---|---|
| 0.00 | 5 | 95 |
| 3.00 | 95 | 5 |
| 4.00 | 95 | 5 |
| 4.10 | 5 | 95 |
| 5.00 | 5 | 95 |

| Time (min) | Acetonitrile (0.05% FA/0.05% TFA)(%) | H₂O (0.05% FA/0.05% TFA)(%) |
|---|---|---|
| 0.00 | 5 | 95 |
| 7.50 | 95 | 5 |
| 8.50 | 95 | 5 |
| 9.00 | 5 | 95 |
| 10 | 5 | 95 |

The following methods were used for Agilent LCMS: Agilent 1260 (binary pump) with single-quadrupole Mass detector, ESI for ionization. Waters analytical column Xbridge C18, 3.5 μm, 4.6×100 mm, 35° C., 1 μL injection volume, 1.0 mL/min, with a gradient of mobile phase according to the following timings:

| Time (min) | Acetonitrile (0.05% NH₄OH)(%) | H₂O (0.05% NH₄OH)(%) |
|---|---|---|
| 0.00 | 10 | 90 |
| 6.50 | 90 | 10 |
| 6.60 | 95 | 5 |
| 8.60 | 95 | 5 |
| 9.00 | 90 | 10 |
| 10.00 | 90 | 10 |

The following systems were used for UPLC (PDA detector, no mass spectrometry) Waters H-Class (quaternary pump), Waters ACQUITY BEH C18 1.7 μm, 2.1×50 mm, 0.5 mL/min, 40° C.; with a gradient of mobile phase according to the following timings:

| Time (min) | Acetonitrile (0.05% TFA)(%) | H₂O (0.05% TFA)(%) |
|---|---|---|
| 0.00 | 5 | 95 |
| 2.00 | 95 | 5 |
| 2.70 | 95 | 5 |
| 2.80 | 5 | 95 |
| 3.50 | 5 | 95 |

The following system was used for HPLC (DAD detector, no mass spectrometry) Agilent 1260 (quaternary pump), Waters Xbridge C18 5 μm, 2.1×50 mm, 0.8 mL/min, 35° C.; with a gradient of mobile phase according to the following timings:

| Time (min) | Acetonitrile (0.1% FA)(%) | H₂O (0.1% FA)(%) |
|---|---|---|
| 0.00 | 1 | 99 |
| 0.60 | 1 | 99 |
| 4.00 | 100 | 0 |
| 4.30 | 1 | 99 |
| 5.50 | 1 | 99 |

NMR spectra were measured with a Bruker/Varian spectrometer operating at 400 MHz (1H), 376 MHz (19F) or 100 MHz (13C). Solvents used for samples are specified in the experimental procedures for each compound.

The known starting materials of the invention are synthesized by the methods known in the art, or are purchased from Bide Chemical ltd., Bridge, Combi Blocks, Wuxi Lab Networks, Acros Organics, Aldrich Chemical Company, Accela ChemBio Inc and Darui Chemical Company etc.

All examples were performed under nitrogen or argon atmosphere and the solution refers to aqueous solution if without special explanation.

In the examples, the reaction process was monitored by thin layer chromatography (TLC), compounds were purified by column chromatography. The eluent used in Column chromatography or TLC were selected from a system of dichloromethane and methanol, n-hexane and ethyl acetate, petroleum ether and ethyl acetate, or acetone and the like, wherein the volume ratio of the solvents might be regulated according to the different polarity of compounds.

DMF refers to dimethylformamide, DMSO refers to dimethylsulfoxide, THF refers to tetrahydrofuran, DIEA refers to N,N-diisopropylethylamine, EA refers to ethyl acetate, PE refers to petroleum ether. BINAP refers to (2R, 3S)-2,2'-bis diphenylphosphino-1,1'-binaphthyl, NBS refers to N-bromosuccinimide, NCS refers to N-chlorosuccinimide, Pd2(dba)3 refers to tris(dibenzylideneacetone)dipalladium, Pd(dppf)Cl2 refers to [1,1'-bis(diphenylphosphino)ferrocene] palladium dichloride.

As used herein, room temperature refers to be about 25° C.

In the examples, compound No. "TJU-AXXX" and "AXXX" means same compounds. For example, compound TJU-A001 and compound A001 are same.

Example 1: 1,1'-methylenebis(naphthalen-2-ol) (A001)

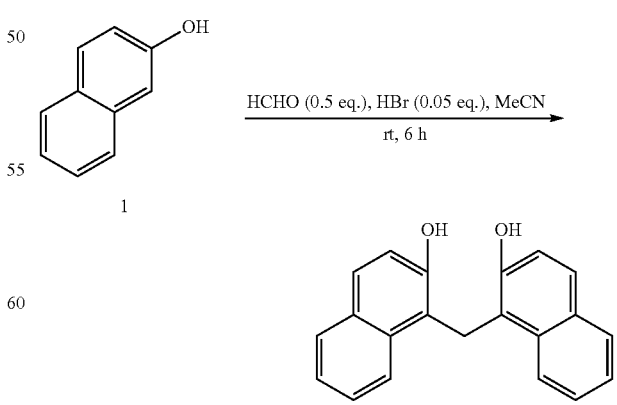

To a solution of naphthalen-2-ol (1.009 g, 7 mmol) and formaldehyde aqueous solution (314 mg, 3.85 mmol) in acetonitrile (9 mL) was added HBr (40% aqueous, 75 mg)-acetonitrile (1 mL) at room temperature. The mixture was stirred at room temperature for 6 h and poured into water (40 mL) and extracted with dichloromethane (30 mL×2), dried over anhydrous sodium sulfate, filtered and concentrated. The residue was purified by flash column chromatography on silica gel flash column chromatography on silica gel (EA/PE=1/4, v/v) to afford 1,1'-methylenebis(naphthalen-2-ol) (570 mg, 27%) as a pale-yellow solid. Mass Spectrum (ESI) m/z=323.1 (M+Na$^+$).

$^1$H NMR (400 MHz, DMSO-d$_6$) δ 10.10 (s, 2H), 8.18 (d, J=8.5 Hz, 2H), 7.63-7.61 (m, 4H), 7.26 (d, J=8.8 Hz, 2H), 7.18-7.16 (m, 2H), 7.12-7.10 (m, 2H), 4.70 (s, 2H).

Example 2:
1,1'-(methylazanediyl)bis(naphthalen-2-ol) (A003)

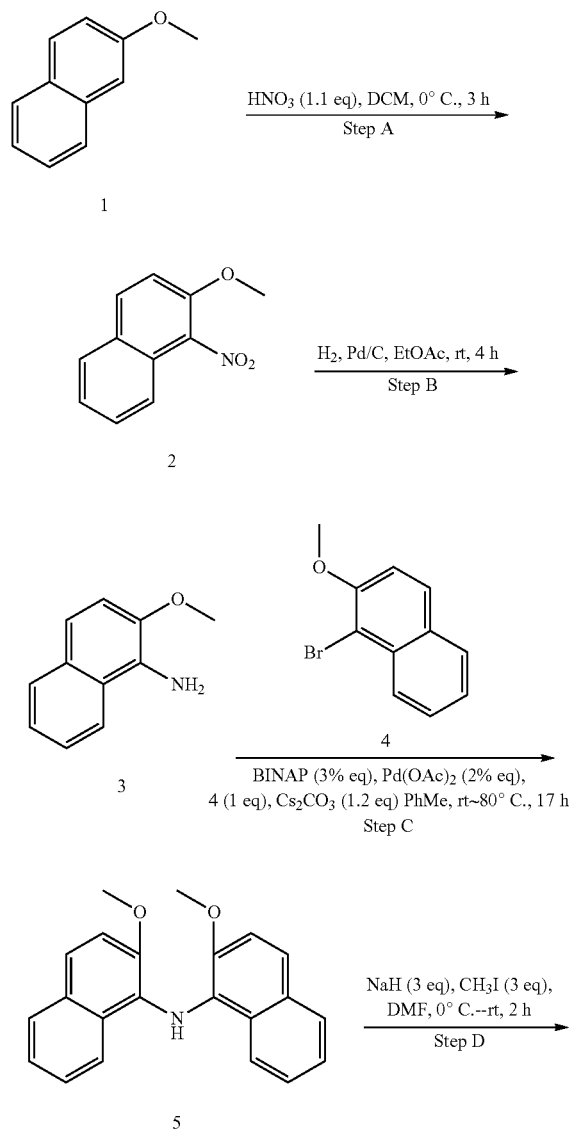

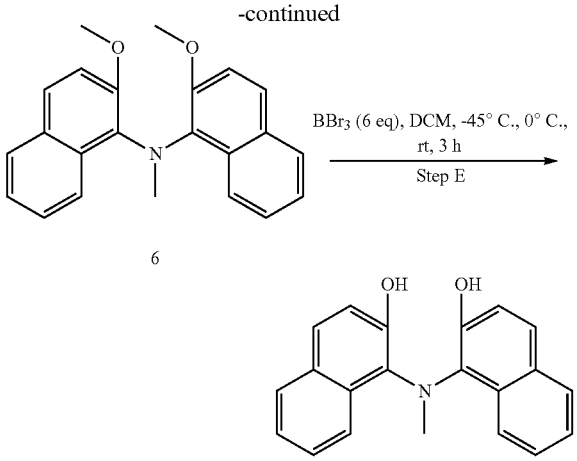

Step A

To a solution of 2-methoxynaphthalene (5 g, 31.6 mmol) in dichloromethane (100 mL) was added fuming nitric acid (2.19 g, 34.77 mmol) dropwise at 0° C. and the reaction mixture was stirred for 3 h. The mixture was washed with saturated sodium bicarbonate (100 mL), brine (60 mL×3), filtered, dried over anhydrous sodium sulfate and concentrated. The residue was purified by column chromatography (EA/PE=1/10, v/v) to afford 2-methoxy-1-nitronaphthalene (3.9 g, 60%) as a yellow solid.

Step B

A suspension of 2-methoxy-1-nitronaphthalene (3.9 g, 19.2 mmol) and 10% Pd/C (600 mg) in ethyl acetate (150 mL) was stirred at room temperature under H$_2$ (60 psi) for 4 h. The catalyst was removed by filtration and the filtrate was evaporated. The crude 2-methoxynaphthalen-1-amine was purified by flash column chromatography on silica gel (EA/PE=1/4, v/v) to afford pure 2-methoxynaphthalen-1-amine (2.8 g, 84%) as a pale violet solid.

Mass Spectrum (ESI) m/z=174.1 (M+H$^+$).

Step C

To a solution of (±)-BINAP (647 mg, 1.04 mmol) in toluene (20 mL) were added Pd(OAc)$_2$ (233 mg, 1.04 mmol), 2-methoxynaphthalen-1-amine (1.8 g, 10.4 mmol), 1-bromo-2-methoxynaphthalene (2.46 g, 10.4 mmol) in toluene (20 mL) and cesium carbonate (4.1 g, 12.48 mmol), the reaction mixture was stirred at 100° C. under nitrogen overnight. After completion, the reaction mixture was cooled to room temperature, diluted with ethyl acetate (100 mL), filtered and concentrated To get a crude bis(2-methoxynaphthalen-1-yl)amine which was purified by flash column chromatography on silica gel flash column chromatography on silica gel (EA/PE=1/4, v/v) to afford pure bis(2-methoxynaphthalen-1-yl)amine (1.7 g, 49%) as a yellowish green solid.

Mass Spectrum (ESI) m/z=330.1 (M+H$^+$).

Step D

To a solution of bis(2-methoxynaphthalen-1-yl)amine (500 mg, 1.52 mmol) in anhydrous N,N-dimethylformamide (6 mL) was added sodium hydride (200 mg, 4.56 mmol) at 0° C. under nitrogen. After stirring for 0.5 h, methyl iodide (650 mg, 4.56 mmol) was added, stirring was continued at room temperature for 2 h. After completion, the reaction mixture was quenched with water (20 mL) and extracted with ethyl acetate (20 mL). The organic layer was washed with brine (10 mL×3), dried over anhydrous sodium sulfate, filtered and concentrated. The residue was purified by flash column chromatography on silica gel (EA/PE=¼, v/v) to afford 2-methoxy-N-(2-methoxynaphthalen-1-yl)-N-methylnaphthalen-1-amine (450 mg, 86%) as a white solid.
Mass Spectrum (ESI) m/z=344.2 (M+H$^+$).
Step E To a solution of 2-methoxy-N-(2-methoxynaphthalen-1-yl)-N-methylnaphthalen-1-amine (100 mg, 0.292 mmol) in anhydrous dichloromethane (2 mL) was added boron tribromide (1.8 mL, 1.752 mmol, 1 M in dichloromethane) under nitrogen at −45° C. The reaction mixture was stirred for 3 h at room temperature. After completion, the reaction mixture was quenched with methanol (20 mL) and concentrated. The residue was extracted with ethyl acetate (10 mL×3), washed with water (20 mL), brine (20 mL), dried over anhydrous sodium sulfate and concentrated. The crude 1,1'-(methylazanediyl)bis(naphthalen-2-ol) was purified by prep-HPLC to afford pure 1,1'-(methylazanediyl)bis(naphthalen-2-ol) (40 mg, 43%) as an off-white solid. Mass Spectrum (ESI) m/z=316.1 (M+H$^+$).

$^1$H NMR (400 MHz, DMSO-d$_6$) δ 9.79 (s, 2H), 8.02-8.00 (m, 2H), 7.69-7.67 (m, 2H), 7.53 (d, J=8.8 Hz, 2H), 7.25 (d, J=8.8 Hz, 2H), 7.15-7.13 (m, 4H), 3.48 (s, 3H).

Example 3: 1,1'-sulfonylbis(naphthalen-2-ol) (A005)

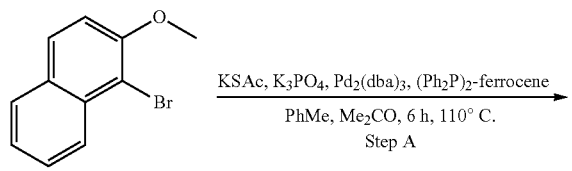

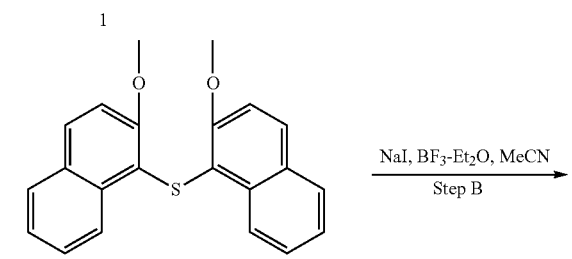

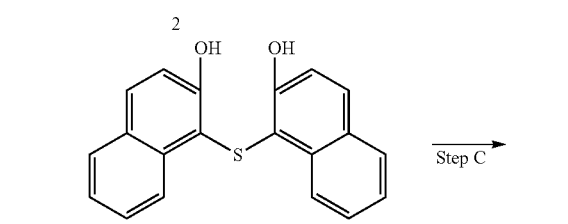

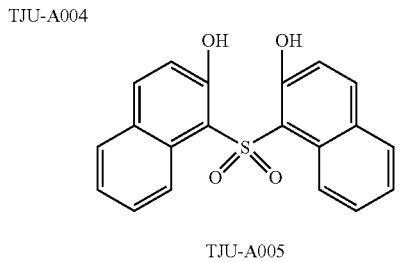

TJU-A005

Step A

A mixture of 1-bromo-2-methoxynaphthalene (948 mg, 4 mmol), KSAc (228 mg, 2 mmol), K$_3$PO$_4$ (509 mg, 2.4 mmol), Pd$_2$(dba)$_3$ (115 mg, 0.2 mmol), (Ph$_2$P)$_2$-ferrocene (155 mg, 0.28 mmol) and Me$_2$CO (1 mL) in toluene (2 mL) was stirred for 16 h at 110° C. After completion, the mixture was diluted with water (30 mL) and extracted with ethyl acetate (30 mL). The organic layer was dried over anhydrous Na$_2$SO$_4$ and concentrated to afford bis(2-methoxynaphthalen-1-yl)sulfane (400 mg, 30%) as a yellow solid.
LCMS: RT=1.72 min; 369 (M+Na$^+$)
$^1$H NMR (400 MHz, CDCl$_3$) δ 8.74 (d, J=8.4 Hz, 2H), 7.74 (d, J=9.2 Hz, 4H), 7.49-7.45 (m, 2H), 7.35-7.31 (m, 2H), 7.14 (d, J=9.2 Hz, 2H), 3.62 (s, 6H).
Step B To a solution of bis(2-methoxynaphthalen-1-yl)sulfane (100 mg, 0.29 mmol) in MeCN (20 mL) were added NaI (8.7 mg, 0.06 mmol) and BF$_3$-Et$_2$O (1 mL), the mixture was stirred at room temperature for 6 h. The mixture was concentrated and the residue was purified by silica gel column (DCM/MeOH=100/1, v/v) to afford 1,1'-thiobis(naphthalen-2-ol) (10 mg, 11%) as a white solid.
LCMS: RT=1.307 min; 341.1(M+Na$^+$)
$^1$H NMR (400 MHz, DMSO-d6) δ 10.19 (s, 2H), 8.53 (d, J=8.4 Hz, 2H), 7.74 (d, J=8.8 Hz, 4H), 7.42-7.39 (m, 2H), 7.27-7.23 (m, 2H), 7.18 (d, J=8.8 Hz, 2H).
Step C A mixture of 1,1'-thiobis(naphthalen-2-ol) (318 mg, 4 mmol) and mCPBA (384 mg, 2.2 mmol) in chloroform (20 mL) was stirred at room temperature for 5 days. After the completion, water (20 mL) was added and extracted with ethyl acetate (20 mL×3). The reaction mixture was concentrated and the residue was purified by prep-HPLC to afford 1,1'-sulfonylbis(naphthalen-2-ol) (110 mg, 29%) as a white solid.
LCMS: RT=1.38 min; 373(M+H$^+$).
$^1$H NMR (400 MHz, DMSO-d6) δ 11.43 (s, 2H), 8.77-8.74 (m, 2H), 7.88 (s, 2H), 7.51-7.49 (m, 2H), 7.47-7.40 (m, 2H), 7.38-7.36 (m, 2H), 7.11-7.10 (m, 2H).

Example 4: 1,1'-sulfinylbis(naphthalen-2-ol) (A006)

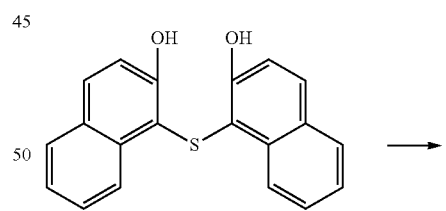

TJU-A004

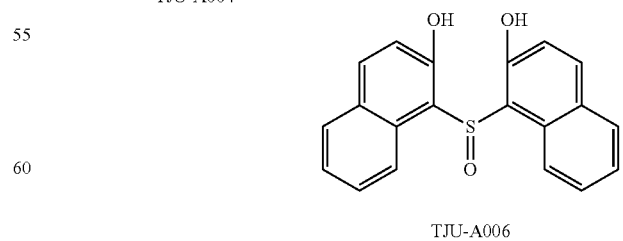

TJU-A006

A mixture of 1,1'-thiobis(naphthalen-2-ol) (318 mg, 1 mmol) and mCPBA (192 mg, 1.1 mmol) in chloroform (20 mL) was stirred at room temperature for 16 h. After the completion, water (20 mL) was added and the mixture was extracted with ethyl acetate (20 mL×3). The reaction mixture was concentrated and the residue was purified by prep-HPLC to afford a white solid of 1,1'-sulfinylbis(naphthalen-2-ol) (10 mg, 29%).

LCMS: RT=1.45 min; 335 (M+H$^+$).

$^1$H NMR (400 MHz, DMSO-d6) δ 12.02 (s, 2H), 8.15-8.13 (m, 2H), 8.00-7.97 (m, 2H), 7.87-7.85 (m, 2H), 7.49-7.45 (m, 2H), 7.36-7.32 (m, 2H), 7.16 (d, J=8 Hz, 2H).

Example 5: bis(2-methoxynaphthalen-1-yl)methanol (A040)

Example 6: bis(2-hydroxynaphthalen-1-yl)methanone (A007)

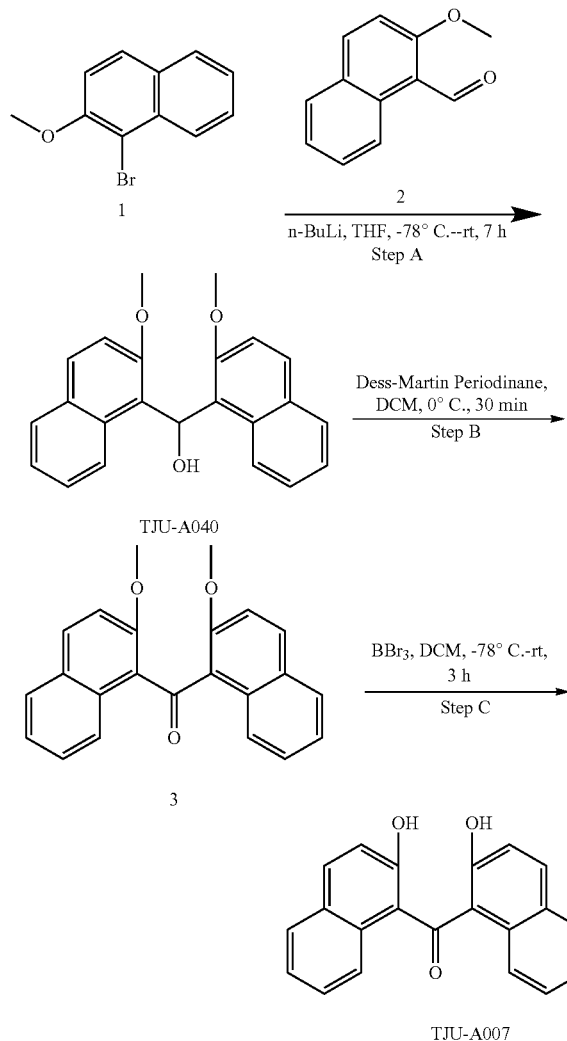

with saturated ammonium chloride (20 mL) at −78° C. and extracted with ethyl acetate (30 mL×3), dried over sodium sulfate, filtered and concentrated in vacuo. The crude bis(2-methoxynaphthalen-1-yl)methanol was purified by flash chromatography (PE/EA=10/1, v/v) to afford bis(2-methoxynaphthalen-1-yl)methanol (2.89 g, 39%) as a white solid.

Mass Spectrum (ESI) m/z=367.1 (M+Na$^+$).

$^1$H NMR (400 MHz, DMSO-d6) δ 8.78 (d, J=8.7 Hz, 2H), 7.81 (d, J=8.9 Hz, 4H), 7.36-7.34 (m, 7H), 5.93 (d, J=5.5 Hz, 1H), 3.47 (s, 6H).

Step B

To a solution of bis(2-methoxynaphthalen-1-yl)methanol (1.00 g, 2.91 mmol) in dichloromethane (10 mL) was added Dess-Martin Periodinane (1.85 g, 4.36 mmol) at 0° C. and the mixture was stirred for 1.5 h at 0° C. Upon completion, the reaction mixture was quenched with a 1:1 mixed solution of saturated sodium bicarbonate and 10% sodium sulphite. The mixture was stirred until both layers became clear. The layers were separated and the organic phase was washed with saturated sodium bicarbonate (20 mL). The aqueous phase was extracted with dichloromethane (20 mL×3). The organic extracts were combined, dried over sodium sulfate, filtered and concentrated in vacuo. The crude bis(2-methoxynaphthalen-1-yl)methanone was purified by flash chromatography (EA/PE=1/10, v/v) to afford bis(2-methoxynaphthalen-1-yl)methanone(95 mg, 9%) as a white solid.

Step C

To a solution of bis(2-methoxynaphthalen-1-yl)methanone (90 mg, 0.26 mL) in dichloromethane (1 mL) was added boron tribromide (2.1 mL, 1.0 M) at −78° C. The reaction mixture was stirred for 3 h at room temperature. Upon completion, the mixture was quenched with methanol (20 mL) at −78° C. and extracted with ethyl acetate (10 mL×3), dried over sodium sulfate, filtered and concentrated in vacuo. The crude bis(2-hydroxynaphthalen-1-yl)methanone was purified by prep-HPLC to afford pure bis(2-hydroxynaphthalen-1-yl)methanone(70 mg, 84%) as a yellow solid.

Mass Spectrum (ESI) m/z=315.1 (M+H$^+$)

$^1$H NMR (400 MHz, DMSO-d6) δ 10.67 (s, 2H), 7.93 (d, J=8.9 Hz, 2H), 7.86-7.84 (m, 2H), 7.76 (d, J=8.3 Hz, 2H), 7.34-7.32 (m, 4H), 7.10 (d, J=8.9 Hz, 2H).

Example 7: 1,1'-(ethane-1,1-diyl) bis (naphthalen-2-ol) (A012)

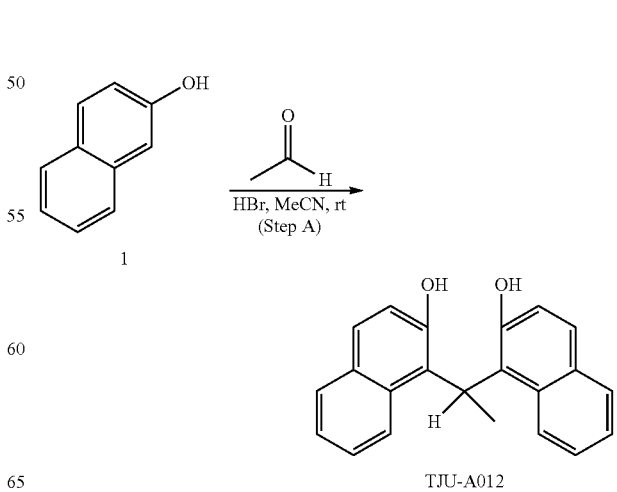

Step A

To a solution of 1-bromo-2-methoxynaphthalene (5 g, 21.09 mmol) in tetrahydrofuran (60 mL) was added n-butyllithium (9.6 mL, 2.4 M) at −78° C. The mixture was stirred for 1 h at room temperature. 2-methoxy-1-naphthaldehyde (2.75 g, 14.76 mmol) in tetrahydrofuran (20 mL) was added at −78° C. and the mixture was stirred for 6 h at room temperature. Upon completion, the mixture was quenched To a solution of naphthalen-2-ol (288 mg, 2 mmol) and acetaldehyde (44 mg, 1 mmol) in acetonitrile (5 mL) at 0° C. was added HBr (134 mg, 40%, 0.33 mmol) under nitrogen. The reaction mixture was stirred at room temperature for 2 h. After completion, the reaction mixture was extracted with ethyl acetate (50 mL×3), dried over sodium sulfate and concentrated under reduced pressure. The crude 1,1'-(ethane-1,1-diyl) bis (naphthalen-2-ol) was purified by silica gel column chromatography (EA/PE=⅕, v/v) to afford 1,1'-(ethane-1,1-diyl) bis (naphthalen-2-ol) as a white solid (27 mg, 4%).

Mass Spectrum (ESI) m/z=313.1(M−H⁻)

$^1$H NMR (400 MHz, DMSO-$d_6$) δ 9.97 (s, 2H), 8.27 (d, J=8.6 Hz, 2H), 7.64 (d, J=7.2 Hz, 2H), 7.59 (d, J=8.8 Hz, 2H), 7.22 (d, J=8.8 Hz, 2H), 7.17 (dd, J=11.3, 4.1 Hz, 2H), 7.11 (t, J=7.1 Hz, 2H), 5.67 (d, J=7.4 Hz, 1H), 1.93 (d, J=7.3 Hz, 3H).

Example 8: 1-((2-methoxynaphthalen-1-yl)methyl)naphthalen-2-ol (A014)

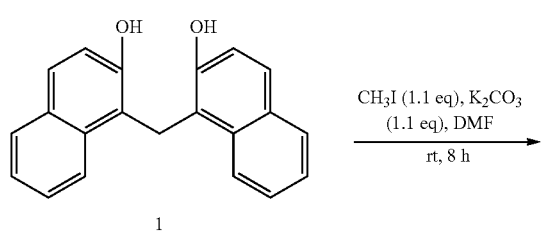
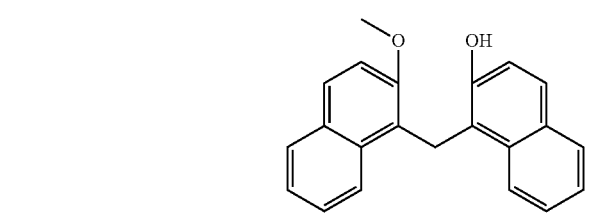

TJU-A014

A mixture of 1,1'-methylenebis(naphthalen-2-ol) (100 mg, 0.333 mmol), potassium carbonate (52 mg, 0.368 mmol) and methyl iodide (53 mg, 0.368 mmol) in anhydrous N,N-dimethylformamide (1 mL) was stirred at room temperature under nitrogen for 8 h. The mixture was diluted with water (5 mL) and extracted with ethyl acetate (10 mL×3). The combined organic layer was washed with brine (10 mL×3), dried over anhydrous sodium sulfate, filtered and concentrated in vacuo. The residue was purified by flash column chromatography on silica gel (EA/PE=⅕, v/v) to afford 1-((2-methoxynaphthalen-1-yl)methyl)naphthalen-2-ol (67 mg, 64%) as a white solid.

Mass Spectrum (ESI) m/z=337.1 (M+Na⁺).

$^1$H NMR (400 MHz, DMSO-$d_6$) δ 10.09 (s, 1H), 8.25 (d, J=8.3 Hz, 1H), 7.96 (d, J=8.5 Hz, 1H), 7.78-7.76 (m, 2H), 7.63-7.61 (m, 2H), 7.52 (d, J=9.0 Hz, 1H), 7.22-7.20 (m, 4H), 7.11 (t, J=7.1 Hz, 1H), 4.76 (s, 2H), 4.09 (s, 3H).

Example 9: bis(2-methoxynaphthalen-1-yl)methane (A015)

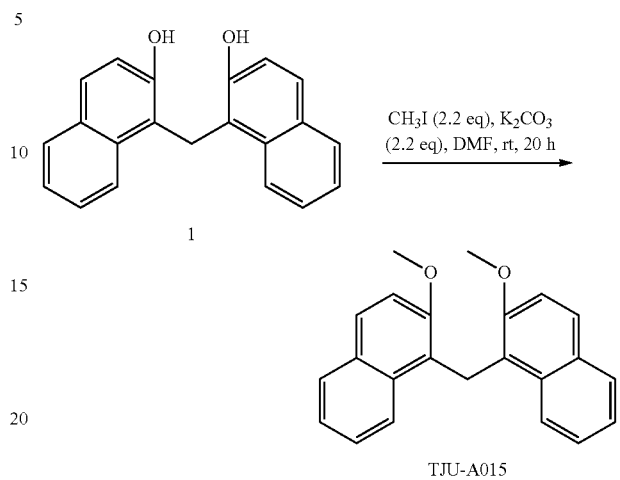

TJU-A015

A mixture of 1,1'-methylenebis(naphthalen-2-ol) (50 mg, 0.167 mmol), potassium carbonate (52 mg, 0.368 mmol) and methyl iodide (53 mg, 0.368 mmol) in anhydrous N,N-dimethylformamide (1 mL) was stirred at room temperature under nitrogen for 20 h. The mixture was diluted with water (5 mL) and extracted with ethyl acetate (10 mL×2). The combined organic layer was washed with brine (10 mL×3), dried over anhydrous sodium sulfate, filtered and concentrated in vacuo. The residue was purified by flash column chromatography on silica gel (EA/PE=⅕, v/v) to afford bis(2-methoxynaphthalen-1-yl)methane (37 mg, 67%) as a white solid.

Mass Spectrum (ESI) m/z=351.1 (M+Na⁺).

$^1$H NMR (400 MHz, DMSO-$d_6$) δ 8.06 (d, J=8.5 Hz, 2H), 7.78-7.76 (m, 4H), 7.49 (d, J=9.0 Hz, 2H), 7.25-7.23 (m, 4H), 4.80 (s, 2H), 4.00 (s, 6H).

Example 10: 2,2'-methylenediphenol (A016)

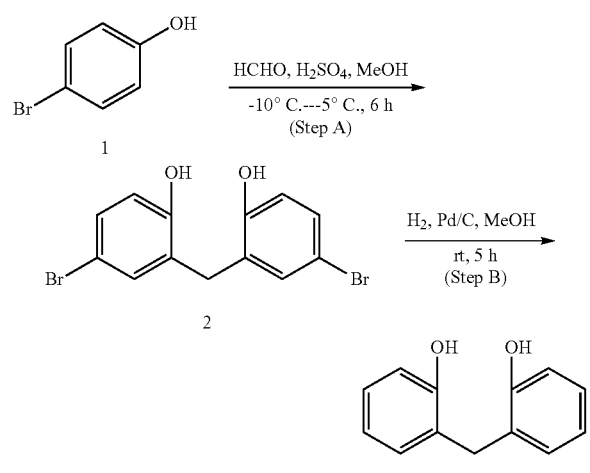

TJU-A016

Step A

Concentrated sulfuric acid (5.3 mL) was added dropwise to a solution of 4-bromophenol (1 g, 5.78 mmol) in methanol (9 mL) while stirring at −10° C. A solution of 38% formalin (0.27 mL) in methanol (1 mL) was added dropwise. Stirring was continued for another 6 h at −10° C. to −5° C. The solution was then poured into cold water (30 mL). The white precipitate was filtered off. The filtrate was extracted with ethyl acetate (20 mL×2), the organic layer was dried over anhydrous sodium sulfate, filtered and concentrated. The residue was purified by flash column chromatography on silica gel (EA/PE=¼, v/v) to afford 2,2'-methylenebis(4-bromophenol) (160 mg, 15%) as a white solid.

Step B

To a solution of 2,2'-methylenebis(4-bromophenol) (100 mg, 0.28 mmol) in methanol (5 mL) was added 10% Pd/C. The reaction mixture was stirred for 5 h under $H_2$ at room temperature. After completion, the reaction mixture was filtered through celite. The filtrate was concentrated and the residue was purified by reversed phase column chromatography to afford 2,2'-methylenediphenol (35 mg, 62%) as a white solid.

Mass Spectrum (ESI) m/z=223.1 (M+Na$^+$).

$^1$H NMR (400 MHz, DMSO-d$_6$) δ 9.29 (s, 2H), 7.02-7.00 (m, 2H), 6.91-6.89 (m, 2H), 6.80-6.78 (m, 2H), 6.69-6.65 (m, 2H), 3.77 (s, 2H).

Example 11: 2,2'-methylenebis(3,4-dimethylphenol) (A017)

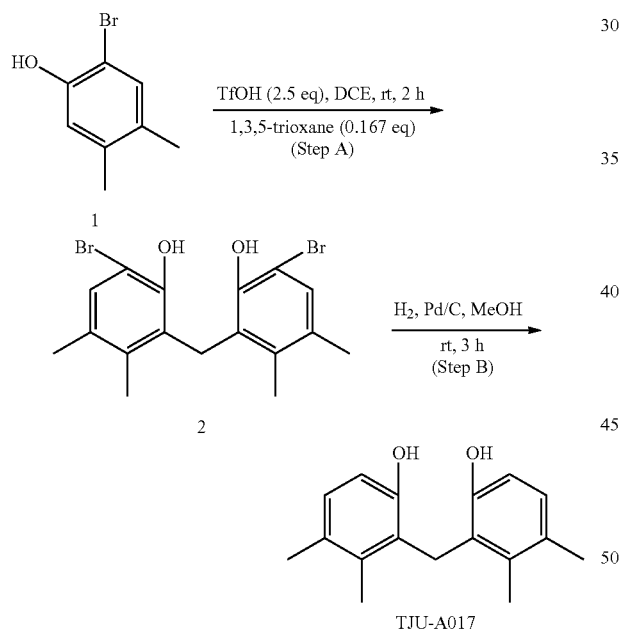

Step A To a solution of 2-bromo-4,5-dimethylphenol (200 mg, 1 mmol) and 1,3,5-trioxane (15 mg, 0.167 mmol) in dichloromethane (5 mL) was added TfOH (375 mg, 2.5 mmol). The reaction mixture was stirred for 2 h at room temperature. The reaction mixture was washed with water (5 mL) and brine (10 mL×3), dried over anhydrous sodium sulfate, and concentrated to afford crude 6,6'-methylenebis(2-bromo-4,5-dimethylphenol) (150 mg) which was used for the next step without purification.

Mass Spectrum (ESI) m/z=413 (M−H$^-$).

Step B

To a solution of crude 6,6'-methylenebis(2-bromo-4,5-dimethylphenol) (100 mg, 0.242 mmol) in methanol (5 mL) was added 10% Pd/C (200 mg) under $H_2$ at room temperature. The reaction mixture was stirred for 3 h. After completion, the catalyst was removed by filtration and the filtrate was concentrated. The residue was purified by prep-HPLC to afford 2,2'-methylenebis(3,4-dimethylphenol) (13.6 mg, 22%) as a white solid.

Mass Spectrum (ESI) m/z=255.2 (M−H$^-$).

$^1$H NMR (400 MHz, DMSO-d$_6$) δ 8.89 (s, 2H), 6.61 (d, J=38.8 Hz, 4H), 3.62 (s, 2H), 2.09 (d, J=13.4 Hz, 6H), 2.01 (s, 6H).

Example 12: 1-((2-aminonaphthalen-1-yl)methyl)naphthalen-2-ol (A021)

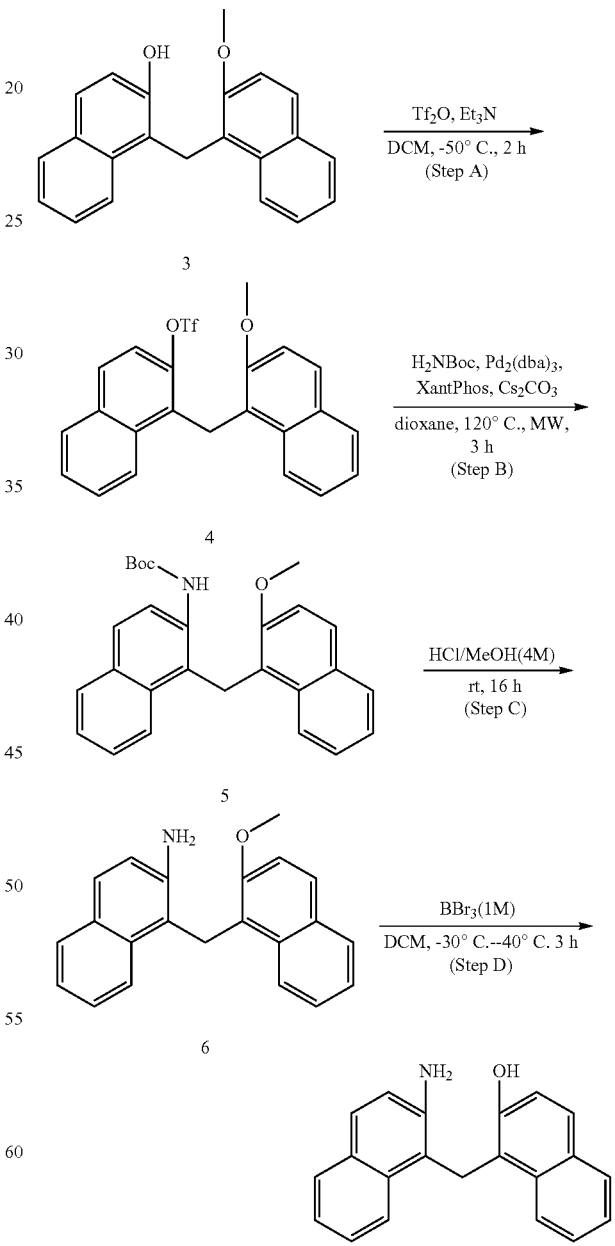

To a solution of 1-((2-methoxynaphthalen-1-yl)methyl)naphthalen-2-ol (1.1 g, 4 mmol) and triethyl amine (1.67 mL, 12 mmol) in anhydrous dichloromethane (20 mL) was added trifluoromethanesulfonic anhydride (2.0 mL, 12 mmol) at −50° C. over a 30 min period. The reaction mixture was stirred at −50° C. for 2 h. After completion, saturated ammonium chloride was added and the mixture was extracted with dichloromethane (50 mL×3). The organic phase was washed with 5% aq. HCl, saturated sodium bicarbonate and brine, dried over sodium sulfate and concentrated under reduced pressure. The residue was purified by silica gel column chromatography (PE/EA=10/1, v/v) to afford the compound 1-((2-methoxynaphthalen-1-yl)methyl)naphthalen-2-yl trifluoromethanesulfonate (1.76 g, 95%) as a white solid.

Step B

To a solution of 1-((2-methoxynaphthalen-1-yl)methyl)naphthalen-2-yl trifluoromethanesulfonate (1 g, 2 mmol) and tert-butyl carbamate (0.52 g, 4 mmol) in dioxane (10 mL) were added $Pd_2(dba)_3$ (0.183 g, 0.2 mmol), XantPhos (0.23 g, 0.4 mmol) and cesium carbonate (1.3 g, 4 mmol). The reaction mixture was stirred at 120° C. for 4 h under argon atmosphere. The reaction mixture was cooled to room temperature and water (50 mL) was added. The aqueous phase was extracted with ethyl acetate (100 mL×3), The organic layer was dried over sodium sulfate and concentrated. The residue was purified by silica gel chromatography (PE/EA=10/1, v/v) to afford tert-butyl (1-((2-methoxynaphthalen-1-yl)methyl)naphthalen-2-yl)carbamate (670 mg, 81%) as a yellow oil.

Mass Spectrum (ESI) m/z=436.2 (M+Na$^+$).

Step C

A solution of tert-butyl (1-((2-methoxynaphthalen-1-yl)methyl)naphthalen-2-yl)carbamate (540 mg, 1.3 mmol) in HCl/methanol (4M, 6 mL) was stirred at room temperature for 16 h. The solvent of the reaction mixture was evaporated under reduced pressure. The crude 1-((2-methoxynaphthalen-1-yl)methyl)naphthalen-2-amine (360 mg, 89%) was used in next step without purification as a yellow solid.

Mass Spectrum (ESI) m/z=336.1 (M+Na$^+$).

Step D

To a solution of 1-((2-methoxynaphthalen-1-yl)methyl)naphthalen-2-amine (220 mg, 0.70 mmol) in anhydrous dichloromethane (10 mL) was added boron tribromide (1 M in $CH_2C_2$, 2.1 mL, 2.1 mmol) under nitrogen at −30° C. dropwise. The reaction mixture was stirred at 40° C. for 3 h. After completion, the reaction mixture was cooled −30° C. and methanol (3 mL) was added dropwise. The mixture was quenched with water (20 mL) and extracted with dichloromethane (100 mL×3). The combined organic layer was washed with saturated sodium bicarbonate (20 mL) and brine (20 mL), dried over anhydrous sodium sulfate and concentrated in vacuo. The solid was recrystallized from (dichloromethane/hexane=1/1) to afford 1-((2-aminonaphthalen-1-yl)methyl)naphthalen-2-ol (200 mg, 95%) as a white solid Mass Spectrum (ESI) m/z=298.1 (M−H$^-$).

$^1$H NMR (400 MHz, DMSO-d6) δ 10.17 (s, 1H), 8.14 (d, J=8.6 Hz, 1H), 7.99-7.91 (m, 1H), 7.64-7.62 (m, 3H), 7.46 (d, J=8.7 Hz, 1H), 7.28-7.17 (m, 2H), 7.13-6.96 (m, 4H), 5.53 (s, 2H), 4.52 (s, 2H).

Example 13: 1,1'-methylenebis(naphthalen-2-amine) (A022)

Example 14: 4-((2-aminonaphthalen-1-yl)methyl)naphthalen-2-amine (A022-2)

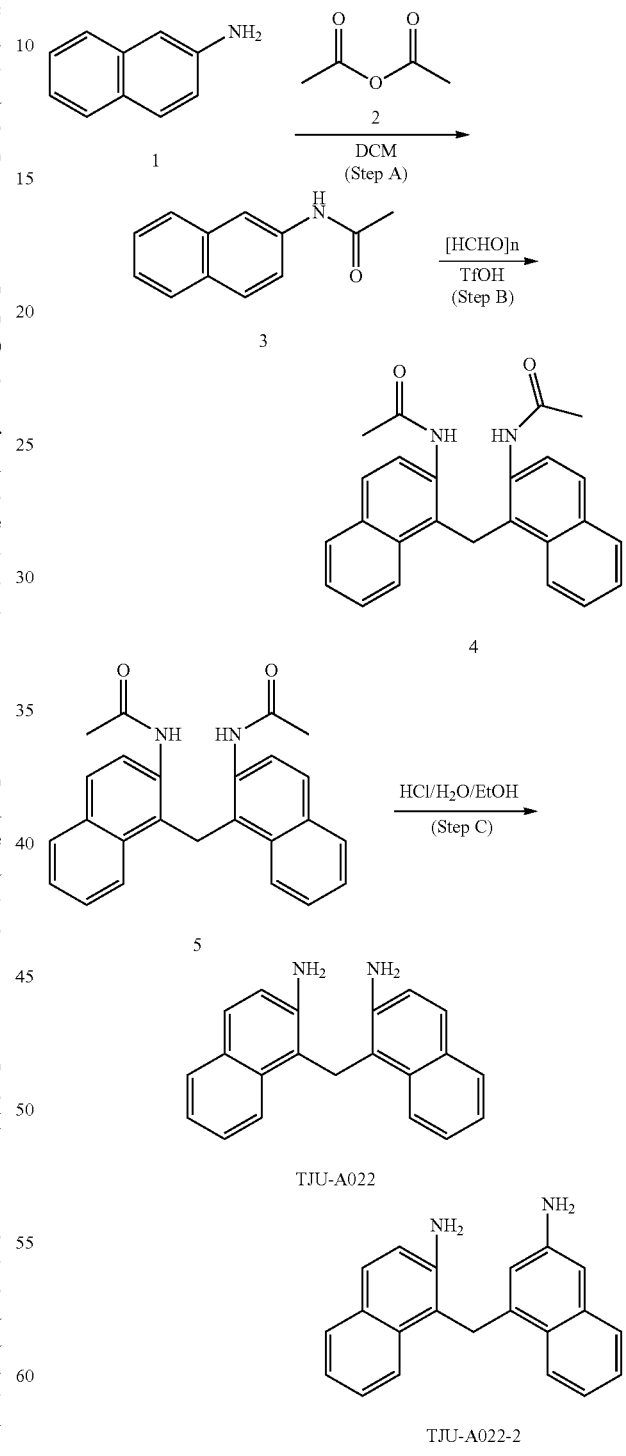

Step A

Naphthalen-2-amine (4.6 g, 32.13 mmol) was dissolved in dichloromethane (30 mL) in a flask purged with $N_2$. Acetic anhydride (3.9 g, 38.2 mmol) was added and the reaction mixture was stirred at room temperature. Upon completion, the reaction mixture was washed with saturated sodium carbonate (30 mL), dried over sodium sulfate and concentrated under vacuum o afford N-(naphthalen-2-yl)acetamide (5 g, 85%).

Mass Spectrum (ESI) m/z=186.1 (M+H⁺).

Step B

To a solution of N-(naphthalen-2-yl)acetamide (3.44 g, 18.59 mmol) and [HCHO]n (835 mg, 9.30 mmol) in dichloroethane (20 mL) was added TfOH (6.97 g, 46.44 mmol). The reaction mixture was stirred at 90° C. for 2 h and then washed with water (15 mL) and brine (30 mL×2). The organic layer was collected, dried over anhydrous sodium sulfate and concentrated under vacuum. The residue was purified by prep-TLC to afford the mixture of N, N'-(methylenebis(naphthalene-1,2-diyl))diacetamide and 4-((2-aminonaphthalen-1-yl)methyl)naphthalen-2-amine (70 mg, 0.9%). The mixture was used directly in the next step without any purification.

Mass Spectrum (ESI) m/z=383.1 (M+H⁺), 405.1(M+Na⁺)

Step C

To a solution of N, N'-(methylenebis(naphthalene-1,2-diyl))diacetamide and 4-((2-aminonaphthalen-1-yl)methyl)naphthalen-2-amine (70 mg, 0.18 mmol) in ethanol (5 mL) was added HCl (4M, 5 mL). The reaction mixture was stirred at 100° C. for 3 h and concentrated under vacuum. The residue was purified by prep-HPLC to afford 1,1'-methylenebis(naphthalen-2-amine) (5.6 mg, 10.43%) and 4-((2-aminonaphthalen-1-yl)methyl)naphthalen-2-amine (2.4 mg, 5%).

1,1'-methylenebis(naphthalen-2-amine)

Mass Spectrum (ESI) m/z=299.1 (M+H⁺)

¹H NMR (400 MHz, CD₃OD) δ 7.72 (d, J=12 Hz, 2H), 7.60 (d, J=8 Hz, 2H), 7.28 (d, J=4 Hz, 2H), 7.10-7.06 (m, 4H), 6.95 (d, J=8 Hz, 2H), 4.65 (s, 2H). 4-((2-aminonaphthalen-1-yl)methyl)naphthalen-2-amine:

Mass Spectrum (ESI) m/z=299.1 (M+H⁺).

¹H NMR (400 MHz, CD₃OD) δ 7.83 (d, J=8 Hz, 1H), 7.68 (d, J=12 Hz, 1H), 7.58 (d, J=8 Hz, 1H), 7.48 (d, J=8 Hz, 1H), 7.23 (d, J=4 Hz, 1H), 7.20-7.17 (m, 1H), 7.07 (d, J=8 Hz, 1H), 7.05-7.00 (m, 3H), 6.92 (d, J=4 Hz, 1H), 6.78 (d, J=8 Hz, 1H), 4.68 (s, 2H).

Example 15: N-(3-((2-(methylsulfonamido)naphthalen-1-yl)methyl)naphthalen-2-yl)methanesulfonamide (A024-3)

Example 16: N,N'-(methylenebis(naphthalene-1,2-diyl))dimethanesulfonamide (A024)

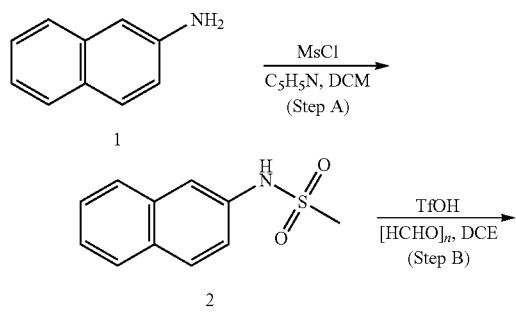

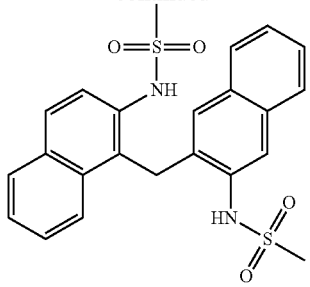

TJU-A024-3

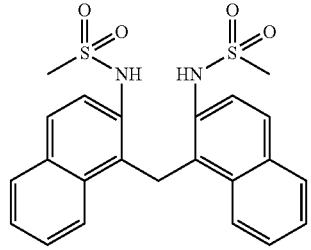

TJU-A024

Step A

To a solution of naphthalen-2-amine (813 mg, 5.68 mmol) in dichloromethane (10 mL) was added triethyl amine (1.72 g, 17.00 mmol) and MsCl (872 mg, 7.61 mmol) successively. The reaction mixture was stirred at room temperature for 2 h. The reaction mixture was concentrated under vacuum and the residue was purified by prep-TLC eluted by PE/dichloromethane=2:3 to afford N-(naphthalen-2-yl)methanesulfonamide (433 mg, 34%) as a yellow solid.

Mass Spectrum (ESI) m/z=244.0 (M+Na⁺).

Step B

To a solution of N-(naphthalen-2-yl)methanesulfonamide (2.77 g, 12.53 mmol) and [HCHO]n (563 mg, 6.26 mmol) in dichloroethane (15 mL) was added TfOH (4.7 g, 31.32 mmol). The reaction mixture was stirred at room temperature for 2 h. The mixture was washed with water (15 mL) and brine (20 mL×2), dried over sodium sulfate and concentrated under vacuum. The residue solid was washed with methanol (20 mL×2) to afford N-(3-((2-(methylsulfonamido)naphthalen-1-yl)methyl)naphthalen-2-yl)methanesulfonamide (48 mg, 1%). The filtrate was concentrated under vacuum and the residue was purified by HPLC to afford N,N'-(methylenebis(naphthalene-1,2-diyl))dimethanesulfonamide (60 mg, 1%). N-(3-((2-(methylsulfonamido)naphthalen-1-yl)methyl)naphthalen-2-yl)methanesulfonamide: Mass Spectrum (ESI) m/z=477.0 (M+Na⁺).

¹H NMR (400 MHz, DMSO-d₆) δ 9.97 (s, 1H), 9.89 (s, 1H), 7.96-7.95 (m, 1H), 7.90 (d, J=8.0 Hz, 1H), 7.79-7.73 (m, 4H), 7.61 (d, J=4.0 Hz, 1H), 7.50 (d, J=4.0 Hz, 1H), 7.42-7.40 (m, 2H), 7.35-7.33 (m, 2H), 4.48 (s, 2H), 3.01 (s, 3H), 2.84 (s, 3H).

N,N'-(methylenebis(naphthalene-1,2-diyl))dimethanesulfonamide: Mass Spectrum (ESI) m/z=477.1 (M+Na⁺).

¹H NMR (400 MHz, DMSO-d₆) δ 9.94 (s, 2H), 7.95 (d, J=12 Hz, 2H), 7.85 (d, J=1.6 Hz, 2H), 7.78 (d, J=8.0 Hz, 2H), 7.45-7.42 (m, 2H), 7.32 (t, J=8.0 Hz, 2H), 7.11 (d, J=8.0 Hz, 2H), 4.73 (s, 2H), 2.89 (s, 6H).

Example 17: N-(1-((3-(methylsulfonamido)naphthalen-1-yl)methyl)naphthalen-2-yl)methanesulfonamide (A024-2)

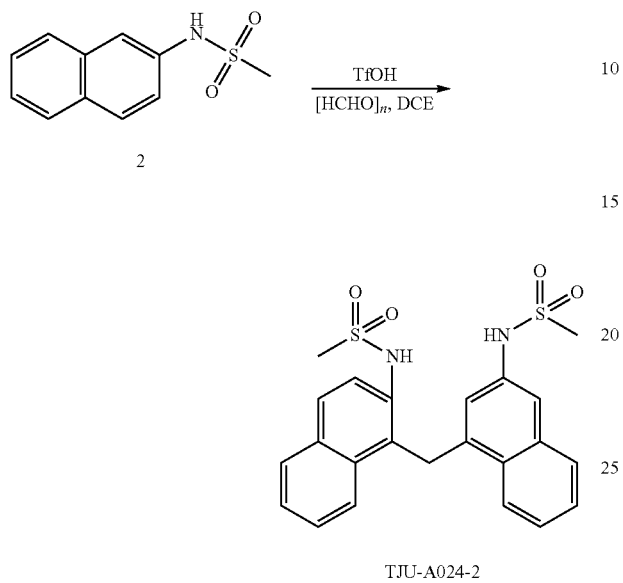

To a solution of N-(naphthalen-2-yl)methanesulfonamide (433 mg, 1.96 mmol) and [HCHO]$_n$ (88.5 mg, 0.98 mmol) in dichloroethane (6 mL) was added TfOH (735.6 mg, 4.9 mmol). The reaction mixture was stirred at room temperature for 2 h. The mixture was washed with water (5 mL) and brine (10 mL×3), dried over sodium sulfate and concentrated under vacuum. The residue was purified by prep-HPLC to afford N-(1-((3-(methylsulfonamido)naphthalen-1-yl)methyl)naphthalen-2-yl)methanesulfonamide (3.2 mg, 1%) as a white solid.

Mass Spectrum (ESI) m/z=477.0 (M+Na$^+$).

$^1$H NMR (400 MHz, DMSO-d$_6$) δ 8.37 (s, 1H), 7.98-7.96 (m, 1H), 7.93-7.88 (m, 2H), 7.69-7.63 (m, 4H), 7.59 (s, 1H), 7.46 (s, 1H), 7.43-7.40 (m, 2H), 7.33-7.28 (m, 2H), 4.76 (s, 2H), 2.99 (s, 3H), 2.93 (s, 3H).

Example 18: N-(1-((2-hydroxynaphthalen-1-yl)methyl)naphthalen-2-yl)methanesulfonamide (A025)

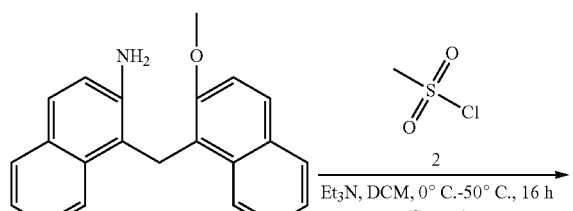

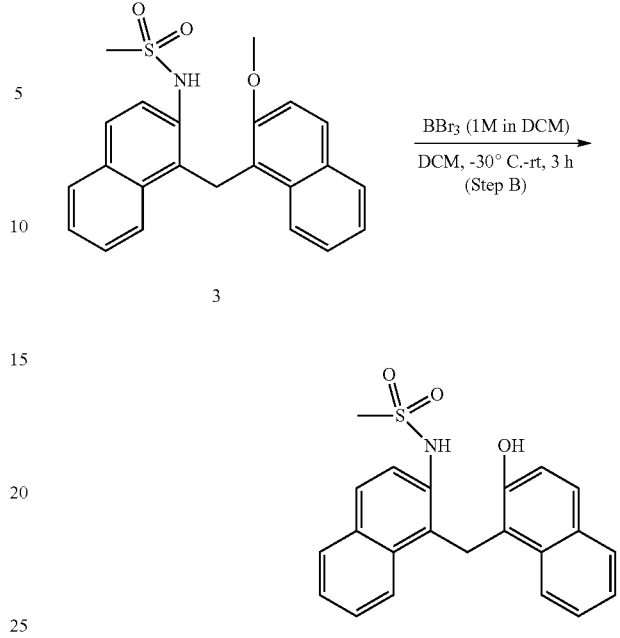

Step A

To a solution of 1-((2-methoxynaphthalen-1-yl)methyl)naphthalen-2-amine (70 mg, 0.224 mmol) in anhydrous dichloromethane (5 mL) at 0° C. was added triethyl amine (0.15 mL, 1.12 mmol) and methanesulfonyl chloride (76.60 mg, 0.672 mmol) dropwise. The reaction mixture was heated to 50° C. for 16 h under nitrogen atmosphere. The reaction mixture was poured into water (10 mL) and extracted with dichloromethane (30 mL×2), dried over anhydrous sodium sulfate and concentrated in vacuo. The residue was purified by silica gel column chromatography (PE/EA=2/1, v/v) to afford N-(1-((2-methoxynaphthalen-1-yl)methyl)naphthalen-2-yl)methanesulfonamide (50 mg, 57%) as a white solid.

Mass Spectrum (ESI) m/z=390.1 (M−H$^-$).

Step B

To a solution of N-(1-((2-methoxynaphthalen-1-yl)methyl)naphthalen-2-yl)methanesulfonamide (40 mg, 0.1 mmol) in anhydrous dichloromethane (5 mL) was added boron tribromide (1 M in CH$_2$C2, 0.3 mL, 0.3 mmol) under nitrogen at −30° C. dropwise. The reaction mixture was stirred at room temperature for 3 h. After completion, the reaction mixture was cooled −30° C. and methanol (2 mL) was added dropwise. The reaction mixture was quenched with water (10 mL), extracted with dichloromethane (20 mL×3). The combined organic layer was washed with saturated sodium bicarbonate (20 mL), brine (20 mL) and dried over anhydrous sodium sulfate and concentrated in vacuo. The resulting solid was recrystallized from (dichloromethane/hexane=1/1) to afford N-(1-((2-hydroxynaphthalen-1-yl)methyl)naphthalen-2-yl)methanesulfonamide (29 mg, 77%) as a white solid.

Mass Spectrum (ESI) m/z=376.1 (M−H$^-$).

$^1$H NMR (400 MHz, DMSO-d6) δ 10.34 (s, 1H), 9.54 (s, 1H), 8.34 (d, J=8.5 Hz, 1H), 7.80 (t, J=8.5 Hz, 2H), 7.75-7.58 (m, 3H), 7.54 (d, J=8.7 Hz, 1H), 7.32-7.30 (m, 3H), 7.20-7.07 (m, 2H), 4.89 (s, 2H), 2.90 (s, 3H).

Example 19: N-(1-((2-hydroxynaphthalen-1-yl)methyl)naphthalen-2-yl)benzenesulfonamide (A026)

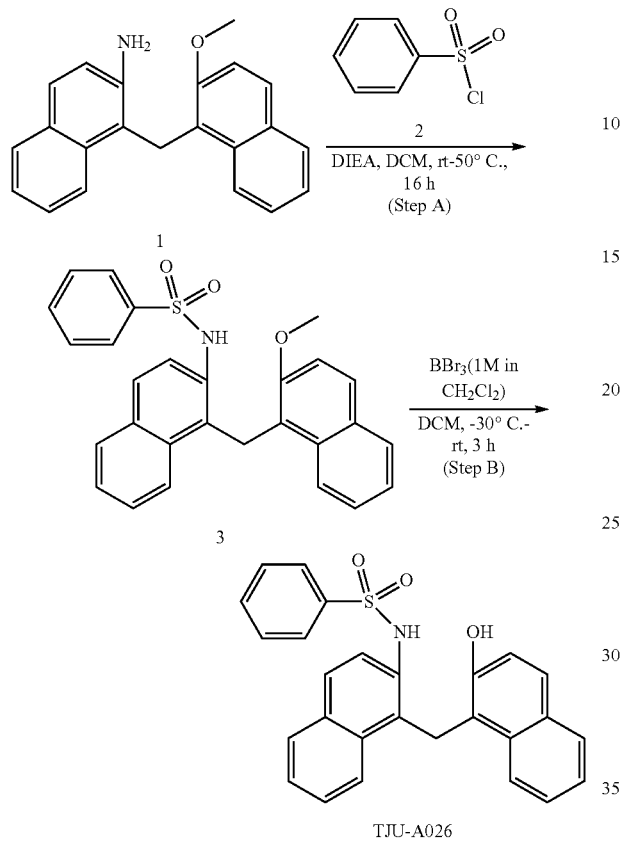

Step A

To a solution of 1-((2-methoxynaphthalen-1-yl)methyl)naphthalen-2-amine (50 mg, 0.1597 mmol) in anhydrous dichloromethane (5 mL) at 0° C. were added diisopropyl ethylamine (0.13 mL, 0.798 mmol) and benzenesulfonyl chloride (36.54 mg, 0.208 mmol). After stirring at 50° C. for 16 h, the reaction mixture was poured into water (10 mL) and extracted with dichloromethane (30 mL×2), dried over anhydrous sodium sulfate and concentrated in vacuo. The residue was purified by prep-TLC (PE/EA=5/1, v/v) to afford N-(1-((2-methoxynaphthalen-1-yl)methyl)naphthalen-2-yl)benzenesulfonamide (40 mg, 56%) as a yellow solid.

Mass Spectrum (ESI) m/z=452.1 (M−H⁻).

Step B

To a solution of N-(1-((2-methoxynaphthalen-1-yl)methyl)naphthalen-2-yl)benzenesulfonamide (40 mg, 0.088 mmol) in anhydrous dichloromethane (5 mL) was added boron tribromide (1 M in CH₂C2, 0.264 mL, 0.264 mmol) under nitrogen at −30° C. dropwise. The reaction mixture was stirred at room temperature for 3 h. After completion, the reaction mixture was cooled to −30° C. and methanol (2 mL) was added dropwise. The reaction mixture was quenched with water (10 mL), extracted with dichloromethane (20 mL×3), washed with saturated sodium bicarbonate (20 mL), brine (20 mL), dried over anhydrous sodium sulfate and concentrated in vacuo. The resulting solid was recrystallized from (dichloromethane/hexane=1/1) to afford N-(1-((2-hydroxynaphthalen-1-yl)methyl)naphthalen-2-yl)benzenesulfonamide (20 mg, 52%) as a white solid.

Mass Spectrum (ESI) m/z=438.1 (M−H⁻).

$^1$H NMR (400 MHz, DMSO-d6) δ 10.30 (s, 1H), 10.11 (s, 1H), 8.29 (d, J=8.4 Hz, 1H), 7.67-7.65 (m, 7H), 7.54-7.52 (m, 3H), 7.29-7.27 (m, 3H), 7.12-7.10 (m, 2H), 6.81 (d, J=8.7 Hz, 1H), 4.87 (s, 2H).

Example 20: 4-((2-hydroxynaphthalen-1-yl)methyl)isoquinolin-3-ol (A027)

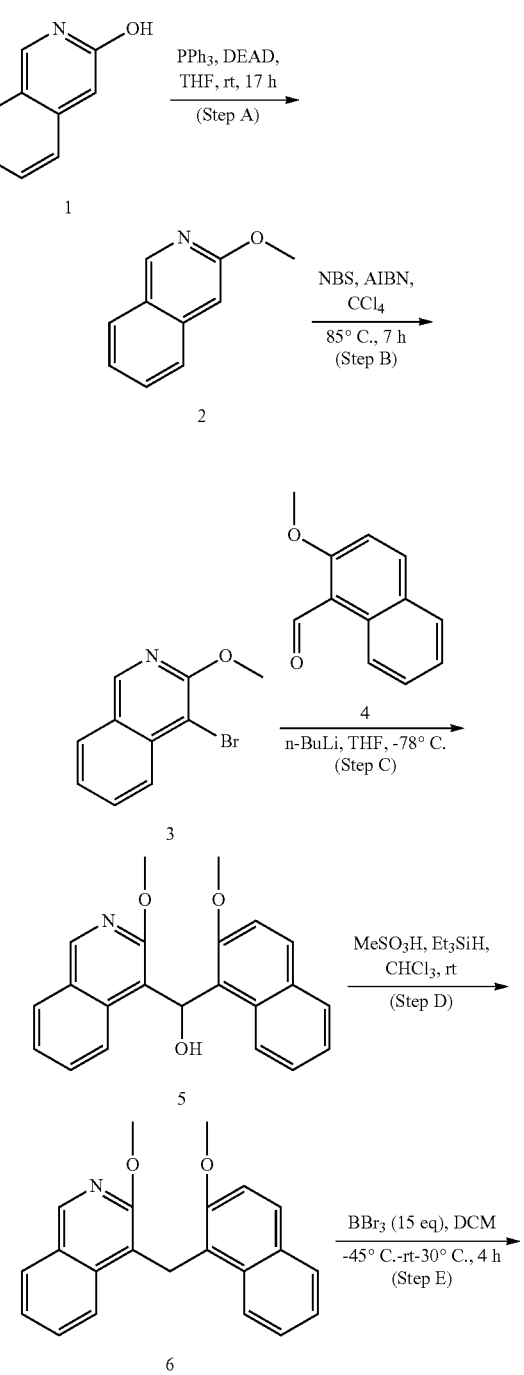

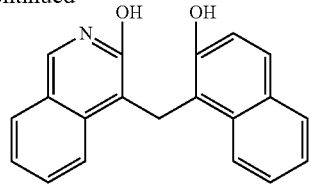

TJU-A027

Step A

To a stirred suspension of isoquinolin-3-ol (5.0 g, 34.48 mmol) and triphenyl phosphine (16.13 g, 41.03 mmol) in dry tetrahydrofuran (60 mL) were added methanol (3.0 mL) and diethyl azodicarboxylate (DEAD, 11.25 mL, 41.03 mmol). The mixture was stirred at room temperature for 20 h. The reaction mixture was diluted with ethyl acetate (60 mL), washed with brine (60 mL), dried over anhydrous sodium sulfate, filtered and concentrated. The residue was purified by flash chromatography on silica gel (PE/EA=10/1, v/v) to afford 3-methoxyisoquinoline (700 mg, 13%) as a colorless oil.

Mass Spectrum (ESI) m/z=160.1 (M+H$^+$).

Step B

To a mixture of 3-methoxyisoquinoline (700 mg, 4.40 mmol) and N-bromosuccinimide (1.57 g, 8.81 mmol) in carbon tetrachloride (15 mL) was added 2,2-azobisisobutyronitrile (cat.) and the reaction mixture was stirred at 85° C. for 7 h. The cooled reaction mixture was filtered and the filtrate was concentrated. The residue was purified by flash chromatography on silica gel (PE/EA=4/1, v/v) to afford 4-bromo-3-methoxyisoquinoline (500 mg, 22%) as a yellow solid.

Mass Spectrum (ESI) m/z=238.0 (M+H$^+$).

Step C

To a solution of 4-bromo-3-methoxyisoquinoline (200 mg, 0.833 mmol) in dry tetrahydrofuran (2 mL) was added n-butyllithium (0.76 mL, 1.67 mmol, 2.4 M in tetrahydrofuran) dropwise at −78° C. The mixture was stirred at −78° C. for 40 min. 2-methoxy-1-naphthaldehyde (520 mg, 2.50 mmol) in dry tetrahydrofuran (1.5 mL) was added dropwise to the solution at −78° C. The mixture was stirred at −78° C. for another 40 min. Upon completion, the mixture was quenched with saturated ammonium chloride (50 mL) at −78° C., extracted with ethyl acetate (50 mL×3), dried over anhydrous sodium sulfate, filtered and concentrated in vacuo. The residue was purified by flash chromatography (PE/EA=10/1, v/v) to afford (3-methoxyisoquinolin-4-yl)(2-methoxynaphthalen-1-yl)methanol (200 mg, 58%) as red oil.

Mass Spectrum (ESI) m/z=346.1 (M+H$^+$).

Step D

A mixture of (3-methoxyisoquinolin-4-yl)(2-methoxynaphthalen-1-yl)methanol (240 mg, 0.694 mmol), triethylsilane (360 mg, 3.121 mmol) and methanesulfonic acid (360 mg, 3.746 mmol) in chloroform (10 mL) was stirred at room temperature for 1 min. Ice and saturated ammonium chloride (10 mL) was added to the reaction mixture. The mixture was extracted with dichloromethane (60 mL), washed brine (60 mL×2), dried over anhydrous sodium sulfate, filtered and concentrated in vacuo. The crude 3-methoxy-4-((2-methoxynaphthalen-1-yl)methyl)isoquinoline was used in the next step without purification.

Mass Spectrum (ESI) m/z=330.2 (M+H$^+$).

Step E

To a solution of 3-methoxy-4-((2-methoxynaphthalen-1-yl)methyl)isoquinoline (100 mg, 0.303 mmol) in anhydrous dichloromethane (1.2 mL) was added boron tribromide (4.6 mL, 4.545 mmol) (1 M in dichloromethane) under nitrogen at −45° C. The reaction mixture was stirred at room temperature for 1 h and at 30° C. for 3 h. After completion, the reaction mixture was quenched with methanol (50 mL), extracted with dichloromethane (50 mL). The organic layer was washed with water (50 mL), brine (50 mL), dried over anhydrous sodium sulfate, filtered and concentrated. The crude 4-((2-hydroxynaphthalen-1-yl)methyl)isoquinolin-3-ol was purified by prep-HPLC to afford 4-((2-hydroxynaphthalen-1-yl)methyl)isoquinolin-3-ol (18 mg, 19%) as a yellow solid.

Mass Spectrum (ESI) m/z=302.1 (M+H$^+$).

$^1$H NMR (400 MHz, DMSO-d$_6$) δ 12.12 (s, 2H), 8.65 (s, 1H), 8.21 (d, J=8.6 Hz, 1H), 8.08 (d, J=8.8 Hz, 1H), 7.74 (d, J=8.2 Hz, 1H), 7.67 (d, J=8.0 Hz, 1H), 7.58 (d, J=8.8 Hz, 1H), 7.37-7.35 (m, 1H), 7.27 (t, J=7.6 Hz, 1H), 7.14-7.12 (m, 2H), 7.06 (t, J=7.3 Hz, 1H), 4.54 (s, 2H).

Example 21: 1-((2-hydroxynaphthalen-1-yl)methyl)-3-methylnaphthalen-2-ol (A031)

Example 22: 1,1′-methylenebis(3-methylnaphthalen-2-ol) (A032)

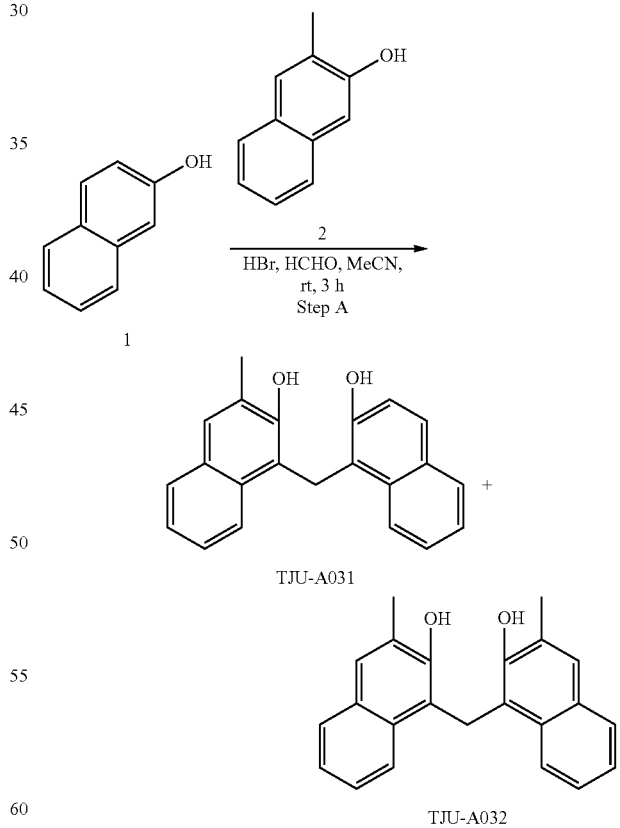

Step A

To a solution of 2-naphthol (91.14 mg, 0.62 mmol) and 3-methylnaphthalen-2-ol (300 mg, 1.90 mmol) in acetonitrile (7 mL) were added HBr (40% aqueous, 42.6 mg)-acetonitrile (1 mL) and HCHO (37% aqueous, 77.04 mg)- acetonitrile (1.5 mL). Upon completion, the reaction mixture was poured into water (30 mL) and extracted with dichloromethane (15 mL×3), dried over anhydrous sodium sulfate, filtered and concentrated in vacuo. The crude was purified by prep-HPLC to afford 1-((2-hydroxynaphthalen-1-yl)methyl)-3-methylnaphthalen-2-ol (110 mg, 55%) as a yellow solid and 1,1'-methylenebis(3-methylnaphthalen-2-ol) (120 mg, 28%) as a yellow solid.

1-((2-hydroxynaphthalen-1-yl)methyl)-3-methyl-naphthalen-2-olYellow solid (110 mg, 55%)

Mass Spectrum (ESI) m/z=313.1 (M−H⁻).
$^1$H NMR (400 MHz, DMSO-d6) δ 10.20 (s, 1H), 9.03 (s, 1H), 8.16 (d, J=7.6 Hz, 1H), 8.05 (d, J=8.4 Hz, 1H), 7.63-7.61 (m, 3H), 7.49 (s, 1H), 7.25 (d, J=8.8 Hz, 1H), 7.15-7.13 (m, 4H), 4.75 (s, 2H), 2.43 (s, 3H).

1,1'-methylenebis(3-methylnaphthalen-2-ol)

Yellow solid (120 mg, 28%)
Mass Spectrum (ESI) m/z=372.2 (M−H⁻)
$^1$H NMR (400 MHz, DMSO-d6) δ 9.15 (s, 2H), 8.07-8.05 (m, 2H), 7.61-7.59 (m, 2H), 7.50 (s, 2H), 7.15-7.13 (m, 4H), 4.80 (s, 2H), 2.43 (s, 6H).

Example 23: 2,2''-methylenebis(([1,1'-biphenyl]-3-ol)) (A034)

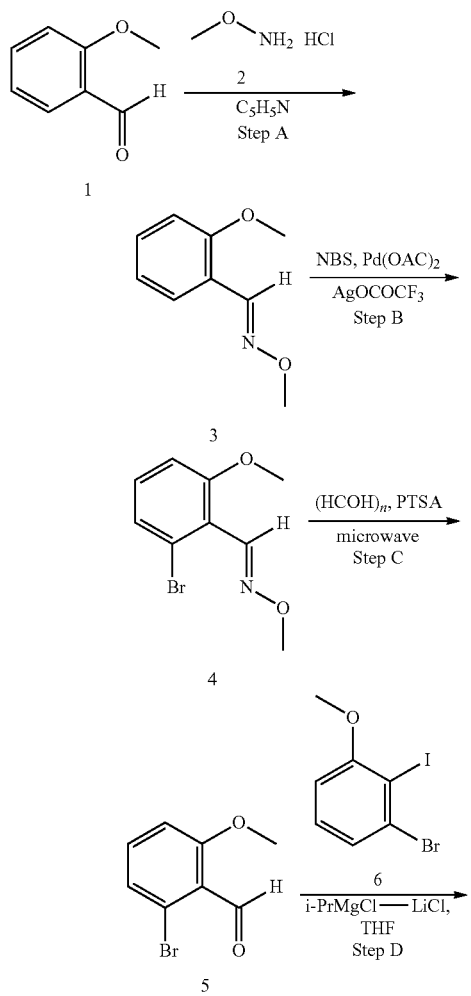

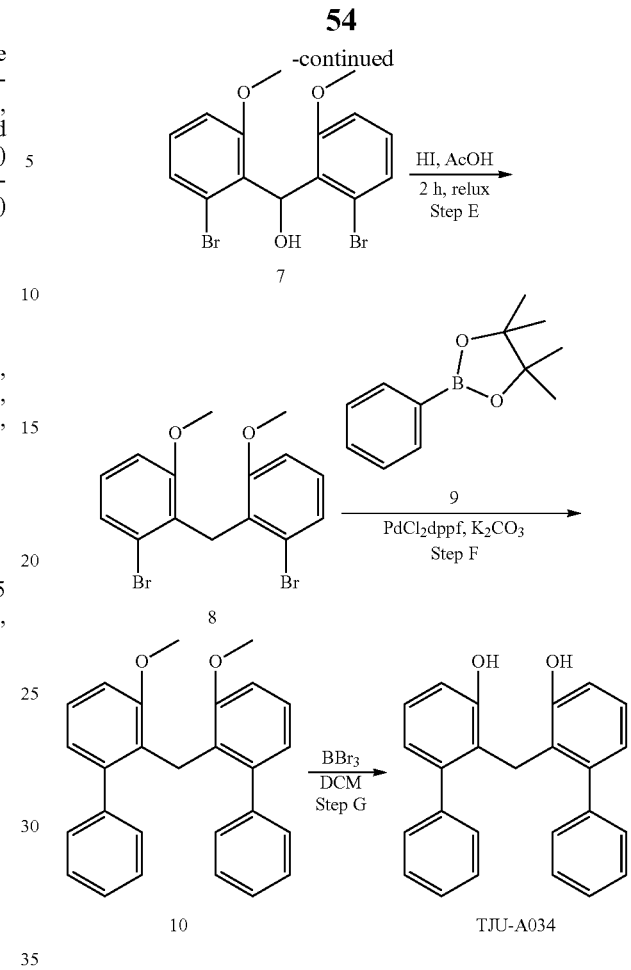

Step A

To a solution of 2-methoxybenzaldehyde (5.44 g, 40.0 mmol) in dichloromethane (50 mL) were added O-methylhydroxylamine hydrochloride (4 g, 48.0 mmol) and pyridine (9.5 g, 120.0 mmol), the reaction mixture was stirred at room temperature for 1 h The reaction mixture was diluted with saturated ammonium chloride (50 mL) and extracted with dichloromethane (50 mL×3). The combined organic layer was dried over anhydrous sodium sulfate, filtered, and concentrated. The residue was purified by column chromatography (PE/EA=5/1, v/v) to afford (E)-2-methoxybenzaldehyde O-methyl oxime (5 g, 76%) as a colorless oil. Mass Spectrum (ESI) m/z=166.2 (M+H⁺)
$^1$H NMR (400 MHz, DMSO-d$_6$) δ 8.35 (s, 1H), 8.66 (dd, J=8.0 Hz, 4.0 Hz, 1H), 7.44-7.40 (m, 1H), 7.09 (d, J=8.0 Hz, 1H), 6.98 (t, J=8.0 Hz, 1H), 3.89 (s, 3H), 3.83 (s, 3H).

Step B

A mixture of (E)-2-methoxybenzaldehyde O-methyl oxime (2.31 g, 14.0 mmol), NBS (2.5 g, 14.0 mmol), Pd(OAc)$_2$ (314 mg, 1.4 mmol), AgOCOCF$_3$ (308 mg, 1.4 mmol) and acetic acid (840 mg, 14.0 mmol) in dichloroethane (20 mL) was heated at 120° C. for 24 h. The mixture was concentrated, and the residue was purified by column chromatography (PE/EA=5/1, v/v), to afford (E)-2-bromo-6-methoxybenzaldehyde O-methyl oxime (1.2 g, 35.7%) as a yellow oil. Mass Spectrum (ESI) m/z=243.9, 245.9 (M+H⁺)
$^1$H NMR (400 MHz, DMSO-d$_6$) δ 8.18 (s, 1H), 7.32-7.28 (m, 2H), 7.13 (dd, J=8.0 Hz, 4.0 Hz, 1H), 3.89 (s, 3H), 3.82 (s, 3H).

Step C

To a solution of (E)-2-bromo-6-methoxybenzaldehyde O-methyl oxime (976 mg, 4.0 mmol) in tetrahydrofuran (10 mL) were added paraformaldehyde (900 mg, 30.0 mmol) and PTSA (1.38 g, 8.0 mmol). The reaction mixture was stirred at 100° C. for 15 min under microwave. The reaction mixture was diluted with saturated ammonium chloride (10 mL) and extracted with ethyl acetate (20 mL×3). The combined organic layer was dried over anhydrous sodium sulfate, filtered, and concentrated. The residue was purified by column chromatography (PE/EA=5/1, v/v) to afford 2-bromo-6-methoxybenzaldehyde (770 mg, 89%) as a light brown solid. Mass Spectrum (ESI) m/z=214.9, 216.9 (M+H$^+$)

$^1$H NMR (400 MHz, CDCl$_3$) δ 10.44 (s, 1H), 7.35 (t, J=8.0 Hz, 1H), 7.29-7.26 (m, 1H), 6.98 (d, J=8.0 Hz, 1H), 3.94 (s, 3H).

Step D

To a solution of 1-bromo-2-iodo-3-methoxybenzene (175 mg, 0.56 mmol) in tetrahydrofuran (5 mL) cooled at −15° C. was added i-PrMgCl LiCl (1M, 0.6 mL, 0.6 mmol). When the exchange was complete, the reaction mixture was cooled to −78° C. and 2-bromo-6-methoxybenzaldehyde was added dropwise via a syringe. The reaction was allowed to warm to room temperature and stirred overnight. The reaction mixture was diluted with diethyl ether and quenched with HCl (6 M). The organic layer was separated and the aqueous layer was extracted with diethyl ether (20 mL×3), The combined organic layer was dried over anhydrous sodium sulfate, filtered, and concentrated. The residue was washed with diethyl ether and filtered to afford bis(2-bromo-6-methoxyphenyl)methanol (130 mg, 58%) as a white powder. Mass Spectrum (ESI) m/z=384.8 (M−H$_2$O+H$^+$)

Step E

To a solution of bis(2-bromo-6-methoxyphenyl)methanol (100 mg, 0.25 mmol) in acetic acid (5 mL) was added hydrogen iodide (55%, 568 mg, 2.5 mmol), the reaction mixture was refluxed for 2 h. The reaction mixture was quenched with saturated solution of sodium sulfite and extracted with ethyl acetate (20 mL×3). The organic layer was dried over anhydrous sodium sulfate, filtered, and concentrated to afford bis(2-bromo-6-methoxyphenyl)methane (75 mg, 78%) as a light yellow solid.

$^1$H NMR (400 MHz, DMSO-d$_6$) δ 7.17-7.15 (m, 2H), 7.12-7.07 (m, 2H), 6.91-6.89 (m, 2H), 4.19 (s, 2H), 3.59 (s, 6H).

Step F

A mixture of bis(2-bromo-6-methoxyphenyl)methane (75 mg, 0.19 mmol), 4,4,5,5-tetramethyl-2-phenyl-1,3,2-dioxaborolane (204 mg, 1.0 mmol), PdCl$_2$dppf (41 mg, 0.05 mmol) and potassium carbonate (276 mg, 2.0 mmol) in dioxane (10 mL) was stirred at 100° C. under nitrogen overnight. The reaction mixture was concentrated and the residue was purified by prep-TLC to afford bis(3-methoxy-[1,1'-biphenyl]-2-yl)methane (40 mg, 55%) as a white solid.

Step G

To a solution of bis(3-methoxy-[1,1'-biphenyl]-2-yl)methane (40 mg, 0.11 mmol) in dry dichloromethane (2 mL) at −78° C. was added boron tribromide (275 mg, 1.1 mmol), the reaction mixture was stirred at room temperature for 2 h. The reaction mixture was quenched with methanol (5 mL), concentrated and the residue was purified by prep-HPLC to afford 2,2''-methylenebis(([1,1'-biphenyl]-3-ol)) as a white solid (5 mg, 13%). Mass Spectrum (ESI) m/z=351.1 (M−H)$^-$ 1H NMR (400 MHz, DMSO-d$_6$) δ 8.92 (br, 2H), 7.31-7.25 (m, 6H), 7.18-7.16 (m, 4H), 6.89 (t, J=8.0 Hz, 2H), 6.55 (d, J=8.0 Hz, 2H), 6.44 (d, J=8.0 Hz, 2H), 3.76 (s, 2H).

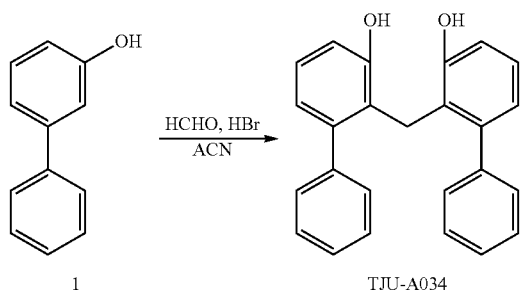 [SMILES: Oc1cccc(-c2ccccc2)c1 ; "ACN" ; Oc1cccc(-c2ccccc2)c1Cc1c(O)cccc1-c1ccccc1]

To a solution of [1,1'-biphenyl]-3-ol (2 g, 11.76 mmol) and 37% formaldehyde aqueous solution (520 mg, 1.35 mmol) in acetonitrile (15 mL) was added HBr (40% aqueous, 280 mg) in acetonitrile (0.5 mL). The reaction mixture was stirred at room temperature for 6 h and then poured into H$_2$O (40 mL) and extracted with dichloromethane (20 mL×2), dried over sodium sulfate and concentrated under vacuum. The residue was purified by prep-HPLC to afford 2,2''-methylenebis(([1,1'-biphenyl]-3-ol)) (150 mg, 7%) as a white solid.

Mass Spectrum (ESI) m/z=350.8 (M−H$^-$).

$^1$H NMR (400 MHz, CDCl$_3$) δ 7.31-7.30 (m, 6H), 7.09-7.08 (m, 4H), 6.89 (d, J=8.0 Hz, 2H), 6.76-6.73 (m, 2H), 6.70-6.69 (m, 2H), 3.71 (s, 2H).

Example 24:
2,2'-methylenebis(3-methylnaphthalen-1-ol) (035)

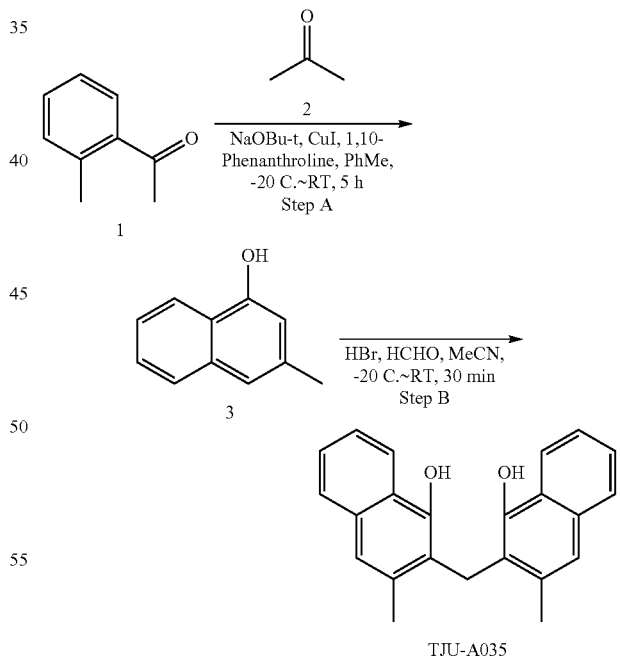

Step A

The 3-neck flask was charged with the mixture of 1-(2-iodophenyl)ethan-1-one (2.46 g, 10.0 mmol), t-BuONa (5.76 g, 60.0 mmol), copper iodide (190 mg, 1.0 mmol), 1,10-phenanthroline (360 mg, 2.0 mmol). After evacuated and recharged with N$_2$ for 3 times, acetone (50.0 mmol) and toluene (40 mL) was added into the flask with three necks at −20° C. The reaction mixture was stirred at room temperature. After completion 2 N HCl aq. was added and mixture was extracted with ethyl acetate (30 ml×3), dried over sodium sulfate and concentrated in vacuo. The crude was purified by prep-HPLC to afford the desired product as a white solid.

Mass Spectrum (ESI) m/z=157.1 (M−H+).

Step B

To a solution of 3-methylnaphthalen-1-ol (100 mg, 0.63 mmol) in acetonitrile (2 mL) was added HBr (40% aqueous, 7.68 mg)-acetonitrile (1 mL) and HCHO (37% aqueous, 28.4 mg)-acetonitrile (0.5 mL). Upon the completion, the reaction mixture was poured into water (15 mL) and extracted with dichloromethane (3×10 mL). The combined organic layers were dried over anhydrous sodium sulfate, filtered, and concentrated in vacuo. The crude was purified by prep-HPLC to afford the desired products.

Mass Spectrum (ESI) m/z=327.1 (M−H$^+$).

1H NMR (400 MHz, DMSO) δ 9.85 (s, 2H), 8.08 (m, 2H), 7.88 (d, J=8.0 Hz, 2H), 7.26 (m, 4H), 6.67 (s, 2H), 4.66 (s, 2H), 2.23 (s, 6H).

Example 25: 1-(2-((1-((2-(2-methoxyethoxy)naphthalen-1-yl)methyl)naphthalen-2-yl)oxy)ethyl)pyrrolidine (A258)

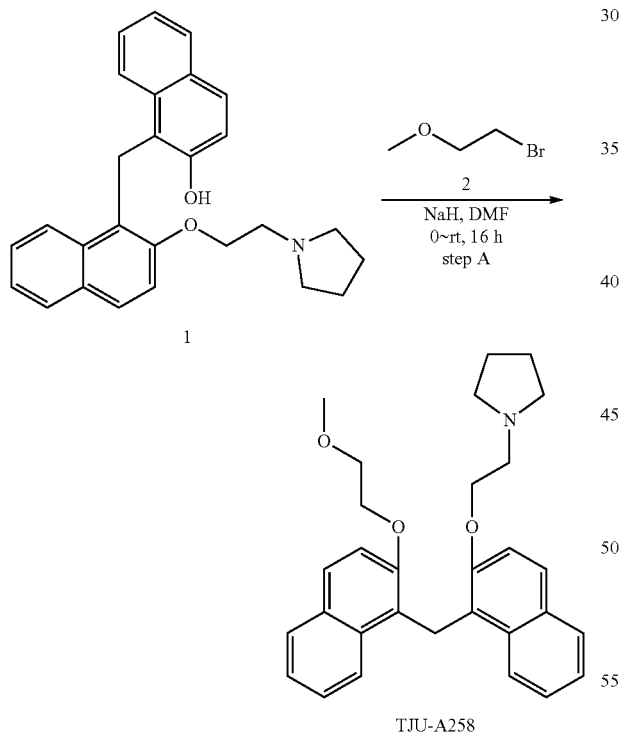

TJU-A258

1-(2-((1-((2-(2-methoxyethoxy)naphthalen-1-yl)methyl)naphthalen-2-yl)oxy)ethyl)pyrrolidine (135.00 mg) was prepared as described for Example 93.

Mass Spectrum (ESI) m/z=456.3 (M+H$^+$).

1H NMR (400 MHz, DMSO-d6) δ 8.09 (t, J=8.0 Hz, 2H), 7.84-7.67 (m, 4H), 7.49 (dd, J=8.0 Hz, 4.0 Hz, 2H), 7.30-7.16 (m, 4H), 4.86 (s, 2H), 4.42-4.22 (m, 4H), 3.68 (t, J=4.0 Hz, 2H), 3.32 (s, 3H), 2.85 (s, 2H), 2.58 (s, 4H), 1.67 (s, 4H).

Example 26: 1-((2-((1-methylpyrrolidin-3-yl)methoxy)naphthalen-1-yl)methyl)naphthalen-2-ol (A262)

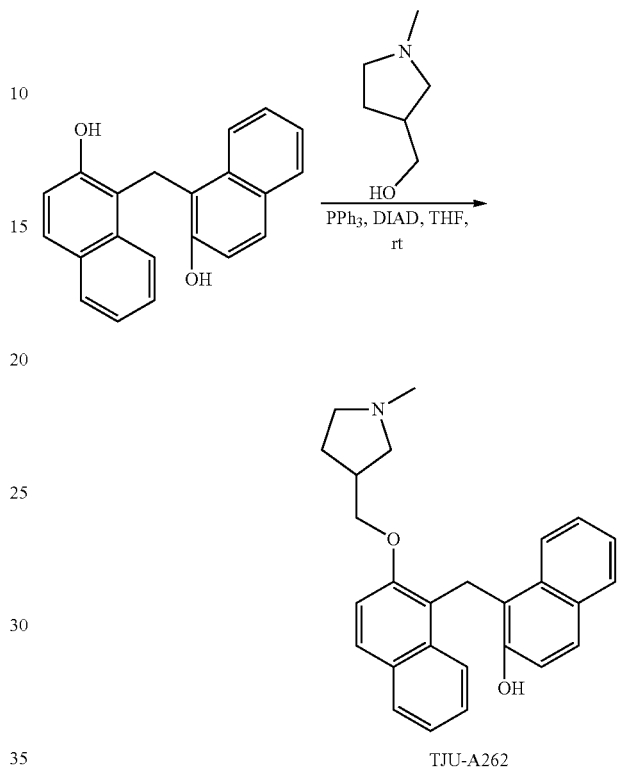

TJU-A262

1-((2-((1-methylpyrrolidin-3-yl)methoxy)naphthalen-1-yl)methyl)naphthalen-2-ol (17.8 mg) was prepared as described for Example 90.

Mass Spectrum (ESI) m/z=398.3 (M+H$^+$).

$^1$H NMR (400 MHz, DMSO-d6) δ 8.24 (d, J=7.8 Hz, 2H), 7.99 (d, J=8.0 Hz, 1H), 7.80-7.71 (m, 2H), 7.63 (dd, J=16.0 Hz, 8.0 Hz, 2H), 7.49 (d, J=8.0 Hz, 1H), 7.31-7.06 (m, 5H), 4.77 (s, 2H), 4.23-4.14 (m, 2H), 2.74 (s, 2H), 2.65-2.54 (m, 3H), 2.31 (d, J=4.0 Hz, 3H), 2.07-1.98 (m, 1H), 1.74-1.64 (m, 1H).

Example 27: 2-((1-((2-(hexyloxy)naphthalen-1-yl)methyl)naphthalen-2-yl)oxy)ethan-1-amine (A247)

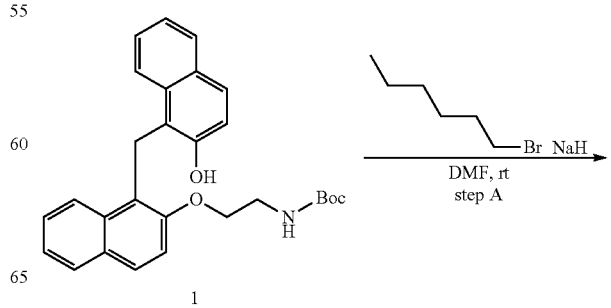

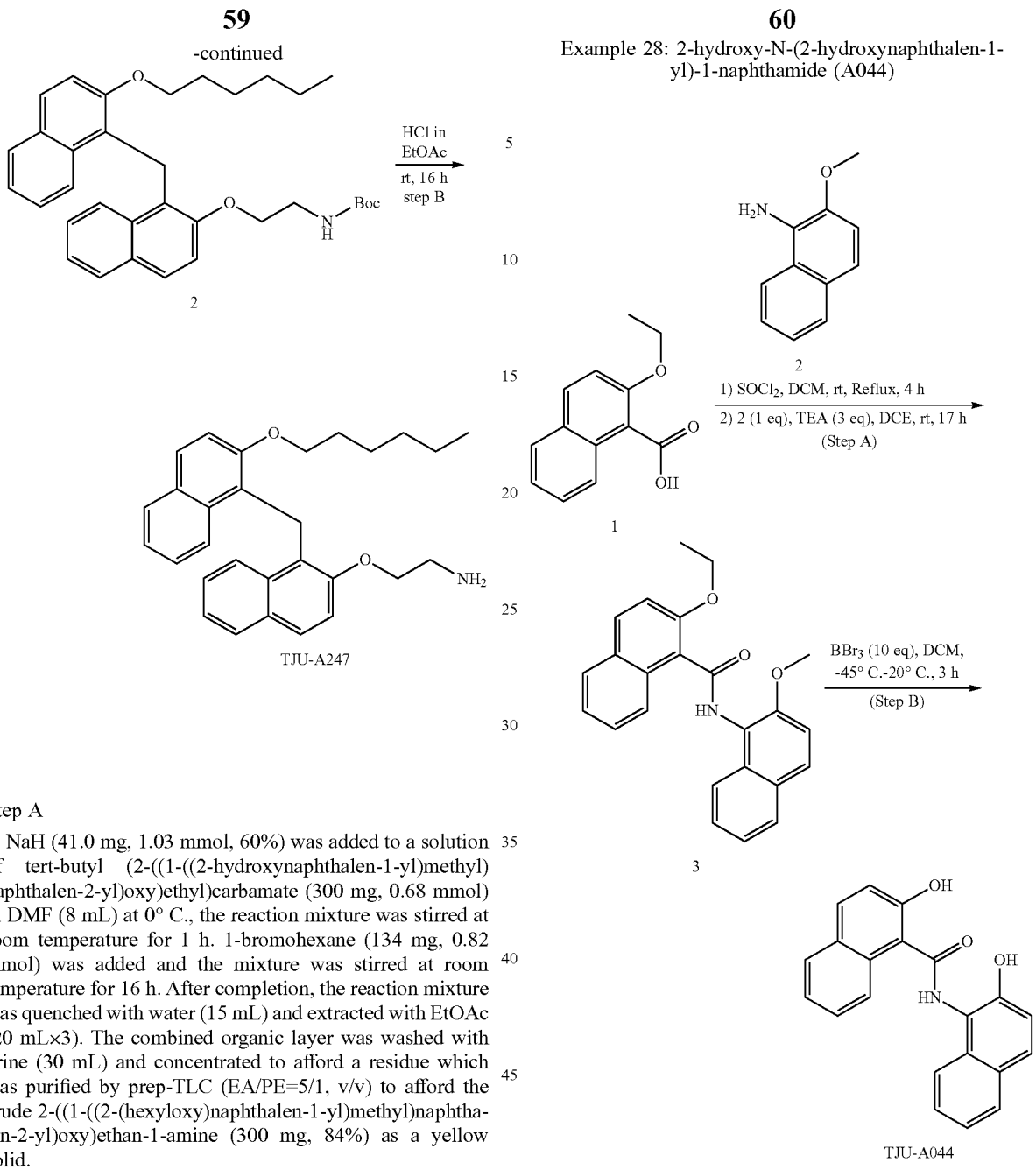

Example 28: 2-hydroxy-N-(2-hydroxynaphthalen-1-yl)-1-naphthamide (A044)

Step A

NaH (41.0 mg, 1.03 mmol, 60%) was added to a solution of tert-butyl (2-((1-((2-hydroxynaphthalen-1-yl)methyl)naphthalen-2-yl)oxy)ethyl)carbamate (300 mg, 0.68 mmol) in DMF (8 mL) at 0° C., the reaction mixture was stirred at room temperature for 1 h. 1-bromohexane (134 mg, 0.82 mmol) was added and the mixture was stirred at room temperature for 16 h. After completion, the reaction mixture was quenched with water (15 mL) and extracted with EtOAc (20 mL×3). The combined organic layer was washed with brine (30 mL) and concentrated to afford a residue which was purified by prep-TLC (EA/PE=5/1, v/v) to afford the crude 2-((1-((2-(hexyloxy)naphthalen-1-yl)methyl)naphthalen-2-yl)oxy)ethan-1-amine (300 mg, 84%) as a yellow solid.

Mass Spectrum (ESI) m/z=550.3 (M+Na$^+$).

Step B

A solution of tert-butyl (2-((1-((2-(hexyloxy)naphthalen-1-yl)methyl)naphthalen-2-yl)oxy)ethyl)carbamate (140 mg, 0.27 mmol) in HCl/EtOAc (5 mL, 2M) was stirred at room temperature for 16 h. After completion, the precipitate was collected by filtration to get 2-((1-((2-(hexyloxy)naphthalen-1-yl)methyl)naphthalen-2-yl)oxy)ethan-1-amine (90 mg, 80%) as a white solid.

Mass Spectrum (ESI) m/z=428.2 (M+H$^+$).

$^1$H NMR (400 MHz, DMSO-d6) δ 8.29 (s, 2H), 8.14-7.97 (m, 2H), 7.82-7.47 (m, 4H), 7.48 (t, J 8.0 Hz, 2H), 7.32 (t, J=8.0 Hz, 1H), 7.29-7.18 (m, 3H), 4.91 (s, 2H), 4.41 (t, J=8.0 Hz, 2H), 4.20 (t, J 8.0 Hz, 2H), 3.20 (t, J=8.0 Hz, 2H), 1.74-1.63 (m, 2H), 1.47-1.37 (m, 2H), 1.35-1.15 (m, 4H), 0.84 (t, J=8.0 Hz, 3H).

Step A

To a solution of 2-ethoxy-1-naphthoic acid (500 mg, 2.32 mmol) in anhydrous dichloromethane (6 mL) was added thionyl chloride (5.53 g, 46.4 mmol) dropwise at room temperature and the mixture was refluxed for 4 h. The reaction mixture was concentrated to give the acyl chloride. The acyl chloride (150 mg, 0.636) was dissolved in dichloroethane (3 mL), triethyl amine (176 mg, 1.734 mmol), 2-methoxynaphthalen-1-amine (100 mg, 0.578 mmol) were added and the mixture was stirred at room temperature overnight. After completion, water (20 mL) was added and the mixture was extracted with ethyl acetate (20 mL×3). The organic layer was dried over anhydrous sodium sulfate, filtrated and the filtrate was concentrated. The residue was purified by flash column chromatography on silica gel (PE/EA=1/1, v/v) to afford 2-ethoxy-N-(2-methoxynaphthalen-1-yl)-1-naphthamide (170 mg, 79%) as a white solid.

Mass Spectrum (ESI) m/z=372.2 (M+H$^+$).

Step B

To a solution of 2-ethoxy-N-(2-methoxynaphthalen-1-yl)-1-naphthamide (75 mg, 0.202 mmol) in anhydrous dichloromethane (2 mL) was added boron tribromide (2 mL, 2 mmol) (1 M in dichloromethane) at −45° C. under nitrogen. The reaction mixture was stirred at −20° C. for 3 h. After completion, the reaction mixture was quenched with methanol (20 mL) and concentrated. The residue was extracted with ethyl acetate (10 mL×3), washed with water (20 mL), brine (20 mL), dried over anhydrous sodium sulfate and concentrated. The crude 2-hydroxy-N-(2-hydroxynaphthalen-1-yl)-1-naphthamide was purified by prep-HPLC to afford pure 2-hydroxy-N-(2-hydroxynaphthalen-1-yl)-1-naphthamide (14 mg, 21%) as a white solid.

Mass Spectrum (ESI) m/z=330.2 (M+H$^+$).

$^1$H NMR (400 MHz, DMSO-d$_6$)) δ 10.03-10.00 (m, 3H), 8.20-8.18 (m, 2H), 7.87-7.85 (m, 3H), 7.79 (d, J=8.8 Hz, 1H), 7.50-7.48 (m, 2H), 7.34 (t, J=7.4 Hz, 2H), 7.28 (m, 2H).

Example 29: 1,1'-methylenebis(3-chloronaphthalen-2-ol) (A046)

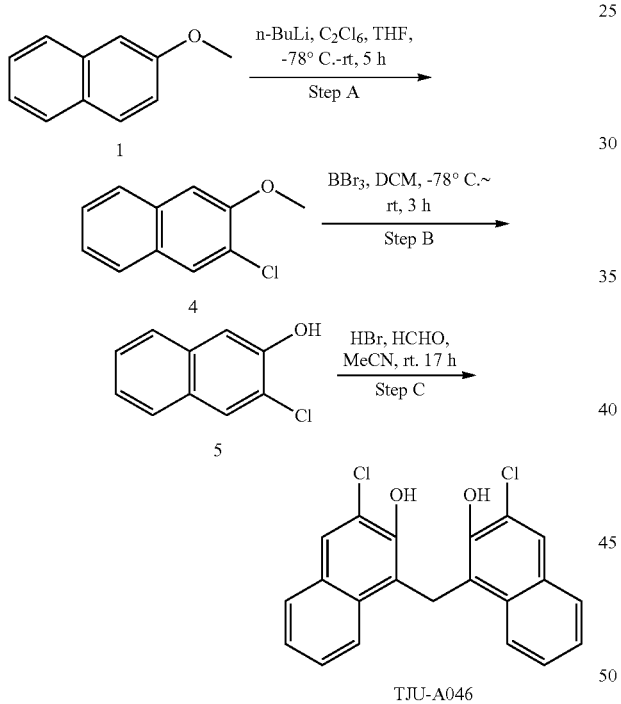

Step A

N-butyllithium (8.4 mL, 2.4 M) was added to a solution of 2-methoxynaphthalene (2.0 g, 12.6 mmol) in tetrahydrofuran (20 mL) at −78° C. dropwise and the mixture was stirred for 1 h at room temperature. hexachloroethane (3.59 g, 15.1 mmol) in tetrahydrofuran (10 mL) was added to the solution at −78° C. and the resulting mixture was stirred for 4 h at room temperature. Upon completion, the mixture was quenched with saturated ammonium chloride (10 mL) at −78° C. and extracted with ethyl acetate (20 mL×3). The organic layer was dried over sodium sulfate, filtered and concentrated in vacuo. The crude product was purified by flash chromatography (PE/EA=10/1, v/v) to afford 2-chloro-3-methoxynaphthalene (1.60 g, 65%) as a white solid.

Step B

To a solution of 2-chloro-3-methoxynaphthalene (300 mg, 1.56 mmol) in dichloromethane (5 mL) was added boron tribromide (1174.31 mg, 4.68 mmol, 1.0 M) at −78° C. and the reaction mixture was stirred for 3 h at room temperature. Upon completion, the mixture was quenched with methanol and water at −78° C. and extracted with ethyl acetate (15 mL×3), the organic layer was dried over sodium sulfate, filtered and concentrated in vacuo. The crude was purified by flash chromatography (PE/EA=7/1, v/v) to afford 3-chloronaphthalen-2-ol (250 mg, 89%) as a white solid.

Mass Spectrum (ESI) m/z=177.1 (M−H$^-$).

Step C

To a solution of 3-chloronaphthalen-2-ol (250 mg, 1.40 mmol) in acetonitrile (5 mL) were added HBr (40% aqueous, 17.06 mg)-acetonitrile (1 mL) and HCHO (37% aqueous, 62.76 mg) in acetonitrile (1.5 mL). Upon completion, the reaction mixture was poured into water (30 mL) and extracted with dichloromethane (20 mL×3). The organic layer was dried over anhydrous sodium sulfate, filtered, and concentrated in vacuo. The crude was purified by prep-HPLC to afford 1,1'-methylenebis(3-chloronaphthalen-2-ol).

Mass Spectrum (ESI) m/z=366.9 (M−H$^-$).

1H NMR (400 MHz, DMSO-d6) δ 9.89 (s, 2H), 8.02 (d, J=8.3 Hz, 2H), 7.91 (s, 2H), 7.70 (d, J=7.6 Hz, 2H), 7.29-7.18 (m, 4H), 4.87 (s, 2H).

Example 30: 1,1'-methylenebis(3-(2-hydroxypropan-2-yl)naphthalen-2-ol) (A047)

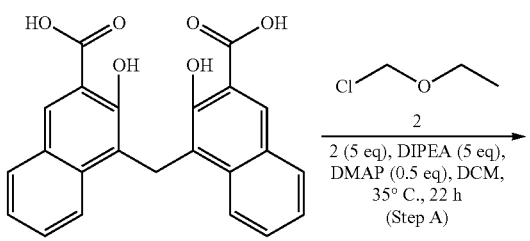

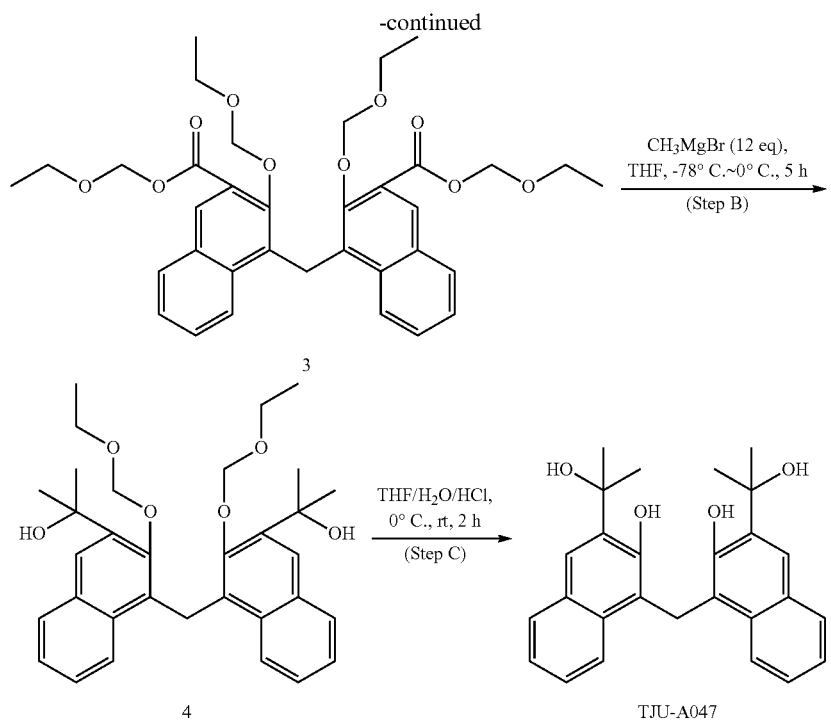

Step A

To a solution of 4,4'-methylenebis(3-hydroxy-2-naphthoic acid) (2 g, 5.15 mmol) in dichloromethane (25 mL) were added chloromethyl ethyl ether (2.44 g, 25.75 mmol), diisopropyl ethyl amine (3.33 g, 25.75 mmol), dimethyl aminopyridine (315 mg, 2.575 mmol) at 0° C. The reaction mixture was stirred at 35° C. for 22 h. After completion, the reaction mixture was quenched with water (20 mL), extracted with dichloromethane (20 mL×3). The combined organic layer was washed with brine (50 mL×3), dried over anhydrous sodium sulfate and concentrated. The residue was purified by column chromatography (PE/EA=10/1, v/v) to afford bis(ethoxymethyl) 4,4'-methylenebis(3-(ethoxymethoxy)-2-naphthoate) (1.6 g, 50%) as a yellow oil.

Mass Spectrum (ESI) m/z=643.3 (M+Na$^+$)

Step B

To a solution of bis(ethoxymethyl) 4,4'-methylenebis(3-(ethoxymethoxy)-2-naphthoate) (300 mg, 0.483 mmol) in anhydrous tetrahydrofuran (3 mL) was added methylmagnesium bromide (3 M in ether, 2 mL, 5.8 mmol) at −78° C. under nitrogen. The reaction mixture was stirred at −78° C. to 0° C. for 5 h. After completion, the reaction mixture was quenched with saturated ammonium chloride (5 mL) at 0° C. and extracted with ethyl acetate (15 mL×3). The combined organic layer was washed with brine (40 mL×3), dried over anhydrous sodium sulfate and concentrated. The residue was purified by flash column chromatography on silica gel (PE/EA=10/1, v/v) to afford 2,2'-(methylenebis(3-(ethoxymethoxy)naphthalene-4,2-diyl))bis(propan-2-ol) (110 mg, 42%) as a white solid.

Mass Spectrum (ESI) m/z=555.3 (M+Na$^+$).

Step C

A solution of 2,2'-(methylenebis(3-(ethoxymethoxy)naphthalene-4,2-diyl))bis(propan-2-ol) (50 mg, 0.094 mmol) in tetrahydrofuran/H$_2$O/HCl (6/2,1, v/v/v) (3 mL) was stirred for 2 h at room temperature. After completion, water (5 mL) was added, and the mixture was extracted with ethyl acetate (10 mL×3). The combined organic layer was washed with saturated sodium bicarbonate (10 mL×3), brine (20 mL×3), dried over anhydrous sodium sulfate and concentrated. The residue was purified by prep-HPLC to afford 1,1'-methylenebis(3-(2-hydroxypropan-2-yl)naphthalen-2-ol) (10.2 mg, 25%) as a yellow solid.

Mass Spectrum (ESI) m/z=415.2 (M−H$^−$).

$^1$H NMR (400 MHz, DMSO-d$_6$) δ 11.13 (s, 2H), 8.23 (d, J=8.5 Hz, 2H), 7.64 (d, J=7.9 Hz, 2H), 7.55 (s, 2H), 7.14-7.12 (m, 6H), 4.74 (s, 2H), 1.70 (s, 12H).

Example 31: 1,1'-methylenebis(3-fluoronaphthalen-2-ol) (A049)

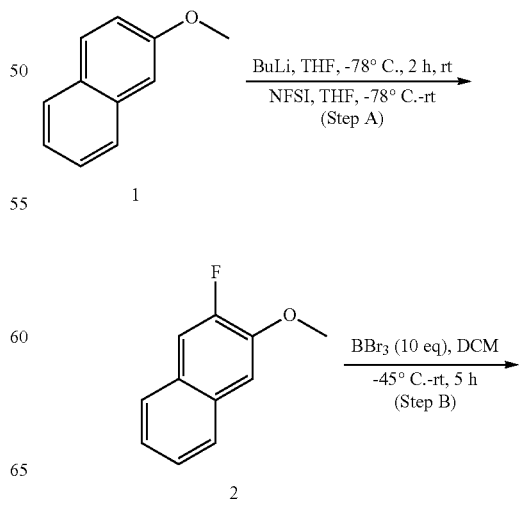

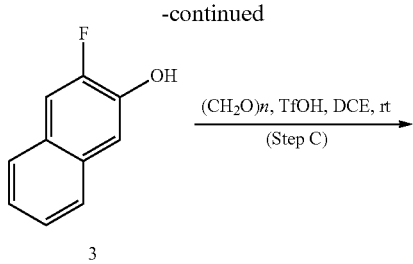

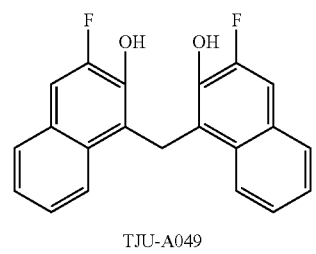

TJU-A049

Step A

To a solution of 2-methoxynaphthalene (4.74 g, 30.0 mmol) in tetrahydrofuran (50 mL) at −78° C. was added n-BuLi 18.75 mL, 2.4 M in hexane, 45.0 mmol)under nitrogen atmosphere. The reaction mixture was stirred at room temperature for 2 h. NFSI (11.4 g, 36.0 mmol) in tetrahydrofuran (10 mL) was added at −78° C. and the reaction mixture was stirred for another 2 h at room temperature. The reaction mixture was quenched with saturated ammonium chloride (30 mL) and extracted with ethyl acetate (50 mL×3). The organic layer was dried over anhydrous sodium sulfate, filtered and concentrated in vacuo. The crude was purified by column chromatography (PE/EA=50/1, v/v) to afford 2-fluoro-3-methoxynaphthalene (2.1 g, 39%) as a pink powder.

$^1$H NMR (400 MHz, DMSO-d6) δ 7.85 (d, J=8.0 Hz, 1H), 7.82 (d, J=8.0 Hz, 1H), 7.73 (d, J=12.0 Hz, 1H), 7.54 (d, J=8.0 Hz, 1H), 7.48-7.44 (m, 1H), 7.42-7.38 (m, 1H), 3.96 (s, 3H).

Step B

To a solution of 2-fluoro-3-methoxynaphthalene (528 mg, 3.0 mmol) in dry dichloromethane (10 mL) at −78° C. was added borontribromide (3.75 g, 1.44 mL, 15.0 mmol). After stirring at room temperature for 2 h, the reaction mixture was quenched with ice water (20 mL) and extracted with dichloromethane (30 mL×2). The organic layer was dried over anhydrous sodium sulfate, filtered and concentrated to afford 3-fluoronaphthalen-2-ol (450 mg, 92%) as a pink solid.

Mass Spectrum (ESI) m/z=161.0 (M−H$^-$).

$^1$H NMR (400 MHz, DMSO-d6) δ 10.30 (s, 1H), 7.77 (d, J=8.0 Hz, 2H), 7.73 (d, J=8.0 Hz, 2H), 7.41-7.37 (m, 1H), 7.34-7.30 (m, 1H).

Step C

To a solution of 3-fluoronaphthalen-2-ol (891 mg, 5.5 mmol) and paraformaldehyde (82.5 mg) in dichloroethane (20 mL) was added TfOH (2.06 g, 13.75 mL). The reaction mixture was stirred at room temperature for 2 h. Another batch of paraformaldehyde (82.5 mg) was added and the mixture was stirred overnight. The reaction mixture was quenched with ice water (20 mL) and extracted with dichloromethane (30 mL×2). The combined organic layer was washed with brine, dried over anhydrous sodium sulfate, filtered and concentrated in vacuo. The crude was purified by prep-TLC and prep-HPLC to afford 1,1'-methylenebis(3-fluoronaphthalen-2-ol) (40 mg, 4%) as a white solid.

Mass Spectrum (ESI) m/z=334.2 (M−H$^-$)

$^1$H NMR (400 MHz, DMSO-d6) δ 10.22 (br, 2H), 7.68-7.58 (m, 6H), 7.30-7.20 (m, 4H), 4.14 (s, 2H).

Example 32: 1,1'-methylenebis(3-methoxynaphthalen-2-ol) (A050)

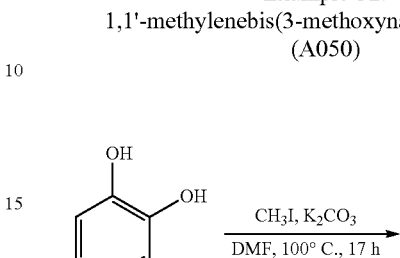

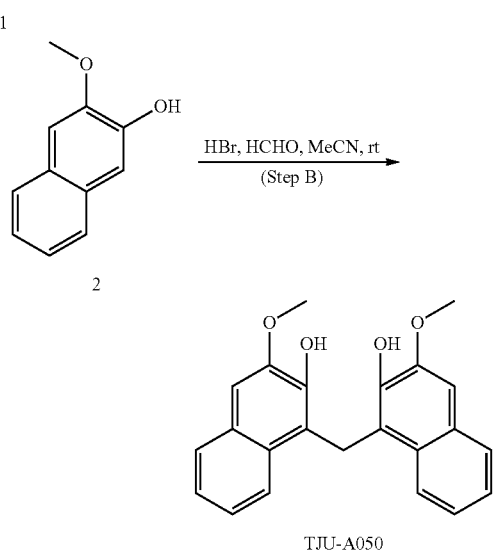

TJU-A050

Step A

Naphthalene-2,3-diol (320 mg, 2 mmol) and potassium carbonate (579 mg, 4.19 mmol) were dissolved in N,N-dimethylformamide (10 mL), the reaction mixture was stirred at 100° C. for 30 min. methyl iodide (283.88 mg, 2 mmol) was added at 25° C. The mixture was stirred under nitrogen atmosphere for 15 h at room temperature. The reaction mixture was diluted with water (100 mL) and extracted with ethyl acetate (100 mL×3). The organic layer was combined and concentrated under vacuum to afford the crude 3-methoxynaphthalen-2-ol (174 mg, 50%) which was used directly in the next step without purification.

Mass Spectrum (ESI) m/z=175.1 (M+H$^+$)

Step B

To a solution of 3-methoxynaphthalen-2-ol (174 mg, 1 mmol) and formaldehyde aqueous solution (44 mg, 1.47 mmol) in acetonitrile (4 mL) was added HBr (40%, 25 mg) in acetonitrile (0.5 mL). After stirring at room temperature for 6 h, the reaction mixture was poured into H$_2$O (40 mL) and extracted with dichloromethane (30 mL×2). The organic layer was dried over sodium sulfate, filtered and concentrated under vacuum. The residue was purified by prep-HPLC to afford 1,1'-methylenebis(3-methoxynaphthalen-2-ol) (35.3 mg, 9%) as a white solid.

Mass Spectrum (ESI) m/z=383.0 (M+Na$^+$).

$^1$H NMR (400 MHz, DMSO-d6) δ 9.41 (s, 2H), 8.06 (d, J=8.0 Hz, 2H), 7.60 (d, J=4.0 Hz, 2H), 7.18 (s, 2H), 7.14-7.11 (m, 2H), 7.07-7.04 (m, 2H), 4.74 (s, 2H), 3.98 (s, 6H).

Example 33: afford 1-(naphthalen-1-ylmethyl)naphthalen-2-ol (A052)

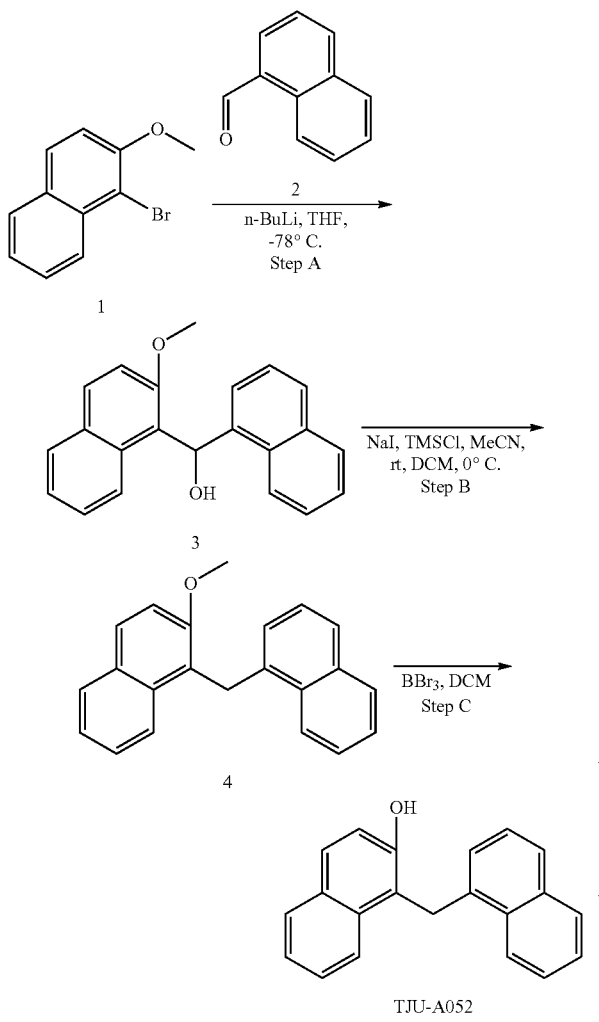

Step A n-BuLi (2.4 M in n-hexane solution, 1.92 mL, 4.61 mmol) was added dropwise to a solution of 1-bromo-2-methoxynaphthalene (1 g, 4.22 mmol) in dry tetrahydrofuran (10 mL) under nitrogen at −78° C. A solution of 1-naphthaldehyde (599 mg, 3.84 mmol) in tetrahydrofuran (6 mL) was added dropwise to the solution at −78° C. The resulting solution was allowed to warm to room temperature with stirring for 2 h. The mixture was quenched with saturated ammonium chloride at 0° C. and diluted with ethyl acetate (50 mL). The organic layer was washed with water (30 mL×3) and brine, dried over sodium sulfate, filtered and concentrated under reduced pressure. The crude product was purified by column chromatography (PE/EA=4/1, v/v) to afford (2-methoxynaphthalen-1-yl)(naphthalen-1-yl)methanol (360 mg, 30%) as a white solid.

Mass Spectrum (ESI) m/z=297.2 (M+1+).

Step B

To a stirred suspension of sodium iodide (143 mg, 0.954 mmol) in acetonitrile (2 mL) under nitrogen at room temperature, was added chlorotrimethylsilane (104 mg, 0.954 mmol). After stirring for 20 min, the reaction mixture was cooled to 0° C., a solution of (2-methoxynaphthalen-1-yl)(naphthalen-1-yl)methanol (50 mg, 0.159 mmol) in dichloromethane (0.5 mL) and acetonitrile (0.5 mL) was added over 1 h. After stirring for 30 min at 0° C., the mixture was allowed to warm to room temperature over 5 min, and then immediately cooled to 0° C., then poured into aqueous sodium hydroxide (1M), additional sodium hydroxide solution was added to adjust pH=7. The biphasic mixture was extracted with ethyl acetate (10 mL×2) and the organic phase was washed with saturated aqueous $Na_2S_2O_3$ to completely remove any color of iodine. The aqueous portion was extracted with ethyl acetate and the combined organic layer was dried over sodium sulfate, filtered and concentrated under reduced pressure. The residue was purified by column chromatography (PE/EA=2/1, v/v) to afford 2-methoxy-1-(naphthalen-1-ylmethyl)naphthalene (20 mg, 43%) as a white solid.

$^1$H NMR (400 MHz, DMSO-d$_6$) δ 8.46 (d, J=8.4 Hz, 1H), 7.96-7.94 (m, 3H), 7.64-7.62 (m, 5H), 7.34-7.32 (m, 2H), 7.20-7.18 (m, 1H), 6.49 (d, J=6.5 Hz, 1H), 4.83 (s, 2H), 3.88 (s, 3H).

Step C

To a solution of 2-methoxy-1-(naphthalen-1-ylmethyl)naphthalene (20 mg, 0.0671 mmol) in anhydrous dichloromethane (1 mL) was added boron tribromide (0.13 mL, 0.134 mmol) at −78° C. under nitrogen. The reaction mixture was stirred at 40° C. for 1 h. The mixture was quenched with methanol and concentrated under reduced pressure. The crude product was purified by column chromatography (PE/EA=2/1, v/v) to afford 1-(naphthalen-1-ylmethyl)naphthalen-2-ol(14.7 mg, 77%) as a yellow solid.

Mass Spectrum (ESI) m/z=283.1 (M−H)$^-$.

$^1$H NMR (400 MHz, CD$_3$OD) δ 8.42 (d, J=8.5 Hz, 1H), 7.87 (d, J=8.1 Hz, 1H), 7.76-7.74 (m, 2H), 7.62-7.60 (m, 2H), 7.54-7.52 (m, 2H), 7.23-7.21 (m, 3H), 7.13-7.11 (m, 1H), 6.66-6.64 (m, 1H), 4.84 (s, 2H).

Example 34: 1-(isoquinolin-1-ylmethyl)naphthalen-2-ol (A053)

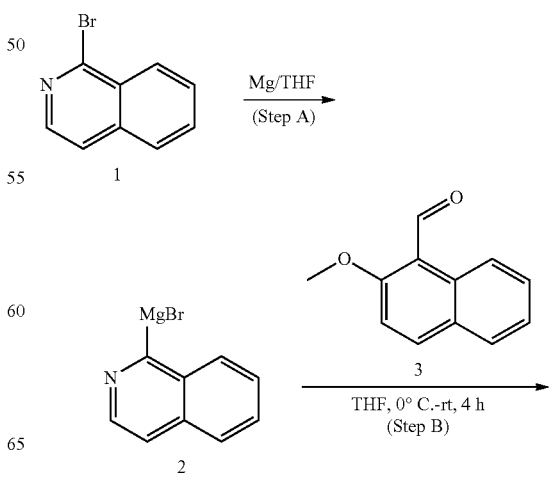

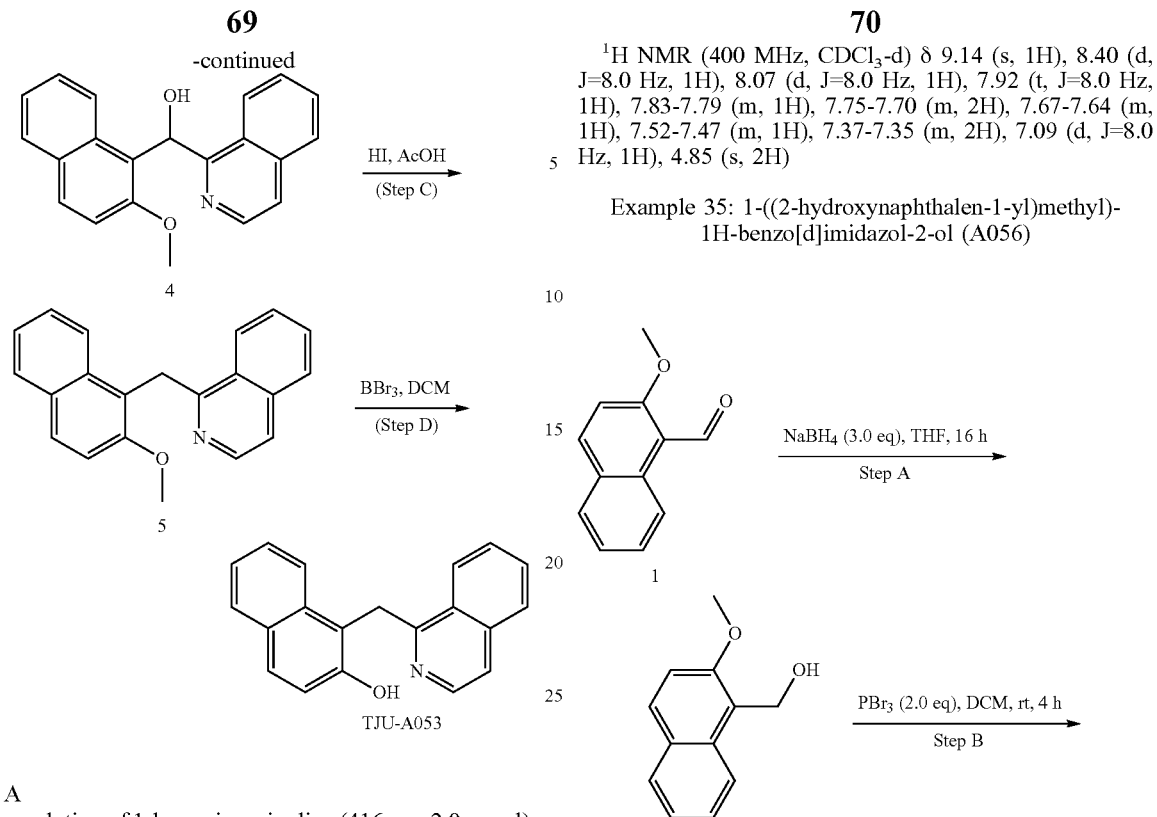

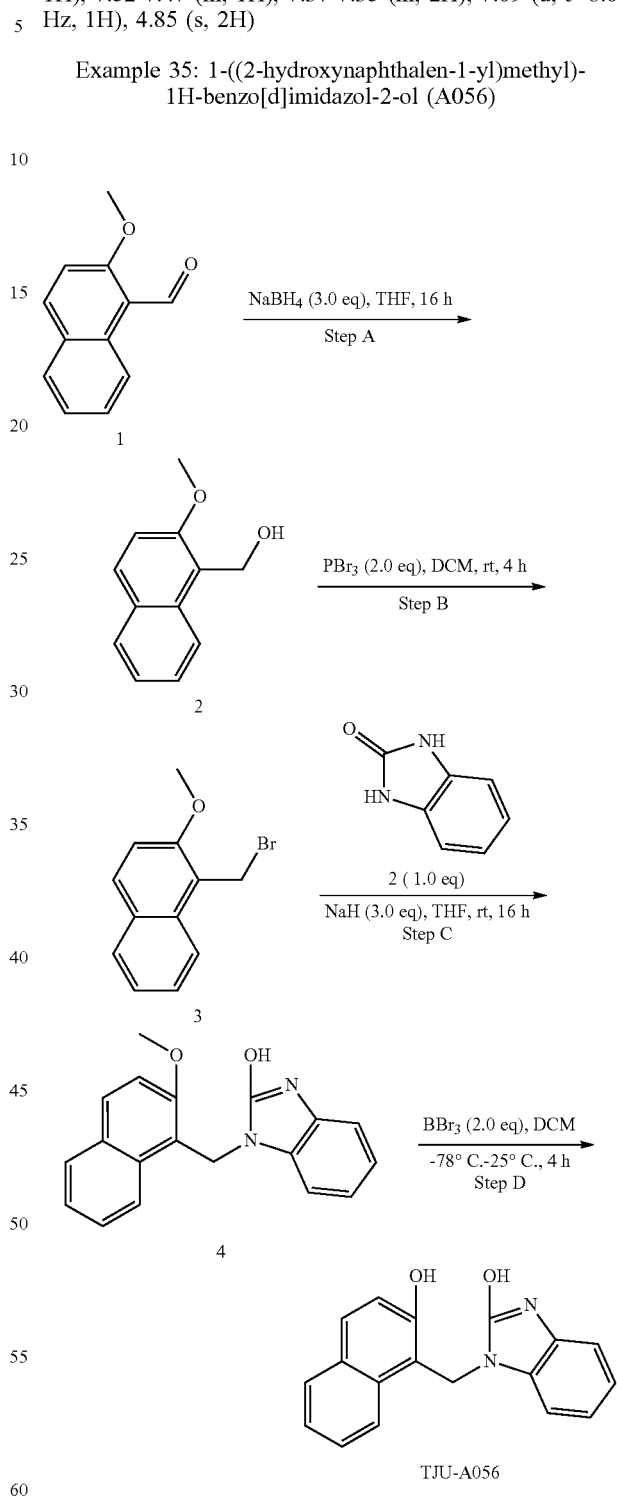

Step A
To a solution of 1-bromoisoquinoline (416 mg, 2.0 mmol) in tetrahydrofuran (4 mL) were added magnesium (240 mg, 10.0 mmol) and $I_2$ of catalytic amount. The reaction mixture was stirred at reflux for 2 h under nitrogen. The solution was used directly for the next step.

Step B
To a solution of 2-methoxy-1-naphthaldehyde (409 mg, 2.2 mmol) in dry tetrahydrofuran (10 mL) at 0° C. was slowly added isoquinolin-1-ylmagnesium bromide (4 mL) under nitrogen. The reaction mixture was stirred at room temperature for 2 h under nitrogen and then quenched with 6 M HCl (5 mL), extracted with ethyl acetate (30 mL×3). The organic layer was dried over anhydrous sodium sulfate, filtered and concentrated. The residue was purified by column chromatography (ethyl acetate) and prep-HPLC to afford isoquinolin-1-yl(2-methoxynaphthalen-1-yl)methanol (20 mg, 3%) as a yellow solid.

Mass Spectrum (ESI) m/z=316.1 (M+H$^+$)

Step C
To a solution of isoquinolin-1-yl(2-methoxynaphthalen-1-yl)methanol (200 mg, 0.64 mmol) in acetic acid (10 mL) was added hydrogen iodide (55%, 583 mg, 2.56 mmol). The reaction mixture was refluxed for 24 h. The reaction mixture was concentrated to afford the crude 1-((2-methoxynaphthalen-1-yl)methyl)isoquinoline which was used in the next step without purification.

Mass Spectrum (ESI) m/z=300.1 (M+H$^+$)

Step D
To a solution of 1-((2-methoxynaphthalen-1-yl)methyl)isoquinoline (150 mg, crude) in dry dichloromethane (10 mL) at −78° C. was added borontribromide (1.0 mL, 10.0 mmol) and the reaction mixture was stirred at room temperature for 2 h. The reaction was quenched with methanol (5 mL) and concentrated. The residue was purified by prep-HPLC to afford 1-(isoquinolin-1-ylmethyl)naphthalen-2-ol (20 mg, 11% over two steps) as a yellow solid.

Mass Spectrum (ESI) m/z=286.1 (M+H$^+$)

$^1$H NMR (400 MHz, CDCl$_3$-d) δ 9.14 (s, 1H), 8.40 (d, J=8.0 Hz, 1H), 8.07 (d, J=8.0 Hz, 1H), 7.92 (t, J=8.0 Hz, 1H), 7.83-7.79 (m, 1H), 7.75-7.70 (m, 2H), 7.67-7.64 (m, 1H), 7.52-7.47 (m, 1H), 7.37-7.35 (m, 2H), 7.09 (d, J=8.0 Hz, 1H), 4.85 (s, 2H)

Example 35: 1-((2-hydroxynaphthalen-1-yl)methyl)-1H-benzo[d]imidazol-2-ol (A056)

Step A
To a solution of 2-methoxy-1-naphthaldehyde (5 g, 26.9 mmol) in tetrahydrofuran (100 mL) was added sodium borohydride (3.0 g, 80.7 mmol) at 0° C. The mixture was stirred at room temperature overnight. Upon completion, the mixture was quenched with water and extracted with ethyl acetate (100 mL×3). The organic layer was dried over sodium sulfate, filtered and concentrated in vacuo. The crude was purified by flash chromatography (PE/EA=4/1, v/v) to afford (2-methoxynaphthalen-1-yl) methanol (4.6 g, 91%) as a white solid.

Mass Spectrum (ESI) m/z=171.2 (M–OH⁻).

Step B

To a solution of (2-methoxynaphthalen-1-yl) methanol (3.0 g, 16.0 mmol) in dichloromethane (80 mL) was added phosphorus tribromide (8.6 g, 32.0 mmol) at 0° C. and the mixture was stirred at room temperature for 4 h. Upon completion, the mixture was quenched with water and extracted with dichloromethane (25 mL×3). The organic layer was dried over sodium sulfate, filtered and concentrated in vacuo to afford crude 1-(bromomethyl)-2-methoxynaphthalene which was used for next step without purification.

Mass Spectrum (ESI) m/z=171.2 (M–Br⁺)

Step C

To a solution of 1,3-dihydro-2H-benzo[d]imidazol-2-one (804 mg, 6.0 mmol) in tetrahydrofuran (40 mL) were added sodium hydride (720 mg, 18.0 mmol) and 1-(bromomethyl)-2-methoxynaphthalene (1.5 g, 6.0 mmol) at 0° C. The mixture was stirred at room temperature overnight. Upon completion, the mixture was quenched with water and extracted with ethyl acetate (60 mL×3). The organic layer was dried over sodium sulfate, filtered and concentrated in vacuo. The crude product was purified by flash chromatography (PE/EA=4/1, v/v) to afford 1-((2-methoxynaphthalen-1-yl) methyl)-1H-benzo[d]imidazol-2-ol (550 mg, 28%) as a white solid.

Mass Spectrum (ESI) m/z=305.1 (M+H⁺)

Step D

To a solution of 1-((2-methoxynaphthalen-1-yl) methyl)-1H-benzo[d]imidazol-2-ol (80 mg, 0.26 mmol) in dichloromethane (10 mL) was added boron tribromide (128 mg, 0.52 mmol) at –78° C. and the mixture was stirred at room temperature for 4 h. Upon completion, the mixture was quenched with water, extracted with dichloromethane (30 mL×3). The organic layer was dried over sodium sulfate, filtered and concentrated in vacuo. The crude product was purified by prep-HPLC to afford 1-((2-hydroxynaphthalen-1-yl)methyl)-1H-benzo[d]imidazol-2-ol (18 mg, 24%) as a white solid.

Mass Spectrum (ESI) m/z=291.1 (M+H⁺).

¹H NMR (400 MHz, DMSO-d₆) δ 10.91 (brs, 2H), 8.17 (d, J=8.5 Hz, 1H), 7.67 (t, J=7.5 Hz, 2H), 7.41 (d, J=7.3 Hz, 1H), 7.33-7.29 (m, 2H), 7.14 (t, J=7.4 Hz, 1H), 6.90-6.77 (m, 3H), 5.39 (s, 2H).

Example 36: 1-((2-hydroxynaphthalen-1-yl)methyl) indolin-2-one (A057)

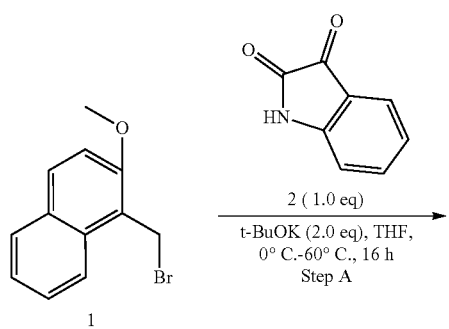

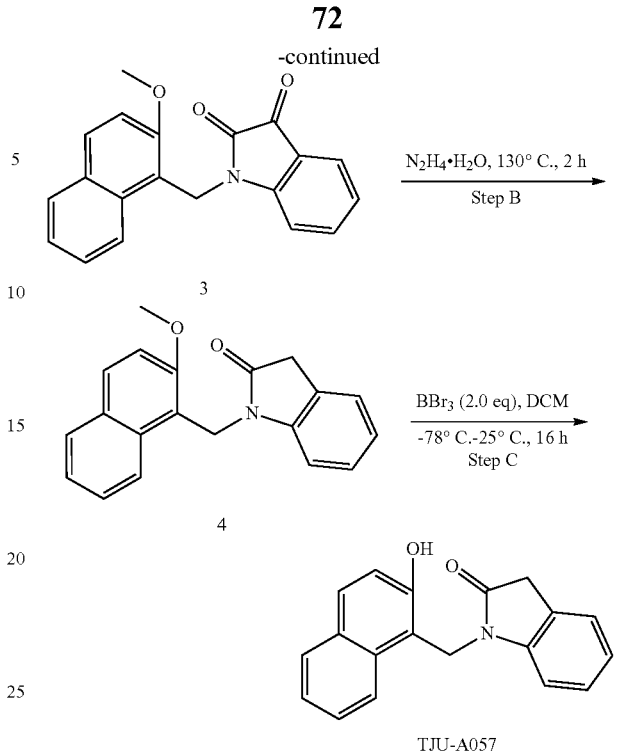

Step A

To a solution of indoline-2,3-dione (117 mg, 0.8 mmol) in tetrahydrofuran (40 mL) were added potassium t-butoxide (179 mg, 1.6 mmol) and 1-(bromomethyl)-2-methoxynaphthalene (200 mg, 0.8 mmol) at 0° C. The mixture was stirred at 60° C. overnight. Upon completion, the mixture was quenched with water and extracted with ethyl acetate (60 mL×3). The organic layer was dried over sodium sulfate, filtered and concentrated in vacuo. The crude 1-((2-methoxynaphthalen-1-yl) methyl) indoline-2,3-dione was purified by flash chromatography (PE/EA=4/1, v/v) to afford 1-((2-methoxynaphthalen-1-yl) methyl) indoline-2,3-dione (60 mg, 24%) as a white solid.

Mass Spectrum (ESI) m/z=340.1 (M+Na⁺).

Step B A solution of 1-((2-methoxynaphthalen-1-yl) methyl) indoline-2,3-dione (50 mg, 0.16 mmol) in N₂H₄·H₂O (10 mL) was stirred at 130° C. for 2 h. Upon completion, the mixture was quenched with water, extracted with dichloromethane (30 mL×3). The organic layer was dried over sodium sulfate, filtered and concentrated in vacuo. The crude 1-((2-methoxynaphthalen-1-yl) methyl) indolin-2-one was purified by flash chromatography (PE/EA=2/1, v/v) to afford 1-((2-methoxynaphthalen-1-yl) methyl) indolin-2-one (30 mg, 64%) as a white solid.

Mass Spectrum (ESI) m/z=304.1 (M+H⁺).

Step C

To a solution of 1-((2-methoxynaphthalen-1-yl) methyl) indolin-2-one (30 mg, 0.10 mmol) in dichloromethane (10 mL) was added boron tribromide (50 mg, 0.20 mmol) at –78° C. The mixture was stirred at room temperature for 16 h. Upon completion, the mixture was quenched with water and extracted with dichloromethane (30 mL×3). The organic layer was dried over sodium sulfate, filtered and concentrated in vacuo. The crude product was purified by prep-HPLC to afford 1-((2-hydroxynaphthalen-1-yl)methyl)indolin-2-one (12 mg, 43%) as a white solid.

Mass Spectrum (ESI) m/z=290.1 (M+H⁺).

$^1$H NMR (400 MHz, DMSO-d6) δ 7.95-7.93 (m, 1H), 7.64-7.52 (m, 3H), 7.28-7.26 (m, 1H), 7.20-7.02 (m, 4H), 6.88-6.85 (m, 1H), 5.27 (s, 2H), 3.60 (s, 2H).

Example 37: 1-((2-hydroxynaphthalen-1-yl)methyl)-4-phenyl-1H-pyrazol-5-ol (A059)

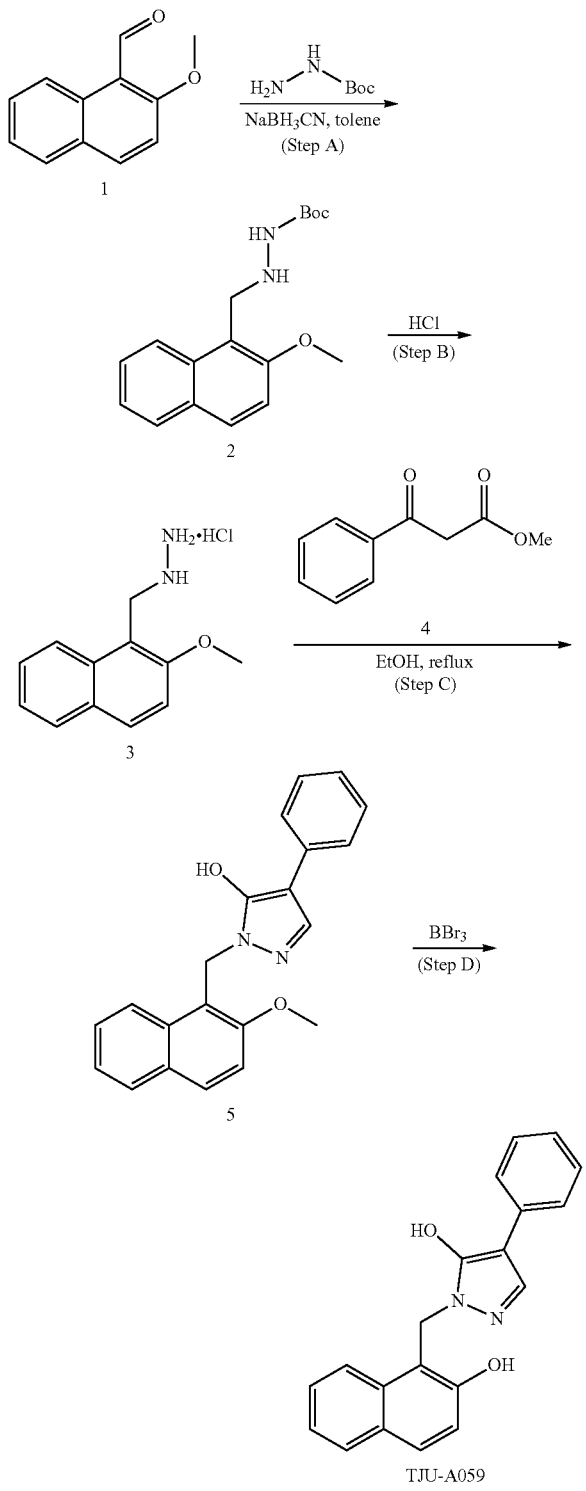

Step A

A solution of 2-methoxy-1-naphthaldehyde (3.84 g, 20.6 mmol) and tert-butyl hydrazinecarboxylate (3 g, 22.7 mmol) in toluene (50 mL) was stirred at 50° C. for 3 h. The reaction mixture was cooled to room temperature and NaBH$_3$CN (3.2 g, 51.6 mmol) in methanol (10 mL) was added. The reaction mixture was stirred at 50° C. for 2 h. After completion, the reaction mixture was quenched with water (20 mL) and extracted with ethyl acetate (50 mL×3). The organic layer was combined and washed with brine (50 mL×3), dried over anhydrous sodium sulfate, filtered and concentrated. The residue was purified by column chromatography (PE/EA=3/1, v/v) to afford tert-butyl 2-((2-methoxynaphthalen-1-yl)methyl)hydrazine-1-carboxylate (4 g, 64%) as a white solid.

Mass Spectrum (ESI) m/z=325.1 (M+Na$^+$)

Step B

A solution of tert-butyl 2-((2-methoxynaphthalen-1-yl)methyl)hydrazine-1-carboxylate (1.5 g, 5 mmol) in 4 M HCl/dioxane (10 mL) was stirred at room temperature for 3 h. After completion, the solvent was removed to afford ((2-methoxynaphthalen-1-yl)methyl)hydrazine (1 g, 100%) as a white solid which was used in next step directly.

Mass Spectrum (ESI) m/z=203.1 (M+H$^+$).

Step C

A solution of ((2-methoxynaphthalen-1-yl)methyl)hydrazine hydrochloride (1.8 g, 7.5 mmol) and methyl 3-oxo-3-phenylpropanoate (1.3 g, 7.5 mmol) in ethanol (50 mL) was refluxed overnight. The reaction mixture was concentrated to afford crude compound which was purified by chromatography (EA/methanol=50/1, v/v) to afford 1-((2-methoxynaphthalen-1-yl)methyl)-1H-pyrazol-5-ol (2 g, 88%).

Mass Spectrum (ESI) m/z=255 (M−HCl+H$^+$)

Step D

To a solution of 1-((2-methoxynaphthalen-1-yl)methyl)-4-phenyl-1H-pyrazol-5-ol (1.9 g, 5.7 mmol) in dichloromethane (50 mL) was added boron tribromide at −78° C. over 30 min. The reaction mixture was warmed to room temperature and stirred for 2 h. The reaction mixture was quenched with ice and filtered to afford the crude compound which was purified by prep-HPLC to afford 1-((2-hydroxynaphthalen-1-yl)methyl)-4-phenyl-1H-pyrazol-5-ol (300 mg, 17%) as a white solid.

Mass Spectrum (ESI) m/z=317.1 (M+H$^+$).

$^1$H NMR (400 MHz, DMSO-d$_6$) δ 10.93 (s, 2H), 8.19 (d, J=8.0 Hz, 1H), 7.79 (t, J=8.0 Hz, 2H), 7.6 (d, J=8 Hz, 2H), 7.49-7.44 (m, 1H), 7.34-7.21 (m, 5H), 5.77 (s, 1H), 5.49 (s, 2H).

Example 38: N,N-bis(2-hydroxynaphthalen-1-yl)acetamide (A075)

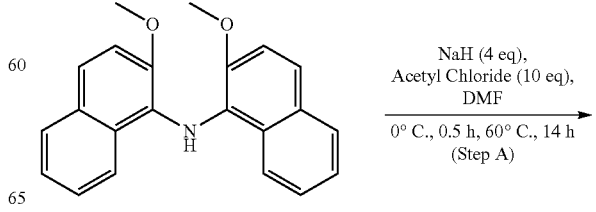

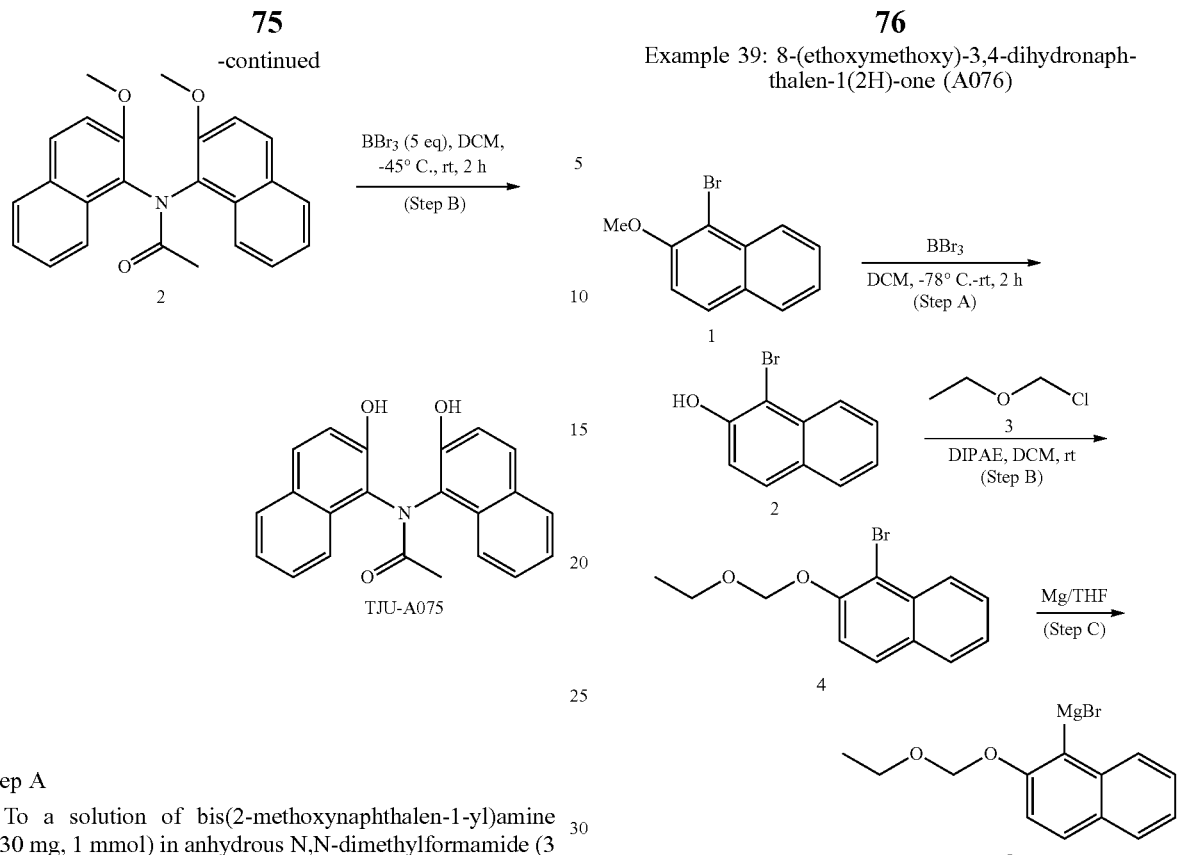

Example 39: 8-(ethoxymethoxy)-3,4-dihydronaphthalen-1(2H)-one (A076)

Step A

To a solution of bis(2-methoxynaphthalen-1-yl)amine (330 mg, 1 mmol) in anhydrous N,N-dimethylformamide (3 mL) was added sodium hydride (160 mg, 4 mmol) at 0° C. After stirring 0.5 h, acetyl chloride (0.7 mL, 10 mmol) was added and the reaction mixture was stirred at 60° C. for 14 h. After completion, the reaction mixture was quenched with water (30 mL) and extracted with ethyl acetate (30 mL×3). The combined organic layer was washed with saturated sodium bicarbonate aqueous (40 mL×3), brine (50 mL×3), dried over anhydrous sodium sulfate, and concentrated. The residue was purified by flash column chromatography on silica gel (PE/EA=2/1, v/v) to afford N,N-bis(2-methoxynaphthalen-1-yl)acetamide (270 mg, 73%) as a pale yellow solid.

Mass Spectrum (ESI) m/z=372.2 (M+H$^+$).

Step B

To a solution of N,N-bis(2-methoxynaphthalen-1-yl)acetamide (100 mg, 0.27 mmol) in anhydrous dichloromethane (1.5 mL) was added boron tribromide (1.4 mL, 1.35 mmol) dropwise under nitrogen at −45° C. The reaction mixture was stirred for 2 h at room temperature. After completion, the reaction mixture was quenched with methanol, diluted with water, extracted with dichloromethane (10 mL×2), and the organic layer was dried over anhydrous sodium sulfate, filtered, and concentrated. The resulting solid was recrystallized in dichloromethane/n-hexane(1/1) to afford N,N-bis(2-hydroxynaphthalen-1-yl)acetamide (70 mg, 75%) as a pale pink solid.

Mass Spectrum (ESI) m/z=342.1 (M−H$^-$).

$^1$H NMR (400 MHz, DMSO-d$_6$) δ 10.97 (s, 0.2H), 10.70 (s, 0.7H), 10.19 (s, 0.7H), 9.36 (s, 0.2H), 8.22 (d, J=8.6 Hz, 0.7H), 8.11 (d, J=8.5 Hz, 0.7H), 7.94 (d, J=8.5 Hz, 0.3H), 7.84 (t, J=8.1 Hz, 0.9H), 7.71-7.69 (m, 3H), 7.56 (t, J=7.4 Hz, 0.2H), 7.35-7.33 (m, 0.9H), 7.21-7.19 (m, 3.2H), 7.06 (d, J=8.8 Hz, 0.2H), 2.04 (s, 0.6H), 1.99 (s, 2.1H), 1.24 (s, 0.5H), 0.86 (t, J=6.8 Hz, 0.3H).

Step A

To a solution of 1-bromo-2-methoxynaphthalene (6.0 g, 25.3 mmol) in dry dichloromethane (10 mL) at −78° C. was added borontribromide (12.0 mL, 126.0 mmol) and the reaction mixture was stirred at room temperature for 2 h. The reaction mixture was quenched with ice water (80 mL) and extracted with dichloromethane (80 mL×3), and the organic layer was dried over anhydrous sodium sulfate, filtered and concentrated to afford 1-bromonaphthalen-2-ol (5.2 g, 92%) as a white solid.

Mass Spectrum (ESI) m/z=222.9, 225.0 (M+H$^+$).

$^1$H NMR (400 MHz, DMSO-d$_6$) δ 10.52 (s, 1H), 8.02 (d, J=8.0 Hz, 1H), 7.86 (d, J=8.0 Hz, 1H), 7.82 (d, J=8.0 Hz, 1H), 7.60-7.56 (m, 1H), 7.40-7.36 (m, 1H), 7.29 (d, J=8.0 Hz, 1H).

Step B

To a mixture of 1-bromonaphthalen-2-ol (5.2 g, 23.3 mmol) in dichloromethane (50 mL) were added (chloromethoxy)ethane (4.38 g, 46.6 mmol) and diisopropyl ethyl amine (9.01 g, 69.9 mmol), the reaction mixture was stirred at room temperature for 4 h. The reaction mixture was quenched with sat ammonium chloride (50 mL) and extracted with dichloromethane (80 mL×2). The organic layer was dried over anhydrous sodium sulfate, filtered and concentrated. The residue was purified by column chromatography (PE/EA=20/1, v/v) to afford 1-bromo-2-(ethoxymethoxy)naphthalene (6.3 g, 96%) as an off-white powder.

$^1$H NMR (400 MHz, DMSO-d$_6$) δ 8.12 (d, J=8.0 Hz, 1H), 7.99 (d, J=8.0 Hz, 1H), 7.95 (d, J=8.0 Hz, 1H), 7.67-7.63 (m, 1H), 7.57 (d, J=8.0 Hz, 1H), 7.51-7.47 (m, 1H), 5.47 (s, 2H), 3.76 (q, J=8.0 Hz, 2H), 1.14 (t, J=8.0 Hz, 3H).

Step C

To a solution of 1-bromo-2-(ethoxymethoxy)naphthalene (984 mg, 3.5 mmol) in tetrahydrofuran (7 mL) was added magnesium (420 mg, 17.5 mmol) and a grain of I$_2$ under nitrogen. The reaction mixture was stirred at reflux for 2 h. The solution was used directly used in the following step.

Step D

A mixture of naphthalene-1,8-diol (10.0 g, 62.4 mmol) and Pd/C (1 g) in ethanol (100 mL) was stirred at 60° C. under H$_2$ for 24 h. The mixture was filtered, and the filtrate was concentrated and the residue was purified by column chromatography (PE/EA=50/1, v/v) to afford 8-hydroxy-3,4-dihydronaphthalen-1(2H)-one (7.5 g, 74%) as a colorless oil.

Mass Spectrum (ESI) m/z=163.1 (M+H$^+$).

Step E

A mixture of 8-hydroxy-3,4-dihydronaphthalen-1(2H)-one (2.65 g, 16.33 mmol), (chloromethoxy)ethane (3.07 g, 32.7 mmol) and diisopropyl ethyl amine (9.01 g, 69.9 mmol) in tetrahydrofuran (40 mL) was stirred at reflux for 24 h under nitrogen. The reaction mixture was concentrated and the residue was purified by column chromatography (PE/EA=20/1, v/v) to afford 8-(ethoxymethoxy)-3,4-dihydronaphthalen-1(2H)-one (450 mg, 12%) as a yellow oil.

Mass Spectrum (ESI) m/z=221.1 (M+H$^+$), m/z=243.1 (M+Na$^+$).

$^1$H NMR (400 MHz, DMSO-d$_6$) δ 7.43 (t, J=8.0 Hz, 1H), 7.03 (d, J=8.0 Hz, 1H), 6.95 (d, J=8.0 Hz, 1H), 5.23 (s, 2H), 3.69 (q, J=8.0 Hz, 2H), 2.91-2.88 (m, 2H), 2.54-2.51 (m, 2H), 1.98-1.95 (m, 2H), 1.13 (t, J=8.0 Hz, 3H).

Step F

To a mixture of 8-(ethoxymethoxy)-3,4-dihydronaphthalen-1(2H)-one (770 mg, 3.5 mmol) and anhydrous cerium chloride (1.73 g, 7.0 mmol) in tetrahydrofuran (20 mL) was added dropwise 0.5 M (2-(ethoxymethoxy)naphthalen-1-yl) magnesium bromide (7.0 mL) at 0° C. The reaction mixture was stirred at room temperature for 2 h and quenched with 6 M HCl (10 mL). The aqueous phase was extracted with ethyl acetate (30 mL×3), and the organic layer was dried over anhydrous sodium sulfate, filtered and concentrated. The residue was purified by prep-TLC and prep-HPLC to afford 3',4'-dihydro-[1,1'-binaphthalene]-2,8'-diol (55 mg, 5%) as yellow powder.

Mass Spectrum (ESI) m/z=289.1 (M+H$^+$), m/z=311.0 (M+Na$^+$).

$^1$H NMR (400 MHz, CDCl$_3$) δ 7.84 (d, J=8.9 Hz, 1H), 7.82-7.78 (m, 1H), 7.60-7.58 (m, 1H), 7.41-7.33 (m, 2H), 7.29 (d, J=8.9 Hz, 1H), 7.12-7.07 (m, 1H), 6.86 (d, J=7.3 Hz, 1H), 6.56 (d, J=8.2 Hz, 1H), 6.25 (t, J=4.8 Hz, 1H), 5.74 (s, 1H), 5.01 (s, 1H), 3.10-2.99 (m, 1H), 2.95-2.93 (m, 1H), 2.53-2.51 (m, 2H).

Example 40: 1',2',3',4'-tetrahydro-[1,1'-binaphthalene]-2,8'-diol (A077)

Example 41: 1',2',3',4',5,6,7,8-octahydro-[1,1'-binaphthalene]-2,8'-diol (A077-2)

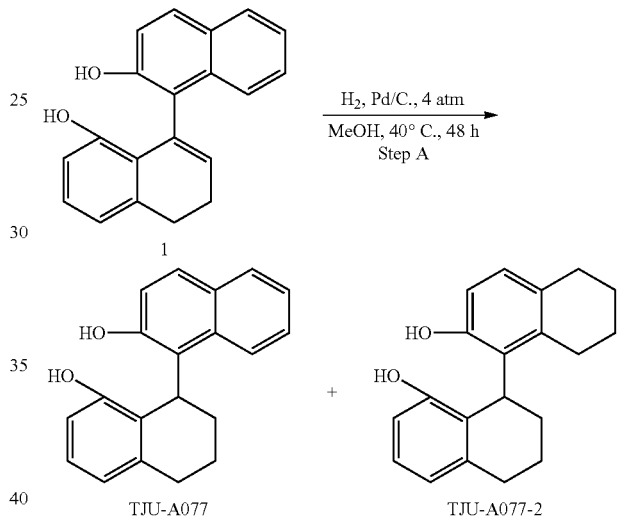

Step A

A mixture of 3',4'-dihydro-[1,1'-binaphthalene]-2,8'-diol (40 mg, 0.14 mmol) and 10% Pd/C (20 mg) in methanol (5 mL) was stirred under H$_2$ at 40° C. for 48 h. After completion, the reaction mixture was filtered and the filtrate was concentrated under reduced pressure. The residue was purified by prep-HPLC to afford 1',2',3',4'-tetrahydro-[1,1'-binaphthalene]-2,8'-diol (25.8 mg, 64%) as a white powder and 1',2',3',4',5,6,7,8-octahydro-[1,1'-binaphthalene]-2,8'-diol (6.3 mg, 15%) as a white powder.

1',2',3',4'-tetrahydro-[1,1'-binaphthalene]-2,8'-diol: Mass Spectrum (ESI) m/z=288.9 (M−H$^-$)$^-$ 1',2',3',4',5,6,7,8-octahydro-[1,1'-binaphthalene]-2,8'-diol: Mass Spectrum (ESI) m/z=292.9 (M−H$^-$)

1',2',3',4'-tetrahydro-[1,1'-binaphthalene]-2,8'-diol: $^1$H NMR (400 MHz, DMSO-d$_6$) δ 8.17 (s, 1H), 7.85 (d, J=4.0 Hz, 1H), 7.73 (d, J=8.0 Hz, 1H), 7.54 (s, 1H), 7.42 (s, 1H), 7.18 (s, 1H), 7.04 (d, J=12.0 Hz, 1H), 6.90 (d, J=4.0 Hz, 1H), 6.70 (s, 1H), 5.36 (s, 1H), 5.04 (s, 1H), 4.67 (s, 1H), 3.00-2.94 (m, 1H), 2.33 (s, 1H), 2.03 (s, 1H), 1.90-1.85 (m, 1H).

1',2',3',4',5,6,7,8-octahydro-[1,1'-binaphthalene]-2,8'-diol: $^1$H NMR (400 MHz, DMSO-d$_6$) δ 7.12-7.06 (m, 1H), 6.96-6.87 (m, 1H), 6.81 (d, J=8.0 Hz, 1H), 6.68-6.62 (m, 2H), 6.06 (t, J=4.6 Hz, 0.4H), 5.33 (s, 0.4H), 5.21 (s, 0.4H), 4.79 (s, 0.6H), 4.69 (s, 0.6H), 4.40 (t, J=8.4 Hz, 0.6H), 3.02-2.83 (m, 4H), 2.76-2.72 (m, 1H), 2.45-2.39 (m, 1H), 2.22-2.17 (m, 1H), 2.05-2.02 (m, 1H), 1.93-1.66 (m, 4H).

Example 42: 1-(4-hydroxy-1H-inden-3-yl)naphthalen-2-ol (A078)

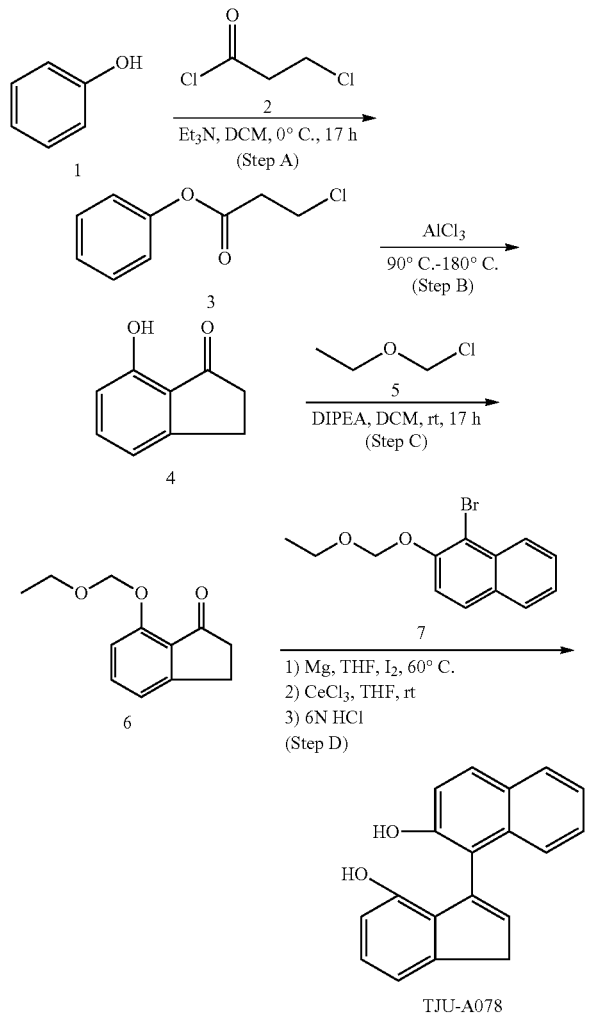

TJU-A078

Step A

To a solution of phenol (5 g, 55.6 mmol) and triethyl amine (6 g, 55.6 mmol) in dichloromethane (100 mL) was slowly added 3-chloropropanoyl chloride (7 g, 55.6 mmol) at 0° C. The reaction mixture was gradually warmed up to room temperature and stirred overnight. After completion, the reaction mixture was concentrated under reduced pressure to afford phenyl 3-chloropropanoate as orange oil (8.9 g, 86%). The crude phenyl 3-chloropropanoate was used directly in next step without purification.

Mass Spectrum (ESI) m/z=185.0 (M+H$^+$)

Step B

A mixture of phenyl 3-chloropropanoate (8.9 g 48 mmol) and aluminum trichloride (18 g, 144 mmol) was heated up to 90° C. for 1 h, 160° C. for 1 h and 180° C. for 2 h. After completion, the reaction mixture was cooled down to ambient temperature and quenched with 6N HCl (30 mL), diluted by water (100 mL), extracted with ethyl acetate (40 mL×3). The combined organic layer was washed with brine, dried over anhydrous sodium sulfate, filtered and concentrated under vacuum. The residue was purified on silica gel (PE/EA=3/1, v/v) to afford 7-hydroxy-2,3-dihydro-1H-inden-1-one (1 g, 12%) as a pale grey solid.

Mass Spectrum (ESI) m/z=149.1 (M+H$^+$).

Step C

To a solution of 7-hydroxy-2,3-dihydro-1H-inden-1-one (1 g, 6.7 mmol) and diisopropyl ethyl amine (1.7 g, 13.5 mmol) in 15 mL dichloromethane was added chloromethyl ethyl ether (1.3 g, 13.5 mmol) dropwise at 0° C. The reaction mixture was stirred overnight at room temperature. After completion, the reaction mixture was quenched with water (50 mL) and extracted with dichloromethane (20 mL×3). The combined organic layer was washed with brine and dried over anhydrous sodium sulfate, filtered and concentrated under vacuum to afford 7-(ethoxymethoxy)-2,3-dihydro-1H-inden-1-one 6 (1.2 g, 87%) as a yellow solid. The crude 7-(ethoxymethoxy)-2,3-dihydro-1H-inden-1-one was directly used in next step without purification.

Mass Spectrum (ESI) m/z=229.1 (M+Na$^+$).

Step D

To a solution of 1-bromo-2-(ethoxymethoxy)naphthalene (1.2 g, 4.3 mmol) in tetrahydrofuran (30 mL) were added magnesium turnings (144 mg) and a few pieces of I$_2$. The reaction mixture was stirred at 60° C. for 30 min. After the solution went to colorless, the mixture was stirred for another 2 h under room temperature.

A mixture of 7-(ethoxymethoxy)-2,3-dihydro-1H-inden-1-one (1.2 g, 5.8 mmol) and cerium chloride (2.7 g, 10.9 mmol) in anhydrous tetrahydrofuran (15 mL) was stirred for 1 h under room temperature. The above solution of newly prepared Grignard reagent was added in one portion and the resulting mixture was stirred for another 2 h.

After completion, the reaction mixture was quenched with water (50 mL), then extracted with dichloromethane (20 mL×3). The combined organic layer was washed with saturated NaCl and dried over anhydrous sodium sulfate, filtered and concentrated under vacuum. The crude was purified by prep-HPLC to afford 1-(4-hydroxy-1H-inden-3-yl)naphthalen-2-ol (30 mg, 2%) as a grey powder.

Mass Spectrum (ESI) m/z=275.1 (M+H$^+$), 297.0 (M+Na$^+$).

$^1$H NMR (300 MHz, DMSO-d$_6$) δ 8.89 (s, 2H), 7.73-7.70 (m, 2H), 7.47 (d, J=7.7 Hz, 1H), 7.27-7.14 (m, 3H), 6.99 (d, J=6.9 Hz, 2H), 6.51 (d, J=6.5 Hz, 1H), 6.22 (s, 1H), 3.55 (d, J=6.8 Hz, 2H).

Example 43: 1-(7-hydroxy-2,3-dihydro-1H-inden-1-yl)naphthalen-2-ol (A079)

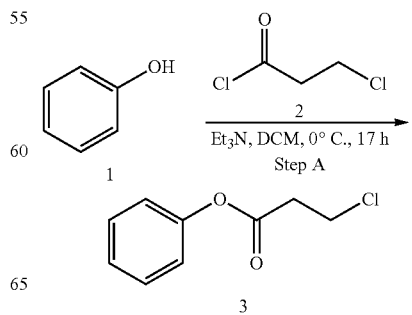

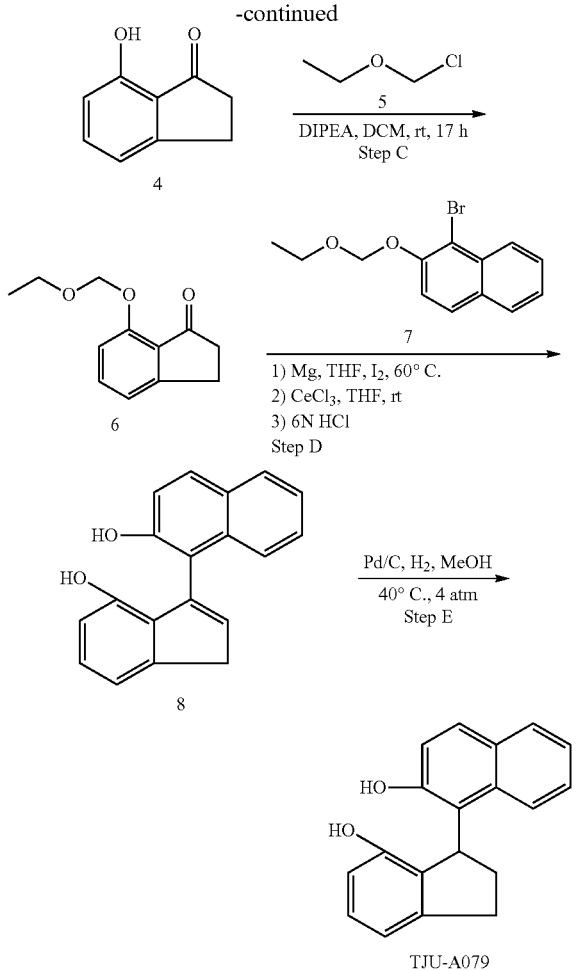

Step A

To a solution of phenol (5 g, 55.6 mmol) and triethyl amine (6 g, 55.6 mmol) in dichloromethane (100 mL) was slowly added 3-chloropropanoyl chloride (7 g, 55.6 mmol) at 0° C. The reaction mixture was gradually warmed up by ambient atmosphere and stirred overnight. After completion, the reaction mixture was concentrated under reduced pressure to afford phenyl 3-chloropropanoate (8.9 g, 86%) as an orange oil. The crude phenyl 3-chloropropanoate was directly used in next step without purification.

Mass Spectrum (ESI) m/z=185.0 (M+H$^+$)

Step B

A mixture of phenyl 3-chloropropanoate (8.9 g 48 mmol) and aluminum chloride (18 g, 144 mmol) was heated up to 90° C. for 1 h, 160° C. for 1 h and 180° C. for 2 h. After completion, the reaction mixture was cooled to ambient temperature, quenched with 6 N HCl (30 mL), diluted by water (100 mL) and extracted with ethyl acetate (40 mL×3). The combined organic layer was washed with brine and dried over anhydrous sodium sulfate, filtered and concentrated under vacuum. The residue was purified on silica gel (PE/EA=3/1, v/v) to afford 7-hydroxy-2,3-dihydro-1H-inden-1-one (1 g, 12%) as a pale grey solid.

Mass Spectrum (ESI) m/z=149.1 (M+H$^+$).

Step C

To a solution of 7-hydroxy-2,3-dihydro-1H-inden-1-one (1 g, 6.7 mmol) and diisopropyl ethyl amine (1.7 g, 13.5 mmol) in dichloromethane (15 mL) was added chloromethyl ethyl ether (1.3 g, 13.5 mmol) dropwise at 0° C. The reaction mixture was stirred overnight at room temperature. After completion, the reaction mixture was quenched with water (50 mL) and extracted with dichloromethane (20 mL×3). The combined organic layer was washed with brine and dried over sodium sulfate, filtered and concentrated under vacuum to afford 7-(ethoxymethoxy)-2,3-dihydro-1H-inden-1-one (1.2 g, 87%) as a yellow solid. The crude 7-(ethoxymethoxy)-2,3-dihydro-1H-inden-1-one was directly used in next step without purification.

Mass Spectrum (ESI) m/z=229.1 (M+Na$^+$).

Step D

To a solution of 1-bromo-2-(ethoxymethoxy)naphthalene (1.2 g, 4.3 mmol) in anhydrous tetrahydrofuran (15 mL) were added magnesium turnings (144 mg) and a piece of I2. The reaction mixture was stirred at 60° C. for 30 min. After the solution went to colorless, the mixture was stirred for another 2 h under room temperature.

To another flask with 15 mL anhydrous tetrahydrofuran was added 7-(ethoxymethoxy)-2,3-dihydro-1H-inden-1-one (1.2 g, 5.8 mmol) and anhydrous cerium(III) chloride (2.7 g, 10.9 mmol). The mixture was stirred for 1 h under room temperature. The above solution of newly prepared Grignard reagent was added in one portion and the resulting mixture was stirred for another 2 h.

After completion, the reaction mixture was quenched with water (50 mL), then extracted with dichloromethane (20 mL×3). The combined organic layer was washed with brine and dried over anhydrous sodium sulfate, filtered and concentrated under vacuum. The crude was purified by prep-HPLC to afford 1-(4-hydroxy-1H-inden-3-yl)naphthalen-2-ol (30 mg, 2%) as a grey powder.

Mass Spectrum (ESI) m/z=275.1 (M+H$^+$), 297.0 (M+Na$^+$).

Step E

To a solution of 1-(4-hydroxy-1H-inden-3-yl)naphthalen-2-ol (20 mg, 0.07 mmol) in methanol (10 mL) was added Pd/C (20 mg). The reaction mixture was stirred at 40° C. for 24 h under H$_2$ (4 atm). After completion, the reaction mixture was filtered and the filtrate was concentrated under reduced pressure. The residue was purified by prep-HPLC to afford 1-(7-hydroxy-2,3-dihydro-1H-inden-1-yl)naphthalen-2-ol (12.1 mg, 62%) as a brown solid.

Mass Spectrum (ESI) m/z=274.8 (M−H$^-$).

$^1$H NMR (300 MHz, CDCl$_3$) δ 7.82 (d, J=7.9 Hz, 1H), 7.73 (d, J=8.8 Hz, 1H), 7.55 (t, J=7.6 Hz, 1H), 7.55 (t, J=7.6 Hz, 1H), 7.42-7.35 (m, 1H), 7.20 (d, J=7.8 Hz, 1H), 7.06 (d, J=8.8 Hz, 1H), 6.96 (d, J=7.5 Hz, 1H), 6.68 (d, J=8.0 Hz, 1H), 5.34 (t, J=9.1 Hz, 1H), 4.51 (s, 1H), 3.15-3.06 (m, 3H), 2.79-2.66 (m, 1H), 2.28-2.20 (m, 1H).

Example 44: bis(2-(((4-methoxybenzyl)oxy)methyl)naphthalen-1-yl)methanol (A080)

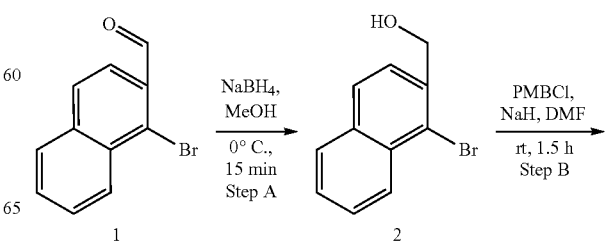

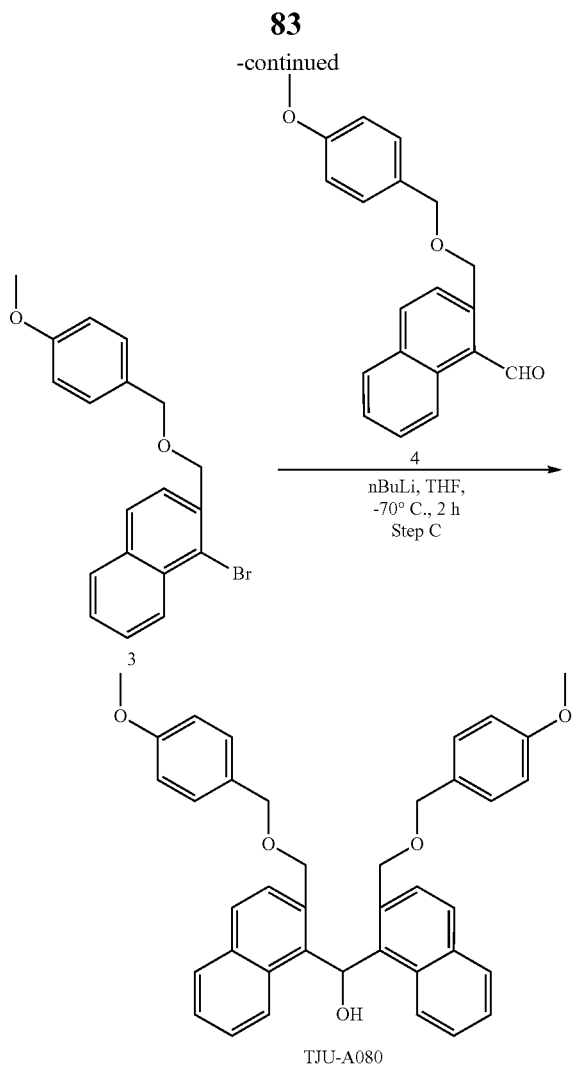

Step C

To a solution of 1-bromo-2-(((4-methoxybenzyl)oxy)methyl)naphthalene (150 mg, 0.42 mmol) in tetrahydrofuran (2 mL) was added nBuLi (2.4 M, 0.19 mL) at −70° C. The mixture was stirred at −70° C. for 1 h. Then 2-(((4-methoxybenzyl)oxy)methyl)-1-naphthaldehyde (154 mg, 0.5 mmol) in tetrahydrofuran (2 mL) was added and the mixture was stirred at −70° C. for 1 h. Upon completion, the mixture was quenched with water and extracted with ethyl acetate (30 mL×3), dried over sodium sulfate, filtered and concentrated in vacuo to afford the crude product which was purified by prep-HPLC to afford bis(2-(((4-methoxybenzyl)oxy)methyl)naphthalen-1-yl)methanol (10 mg, 8%) as a white solid.

$^1$H NMR (400 MHz, DMSO-d6) δ 8.17 (s, 2H), 7.88 (d, J=8.6 Hz, 4H), 7.67 (d, J=8.6 Hz, 2H), 7.41 (t, J=7.3 Hz, 3H), 7.26 (t, J=7.7 Hz, 2H), 7.11 (d, J=8.3 Hz, 4H), 6.83 (d, J=8.4 Hz, 4H), 6.21 (d, J=5.3 Hz, 1H), 4.78 (d, J=13.0 Hz, 2H), 4.55 (d, J=12.8 Hz, 2H), 4.29-4.19 (m, 4H), 3.72 (s, 6H).

Example 45: 1,1'-methylenebis(3-isopropylnaphthalen-2-ol) (A081)

Step A

To a solution of 1-bromo-2-naphthaldehyde (2.4 g, 10 mmol) in methanol (15 mL) was added NaBH$_4$ (567 mg, 15 mmol) and the mixture was stirred at 0° C. for 15 min. Upon completion, the mixture was quenched with water and extracted with ethyl acetate (100 mL×3), dried over sodium sulfate, filtered and concentrated in vacuo. The crude was purified by flash chromatography (PE/EA=3/1, v/v) to afford (1-bromonaphthalen-2-yl)methanol (1.8 g, 76%) as a white liquid.

Mass Spectrum (ESI) m/z=237.1 (M+H$^+$).

Step B

To a solution of (1-bromonaphthalen-2-yl)methanol (1.8 g, 7.6 mmol) in N,N-dimethylformamide (10 mL) was added sodium hydride (458 mg, 11.4 mmol) at 0° C. and the reaction mixture was stirred for 1 h. p-methoxy benzyl chloride (1.4 g, 9.1 mmol) was added and the mixture was stirred at room temperature for 1.5 h. Upon completion, the mixture was quenched with water and extracted with ethyl acetate (150 mL×3), dried over sodium sulfate, filtered and concentrated in vacuo. The crude was purified by flash chromatography (PE/EA=10/1, v/v) to afford 1-bromo-2-(((4-methoxybenzyl)oxy)methyl)naphthalene (1 g, 37%) as a yellow solid.

Mass Spectrum (ESI) m/z=356.1 (M+H$^+$).

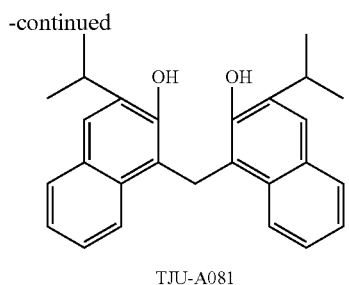

TJU-A081

Step A

A mixture of 2-bromobenzaldehyde(5 g, 27 mmol), ethynyltrimethylsilane (3.2 g, 32.4 mmol), triethyl amine (20 mL), PdCl$_2$(triphenyl phosphine)$_2$ (378 mg, 0.54 mmol) and copper iodide (205 mg, 1.08 mmol) in tetrahydrofuran (50 mL) was stirred at 50° C. for 3 h. The reaction mixture was concentrated and the residue was purified by column chromatography (PE/EA=20/1, v/v) to afford 2-((trimethylsilyl)ethynyl)benzaldehyde (3 g, 55%) as a white solid.

$^1$H NMR (300 MHz, DMSO-d$_6$) δ 10.34 (s, 1H), 7.83-7.81 (m, 1H), 7.67-7.52 (m, 3H), 0.26 (s, 9H).

Step B

To a solution of isobutyltriphenylphosphonium bromide (8.9 g, 22.3 mmol) in tetrahydrofuran (30 mL) at −78° C. was added dropwise n-BuLi (8.1 mL, 19.3 mmol). After addition, the reaction mixture was allowed to warm to room temperature and stirred for 0.5 h. After cooling to 0° C., 2-((trimethylsilyl)ethynyl)benzaldehyde (3 g, 14.85 mmol) in tetrahydrofuran (3 mL) was added dropwise.

The reaction mixture was stirred at 0° C. for 2 h. The reaction mixture was quenched with aqueous ammonium chloride and extracted with ethyl acetate (100 mL×2). The organic layer was washed with brine (20 mL×2), dried over sodium sulfate, filtered, and concentrated in vacuum. The residue was purified by column chromatography (PE/EA=10/1, v/v) to afford trimethyl((2-(3-methylbut-1-en-1-yl)phenyl)ethynyl)silane (2 g, 56%) as a colorless oil.

Step C

Tributyl ammonium fluoride (2.4 g, 9.13 mmol) was added slowly into a solution of trimethyl((2-(3-methylbut-1-en-1-yl)phenyl)ethynyl)silane (2 g, 8.3 mmol) in tetrahydrofuran (20 mL). After stirring at room temperature for 1 h, the reaction mixture was concentrated and the residue was purified by column chromatography (PE/EA=10/1, v/v) to afford 1-ethynyl-2-(3-methylbut-1-en-1-yl)benzene (1.2 g, 85%) as a colorless oil.

Step D

To a mixture of 1-ethynyl-2-(3-methylbut-1-en-1-yl)benzene (500 mg, 2.94 mmol), Rh(COD)$_2$OTf (82 mg, 0.18 mmol) in chlorobenzene (20 mL) was added pyridine N-oxide (559 mg, 5.88 mmol) and Tri(p-tolyl)P (214 mg, 0.7 mmol). The reaction mixture was stirred at 100° C. overnight. After concentration, the residue was purified by column chromatography (PE/EA=2/1, v/v) to afford 3-isopropylnaphthalen-2-ol (100 mg, 18%) as a black solid.

Mass Spectrum (ESI) m/z=185.0 (M−H$^-$).

Step E

To a solution of 3-isopropylnaphthalen-2-ol (180 mg, 0.97 mmol) and formaldehyde aqueous solution (180 mg, 2.4 mmol) in acetonitrile (5 mL) was added HBr (40% aqueous, 200 mg) and the reaction mixture was stirred at room temperature for 2 h. The mixture was concentrated and the residue was purified by prep-HPLC to afford 1,1'-methylenebis(3-isopropylnaphthalen-2-ol) (100 mg, 52%) as a light yellow powder.

Mass Spectrum (ESI) m/z=383.2 (M−H$^-$).

$^1$H NMR (400 MHz, DMSO-d$_6$) δ 9.19 (s, 2H), 8.12-8.09 (m, 2H), 7.67-7.65 (m, 2H), 7.52 (s, 2H), 7.16-7.11 (m, 4H), 4.82 (s, 2H), 3.57-3.50 (m, 2H), 1.32 (d, J=8.0 Hz, 12H).

Example 46: 1-((2-(2-(diethylamino)ethoxy)naphthalen-1-yl)methyl)naphthalen-2-ol formate (A093)

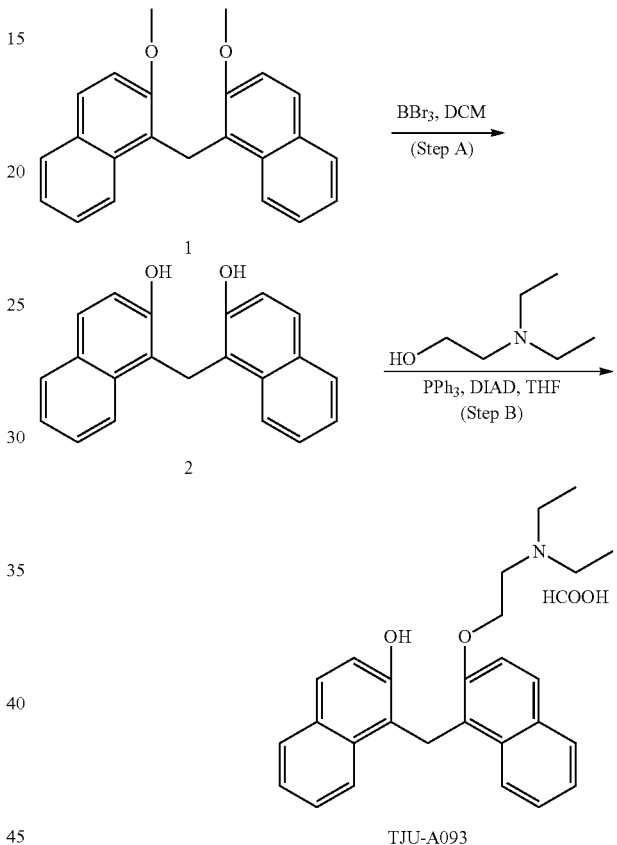

TJU-A093

Step A

To a solution of bis(2-methoxynaphthalen-1-yl)methane (175 mg, 0.53 mmol) in dry dichloromethane (10 mL) at −78° C. was added borontribromide (0.5 mL, 5.3 mmol). The reaction mixture was stirred at room temperature for 2 h and then diluted with ice water (10 mL), extracted with dichloromethane (20 mL×2), dried over anhydrous sodium sulfate, filtered and concentrated. The crude was purified by prep-TLC to afford 1,1'-methylenebis(naphthalen-2-ol) (120 mg, 75%) as a light pink solid.

Mass Spectrum (ESI) m/z=298.3 (M−H$^-$).

Step B

To a solution of 1,1'-methylenebis(naphthalen-2-ol) (120 mg, 0.4 mmol) and 2-(diethylamino)ethan-1-ol (51.8 mg, 0.44 mmol) in tetrahydrofuran (10 mL) were added triphenyl phosphine (126 mg, 0.48 mmol) and DIAD (97 mg, 0.48 mmol) and the reaction mixture was stirred at room temperature for 2 h. After quenching with saturated ammonium chloride (10 mL), the mixture was extracted with ethyl acetate (30 mL×2). The combined organic layer was washed with brine, dried over anhydrous sodium sulfate, filtered and concentrated. The crude was purified by prep-HPLC to afford 1-((2-(2-(diethylamino)ethoxy)naphthalen-1-yl)methyl)naphthalen-2-ol formate (75 mg, 42%) as a white solid.

Mass Spectrum (ESI) m/z=400.2 (M+H⁺)

¹H NMR (400 MHz, DMSO-d₆) δ 8.26 (d, J=8.0 Hz, 1H), 8.20 (br, 1H), 8.02 (d, J=8.0 Hz, 1H), 7.79-7.73 (m, 2H), 7.67-7.64 (m, 1H), 7.61 (d, J=8.0 Hz, 1H), 7.52 (d, J=12.0 Hz, 1H), 7.27-7.19 (m, 3H), 7.18-7.10 (m, 2H), 4.79 (s, 2H), 4.32 (t, J=8.0 Hz, 2H), 2.93 (t, J=8.0 Hz, 2H), 2.64 (q, J=8.0 Hz, 4H), 1.01 (t, J=8.0 Hz, 6H).

Example 47: 1-((2-(2-(diethylamino)ethoxy)naphthalen-1-yl)methyl)-3-methylnaphthalen-2-ol (A098)

(240 mg, 3.1 mmol) in acetonitrile (10 mL) was added HBr (40% aqueous, 300 mg) at room temperature. The reaction mixture was stirred for 2 h. After concentration, the residue was purified by prep-HPLC to afford 1-((2-(2-(diethylamino)ethoxy)naphthalen-1-yl)methyl)-3-methylnaphthalen-2-ol (22 mg, 8%) as a yellow powder.

Mass Spectrum (ESI) m/z=414.3 (M+H⁺).

¹H NMR (400 MHz, DMSO-d₆) δ 9.07 (br, 1H), 8.19 (d, J=8.0 Hz, 1H), 7.96 (d, J=8.0 Hz, 1H), 7.79-7.76 (m, 2H), 7.61-7.59 (m, 1H), 7.50-7.48 (m, 2H), 7.29-7.22 (m, 2H), 7.14-7.07 (m, 2H), 4.83 (s, 2H), 4.24 (t, J=8.0 Hz, 2H), 2.84 (br, 2H), 2.62-2.60 (m, 4H), 2.44 (s, 3H), 0.99 (t, J=8.0 Hz, 6H).

Example 48: 1,1'-methylenebis(2-naphthoic acid) (A100)

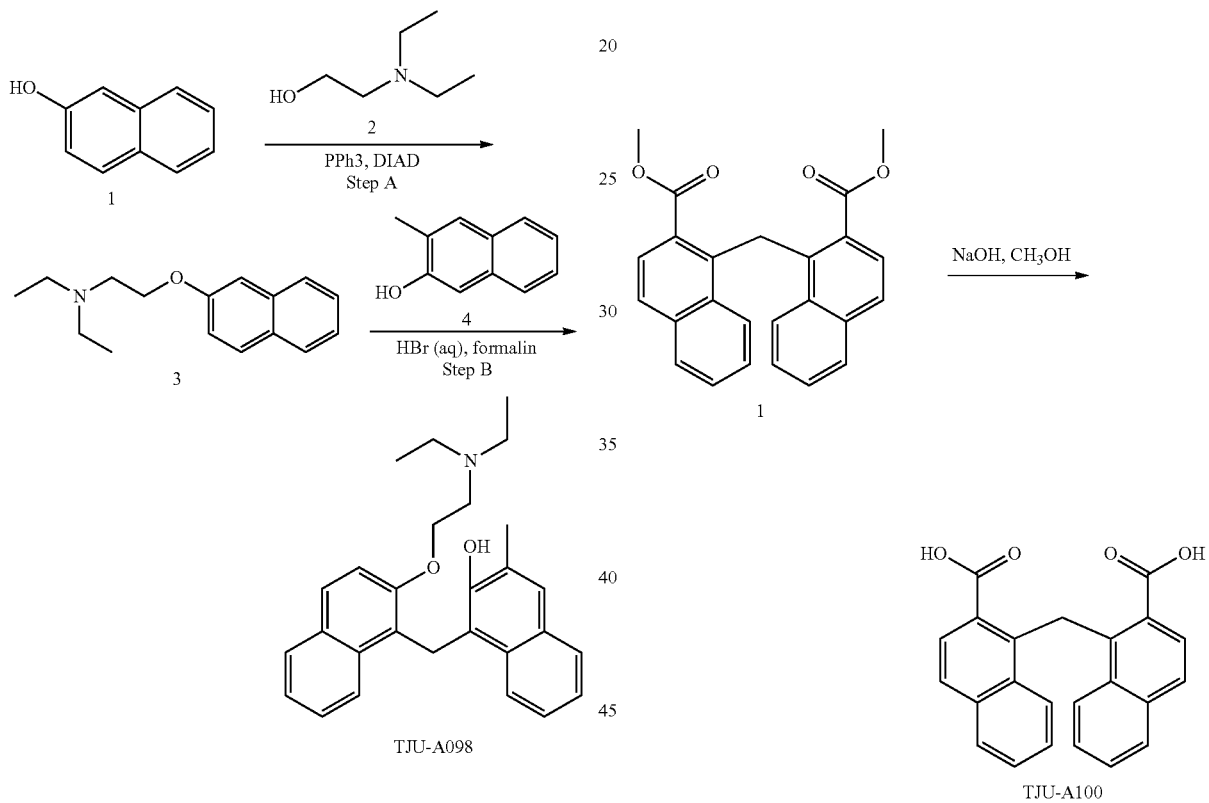

Step A

To a solution of naphthalen-2-ol (2.88 g, 20.0 mmol) and 2-(diethylamino)ethan-1-ol (2.58 g, 0.44 mmol) in tetrahydrofuran (50 mL) at 0° C. were added triphenyl phosphine (6.3 g, 24.0 mmol) and diisopropylazodicarboxylate (4.85 mg, 2.4 mmol). The reaction mixture was stirred at room temperature for 2 h. After quenching with sat ammonium chloride (10 mL), the mixture was extracted with ethyl acetate (30 mL×2). The combined organic layer was washed with brine, dried over anhydrous sodium sulfate, filtered and concentrated in vacuo. The crude product was purified column chromatography (petroleum ether/ethyl acetate=4/1, v/v) to afford N,N-diethyl-2-(naphthalen-2-yloxy)ethan-1-amine (4.5 g, 93%) as a white solid.

Mass Spectrum (ESI) m/z=244.2 (M+H⁺)

Step B

To a solution of 3-methylnaphthalen-2-ol (100 mg, 0.63 mmol), N,N-diethyl-2-(naphthalen-2-yloxy)ethan-1-amine (155 mg, 0.63 mmol) and formaldehyde aqueous solution To a solution of dimethyl 1,1'-methylenebis(2-naphthoate) (280 mg, 0.73 mmol) in methanol (12 mL) was added aqueous solution sodium hydroxide (2M, 12 mL) and the reaction mixture was stirred at 80° C. overnight. The reaction mixture was acidified to pH=1-2 with 6 M HCl and extracted with ethyl acetate (20 mL×3). The organic layer was dried over sodium sulfate, filtered and concentrated under vacuum. The residue was purified by prep-HPLC to afford 1,1'-methylenebis(2-naphthoic acid) (56 mg, 21%) as a white solid.

Mass Spectrum (ESI) m/z=354.8 (M+H⁺).

¹H NMR (400 MHz, DMSO-d₆) δ 8.02 (d, J=8.0 Hz, 2H), 7.89-7.83 (m, 4H), 7.70 (d, J=8.0 Hz, 2H), 7.42 (t, J=8.0, 2H), 7.27-7.23 (m, 2H), 5.54 (s, 2H).

Example 49: 1,1'-methylenebis(2-naphthamide) (A101)

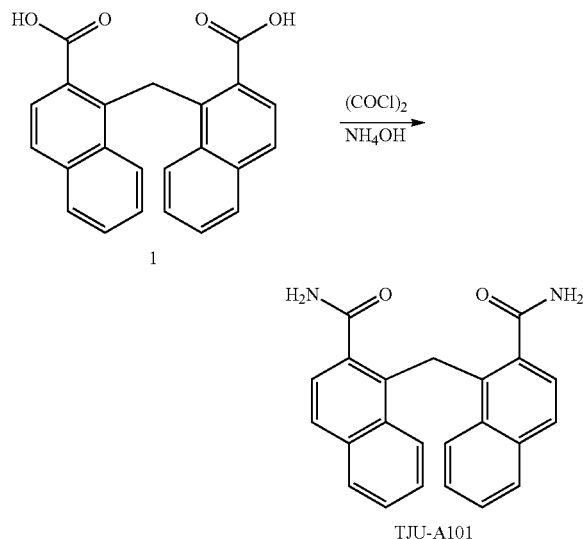

To a slurry of 1,1'-methylenebis(2-naphthoic acid) (150 mg, 0.42 mmol) in dichloromethane (10 mL) at room temperature was added a drop of N,N-dimethylformamide, followed by the dropwise addition of oxalyl chloride (0.1 mL) at such a rate to keep gas evolution under control. The reaction mixture was stirred for an additional hour at room temperature and then concentrated under vacuum. The residue was dissolved in tetrahydrofuran (5 mL) and added to a solution of ammonium (6 mL) in tetrahydrofuran (15 mL). The mixture was stirred at room temperature for 4 h and then concentrated under vacuum. The residue was purified by prep-TLC (Petroleum ether/dichloromethane=½, v/v) to afford 1,1'-methylenebis(2-naphthamide) (3.5 mg, 2%) as a white solid.

Mass Spectrum (ESI) m/z=355.1 (M+H$^+$).

$^1$H NMR (400 MHz, DMSO-d$_6$) δ 8.12-8.08 (m, 4H), 7.86-7.80 (m, 4H), 7.70 (br, 2H), 7.52 (d, J=8.0 Hz, 2H), 7.36-7.32 (m, 2H), 7.18-7.14 (m, 2H), 5.15 (s, 2H).

Example 50: 1-((2-(2-(diethylamino)ethoxy)-3-isopropylnaphthalen-1-yl)methyl)-3-isopropylnaphthalen-2-ol hydrochloride Salt (A102)

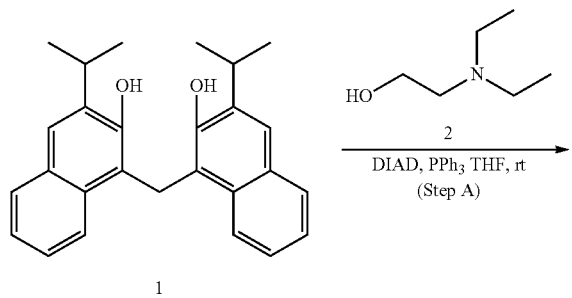

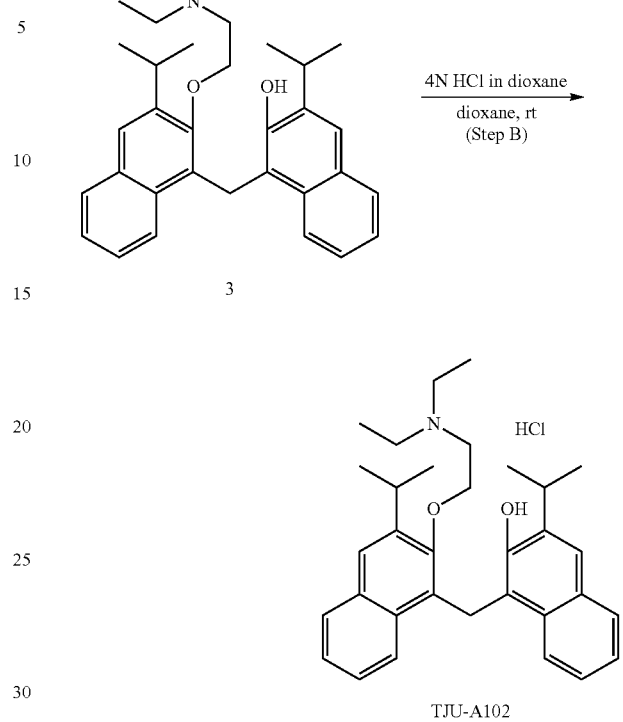

Step A

To a solution of 1,1'-methylenebis(3-isopropylnaphthalen-2-ol) (85 mg, 0.22 mmol) in tetrahydrofuran (10 mL) were added 2-(diethylamino)ethan-1-ol (25 mg, 0.22 mmol), diisopropylazodicarboxylate (45 g, 0.22 mmol) and triphenylphosphine (58 mg, 0.22 mmol). The reaction mixture was stirred at room temperature for 4 h. After completion, the reaction mixture was diluted by water (40 mL) and extracted with ethyl acetate (10 mL×3). The combined organic layer was washed with brine, dried over anhydrous sodium sulfate, filtered and concentrated under vacuum. The residue was purified by prep-HPLC to afford 1-((2-(3-(diethylamino)propoxy)-3-isopropylnaphthalen-1-yl)methyl)-3-isopropylnaphthalen-2-ol (14.0 mg, 13%) as a yellow powder.

Mass Spectrum (ESI) m/z=481.9 (M−H$^-$).

Step B

To a solution of 1-((2-(3-(diethylamino)propoxy)-3-isopropylnaphthalen-1-yl)methyl)-3-isopropylnaphthalen-2-ol (14.0 mg, 0.02 mmol) in anhydrous dioxane (5 mL) was added HCl solution (4 N in dioxane, 1 mL). The reaction mixture was stirred at room temperature for 5 h. After completion, the reaction mixture was directly concentrated under vacuum to afford 1-((2-(2-(diethylamino)ethoxy)-3-isopropylnaphthalen-1-yl)methyl)-3-isopropylnaphthalen-2-ol hydrochloride salt (12.1 mg, 80%) as an orange solid.

Mass Spectrum (ESI) m/z=484.2 (M−Cl$^+$).

$^1$H NMR (400 MHz, CD$_3$OD) δ 8.19 (d, J=8.4 Hz, 1H), 7.97 (d, J=7.8 Hz, 1H), 7.76-7.65 (m, 3H), 7.56 (s, 1H), 7.30 (t, J=7.0 Hz, 1H), 7.23-7.12 (m, 3H), 4.99 (s, 2H), 4.34-4.28 (m, 2H), 3.62 (s, 2H), 3.43 (m, 6H), 1.44 (d, J=6.8 Hz, 6H), 1.36 (m, 12H).

Example 51: 2,2'-((methylenebis(naphthalene-1,2-diyl))bis(oxy))bis(N,N-diethylethan-1-amine) formic acid (A103)

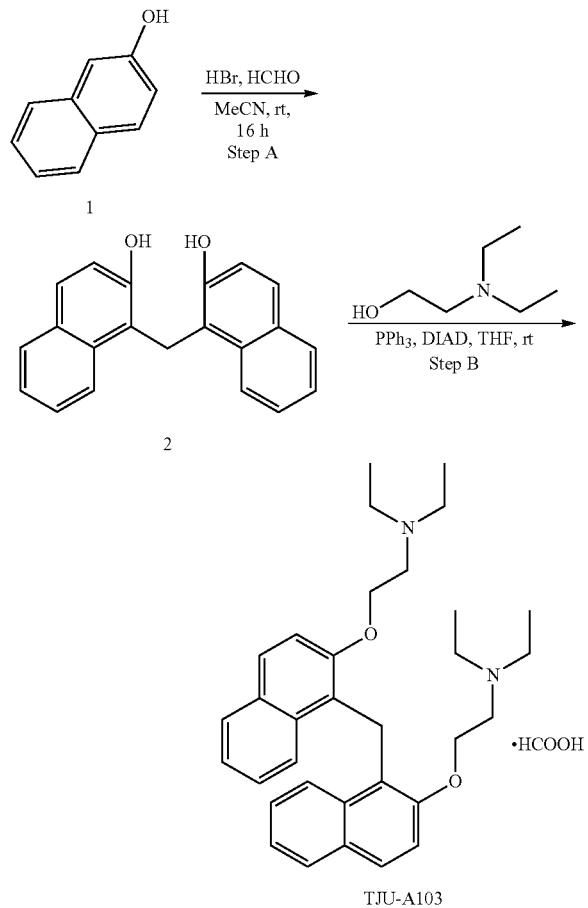

Step A
To a solution of naphthalen-2-ol (8 g, 55.5 mmol) in acetonitrile (80 mL) were added HBr (40% aqueous, 0.6 g, 2.94 mmol) and HCHO (37% aqueous, 2.51 g, 30.53 mmol). Upon completion, the reaction mixture was poured into water (30 mL) and concentrated in vacuo and then extracted with ethyl acetate (30 mL×3), dried over anhydrous sodium sulfate, filtered and concentrated in vacuo. and the residue was purified by flash chromatography (Petroleum ether/ethyl acetate=4/1, v/v) to afford 1,1'-methylenebis(naphthalen-2-ol) (7.9 g, 88%) as a light yellow solid.

Mass Spectrum (ESI) m/z=323.1 (M+Na$^+$).

Step B
To a solution of 1,1'-methylenebis(naphthalen-2-ol) (500 mg, 1.67 mmol) in anhydrous tetrahydrofuran (20 mL) were added triphenyl phosphine (874 mg, 3.33 mmol), 2-(diethylamino)ethan-1-ol (390 mg, 3.33 mmol) and diisopropylazodicarboxylate (674 mg, 3.33 mmol). The reaction mixture was stirred for 2 h at room temperature. After completion, the reaction mixture was quenched with water (50 mL) at 0° C., concentrated in vacuo to remove tetrahydrofuran and the residue was extracted with ethyl acetate (30 mL×3). The combined organic layer was washed with brine (40 mL×3), dried over anhydrous sodium sulfate and concentrated in vacuo. The residue was purified by prep-HPLC to afford 2,2'-((methylenebis(naphthalene-1,2-diyl))bis(oxy))bis(N,N-diethylethan-1-amine) formic acid (68 mg, 7%) as a white solid.

Mass Spectrum (ESI) m/z=498.9 (M+H$^+$).

$^1$H NMR (400 MHz, DMSO-d$_6$) δ 8.13-8.10 (m, 2H), 7.79-7.74 (m, 4H), 7.49 (d, J=9.1 Hz, 2H), 7.27-7.20 (m, 4H), 4.86 (s, 2H), 4.24 (t, J=6.1 Hz, 4H), 2.79 (t, J=6.1 Hz, 4H), 2.61-2.56 (m, 8H), 0.96 (t, J=7.1 Hz, 12H).

Example 52: 1,1'-methylenebis(2-naphthoic acid) (A107)

Example 53: 1-((2-hydroxynaphthalen-1-yl)methyl)-2-naphthoic acid (A106)

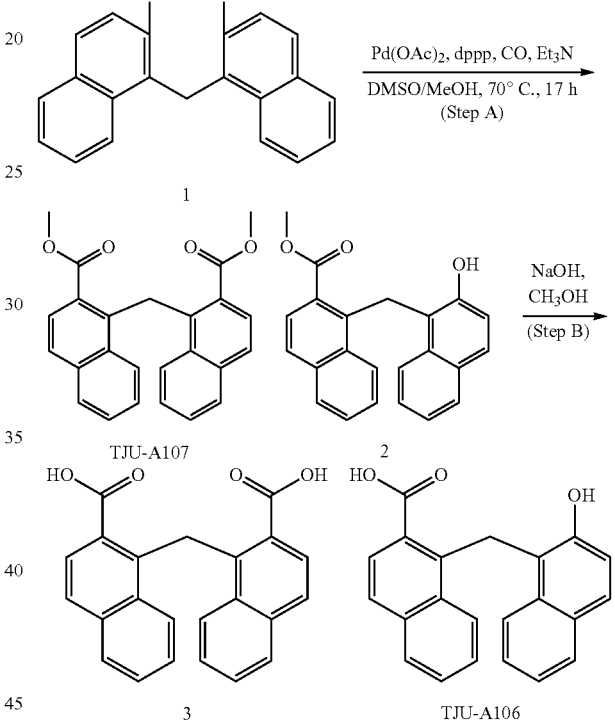

Step A
A mixture of methylenebis(naphthalene-1,2-diyl) bis(trifluoromethanesulfonate) (4.7 g, 8.33 mmol), Pd(OAc)$_2$ (559 mg, 2.49 mmol), triethyl amine (16.5 mL) and dppp (1.35 g, 2.50 mmol) in DMSO (244 mL) and methanol (165 mL) was stirred under CO (1 atm) at 70° C. for 18 h. The mixture was filtered through celite and concentrated under vacuum. The residue was purified by silica gel chromatography (Petroleum ether/ethyl acetate=2/1, v/v) to afford crude dimethyl 1,1'-methylenebis(2-naphthoate) (2 g, 62%) containing 28% of methyl 1-((2-hydroxynaphthalen-1-yl)methyl)-2-naphthoate.

Mass Spectrum (ESI) m/z=407.0 (M+Na$^+$)

Step B
To a solution of dimethyl 1,1'-methylenebis(2-naphthoate) (2 g crude product containing 28% of methyl 1-((2-hydroxynaphthalen-1-yl)methyl)-2-naphthoate) in methanol (60 mL) was added aqueous solution sodium hydroxide (2M, 60 mL). The reaction mixture was stirred at 80° C. overnight and acidified to pH 1-2 with 6 M HCl. The mixture was extracted with ethyl acetate (100 mL×3) and the organic layer was concentrated under vacuum. The residue was purified by prep-HPLC to afford 1,1'-methylenebis(2-naphthoic acid) (210 mg, 10%) as a white solid, 1-((2-hydroxynaphthalen-1-yl)methyl)-2-naphthoic acid (77 mg, 4%) as a white solid and unreacted dimethyl 1,1'-methylenebis(2-naphthoate) (200 mg).

1,1'-methylenebis(2-naphthoic acid) Mass Spectrum (ESI) m/z=326.8 (M−H⁻)

$^1$H NMR (400 MHz, DMSO-$d_6$) δ 8.15 (d, J=12.0 Hz, 1H), 7.98 (d, J=8.0 Hz, 1H), 7.84 (d, J=8.0 Hz, 1H), 7.80-7.77 (m, 2H), 7.70 (d, J=8.0 Hz, 1H), 7.62 (d, J=8.0 Hz, 1H), 7.40 (t, J=8.0 Hz, 1H), 7.23-7.21 (m, 2H), 7.18-7.13 (m, 2H), 5.16 (s, 2H).

1-((2-hydroxynaphthalen-1-yl)methyl)-2-naphthoic acid: Mass Spectrum (ESI) m/z=407.1 (M+Na⁺)

$^1$H NMR (400 MHz, DMSO-$d_6$) δ 8.22 (d, J=8.0 Hz, 2H), 7.98 (d, J=4.0 Hz, 2H), 7.89 (d, J=8.0 Hz, 2H), 7.59-7.55 (m, 4H), 7.48-7.44 (m, 2H), 5.55 (s, 2H), 3.36 (s, 6H).

Example 54: 1-((2-(2-(diethylamino)ethoxy)-3-methylnaphthalen-1-yl)methyl)-3-methylnaphthalen-2-ol (A108)

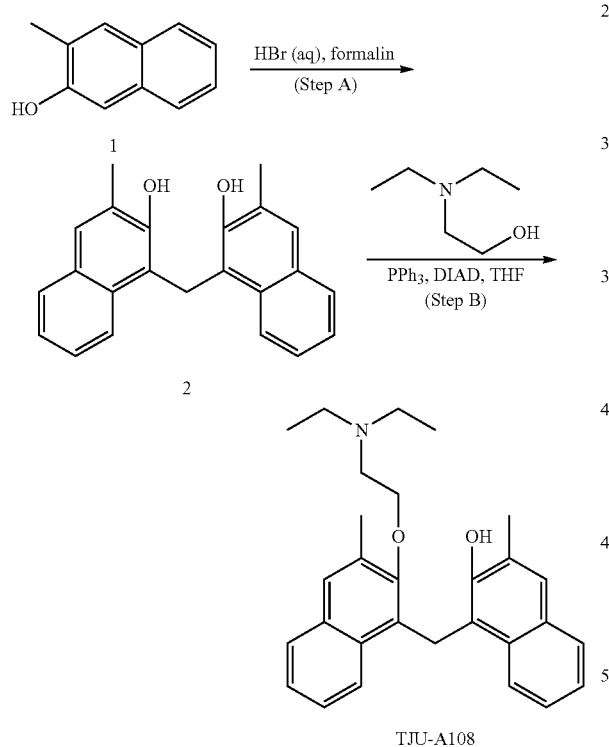

Step A

To a solution of 3-methylnaphthalen-2-ol (200 mg, 1.26 mmol) and formaldehyde aqueous solution (240 mg, 3.1 mmol) in acetonitrile (10 mL) was added HBr (40% aqueous, 300 mg) at room temperature and the reaction mixture was stirred at room temperature for 3 h. The reaction mixture was poured into water (10 mL) and extracted with dichloromethane (20 mL×2). The combined organic layer was collected, dried over anhydrous sodium sulfate, filtered and concentrated. The residue was purified by prep-TLC to afford 1,1'-methylenebis(3-methylnaphthalen-2-ol) (132 mg, 64%) as a light yellow solid.

Mass Spectrum (ESI) m/z=326.9 (M−H⁻)⁻.

Step B

To a solution of 1,1'-methylenebis(3-methylnaphthalen-2-ol) (132 mg, 0.4 mmol) and 2-(diethylamino)ethan-1-ol (51.8 mg, 0.44 mmol) in tetrahydrofuran (10 mL) were added triphenyl phosphine (126 mg, 0.48 mmol) and DIAD (97 mg, 0.48 mmol). After stirring at room temperature for 2 h, the reaction mixture was diluted with sat ammonium chloride (10 mL) and extracted with ethyl acetate (30 mL×2). The combined organic layer was washed with brine, dried over anhydrous sodium sulfate, filtered and concentrated in vacuo. The crude product was purified by prep-HPLC to afford 1-((2-(2-(diethylamino)ethoxy)-3-methylnaphthalen-1-yl)methyl)-3-methylnaphthalen-2-ol (120 mg, 70%) as a white powder.

Mass Spectrum (ESI) m/z=428.2 (M+H⁺)

$^1$H NMR (400 MHz, DMSO-$d_6$) δ 8.17-8.14 (m, 2H), 8.04-8.02 (m, 1H), 7.68 (d, J=4.0 Hz, 1H), 7.61-7.58 (m, 2H), 7.50 (s, 1H), 7.25 (t, J=8.0 Hz, 1H), 7.21-7.17 (m, 1H), 7.14-7.10 (m, 2H), 4.91 (s, 2H), 3.98 (t, J=8.0 Hz, 2H), 2.94 (t, J=8.0 Hz, 2H), 2.65 (q, J=8.0 Hz, 4H), 2.51 (s, 3H), 2.44 (s, 3H), 1.00 (t, J=8.0 Hz, 6H).

Example 55: 8-((2-hydroxynaphthalen-1-yl)methyl)isoquinolin-7-ol (A109)

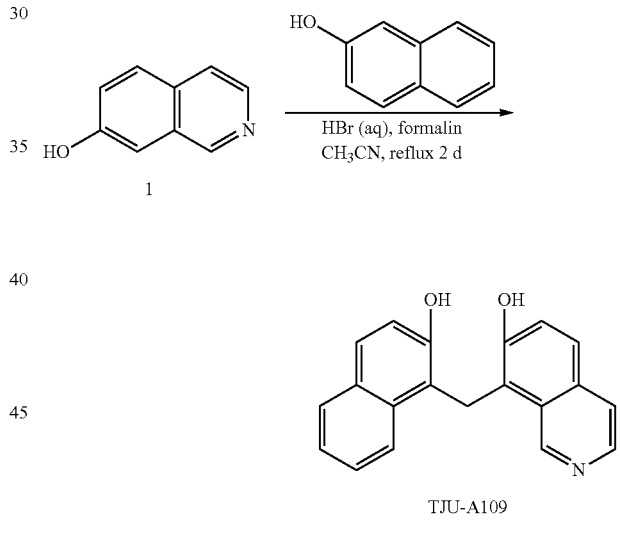

To a solution of isoquinolin-7-ol (120 mg, 0.83 mmol), naphthalen-2-ol (120 mg, 0.83 mmol) and formaldehyde aqueous solution (321 mg, 4.2 mmol) in acetonitrile (10 mL) was added HBr (40% aqueous, 400 mg) and the reaction mixture was refluxed for 2 days. After concentration, the residue was diluted with sat sodium bicarbonate (10 mL) and extracted with dichloromethane (30 mL×3), dried over anhydrous sodium sulfate, filtered and concentrated. The residue was purified by prep-HPLC to afford 8-((2-hydroxynaphthalen-1-yl)methyl)isoquinolin-7-ol (15 mg, 6%) as a yellow powder.

Mass Spectrum (ESI) m/z=302.0 (M+H⁺)

$^1$H NMR (400 MHz, DMSO-$d_6$) δ 10.41 (br, 2H), 9.52 (s, 1H), 8.15-8.15 (m, 2H), 7.69-7.63 (m, 3H), 7.55 (d, J=8.0 Hz, 1H), 7.51 (d, J=12.0 Hz, 1H), 7.29 (d, J=8.0 Hz, 1H), 7.24-7.20 (m, 1H), 7.16-7.13 (m, 1H), 4.17 (s, 2H).

Example 56: 2-(2-(diethylamino)ethoxy)-N-(2-methoxynaphthalen-1-yl)naphthalen-1-amine (A111-1-1)

Example 57: 2-(2-(diethylamino)ethoxy)-N-(2-methoxynaphthalen-1-yl)-N-methylnaphthalen-1-amine 2,2,2-trifluoroacetate (A111-I-2)

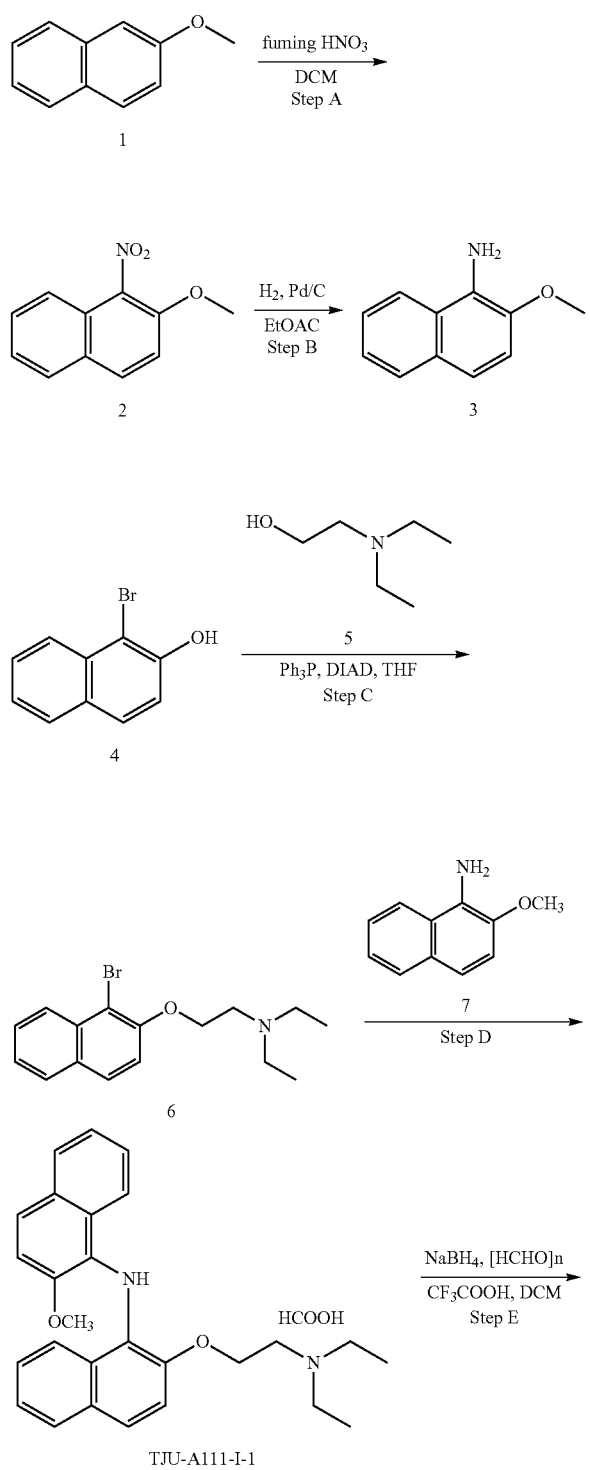

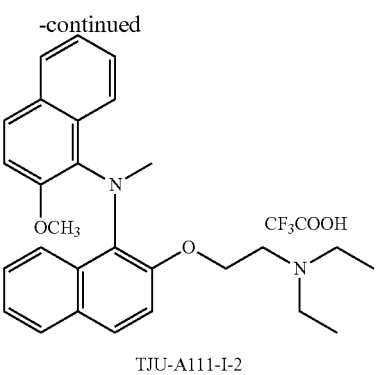

TJU-A111-I-2

Step A

To a solution of 2-methoxynaphthalene (5 g, 31.6 mmol) in dichloromethane (100 mL) was added fuming HNO₃ (2.19 g, 34.77 mmol) dropwise at 0° C. and the reaction mixture was stirred for 3 h at room temperature. The mixture was washed with saturated sodium bicarbonate aqueous solution (100 mL×2), brine (100 mL×2), dried over anhydrous sodium sulfate and concentrated under vacuum. The residue was purified by silica gel chromatography (PE/EA=8/1, v/v) to afford 2-methoxy-1-nitronaphthalene (1.77 g, 26%).

Mass Spectrum (ESI) m/z=204.1 (M+H⁺)

Step B

A suspension of 2-methoxy-1-nitronaphthalene (1.77 g, 8.72 mmol) in ethyl acetate (100 mL) was hydrogenated at room temperature in the presence of as a catalyst (20% Pd/C, 354 mg) at the pressure of 60 psi for 5 h. The mixture was filtered through celite and the filtrate was dried over anhydrous sodium sulfate and concentrated under vacuum. The residue was purified by silica gel chromatography eluted with (PE/EA=4/1, v/v) to afford 2-methoxynaphthalen-1-amine (1.4 g, 93%).

Mass Spectrum (ESI) m/z=174.2 (M+H⁺)

Step C

To a solution of 1-bromonaphthalen-2-ol (1 g, 4.48 mmol) and triphenylphosphine (1.53 g, 5.83 mmol) in tetrahydrofuran (20 mL) were added 2-(diethylamino)ethan-1-ol (683 mg, 5.83 mmol) and diisopropyl azodiformate (1.18 g, 5.83 mmol). The reaction mixture was stirred for 3 h at ambient temperature and then diluted with water (40 mL). The resulting solution was extracted with ethyl acetate (40 mL×3). The combined organic layer was dried over anhydrous sodium sulfate and concentrated under vacuum. The residue was purified by silica gel chromatography eluted with (dichloromethane/methanol=80/1, v/v) to afford 2-((1-bromonaphthalen-2-yl)oxy)-N,N-diethylethan-1-amine (1 g, 71.4%).

Mass Spectrum (ESI) m/z=322.1 [M]⁺, 324.1 [M+2]⁺

Step D

To a solution of 2-((1-bromonaphthalen-2-yl)oxy)-N,N-diethylethan-1-amine (1.06 g, 3.28 mmol) and 2-methoxynaphthalen-1-amine (572 mg, 3.30 mmol) in 1,4-dioxane (20 mL) were added Pd(OAC)₂ (148 mg, 0.66 mmol), (t-Bu)₃P (10%) (2.6 g, 1.28 mmol) and t-BuONa (953 mg, 9.90 mmol). The reaction mixture was stirred at 110° C. overnight under nitrogen. The mixture was filtered through celite and the filtrate was concentrated under vacuum. The residue was purified by silica gel chromatography (dichloromethane/methanol=40/1, v/v). to afford crude 2-(2-(diethylamino)ethoxy)-N-(2-methoxynaphthalen-1-yl)naphthalen-1-amine (470 mg, 34.6%). and then 80 mg crude 2-(2-(diethylamino)ethoxy)-N-(2-methoxynaphthalen-1-yl)naphthalen-1-amine formate was purified by prep-HPLC to afford 2-(2-(diethylamino)ethoxy)-N-(2-methoxynaphthalen-1-yl)naphthalen-1-amine formate (70 mg) as a purple oil.

Mass Spectrum (ESI) m/z=415.2 [M+H]⁺

¹H NMR (400 MHz, DMSO-d₆) δ 7.98 (d, J=8.0 Hz, 1H), 7.82 (d, J=8.0 Hz, 3H), 7.59 (d, J=8.0 Hz, 1H), 7.52 (d, J=8.0 Hz, 1H), 7.38-7.20 (m, 7H), 3.76 (br, 2H), 3.58 (s, 3H), 2.33 (q, J=8.0 Hz, 4H), 2.14 (br, 2H), 0.78 (t, J=8.0 Hz, 6H).

Step E

To CF₃COOH (3 mL) stirred at 0-5° C. under nitrogen atmosphere were added NaBH₄ (172 mg, 4.53 mmol), [HCHO]~ (101 mg, 3.48 mmol) and a solution of 2-(2-(diethylamino)ethoxy)-N-(2-methoxynaphthalen-1-yl)naphthalen-1-amine formate (144 mg, 0.32 mmol) in dichloromethane (3 mL). The resulting mixture was stirred at room temperature for 10 min and then extracted with dichloromethane (6 mL×3). The combined organic layer was dried over anhydrous sodium sulfate and concentrated under vacuum. The residue was purified by prep-TLC (dichloromethane/methanol=20/1,v/v) to afford 2-(2-(diethylamino)ethoxy)-N-(2-methoxynaphthalen-1-yl)-N-methylnaphthalen-1-amine 2,2,2-trifluoroacetate (70 mg, 40%) as a purple oil.

Mass Spectrum (ESI) m/z=429.2 [M+H]⁺

¹H NMR (400 MHz, DMSO-d₆) δ 8.04-8.01 (m, 1H), 7.93-7.91 (m, 1H), 7.84-7.80 (m, 2H), 7.73 (d, J=4.0 Hz, 1H), 7.71 (d, J=4.0 Hz, 1H), 7.51 (d, J=4.0 Hz, 1H), 7.49 (d, J=4.0 Hz, 1H), 7.31-7.24 (m, 4H), 4.38-4.35 (m, 2H), 3.87 (s, 3H), 3.55 (s, 3H), 3.42-3.37 (m, 2H), 3.23-3.11 (m, 4H), 1.14 (t, J=8 Hz, 6H).

Example 58: 6-hydroxy-5-((2-hydroxynaphthalen-1-yl)methyl)-2-naphthoic acid (A114)

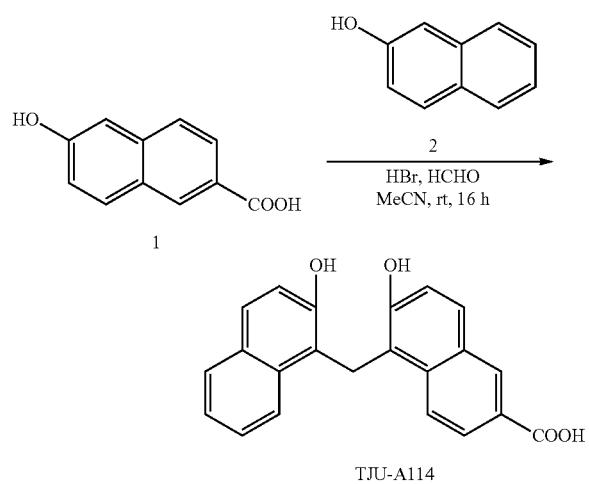

To a solution of 6-hydroxy-2-naphthoic acid (1 g, 5.11 mmol) and naphthalen-2-ol (766 mg, 5.11 mmol) in acetonitrile (30 mL) were added HBr (40% aqueous, 114 mg) and HCHO (37% aqueous, 476 mg). Upon completion, the reaction mixture was poured into water (30 mL), concentrated in vacuo, and extracted with dichloromethane (30 mL×3), dried over anhydrous sodium sulfate, filtered and concentrated in vacuo. The crude product was purified by prep-HPLC to afford 6-hydroxy-5-((2-hydroxynaphthalen-1-yl)methyl)-2-naphthoic acid (20 mg, 1%) as a white solid.

Mass Spectrum (ESI) m/z=342.8 (M−H⁻).

¹H NMR (400 MHz, DMSO-d6) δ 12.63 (s, 1H), 10.53 (s, 1H), 10.17 (s, 1H), 8.34 (s, 1H), 8.27 (d, J=9.0 Hz, 1H), 8.15 (d, J=8.6 Hz, 1H), 7.81 (d, J=8.8 Hz, 1H), 7.69-7.59 (m, 3H), 7.35 (d, J=8.8 Hz, 1H), 7.28 (d, J=8.8 Hz, 1H), 7.20 (t, J=7.1 Hz, 1H), 7.13 (t, J=7.2 Hz, 1H), 4.71 (s, 2H).

Example 59: 2,2'-methylenebis(3-(pyridin-3-yl)phenol) (A117)

Example 60: 2-(2-methoxy-6-(pyridin-3-yl)benzyl)-3-(pyridin-3-yl)phenol (A117-I-1)

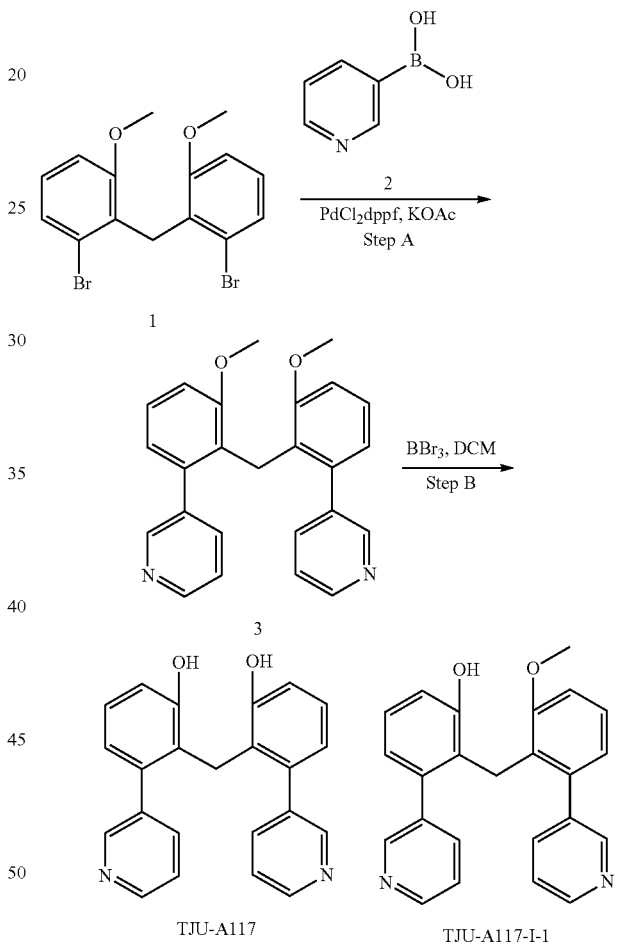

Step A

A mixture of bis(2-bromo-6-methoxyphenyl)methane (100 mg, 0.26 mmol), pyridin-3-ylboronic acid (154 mg, 1.25 mmol), PdCl₂dppf (82 mg, 0.1 mmol) and potassium carbonate (345 mg, 2.5 mmol) in dioxane (15 mL) was stirred at 100° C. under nitrogen overnight. The reaction mixture was concentrated and the residue was purified by prep-TLC to afford bis(2-methoxy-6-(pyridin-3-yl)phenyl)methane (30 mg, 31%) as a white solid. Mass Spectrum (ESI) m/z=383.1 (M+H⁺)

Step B

To a solution of bis(2-methoxy-6-(pyridin-3-yl)phenyl)methane (30 mg, 0.08 mmol) in dry dichloromethane (2 mL)

at −78° C. was added boron tribromide (375 mg, 1.5 mmol). The reaction mixture was stirred at room temperature overnight. Next, the reaction mixture was quenched with methanol (5 mL). It was concentrated and purified by prep-HPLC to afford 2,2'-methylenebis(3-(pyridin-3-yl)phenol) (TJU-A117) (10 mg, 36%) as a white solid. Mass Spectrum (ESI) m/z=355.1 (M+H$^+$)

$^1$H NMR (400 MHz, DMSO-d$_6$) δ 9.16 (s, 2H), 8.47 (d, J=4.0, 2H), 8.36 (s, 2H), 7.62-7.60 (m, 2H), 7.35-7.32 (m, 2H), 6.88 (t, J=8.0 Hz, 2H), 6.50 (d, J=8.0 Hz, 2H), 6.42 (d, J=8.0 Hz, 2H), 3.92 (s, 2H). 2-(2-methoxy-6-(pyridin-3-yl)benzyl)-3-(pyridin-3-yl)phenol (TJU-A117-I-1) (3 mg, 10%) as a white solid. Mass Spectrum (ESI) m/z=369.1 (M+H$^+$)

$^1$H NMR (400 MHz, CD$_3$OD) δ 8.32 (d, J=8.0 Hz, 2H), 8.13-8.12 (m, 2H), 7.50-7.47 (m, 1H), 7.42-7.40 (m, 1H), 7.24-7.18 (m, 2H), 7.02 (t, J=8.0 Hz, 1H), 6.86 (t, J=8.0 Hz, 1H), 6.55-6.52 (m, 2H), 6.41-6.38 (m, 2H), 4.21 (s, 2H), 3.59 (s, 3H).

Example 61: 2,2'-methylenebis(3-(pyridin-4-yl)phenol) (A118)

Example 62: 2-(2-methoxy-6-(pyridin-4-yl)benzyl)-3-(pyridin-4-yl)phenol (A118-I-1)

Step A

A mixture of bis(2-bromo-6-methoxyphenyl)methane (200 mg, 0.52 mmol), pyridin-4-ylboronic acid (308 mg, 2.5 mmol), PdCl$_2$dppf (164 mg, 0.2 mmol) and potassium carbonate (690 mg, 5.0 mmol) in dioxane (15 mL) was stirred at 100° C. under nitrogen overnight. The reaction mixture was concentrated and the residue was purified by prep-TLC to afford bis(2-methoxy-6-(pyridin-4-yl)phenyl)methane (75 mg, 39%) as a white solid. Mass Spectrum (ESI) m/z=383.1 (M+H$^+$)

$^1$H NMR (400 MHz, DMSO-d$_6$) δ 8.43-8.41 (m, 4H), 7.09-7.07 (m, 6H), 6.64 (d, J=8.0 Hz, 2H), 6.56 (d, J=8.0 Hz, 2H), 4.07 (s, 2H), 3.49 (s, 6H).

Step B

To a solution of bis(2-methoxy-6-(pyridin-4-yl)phenyl)methane (75 mg, 0.20 mmol) in dry dichloromethane (5 mL) at −78° C. was added tribromoborane (750 mg, 3.0 mmol) and the reaction mixture was stirred at room temperature overnight. After quenching with methanol (10 mL), the mixture was concentrated and the residue was purified by prep-HPLC to afford 2-(2-methoxy-6-(pyridin-4-yl)benzyl)-3-(pyridin-4-yl)phenol (TJU-A118) (40 mg, 56%) as a white solid.

Mass Spectrum (ESI) m/z=355.1 (M+H$^+$)

$^1$H NMR (400 MHz, DMSO-d$_6$) δ 9.42 (s, 2H), 8.55 (d, J=4.0 Hz, 4H), 7.47-7.46 (m, 4H), 6.92 (t, J=8.0 Hz, 2H), 6.47 (d, J=8.0 Hz, 2H), 6.44 (d, J=8.0 Hz, 2H), 4.06 (s, 2H).

2-(2-methoxy-6-(pyridin-4-yl)benzyl)-3-(pyridin-4-yl)phenol (TJU-A118-I-1) (10 mg, 13.5%) as a white solid. Mass Spectrum (ESI) m/z=369.1 (M+H$^+$)

$^1$H NMR (400 MHz, DMSO-d$_6$) δ 9.21 (br, 1H), 8.41 (t, J=4.0 Hz, 4H), 7.12-7.05 (m, 5H), 6.89 (t, J=8.0 Hz, 1H), 6.65 (d, J=8.0 Hz, 1H), 6.55 (d, J=8.0 Hz, 1H), 6.49 (d, J=8.0 Hz, 1H), 6.40 (d, J=8.0 Hz, 1H), 3.99 (s, 2H), 3.49 (s, 3H).

Example 63: 6-hydroxy-5-((2-hydroxynaphthalen-1-yl)methyl)-2-naphthamide (A122)

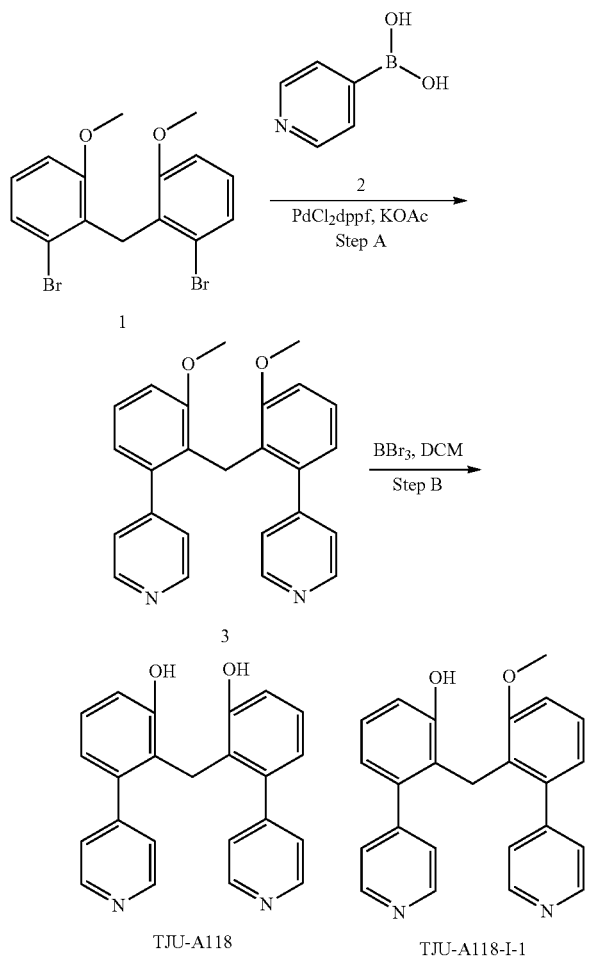

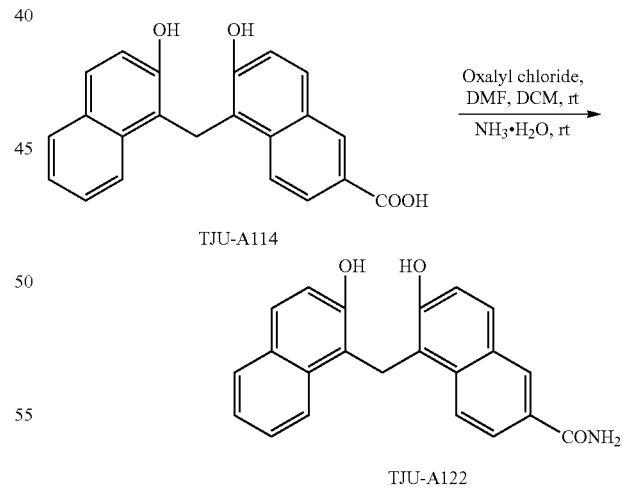

To a solution of 6-hydroxy-5-((2-hydroxynaphthalen-1-yl)methyl)-2-naphthoic acid (200 mg, 0.58 mmol) in dichloromethane (20 mL) was added N,N-dimethylformamide (two drops). Oxalyl chloride (88.5 mg, 0.70 mmol) was added dropwise to the reaction. The reaction mixture was stirred at room temperature for 2 h, NH$_3$·H$_2$O (2 mL) was then added. The reaction mixture was stirred at room temperature for 16 h and concentrated in vacuo. The crude was purified by prep-HPLC to afford 6-hydroxy-5-((2-hydroxynaphthalen-1-yl)methyl)-2-naphthamide (40 mg, 20%) as a white solid.

Mass Spectrum (ESI) m/z=344.0 (M+H$^+$).

$^1$H NMR (400 MHz, DMSO-d6) δ 10.40 (s, 1H), 10.17 (s, 1H), 8.24-8.20 (m, 2H), 8.15 (d, J=8.5 Hz, 1H), 7.88 (s, 1H), 7.70 (d, J=8.9 Hz, 1H), 7.67-7.59 (m, 3H), 7.33 (d, J=8.9 Hz, 1H), 7.28 (d, J=8.8 Hz, 1H), 7.24-7.16 (m, 2H), 7.15-7.11 (m, 1H), 4.71 (s, 2H).

Example 64:
5,5'-methylenebis(6-hydroxy-2-naphthamide) (A123)

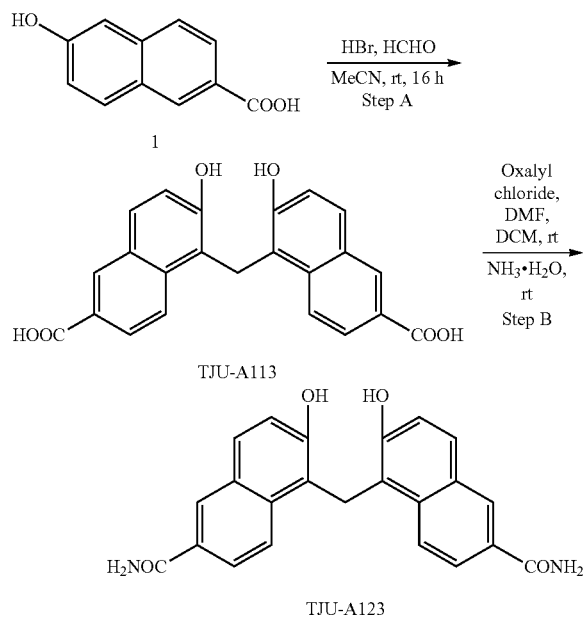

Step A

To a solution of 6-hydroxy-2-naphthoic acid (1 g, 5.11 mmol) in acetonitrile (20 mL) were added HBr (40% aqueous, 57 mg) and HCHO (37% aqueous, 238 mg). Upon completion, the reaction mixture was poured into water (30 mL) and concentrated in vacuo, then extracted with dichloromethane (15 mL×3). The combined organic layer was dried over anhydrous sodium sulfate, filtered, and concentrated in vacuo. The crude was purified by prep-HPLC to afford the 5,5'-methylenebis(6-hydroxy-2-naphthoic acid) as a white solid (225 mg, 21.8%). Mass Spectrum (ESI) m/z=386.8 (M−H$^−$).

$^1$H NMR (400 MHz, DMSO-d$_6$) δ 12.70 (s, 2H), 10.62 (s, 2H), 8.34 (d, J=1.7 Hz, 2H), 8.22 (d, J=9.0 Hz, 2H), 7.82 (d, J=8.9 Hz, 2H), 7.65-7.63 (m, 2H), 7.35 (d, J=8.8 Hz, 2H), 4.72 (s, 2H).

Step B

To a solution of 5,5'-methylenebis(6-hydroxy-2-naphthoic acid) (200 mg, 0.515 mmol) in dichloromethane (20 mL) was added N,N-dimethylformamide (two drops). Oxalyl chloride (144 mg, 1.134 mmol) was added dropwise to the reaction. The reaction mixture was stirred at room temperature for 2 h, NH$_3$·H$_2$O (2 mL) was then added. The reaction mixture was stirred at room temperature for 16 h and concentrated in vacuo. The crude was purified by prep-HPLC to afford 5,5'-methylenebis(6-hydroxy-2-naphthamide) (4.9 mg, 2%) as a light brown solid. Mass Spectrum (ESI) m/z=384.8 (M−H$^+$).

$^1$H NMR (400 MHz, DMSO-d$_6$) δ 10.49 (s, 2H), 8.24 (d, J=1.6 Hz, 2H), 8.17 (d, J=9.0 Hz, 2H), 7.89 (s, 2H), 7.71 (d, J=8.9 Hz, 2H), 7.65-7.63 (m, 2H), 7.34 (d, J=8.8 Hz, 2H), 7.23 (s, 2H), 4.71 (s, 2H).

Example 65: 5-((6-carboxy-2-(2-(diethylamino)ethoxy)naphthalen-1-yl)methyl)-6-hydroxy-2-naphthoic acid (A125)

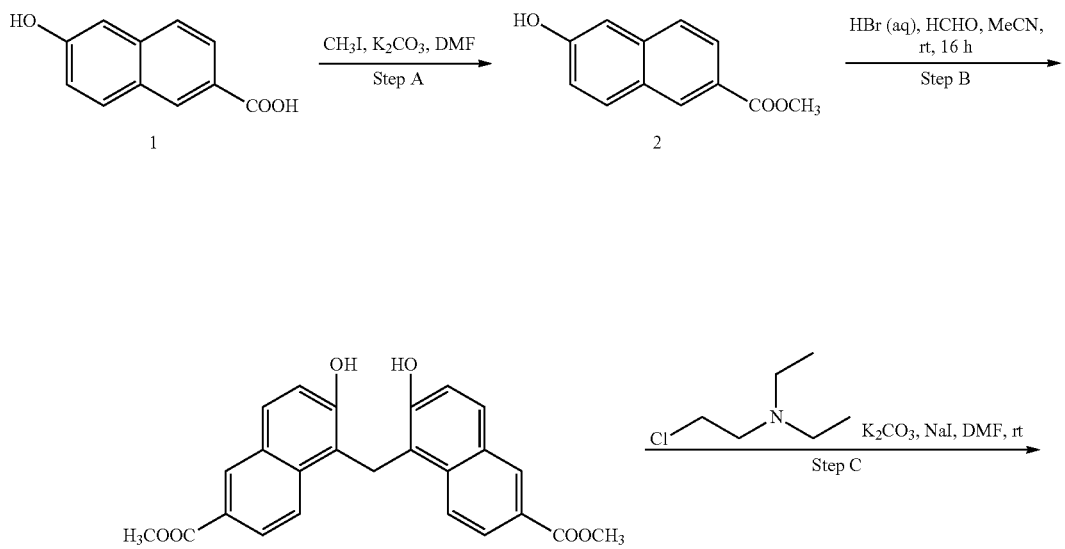

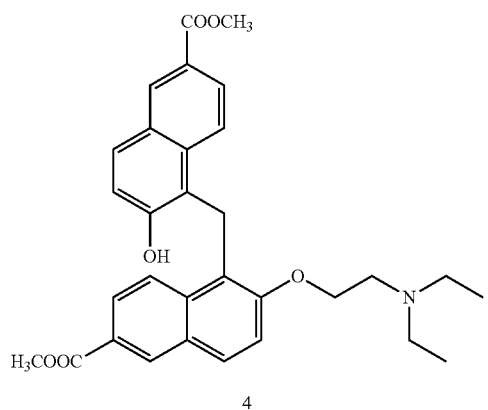

4

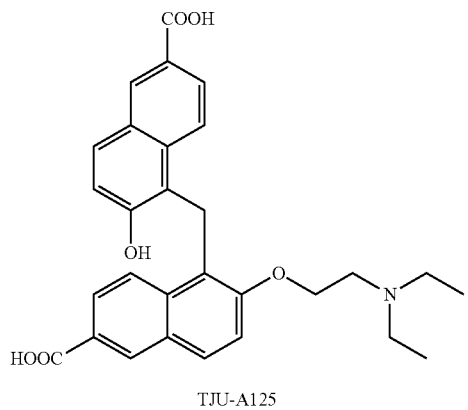

TJU-A125

Step A

To a solution of 6-hydroxy-2-naphthoic acid (2 g, 10.62 mmol) in N,N-dimethylformamide (10 mL) was added potassium carbonate (1.62 g, 11.69 mmol) at room temperature, following the addition of methyl iodide (0.72 mL, 11.69 mmol) at 0° C. The reaction mixture was stirred at room temperature for 16 h. Upon completion, the reaction mixture was poured into water (30 mL) and extracted with ethyl acetate (30 mL×3). The combined organic layer was dried over anhydrous sodium sulfate, filtered and concentrated in vacuo. The residue was purified by flash chromatography (PE/EA=4/1, v/v) to afford methyl 6-hydroxy-2-naphthoate (2.4 g) as a white solid. Mass Spectrum (ESI) m/z=203.1 (M+H$^+$).

$^1$H NMR (400 MHz, DMSO-d$_6$) δ 10.21 (s, 1H), 8.51 (s, 1H), 7.99 (d, J=8.7 Hz, 1H), 7.87 (dd, J=8.6, 1.7 Hz, 1H), 7.78 (d, J=8.7 Hz, 1H), 7.21-7.15 (m, 2H), 3.89 (s, 3H).

Step B

To a solution of methyl 6-hydroxy-2-naphthoate (1.4 g, 6.92 mmol) in acetonitrile (30 mL) were added HBr (40% aqueous, 74 mg, 0.37 mmol) and HCHO (37% aqueous, 0.31 g, 3.8 mmol). Upon completion, the reaction mixture was poured into water (30 mL) and extracted with ethyl acetate (30 mL×3). The combined organic layer was dried over anhydrous sodium sulfate, filtered and concentrated in vacuo. The residue was purified by flash chromatography (PE/EA=1/1, v/v) to afford dimethyl 5,5'-methylenebis(6-hydroxy-2-naphthoate) (1.0 g, 69%) as a white solid. Mass Spectrum (ESI) m/z=439.0 (M+Na$^+$).

Step C

To a solution of dimethyl 5,5'-methylenebis(6-hydroxy-2-naphthoate) (400 mg, 0.96 mmol) in N,N-dimethylformamide (30 mL) were added 2-chloro-N,N-diethylethan-1-amine (200 mg, 1.15 mmol), potassium carbonate (265 mg, 1.92 mmol) and sodium iodide (cat.) at room temperature, the reaction mixture was stirred at room temperature for 16 h. Upon completion, the reaction mixture was poured into water (30 mL) and extracted with ethyl acetate (30 mL×3). The combined organic layer was washed with brine (30 mL×3), dried over anhydrous sodium sulfate, filtered and concentrated in vacuo to afford crude product methyl 6-(2-(diethylamino)ethoxy)-5-((2-hydroxy-6-(methoxycarbonyl)naphthalen-1-yl)methyl)-2-naphthoate (1.5 g) as a yellow oil. Mass Spectrum (ESI) m/z=516.2 (M+H$^+$).

Step D

To a solution of methyl 6-(2-(diethylamino)ethoxy)-5-((2-hydroxy-6-(methoxycarbonyl)naphthalen-1-yl)methyl)-2-naphthoate (1.5 g, 2.9 mmol) in methanol (15 mL) and H$_2$O (8 mL) was added sodium hydroxide (1.2 g, 30 mmol) at room temperature, the reaction mixture was stirred at 25° C. for 16 h. Upon completion, the reaction mixture was concentrated in vacuo, and acidified with 2N HCl to pH=5-6, then concentrated in vacuo. The residue was dissolved in methanol (10 mL) and filtered. The filtrate was concentrated in vacuo to afford crude product (930 mg) as a yellow solid. The residue was purified by prep-HPLC to afford 5-((6-carboxy-2-(2-(diethylamino)ethoxy)naphthalen-1-yl)methyl)-6-hydroxy-2-naphthoic acid (9 mg) as a light orange solid. Mass Spectrum (ESI) m/z=488.1 (M+H$^+$).

$^1$H NMR (400 MHz, DMSO-d$_6$) δ 8.44 (d, J=1.6 Hz, 1H), 8.35 (d, J=1.7 Hz, 1H), 8.31 (d, J=9.1 Hz, 1H), 8.07 (d, J=9.0 Hz, 1H), 8.01 (d, J=9.1 Hz, 1H), 7.83 (d, J=8.9 Hz, 1H), 7.72-7.67 (m, 2H), 7.61 (d, J=9.1 Hz, 1H), 7.33 (d, J=8.9 Hz, 1H), 4.80 (s, 2H), 4.39 (t, J=5.6 Hz, 2H), 3.00 (s, 2H), 2.76-2.67 (m, 4H), 1.03 (t, J=7.1 Hz, 6H).

Example 66: 5,5'-methylenebis(6-(2-(diethylamino)ethoxy)-2-naphthoic acid) (A127)

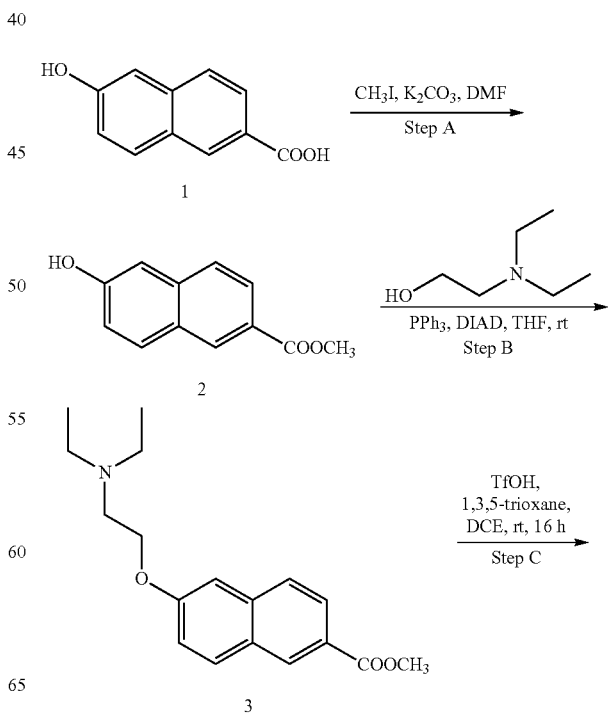

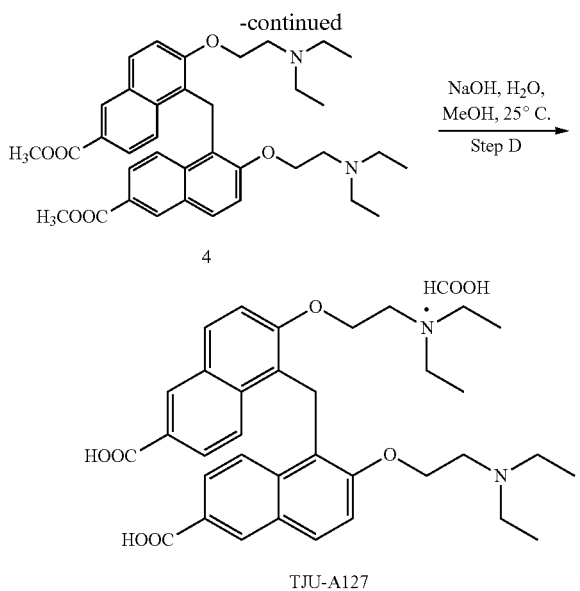

Step A

To a solution of 6-hydroxy-2-naphthoic acid (2 g, 10.62 mmol) in N,N-dimethylformamide (10 mL) was added potassium carbonate (1.62 g, 11.69 mmol) at room temperature, followed by addition of methyl iodide (0.72 mL, 11.69 mmol) at 0° C. The reaction mixture was stirred at room temperature for 16 h. Upon completion, the reaction mixture was poured into water (30 mL) and extracted with ethyl acetate (30 mL×3). The combined organic layer was dried over anhydrous sodium sulfate, filtered and concentrated in vacuo. The residue was purified by flash chromatography (PE/EA=4/1, v/v) to afford methyl 6-hydroxy-2-naphthoate (2.4 g) as a white solid.

Mass Spectrum (ESI) m/z=203.1 (M+H+).

$^1$H NMR (400 MHz, DMSO-d$_6$) δ 10.21 (s, 1H), 8.51 (s, 1H), 7.99 (d, J=8.7 Hz, 1H), 7.87 (dd, J=8.6, 1.7 Hz, 1H), 7.78 (d, J=8.7 Hz, 1H), 7.21-7.15 (m, 2H), 3.89 (s, 3H).

Step B

To a solution of methyl 6-hydroxy-2-naphthoate (500 mg, 2.47 mmol) in anhydrous tetrahydrofuran (20 mL) were added triphenyl phosphine (650 mg, 2.47 mmol), 2-(diethylamino)ethan-1-ol (290 mg, 2.47 mmol) and DIAD (500 mg, 2.47 mmol), the reaction mixture was stirred for 16 h at room temperature. After completion, the reaction mixture was quenched with water (50 mL) at 0° C., concentrated in vacuo to remove tetrahydrofuran and extracted with ethyl acetate (30 mL×3). The combined organic layer was washed with brine (40 mL×3), dried over anhydrous sodium sulfate and concentrated in vacuo. The residue was purified by flash chromatography (PE/EA=1/1, v/v) to afford methyl 6-(2-(diethylamino)ethoxy)-2-naphthoate (1.1 g) as a light yellow solid. Mass Spectrum (ESI) m/z=302.0 (M+H+).

Step C

To a solution of methyl 6-(2-(diethylamino)ethoxy)-2-naphthoate (200 mg, 0.66 mmol) in dichloroethane (10 mL) were added 1,3,5-trioxane (10 mg, 0.11 mmol) and TfOH (249 mg, 1.66 mmol), the reaction mixture was stirred at room temperature for 16 h. Upon completion, the reaction mixture was poured into water (30 mL) and extracted with dichloromethane (30 mL×3). The combined organic layer was dried over anhydrous sodium sulfate, filtered and concentrated in vacuo to afford crude product dimethyl 5,5'-methylenebis(6-(2-(diethylamino)ethoxy)-2-naphthoate) (300 mg) as a white solid. Mass Spectrum (ESI) m/z=615.2 (M+H+).

Step D

To a solution of dimethyl 5,5'-methylenebis(6-(2-(diethylamino)ethoxy)-2-naphthoate) (300 mg, 0.488 mmol) in methanol (15 mL) and H$_2$O (7.5 mL) was added sodium hydroxide (1.2 g, 30 mmol) at room temperature, the reaction mixture was stirred at 25° C. for 2 h. Upon completion, the reaction mixture was concentrated in vacuo, and acidified with 2N HCl to pH 2-3. The mixture was extracted with ethyl acetate (30 mL). The aqueous layer was basified with saturated sodium bicarbonate to pH=7 and concentrated in vacuo. The residue was dissolved in methanol (10 mL), filtered and the filtrate was concentrated in vacuo to afford crude product which was purified by prep-HPLC to afford 5,5'-methylenebis(6-(2-(diethylamino)ethoxy)-2-naphthoic acid) (18.7 mg, 6%) as a white solid. Mass Spectrum (ESI) m/z=587.2 (M+H+).

$^1$H NMR (400 MHz, DMSO-d6) δ 8.44 (s, 2H), 8.22 (d, J=3.8 Hz, 2H), 8.20 (s, 1H), 7.98 (d, J=9.0 Hz, 2H), 7.79-7.74 (m, 2H), 7.55 (d, J=9.2 Hz, 2H), 4.85 (s, 2H), 4.22 (t, J=6.1 Hz, 4H), 2.66 (t, J=6.0 Hz, 4H), 2.55-2.51 (m, 8H), 0.92 (t, J=7.1 Hz, 12H).

Example 67: 1-((2-(2-(pyrrolidin-1-yl)ethoxy)naphthalen-1-yl)methyl)naphthalen-2-ol (A129)

Example 68: 1-(2-((1-((2-methoxynaphthalen-1-yl)methyl)naphthalen-2-yl)oxy)ethyl)-1-methylpyrrolidin-1-ium formate (A129-2)

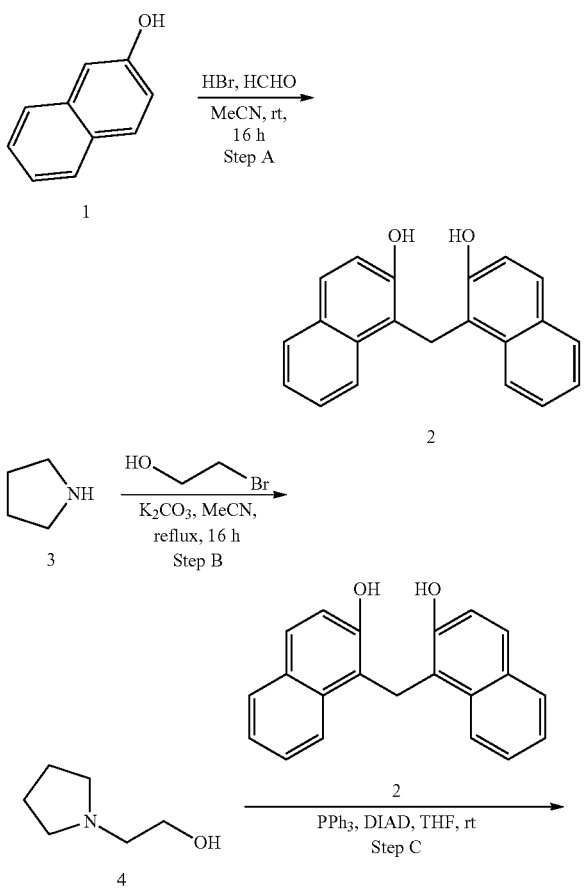

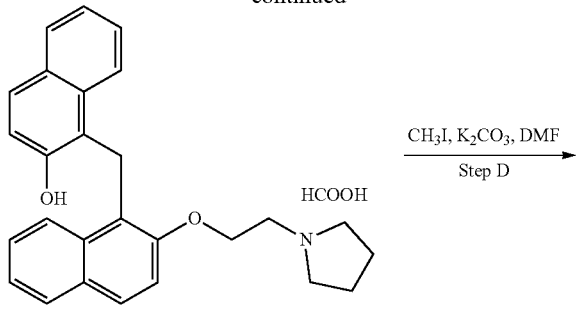

TJU-A129

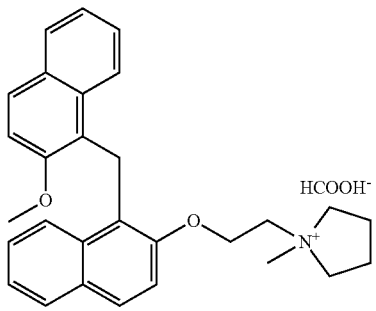

TJU-A129-2

Step A

To a solution of naphthalen-2-ol (8 g, 55.5 mmol) in acetonitrile (80 mL) were added HBr (40% aqueous, 0.6 g, 2.94 mmol) and HCHO (37% aqueous, 2.51 g, 30.53 mmol). Upon completion, the reaction mixture was poured into water (30 mL), concentrated in vacuo and extracted with ethyl acetate (30 mL×3). The combined organic layer was dried over anhydrous sodium sulfate, filtered, and concentrated in vacuo, the residue was purified by flash chromatography (PE/EA=4/1, v/v) to afford 1,1'-methylenebis(naphthalen-2-ol) (7.9 g, 88%) as a light-yellow solid.

Mass Spectrum (ESI) m/z=323.1 (M+Na)$^+$.

Step B 2-bromoethan-1-ol (1.8 mL, 25.1 mmol) in dry acetonitrile (20 mL) was added dropwise under nitrogen atmosphere to a refluxing mixture of pyrrolidine (2.2 mL, 26.7 mmol) and potassium carbonate (3.1 g, 22.6 mmol) in dry acetonitrile (30 mL). After 15 h, the mixture was cooled to 25° C. Solid was filtered off, and the filtrate was concentrated under reduced pressure to afford 2-(pyrrolidin-1-yl)ethan-1-ol (600 mg) as an orange oil.

Mass Spectrum (ESI) m/z=116.2 (M+H$^+$).

Step C

To a solution of 1,1'-methylenebis(naphthalen-2-ol) (200 mg, 0.67 mmol) in anhydrous tetrahydrofuran (20 mL) were added triphenyl phosphine (175 mg, 0.67 mmol), 2-(pyrrolidin-1-yl)ethan-1-ol (77 mg, 0.67 mmol) and DIAD (135 mg, 0.67 mmol), the reaction mixture was stirred for 16 h at room temperature. After completion, the reaction mixture was quenched with water (50 mL), concentrated in vacuo to remove tetrahydrofuran and extracted with ethyl acetate (30 mL×3). The combined organic layer was washed with brine (40 mL×3), dried over anhydrous sodium sulfate and concentrated in vacuo. The residue was purified by prep-HPLC to afford 1-((2-(2-(pyrrolidin-1-yl)ethoxy)naphthalen-1-yl)methyl)naphthalen-2-ol formate (55 mg, 18%) as a white solid.

Mass Spectrum (ESI) m/z=397.8 (M+H$^+$).

$^1$H NMR (400 MHz, DMSO-d6) δ 8.25 (d, J=8.2 Hz, 1H), 8.17 (s, 1H), 7.99 (d, J=8.2 Hz, 1H), 7.81-7.73 (m, 2H), 7.68-7.57 (m, 2H), 7.51 (d, J=9.1 Hz, 1H), 7.27-7.20 (m, 3H), 7.18-7.10 (m, 2H), 4.79 (s, 2H), 4.40 (t, J=5.9 Hz, 2H), 3.01 (t, J=5.8 Hz, 2H), 2.72-2.70 (m, 4H), 1.78-1.65 (m, 4H).

Step D

To a solution of 1-((2-(2-(pyrrolidin-1-yl)ethoxy)naphthalen-1-yl)methyl)naphthalen-2-ol formate (50 mg, 0.11 mmol) in anhydrous N,N-dimethylformamide (10 mL) was added potassium carbonate (24 mg, 0.17 mmol) followed by dropwise addition of methyl iodide (20 mg, 0.14 mmol) at 0° C. The reaction mixture was stirred for 16 h at room temperature. After completion, the reaction mixture was concentrated in vacuo to remove N,N-dimethylformamide. The residue was purified by prep-HPLC to afford 1-(2-((1-((2-methoxynaphthalen-1-yl)methyl)naphthalen-2-yl)oxy)ethyl)-1-methyl-14-pyrrolidine, formate salt (10 mg, 19%) as a white solid.

Mass Spectrum (ESI) m/z=425.9 (M+H$^+$).

$^1$H NMR (400 MHz, DMSO-d6) δ 8.45 (s, 1H), 8.08-8.00 (m, 2H), 7.92-7.76 (m, 4H), 7.58 (d, J=9.1 Hz, 1H), 7.52 (d, J=9.1 Hz, 1H), 7.36-7.21 (m, 4H), 4.85 (s, 2H), 4.69 (s, 2H), 3.97 (s, 3H), 3.86 (s, 2H), 3.58-3.56 (m, 4H), 3.13 (s, 3H), 2.08 (s, 4H).

Example 69: 1-((2-(2-morpholinoethoxy)naphthalen-1-yl)methyl)naphthalen-2-ol (A130)

Example 70: 4-(2-((1-((2-methoxynaphthalen-1-yl)methyl)naphthalen-2-yl)oxy)ethyl)-4-methylmorpholin-4-ium formate (A130-2)

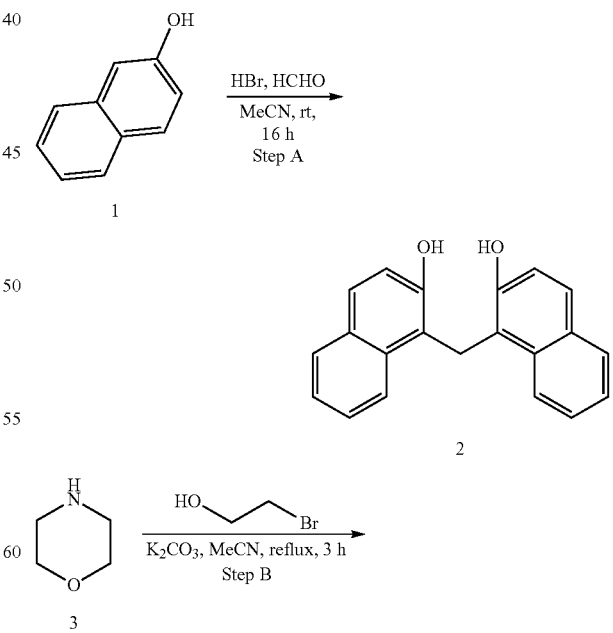

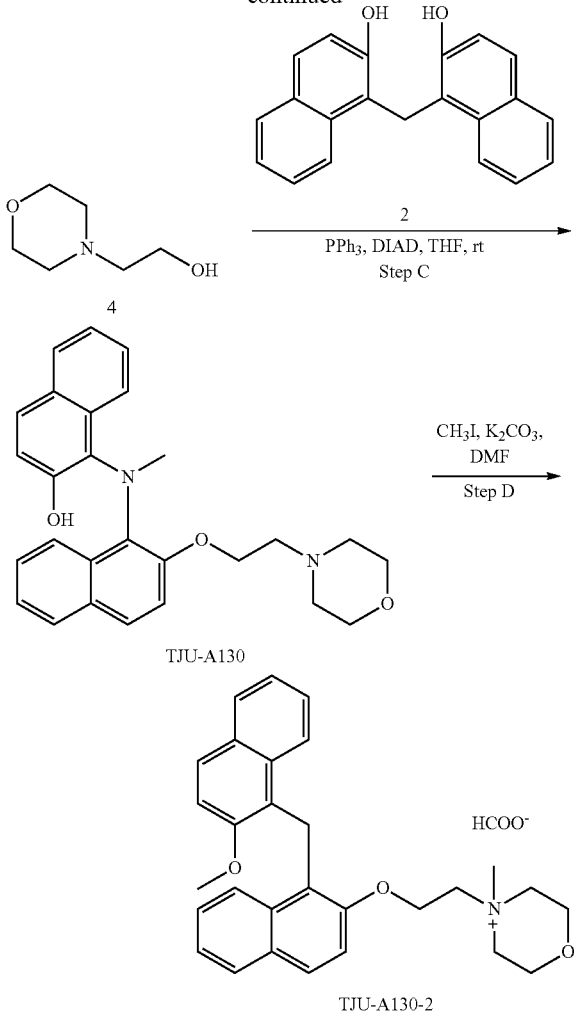

pholinoethan-1-ol (87 mg, 0.67 mmol) and DIAD (135 mg, 0.67 mmol), the reaction mixture was stirred for 16 h at room temperature. After completion, the reaction mixture was quenched with water (50 mL), concentrated in vacuo and extracted with ethyl acetate (30 mL×3). The combined organic layer was washed with brine (40 mL×3), dried over anhydrous sodium sulfate and concentrated in vacuo. The residue was purified by prep-HPLC to afford 1-((2-(2-morpholinoethoxy)naphthalen-1-yl)methyl)naphthalen-2-ol (88 mg, 32%) as a white solid.

Mass Spectrum (ESI) m/z=414.1 (M+H⁺).

¹H NMR (400 MHz, DMSO-d6) δ 10.09 (s, 1H), 8.25 (d, J=8.1 Hz, 1H), 8.00 (d, J=8.2 Hz, 1H), 7.80-7.73 (m, 2H), 7.68-7.60 (m, 2H), 7.52 (d, J=9.0 Hz, 1H), 7.27-7.20 (m, 3H), 7.18-7.11 (m, 2H), 4.78 (s, 2H), 4.39 (t, J=5.8 Hz, 2H), 3.60-3.53 (m, 4H), 2.82 (t, J=5.8 Hz, 2H), 2.57-2.52 (m, 4H).

Step D

To a solution of 1-((2-(2-morpholinoethoxy)naphthalen-1-yl)methyl)naphthalen-2-ol (83 mg, 0.2 mmol) in anhydrous N,N-dimethylformamide (10 mL) was added potassium carbonate (42 mg, 0.3 mmol) followed by dropwise addition of methyl iodide (34 mg, 0.24 mmol) at 0° C. The reaction mixture was stirred for 16 h at room temperature. After completion, the reaction mixture was concentrated in vacuo to remove N,N-dimethylformamide. The residue was purified by prep-HPLC to afford 4-(2-((1-((2-methoxynaphthalen-1-yl)methyl)naphthalen-2-yl)oxy)ethyl)-4-methylmorpholin-4-ium formate (17 mg, 17%) as a white solid.

Mass Spectrum (ESI) m/z=441.8 (M+H⁺).

¹H NMR (400 MHz, DMSO-d6) δ 8.49 (s, 1H), 8.07-7.99 (m, 2H), 7.93-7.75 (m, 4H), 7.59 (d, J=9.1 Hz, 1H), 7.53 (d, J=9.1 Hz, 1H), 7.36-7.20 (m, 4H), 4.86 (s, 2H), 4.73 (s, 2H), 4.01 (s, 2H), 3.98 (s, 3H), 3.94-3.92 (m, 4H), 3.64-3.52 (m, 4H), 3.32 (s, 3H).

Example 71: 1-((2-(2-(dimethylamino)ethoxy)naphthalen-1-yl)methyl)naphthalen-2-ol (A134)

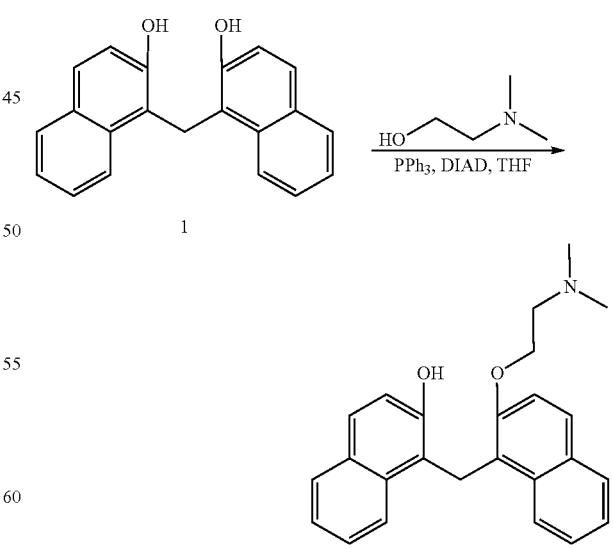

Step A

To a solution of naphthalen-2-ol (8 g, 55.5 mmol) in acetonitrile (80 mL) were added HBr (40% aqueous, 0.6 g, 2.94 mmol) and HCHO (37% aqueous, 2.51 g, 30.53 mmol). Upon completion, the reaction mixture was poured into water (30 mL), concentrated in vacuo and extracted with ethyl acetate (30 mL×3). The combined organic layer was dried over anhydrous sodium sulfate, filtered, and concentrated in vacuo. The residue was purified by flash chromatography (PE/EA=1/1, v/v) to afford 1,1'-methylenebis(naphthalen-2-ol) (7.9 g, 88%) as a light-yellow solid.

Mass Spectrum (ESI) m/z=323.1 (M+Na⁺).

Step B

To a solution of morpholine (2 g, 23 mmol) in dry acetonitrile (20 mL) were added 2-bromoethan-1-ol (1.4 g, 11 mmol) and potassium carbonate (2.42 g, 17.3 mmol) at room temperature, the mixture was refluxed under nitrogen for 3 h. After cooling to the room temperature, the solid was filtered off, and the filtrate was concentrated under reduced pressure to afford product 2-morpholinoethan-1-ol (1.4 g) as a yellow oil.

Mass Spectrum (ESI) m/z=132.1 (M+H⁺).

Step C

To a solution of 1,1'-methylenebis(naphthalen-2-ol) (200 mg, 0.67 mmol) in anhydrous tetrahydrofuran (20 mL) were added triphenyl phosphine (175 mg, 0.67 mmol), 2-mor- To a solution of 1,1'-methylenebis(naphthalen-2-ol) (120 mg, 0.4 mmol) and 2-(dimethylamino)ethan-1-ol (39.2 mg, 0.44 mmol) in tetrahydrofuran (10 mL) were added triphenyl phosphine (126 mg, 0.48 mmol) and DIAD (97 mg, 0.48 mmol), the reaction mixture was stirred at room temperature for 2 h. The reaction mixture was diluted with sat ammonium chloride (10 mL) and extracted with ethyl acetate (30 mL×2). The combined organic layer was washed with brine (30 mL), dried over anhydrous sodium sulfate, filtered, and concentrated in vacuo. The crude was purified by prep-HPLC to afford 1-((2-(2-(dimethylamino)ethoxy)naphthalen-1-yl)methyl)naphthalen-2-ol (40 mg, 27%) as a white solid.

Mass Spectrum (ESI) m/z=372.2 (M+H⁺)

$^1$H NMR (400 MHz, DMSO-$d_6$) δ 8.25 (d, J=8.0 Hz, 1H), 8.18 (s, 1H), 7.99 (d, J=8.0 Hz, 1H), 7.78 (d, J=8.0 Hz, 1H), 7.76-7.74 (m, 1H), 7.67-7.65 (m, 1H), 7.61 (d, J=8.0 Hz, 1H), 7.52 (d, J=12.0 Hz, 1H), 7.27-7.20 (m, 3H), 7.18-7.10 (m, 2H), 4.79 (s, 2H), 4.37 (t, J=8.0 Hz, 2H), 2.81 (t, J=8.0 Hz, 2H), 2.33 (s, 6H).

Example 72: 1-((2-(3-(diethylamino)propoxy)naphthalen-1-yl)methyl)naphthalen-2-ol (A135)

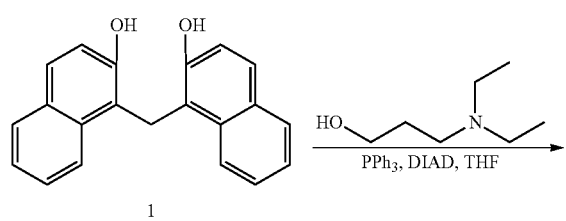

To a solution of 1,1'-methylenebis(naphthalen-2-ol) (110 mg, 0.36 mmol) and 3-(diethylamino)propan-1-ol (52 mg, 0.4 mmol) in tetrahydrofuran (10 mL) were added triphenyl phosphine (105 mg, 0.4 mmol) and DIAD (84 mg, 0.4 mmol), the reaction mixture was stirred for 2 h at room temperature. The reaction mixture was diluted with saturated ammonium chloride (10 mL) and extracted with ethyl acetate (30 mL×2). The combined organic layer was washed with brine, dried over anhydrous sodium sulfate, filtered, and concentrated in vacuo. The crude was purified by prep-HPLC to afford 1-((2-(3-(diethylamino)propoxy)naphthalen-1-yl)methyl)naphthalen-2-ol (70 mg, 47%) as a white solid.

Mass Spectrum (ESI) m/z=414.2 (M+H⁺)

$^1$H NMR (400 MHz, DMSO-$d_6$) δ 10.17 (br, 1H), 8.26 (d, J=8.0 Hz, 1H), 8.21 (s, 1H), 8.00 (d, J=8.0 Hz, 1H), 7.78 (d, J=8.0 Hz, 1H), 7.76-7.73 (m, 1H), 7.67-7.65 (m, 1H), 6.62 (d, J=12.0 Hz, 1H), 7.49 (d, J=8.0 Hz, 1H), 7.28-7.11 (m, 5H), 4.78 (s, 2H), 4.33 (t, J=8.0 Hz, 2H), 2.78 (t, J=8.0 Hz, 2H), 2.60 (q, J=8.0 Hz, 4H), 2.04-1.97 (m, 2H), 0.98 (t, J=8.0 Hz, 6H).

Example 73: 1-((2-(2-(piperidin-1-yl)ethoxy)naphthalen-1-yl)methyl)naphthalen-2-ol (A138)

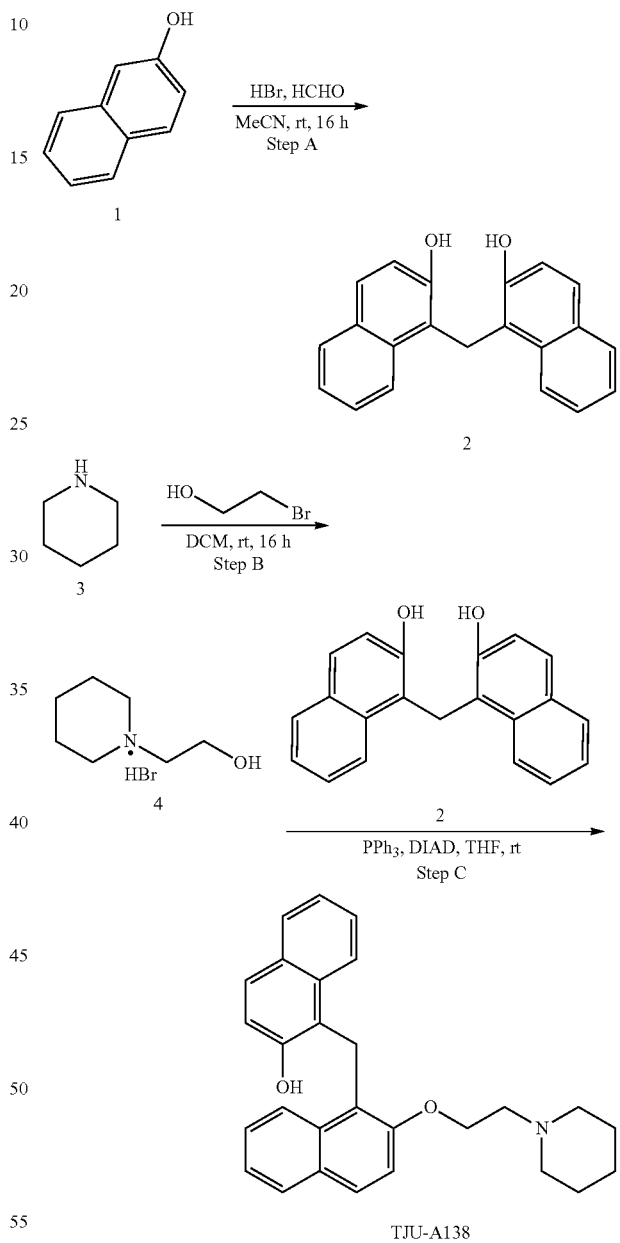

Step A

To a solution of naphthalen-2-ol (8 g, 55.5 mmol) in acetonitrile (80 mL) were added HBr (40% aqueous, 0.6 g, 2.94 mmol) and HCHO (37% aqueous, 2.51 g, 30.53 mmol), the reaction mixture was stirred for 16 h. Upon completion, the reaction mixture was poured into water (30 mL), concentrated in vacuo and extracted with ethyl acetate (30 mL×3). The combined organic layer was dried over anhydrous sodium sulfate, filtered, and concentrated in vacuo. The residue was purified by flash chromatography (PE/

EA=4/1, v/v) to afford 1,1'-methylenebis(naphthalen-2-ol) (7.9 g, 88%) as a light yellow solid. Mass Spectrum (ESI) m/z=323.1 (M+Na⁺).

Step B

To a solution of 2-bromoethan-1-ol (1 g, 8 mmol) in dichloromethane (25 mL) was added piperidine (2 mL) and the reaction mixture was stirred at room temperature for 16 h. The solvent was removed under reduced pressure to afford product 2-(piperidin-1-yl)ethan-1-ol hydrogen bromide (2.0 g) as a white solid.

Mass Spectrum (ESI) m/z=130.2 (M+H⁺).

Step C

To a solution of 1,1'-methylenebis(naphthalen-2-ol) (200 mg, 0.67 mmol) in anhydrous tetrahydrofuran (20 mL) were added triphenyl phosphine (175 mg, 0.67 mmol), 2-(piperidin-1-yl)ethan-1-ol hydrogen bromide (140 mg, 0.67 mmol) and DIAD (135 mg, 0.67 mmol), the reaction mixture was stirred for 16 h at room temperature. After completion, the reaction mixture was quenched with water (50 mL), concentrated in vacuo to remove tetrahydrofuran and extracted with ethyl acetate (30 mL×3). The combined organic layer was washed with brine (40 mL×3), dried over anhydrous sodium sulfate and concentrated in vacuo. The residue was purified by prep-HPLC to afford 1-((2-(2-(piperidin-1-yl)ethoxy)naphthalen-1-yl)methyl)naphthalen-2-ol (27 mg, 10%) as a white solid.

Mass Spectrum (ESI) m/z=412.2 (M+H⁺).

¹H NMR (400 MHz, DMSO-d6) δ 8.26 (d, J=8.3 Hz, 1H), 8.00 (d, J=8.3 Hz, 1H), 7.81-7.72 (m, 2H), 7.68-7.58 (m, 2H), 7.51 (d, J=9.1 Hz, 1H), 7.32-7.07 (m, 5H), 4.78 (s, 2H), 4.38 (t, J=5.9 Hz, 2H), 2.82 (t, J=5.8 Hz, 2H), 1.54-1.48 (m, 4H), 1.40-1.34 (m, 2H), 1.31-1.11 (m, 4H).

Example 74: 2-((1-((2-methoxynaphthalen-1-yl)methyl)naphthalen-2-yl)oxy)ethan-1-ol (A139-2)

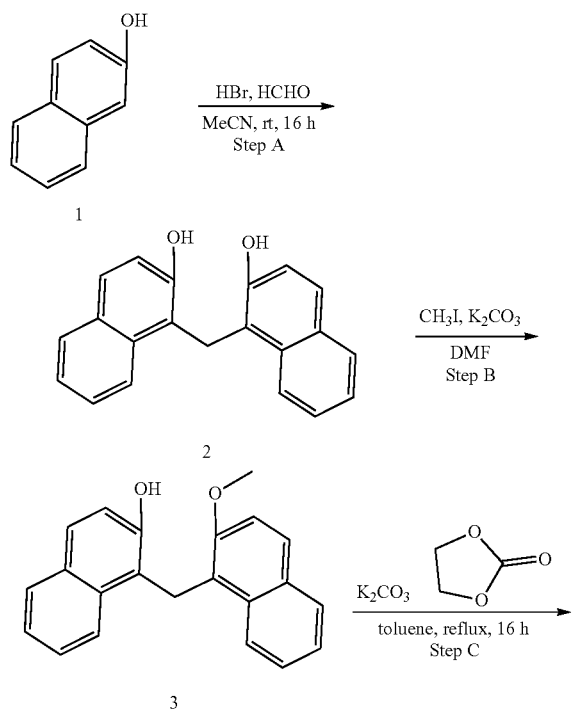

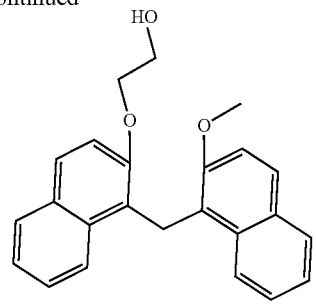

TJU-A139-2

Step A

To a solution of naphthalen-2-ol (8 g, 55.5 mmol) in acetonitrile (80 mL) were added HBr (40% aqueous, 0.6 g, 2.94 mmol) and HCHO (37% aqueous, 2.51 g, 30.53 mmol) and the reaction mixture was stirred for 16 h. Upon completion, the reaction mixture was poured into water (30 mL), concentrated in vacuo and extracted with ethyl acetate (30 mL×3). The combined organic layer was dried over anhydrous sodium sulfate, filtered, and concentrated in vacuo. The residue was purified by flash chromatography (PE/EA=4/1, v/v) to afford 1,1'-methylenebis(naphthalen-2-ol) (7.9 g, 88%) as a light-yellow solid.

Mass Spectrum (ESI) m/z=323.1 (M+Na⁺).

Step B

To a solution of 1,1'-methylenebis(naphthalen-2-ol) (4.0 g, 13.3 mmol) in anhydrous N,N-dimethylformamide (50 mL) was added potassium carbonate (1.84 g, 14.7 mmol), followed by dropwise addition of methyl iodide (0.83 mL, 14.7 mmol) at 0° C. The reaction mixture was stirred for 16 h at room temperature. After completion, the reaction mixture was quenched with water (50 mL) at 0° C. and extracted with ethyl acetate (30 mL×3). The combined organic layer was washed with brine (40 mL×3), dried over anhydrous sodium sulfate and concentrated in vacuo. The residue was purified by flash chromatography (PE/EA=4/1, v/v) to afford 1-((2-methoxynaphthalen-1-yl)methyl)naphthalen-2-ol (4.0 g, 95%) as a yellow solid.

Mass Spectrum (ESI) m/z=336.8 (M+Na⁺).

Step C

To a solution of 1-((2-methoxynaphthalen-1-yl)methyl)naphthalen-2-ol (4.0 g, 12.72 mmol) in toluene (50 mL) were added potassium carbonate (5.28 g, 38.17 mmol) and 1,3-dioxolan-2-one (3.36 g, 38.17 mmol), the reaction mixture was refluxed for 16 h. After completion, the reaction mixture was quenched with water (50 mL) at 0° C. and extracted with ethyl acetate (30 mL×3). The combined organic layer was washed with brine (40 mL×3), dried over anhydrous sodium sulfate and concentrated in vacuo. The residue was washed with methanol (20 mL), filtered to afford 2-((1-((2-methoxynaphthalen-1-yl)methyl)naphthalen-2-yl)oxy)ethan-1-ol (2.0 g, 44%) as a white solid. 100 mg crude product was purified by prep-HPLC to afford 2-((1-((2-methoxynaphthalen-1-yl)methyl)naphthalen-2-yl)oxy)ethan-1-ol as white solid (20 mg).

Mass Spectrum (ESI) m/z=380.7 (M+Na)⁺.

¹H NMR (400 MHz, DMSO-d6) δ 8.14 (d, J=8.3 Hz, 1H), 8.06 (d, J=8.5 Hz, 1H), 7.78 (d, J=20.6, 8.8 Hz, 4H), 7.50 (t, J=9.3 Hz, 2H), 7.29-7.19 (m, 4H), 4.93 (t, J=5.6 Hz, 1H), 4.86 (s, 2H), 4.25 (t, J=5.1 Hz, 2H), 4.03 (s, 3H), 3.79 (dd, J=10.5, 5.3 Hz, 2H).

Example 75: 8-((2-hydroxynaphthalen-1-yl)methyl)-1,2,3,4-tetrahydroisoquinolin-7-ol (A141)

Example 76: 8-((2-hydroxy-5,6,7,8-tetrahydronaphthalen-1-yl)methyl)-1,2,3,4-tetrahydroisoquinolin-7-ol (A141-I-1)

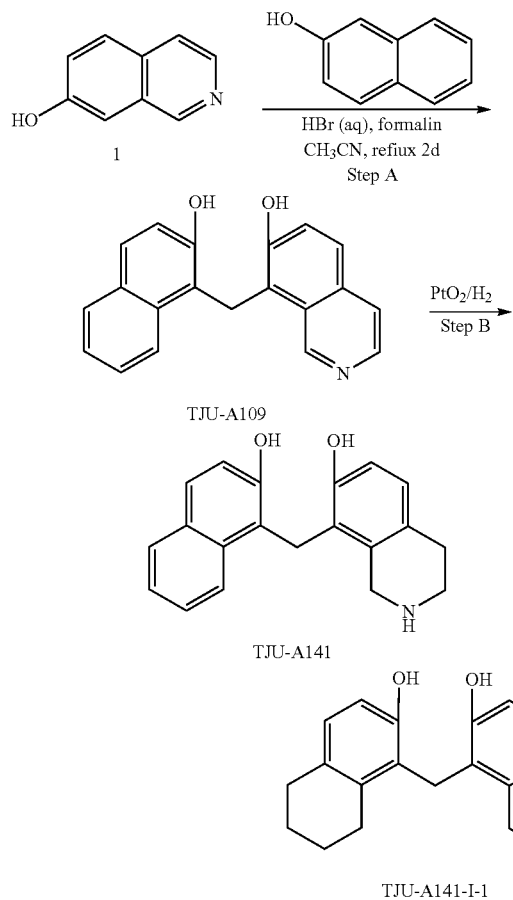

Step A

To a solution of isoquinolin-7-ol (120 mg, 0.83 mmol), naphthalen-2-ol (120 mg, 0.83 mmol) and formaldehyde aqueous solution (321 mg, 4.2 mmol) in acetonitrile (10 mL) was added HBr (40% aqueous, 400 mg) and the reaction mixture was refluxed for 2 days. After concentration, the residue was diluted with sat sodium bicarbonate (10 mL) and extracted with dichloromethane (30 mL×3), dried over anhydrous sodium sulfate, filtered and concentrated. The residue was purified by prep-HPLC to afford 8-((2-hydroxynaphthalen-1-yl)methyl)isoquinolin-7-ol (15 mg, 6%) as a yellow powder.

Mass Spectrum (ESI) m/z=302.0 (M+H$^+$)

$^1$H NMR (400 MHz, DMSO-d$_6$) δ 10.41 (br, 2H), 9.52 (s, 1H), 8.15-8.15 (m, 2H), 7.69-7.63 (m, 3H), 7.55 (d, J=8.0 Hz, 1H), 7.51 (d, J=12.0 Hz, 1H), 7.29 (d, J=8.0 Hz, 1H), 7.24-7.20 (m, 1H), 7.16-7.13 (m, 1H), 4.17 (s, 2H).

Step B

A mixture of 8-((2-hydroxynaphthalen-1-yl)methyl)isoquinolin-7-ol (250 mg, 0.83 mmol), PtO$_2$ (150 mg) in methanol (30 mL) was stirred under hydrogen (0.4 MPa) for 36 h. The reaction mixture was filtered and washed with methanol, the filtrate was concentrated and the residue was purified by prep-HPLC to afford 8-((2-hydroxynaphthalen-1-yl)methyl)-1,2,3,4-tetrahydroisoquinolin-7-ol (5 mg, 2%) as a white powder.

Mass Spectrum (ESI) m/z=306.1 (M+H$^+$)

$^1$H NMR (400 MHz, CD$_3$OD) δ 8.52 (br, 1H), 8.02 (d, J=8.0 Hz, 1H), 7.70 (d, J=8.0 Hz, 1H), 7.66 (d, J=8.0 Hz, 1H), 7.26-7.20 (m, 2H), 7.16 (d, J=8.0 Hz, 1H), 6.93-6.92 (m, 2H), 4.52 (s, 2H), 4.05 (s, 2H), 3.19 (t, J=8.0 Hz, 2H), 2.91 (t, J=8.0 Hz, 2H). 8-((2-hydroxy-5,6,7,8-tetrahydronaphthalen-1-yl)methyl)-1,2,3,4-tetrahydroisoquinolin-7-ol (15 mg, 6% yield) as a white powder.

Mass Spectrum (ESI) m/z=310.2 (M+H$^+$)

$^1$H NMR (400 MHz, CD$_3$OD) δ 8.53 (s, 1H), 6.93 (d, J=8.0 Hz, 1H), 6.79 (t, J=8.0 Hz, 2H), 6.62 (d, J=8.0 Hz, 1H), 4.13 (s, 2H), 4.06 (s, 2H), 3.28 (t, J=8.0 Hz, 2H), 2.97 (t, J=8.0 Hz, 2H), 2.66-2.63 (m, 2H), 2.46-2.43 (m, 2H), 1.62-1.61 (m, 4H).

Example 77: 1-((2-(2-(diethylamino)ethoxy)naphthalen-1-yl)thio)naphthalen-2-ol (A151)

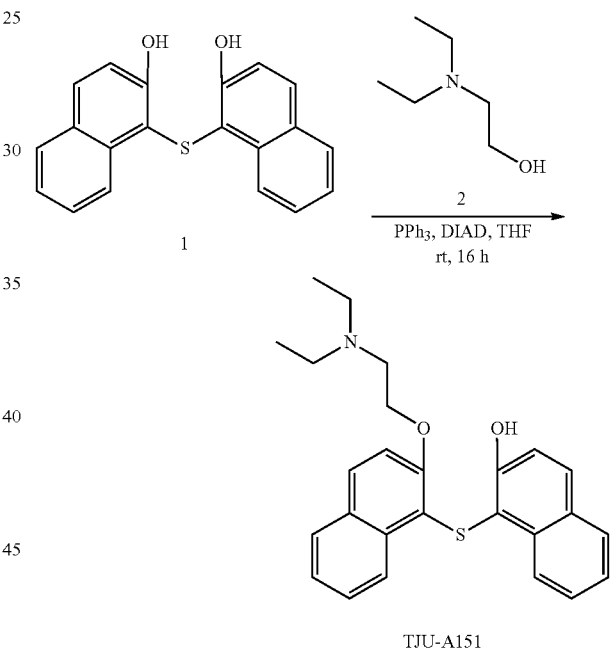

To a stirred suspension of 1,1'-thiobis(naphthalen-2-ol) (500 mg, 1.57 mmol) and triphenyl phosphine (438 mg, 1.67 mmol) in dry tetrahydrofuran (20 mL) were added 2-(diethylamino)ethan-1-ol (184 mg, 1.57 mmol) and DIAD (337 mg, 1.67 mmol) dropwise, the mixture was stirred at room temperature for 16 h. The reaction mixture was diluted with ethyl acetate, washed with brine, dried over anhydrous sodium sulfate, filtered, and concentrated. The residue was purified by prep-HPLC to afford 1-((2-(2-(diethylamino)ethoxy)naphthalen-1-yl)thio)naphthalen-2-ol (13.4 mg, 2%) as an off-white solid.

Mass Spectrum (ESI) m/z=418.1 (M+H$^+$).

$^1$H NMR (400 MHz, DMSO-d$_6$) δ 8.70 (d, J=12.0 Hz, 1H), 8.37 (d, J=8.0 Hz, 1H), 8.30 (s, 1H), 7.85 (t, J=8.0 Hz, 2H), 7.75-7.71 (m, 2H), 7.52-7.48 (m, 1H), 7.41-7.31 (m, 3H), 7.25-7.21 (m, 1H), 7.15 (d, J=12.0 Hz, 1H), 4.01 (t, J=8.0 Hz, 2H), 2.46-2.39 (m, 6H), 0.89 (t, J=4.0 Hz, 6H).

117

Example 78: N,N-diethyl-2-((1-((2-methoxynaphthalen-1-yl)thio)naphthalen-2-yl)oxy)ethan-1-amine (A152)

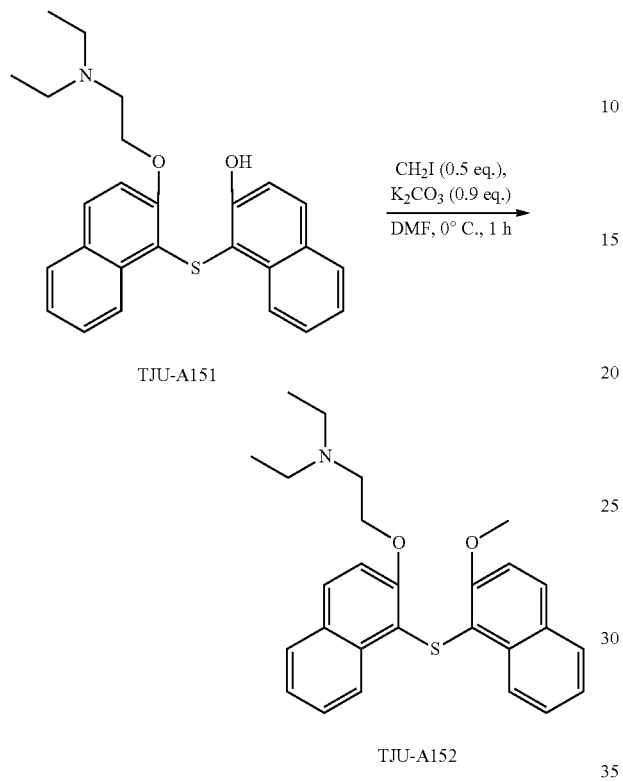

To a solution of 1-((2-(2-(diethylamino)ethoxy)naphthalen-1-yl)thio)naphthalen-2-ol (125 mg, 0.30 mmol) and potassium carbonate (124 mg, 0.27 mmol) in anhydrous N,N-dimethylformamide (2 mL) was added methyl iodide (21 mg, 0.15 mmol) under nitrogen at 0° C. and the reaction mixture was stirred for 1 h at 0° C. After completion, the reaction mixture was purified by flash chromatography (dichloromethane/methanol=1/0 to 10/1, v/v) to afford crude product which was purified by prep-HPLC to afford N,N-diethyl-2-((1-((2-methoxynaphthalen-1-yl)thio)naphthalen-2-yl)oxy)ethan-1-amine (8 mg, 6%) as a white solid.

Mass Spectrum (ESI) m/z=432.2 (M+H$^+$).

$^1$H NMR (400 MHz, CD$_3$OD) δ 8.70 (d, J=8.0 Hz, 1H), 8.56 (d, J=8.0 Hz, 1H), 7.88-7.81 (m, 4H), 7.57-7.53 (m, 2H), 7.44-7.33 (m, 4H), 7.26 (d, J=8.0 Hz, 1H), 4.16 (t, J=8.0 Hz, 2H), 3.43 (s, 3H), 2.97-2.89 (m, 6H), 1.11 (t, J=8.0 Hz, 6H).

Example 79: 1-((6-(2-(diethylamino)ethoxy)quinoxalin-5-yl)methyl)naphthalen-2-ol (A168)

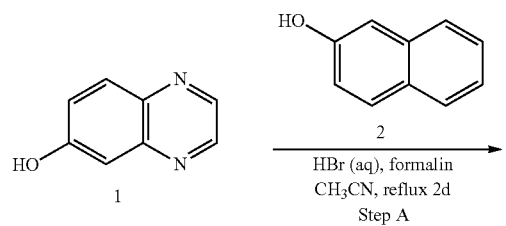

118

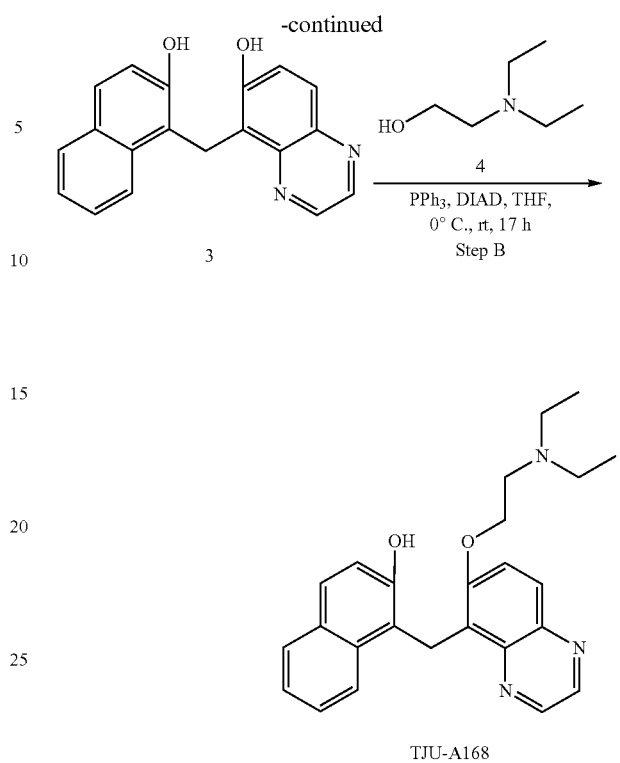

Step A

To a solution of quinoxalin-6-ol (400 mg, 2.74 mmol), naphthalen-2-ol (394.5 mg, 2.74 mmol) and formaldehyde aqueous solution (1.02 g, 13.7 mmol) in acetonitrile (30 mL) was added HBr (40% aqueous, 1.46 g, 2.4 mmol), the reaction mixture was refluxed for 2 days. The resulting reaction was concentrated, the residue was diluted with sat. NaHCO$_3$ (50 mL) and extracted with DCM (30 mL×3). The combined organic layer was dried over anhydrous Na$_2$SO$_4$ and concentrated. The residue was purified by silica gel chromatography (PE/EA=4/1, v/v) to afford 5-((2-hydroxynaphthalen-1-yl)methyl)quinoxalin-6-ol (40 mg, 5%).

Mass Spectrum (ESI) m/z=325.1 (M+H$^+$).

Step B

To a stirred solution of 5-((2-hydroxynaphthalen-1-yl)methyl)quinoxalin-6-ol (30.2 mg, 0.1 mmol), 2-(diethylamino)ethan-1-ol (15.2 mg, 0.13 mmol) and Ph$_3$P (39.3 mg, 0.13 mmol) in dry THF (1 mL) was added DIAD (30.3 mg, 0.15 mmol). The mixture was stirred at room temperature for 17 h. The reaction mixture was diluted with ethyl acetate (60 mL), washed with brine (60 mL), dried over anhydrous Na$_2$SO$_4$, filtered and concentrated. The residue was purified by prep-TLC (DCM/MeOH=20/1, v/v) to 1-((6-(2-(diethylamino)ethoxy)quinoxalin-5-yl)methyl)naphthalen-2-ol (7.74 mg, 19.2%).

Mass Spectrum (ESI) m/z=402.3 (M+H$^+$).

$^1$H NMR (400 MHz, DMSO-d6) δ 10.32 (br, 1H), 8.98 (d, J=1.8 Hz, 1H), 8.85 (d, J=1.8 Hz, 1H), 8.13 (d, J=8.1 Hz, 1H), 7.96 (d, J=9.2 Hz, 1H), 7.77-7.59 (m, 3H), 7.21-7.12 (m, 3H), 4.87 (s, 2H), 4.12 (t, J=6.4 Hz, 2H), 3.29-3.27 (m, 2H), 2.64-2.62 (m, 2H), 2.53-2.50 (m, 2H), 0.92 (t, J=16.0 Hz, 6H).

119

Example 80: diethyl(2-((1-((2-methoxynaphthalen-1-yl)thio)naphthalen-2-yl)oxy)ethyl)(methyl)-14-azane, iodide salt (A191)

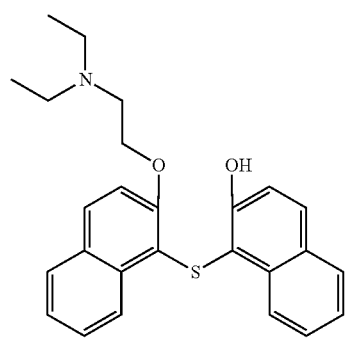

TJU-A151

CH₃I (1.0 eq.),
K₂CO₃ (0.9 eq.)
───────────→
DMF, rt, 16 h
Step A

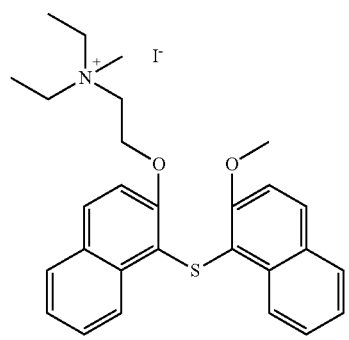

TJU-A191

Step A

To a solution of 1-((2-(2-(diethylamino)ethoxy)naphthalen-1-yl)thio)naphthalen-2-ol (300.0 mg, 0.72 mmol) and potassium carbonate (119.0 mg, 0.86 mmol) in anhydrous DMF (4 mL) was added CH₃I (102.0 mg, 0.72 mmol) under N₂ at room temperature and the reaction mixture was stirred for 16 h at room temperature. After completion, the reaction mixture was purified by flash chromatography (DCM/MeOH=1/0 to 10/1, v/v) to afford diethyl(2-((1-((2-methoxynaphthalen-1-yl)thio)naphthalen-2-yl)oxy)ethyl)(methyl)-14-azane, iodide salt (391.1 mg, 95%) as a white solid.

Mass Spectrum (ESI) m/z=446.2 (M+H⁺).

¹H NMR (400 MHz, DMSO-d₆) δ 8.54 (d, J=8.0 Hz, 1H), 8.48-8.35 (m, 1H), 8.05-7.83 (m, 4H), 7.65-7.49 (m, 2H), 7.47-7.31 (m, 4H), 4.51 (s, 2H), 3.63 (s, 3H), 3.48-3.41 (m, 2H), 3.30 (q, J=8.0 Hz, 4H), 2.93 (s, 3H), 1.14 (t, J=8.0 Hz, 6H).

120

Example 81: 1-((2-(diethylamino)ethyl)(3,4-dimethoxyphenyl)amino)naphthalen-2-ol (A194)

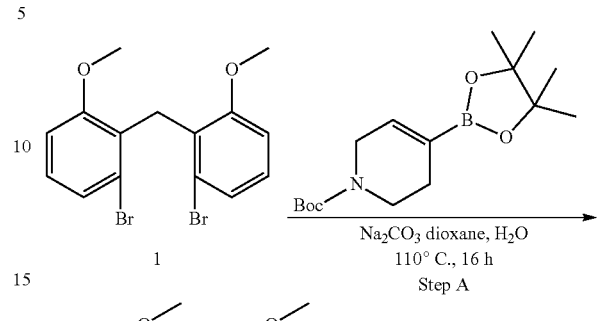

Na₂CO₃ dioxane, H₂O
───────────────→
110° C., 16 h
Step A

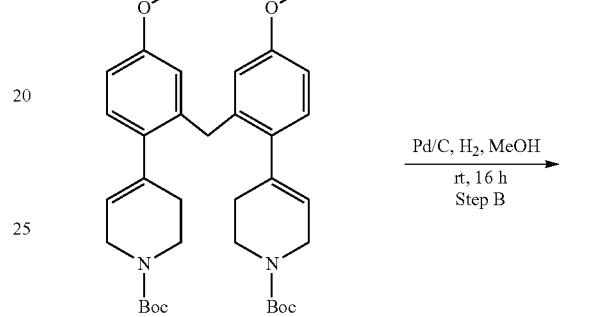

Pd/C, H₂, MeOH
──────────────→
rt, 16 h
Step B

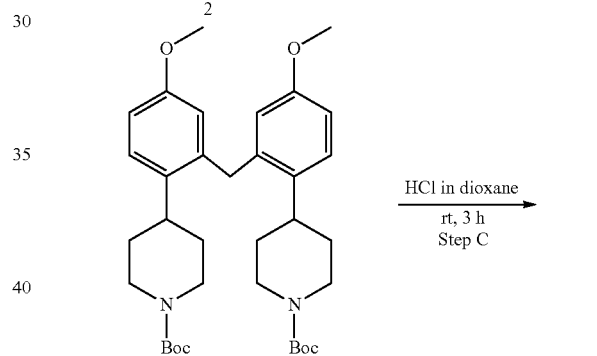

HCl in dioxane
──────────────→
rt, 3 h
Step C

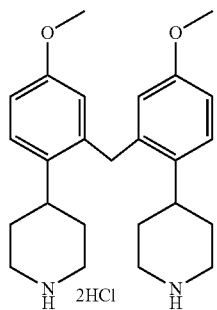

TJU-A194

Step A

To a solution of bis(2-bromo-6-methoxyphenyl)methane (300 mg, 0.78 mmol) and tert-butyl 4-(4,4,5,5-tetramethyl-1,3,2-dioxaborolan-2-yl)-3,6-dihydropyridine-1(2H)-carboxylate (602 mg, 1.95 mmol) in dioxane (12 mL) and H₂O (3 mL) were added Pd(dppf)Cl₂·dichloromethane (57 mg, 0.08 mmol) and sodium carbonate (248 mg, 2.34 mmol) under nitrogen, the reaction mixture was stirred at 110° C.

for 16 h. After completion, the reaction mixture was quenched with water (20 mL) and extracted with ethyl acetate (30 mL×3). The combined organic layer was washed with brine (50 mL), dried over sodium sulfate, concentrated to afford a residue which was purified by prep-TLC (EA/PE=1/4, v/v) to afford di-tert-butyl 4,4'-(methylenebis(3-methoxy-2,1-phenylene))bis(3,6-dihydropyridine-1(2H)-carboxylate) (250 mg, 54%) as a yellow oil.

Mass Spectrum (ESI) m/z=613.3 (M+Na)$^+$.

Step B

To a solution of di-tert-butyl 4,4'-(methylenebis(3-methoxy-2,1-phenylene))bis(3,6-dihydropyridine-1(2H)-carboxylate) (220 mg, 0.37 mmol) in methanol (10 mL) was added Pd/C (50 mg, 10%) under H$_2$ and the reaction mixture was stirred for 16 h. After completion, the reaction mixture was filtered and the filtrate was concentrated to afford a residue which was purified by prep-TLC (EA/PE=1/5, v/v) to get di-tert-butyl 4,4'-(methylenebis(3-methoxy-2,1-phenylene))bis(piperidine-1-carboxylate) (165 mg, 74%) as a white solid.

Mass Spectrum (ESI) m/z=618.2 (M+Na)$^+$.

Step C

A solution of di-tert-butyl 4,4'-(methylenebis(3-methoxy-2,1-phenylene))bis(piperidine-1-carboxylate) (20 mg, 0.03 mmol) in 4M HCl in dioxane (4 mL) was stirred at room temperature for 3 h. After completion, the reaction mixture was concentrated to get bis(2-methoxy-6-(piperidin-4-yl)phenyl)methane (15.60 mg, 82%) as a white solid.

Mass Spectrum (ESI) m/z=198.3 (1/2M+H)$^+$.

$^1$H NMR (400 MHz, DMSO-d6) δ 8.78-8.54 (m, 4H), 7.23 (t, J=8.0 Hz, 2H), 6.91 (d, J=8.0 Hz, 2H), 6.73 (d, J=8.0 Hz, 2H), 4.17 (s, 2H), 3.87 (s, 6H), 3.21 (d, J=12.0 Hz, 4H), 2.89-2.84 (m, 2H), 2.45-2.40 (m, 4H), 1.66 (dd, J=24.0 Hz, 12.0 Hz, 4H), 1.05 (d, J=12.0 Hz, 4H).

Example 82: 2,2'-((2-((1-((2-methoxynaphthalen-1-yl)methyl)naphthalen-2-yl)oxy)ethyl)azanediyl)bis(ethan-1-ol) (A195)

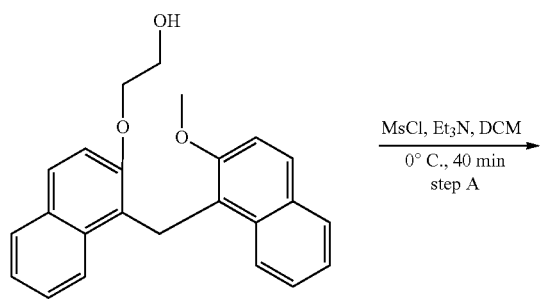

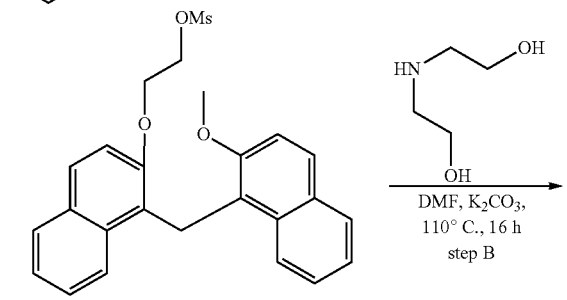

Step A

To a solution of 2-((1-((2-methoxynaphthalen-1-yl)methyl)naphthalen-2-yl)oxy)ethan-1-ol (500 mg, 1.40 mmol) and triethylamine (424 mg, 4.20 mmol) in dichloromethane (8 mL) at 0° C. was added MsCl (209 mg, 1.82 mmol), the reaction mixture was stirred at 0° C. for 40 min. After completion, the reaction mixture was quenched with water (20 mL×3), washed with brine (20 mL), dried over with sodium sulfate, concentrated to afford 2-((1-((2-methoxynaphthalen-1-yl)methyl)naphthalen-2-yl)oxy)ethyl methanesulfonate (610 mg, 99%) as a white solid.

Mass Spectrum (ESI) m/z=459.1 (M+Na)$^+$.

Step B

To a solution of 2-((1-((2-methoxynaphthalen-1-yl)methyl)naphthalen-2-yl)oxy)ethyl methanesulfonate (610 mg, 1.40 mmol) in N,N-dimethylformamide (20 mL) were added 2,2'-azanediylbis(ethan-1-ol) (191 mg, 1.82 mmol) and potassium carbonate (580 mg, 4.20 mmol), the reaction mixture was stirred at 100° C. for 16 h. After completion, the reaction mixture was quenched with water (25 mL) and extracted with dichloromethane (40 mL×3). The combined organic layer washed with brine (80 mL), dried over sodium sulfate and concentrated to afford a residue which was purified by prep-TLC (ethyl acetate, R$_f$=0.3 to afford 2,2'-((2-((1-((2-methoxynaphthalen-1-yl)methyl)naphthalen-2-yl)oxy)ethyl)azanediyl)bis(ethan-1-ol) (100 mg, 16%) as a colorless oil.

Mass Spectrum (ESI) m/z=446.1 (M+H$^+$).

$^1$H NMR (400 MHz, DMSO-d6) δ 8.04 (dd, J=12.0 Hz, 8.0 Hz, 2H), 7.82-7.65 (m, 4H), 7.48-7.44 (m, 2H), 7.30-7.10 (m, 4H), 4.79 (s, 2H), 4.34 (s, 2H), 4.23 (t, J=8.0 Hz, 2H), 3.99 (s, 3H), 3.42 (dd, J=8.0 Hz, 4.0 Hz, 4H), 2.92 (s, 2H), 2.68-2.63 (m, 4H).

Example 83: 2-methoxy-N-(2-nitronaphthalen-1-yl)naphthalen-1-amine (A196)

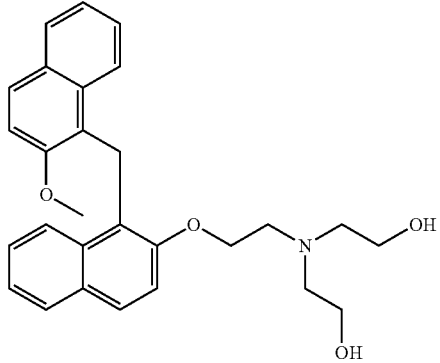

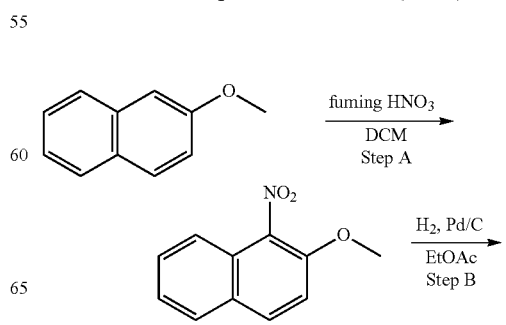

-continued

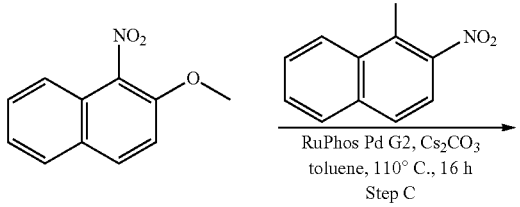

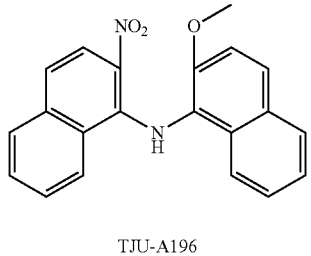

TJU-A196

Step A

To a solution of 2-methoxynaphthalene (5 g, 31.6 mmol) in DCM (100 mL) was added fuming HNO₃ (2.19 g, 34.77 mmol) dropwise at 0° C. and the reaction mixture was stirred for 3 h at room temperature. The mixture was washed with sat. NaHCO₃ (100 mL×2), brine (100 mL×2), dried over anhydrous Na₂SO₄ and concentrated under vacuum. The residue was purified by silica gel chromatography (PE/EA=8/1, v/v) to afford 2-methoxy-1-nitronaphthalene (1.77 g, 26%).

Mass Spectrum (ESI) m/z=204.1 (M+H⁺)

Step B

A suspension of 2-methoxy-1-nitronaphthalene (1.77 g, 8.72 mmol) and Pd/C (10%, 354 mg) in EtOAc (100 mL) was hydrogenated at the pressure of 60 psi for 5 h at room temperature. The mixture was filtered through celite and the filtrate was concentrated under vacuum. The residue was purified by silica gel chromatography eluted with (PE/EA=4/1, v/v) to afford 2-methoxynaphthalen-1-amine (1.4 g, 93%).

Mass Spectrum (ESI) m/z=174.2 (M+H⁺)

Step C

A mixture of 2-methoxynaphthalen-1-amine (350 mg, 2.02 mmol), 1-bromo-2-nitronaphthalene (508 mg, 2.02 mmol), RuPhos Pd G2 (155.4 mg, 0.20 mmol) and Cs₂CO₃ (1.98 g, 6.06 mmol),) in toluene (30 mL) was stirred at 110° C. under N₂ for 17 h. The reaction mixture was concentrated and the residue was purified by silica gel chromatography eluted with (PE/EA=4/1, v/v) to afford 2-methoxy-N-(2-nitronaphthalen-1-yl)naphthalen-1-amine (180 mg, 26%).

Mass Spectrum (ESI) m/z=345.2 (M+H⁺); 367.1 (M+Na⁺).

¹H NMR (400 MHz, DMSO-d6) δ 9.84 (s, 1H), 8.17 (d, J=8.5 Hz, 1H), 8.01-7.85 (m, 5H), 7.63-7.54 (m, 2H), 7.45-7.37 (m, 3H), 7.26-7.18 (m, 1H), 3.40 (s, 3H).

Step D

To a solution of 2-methoxy-N-(2-nitronaphthalen-1-yl) naphthalen-1-amine (90 mg, 0.26 mmol) in THF (5 mL) was added NaH (104.8 mg, 2.62 mmol) at 0° C. The reaction mixture was stirred at 0° C. for 0.5 h, then CH₃I (184.6 mg, 1.3 mmol) was added, the reaction mixture was stirred at 70° C. for 16 h. After completion, the reaction mixture was quenched with H₂O (50 mL) at 0° C. and extracted with ethyl acetate (10 mL×3). The combined organic layer was washed with brine (40 mL×3), dried over anhydrous Na₂SO₄ and concentrated in vacuo. The residue was purified by prep-TLC (PE/EA=1/1, v/v) to afford 2-methoxy-N-methyl-N-(2-nitronaphthalen-1-yl)naphthalen-1-amine (50 mg, 55%) as a brown oil.

Mass Spectrum (ESI) m/z=360.0 (M+H⁺), 382.1 (M+Na⁺).

¹H NMR (400 MHz, CDCl₃) 8.10 (d, J=8.5 Hz, 1H), 7.90 (d, J=8.8 Hz, 1H), 7.80-7.73 (m, 4H), 7.47-7.29 (m, 5H), 7.11-7.07 (m, 1H), 3.85 (s, 3H), 3.48 (s, 3H).

Example 84: 1-((2-methoxynaphthalen-1-yl)methyl)naphthalen-2-yl diethylglycinate (A232)

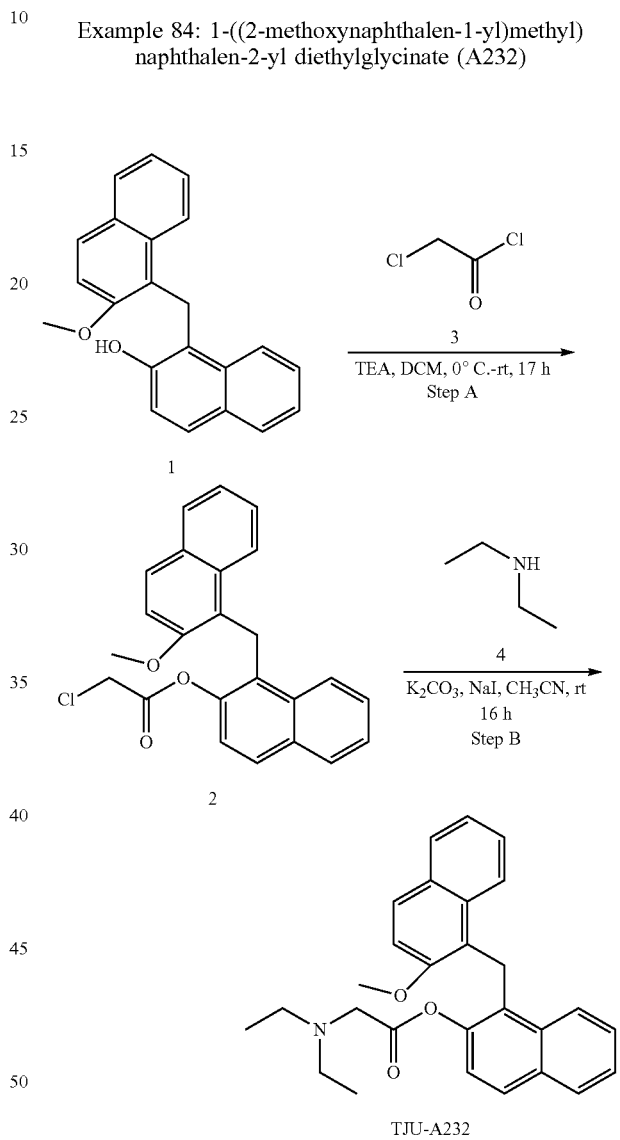

TJU-A232

Step A

To a solution of 1-((2-methoxynaphthalen-1-yl)methyl)naphthalen-2-ol (100 mg, 0.26 mmol) and triethyl amine (79 mg, 0.78 mmol) in dry dichloromethane (3 mL) was chloroacetyl chloride (35 mg, 0.31 mmol) under 0° C. The mixture was stirred for 17 h at room temperature. After completion, the mixture was diluted with water (10 mL) and extracted with dichloromethane (10 mL×3). The organic phase was dried over anhydrous sodium sulfate and concentrated to afford crude 1-((2-methoxynaphthalen-1-yl)methyl)naphthalen-2-yl 2-chloroacetate (170 mg) as yellow oil which was used to next step without purification.

Mass Spectrum (ESI) m/z=413.1 (M+Na⁺).

Step B

To a solution of 1-((2-methoxynaphthalen-1-yl)methyl)naphthalen-2-yl 2-chloroacetate (170 mg, 0.44 mmol) and diethylamine (35 mg, 0.48 mmol) in acetonitrile (30 mL) were added sodium iodide (33 mg, 0.22 mmol) and potassium carbonate (121 mg, 0.88 mmol), the reaction mixture was stirred at room temperature for 16 h. After concentration, the residue was purified by flash column chromatography (dichloromethane/methanol=15/1, v/v) to afford 1-((2-methoxynaphthalen-1-yl)methyl)naphthalen-2-yl diethylglycinate (60 mg, 0.14 mmol, 31%) as a white solid.

Mass Spectrum (ESI) m/z=428.2 (M+H$^+$).

$^1$H NMR (400 MHz, CD$_3$OD) δ 8.31-8.34 (m, 1H), 8.07 (d, J=8.0 Hz, 1H), 7.87-7.85 (m, 1H), 7.80-7.73 (m, 3H), 7.46-7.44 (m, 2H), 7.32-7.28 (m, 3H), 7.10 (d, J=8.0 Hz, 1H), 4.81 (s, 2H), 3.62 (s, 3H), 2.90 (s, 2H), 2.51-2.45 (m, 4H), 0.96 (t, J=8.0 Hz, 6H).

Example 85: (2-hydroxynaphthalen-1-yl)(2-(2-(pyrrolidin-1-yl)ethoxy)naphthalen-1-yl)methanone (A234)

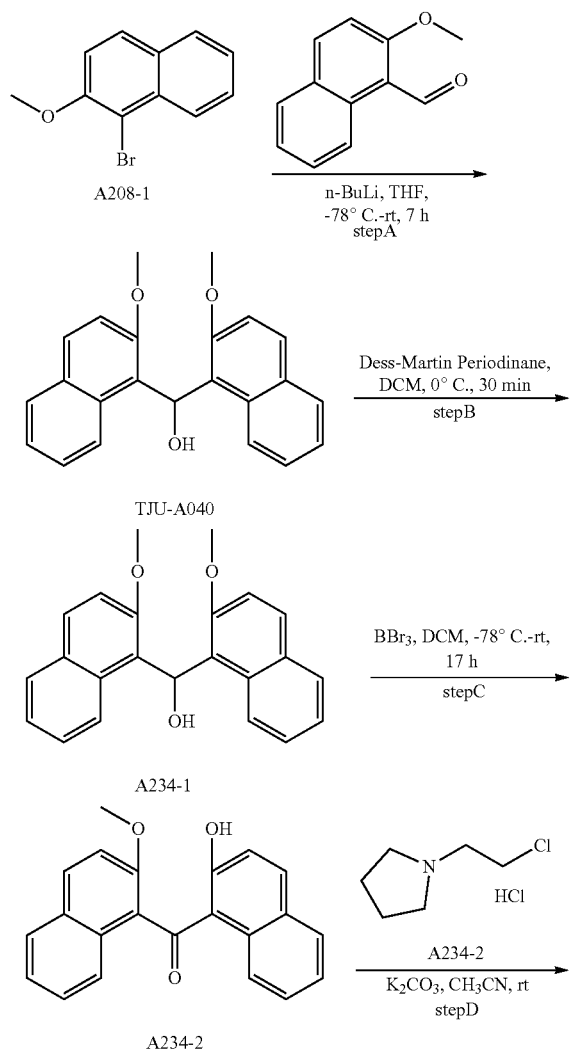

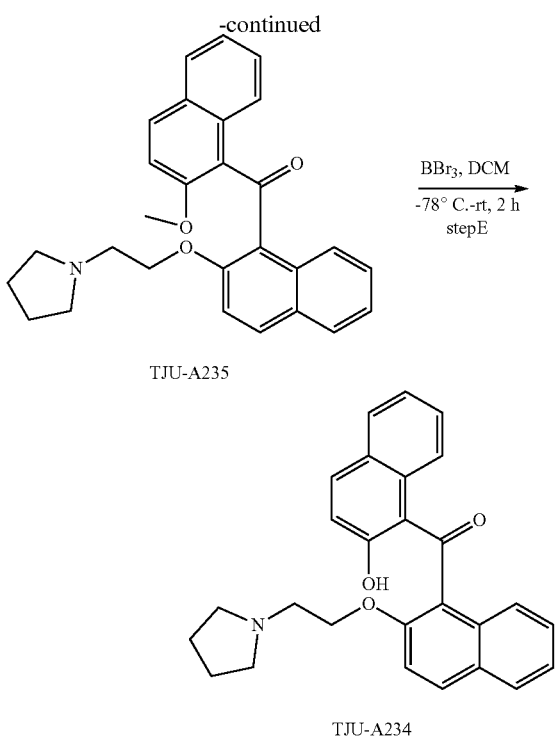

To a solution of 1-bromo-2-methoxynaphthalene (5.0 g, 21.09 mmol) in THF (60 mL) was added n-butyllithium (9.6 mL, 2.4 M) at −78° C. The mixture was stirred for 1 h at room temperature. 2-methoxy-1-naphthaldehyde (2.8 g, 14.76 mmol) in THF (20 mL) was added at −78° C. and the mixture was stirred for 6 h at room temperature. Upon completion, the mixture was quenched with sat. NH$_4$Cl (20 mL) at −78° C. and extracted with EtOAc (30 mL×3), dried over Na$_2$SO$_4$, filtered and concentrated in vacuo. The crude bis(2-methoxynaphthalen-1-yl)methanol was purified by flash chromatography (PE/EA=10/1, v/v) to afford bis(2-methoxynaphthalen-1-yl)methanol(3.0 g, 42%) as a white solid.

Mass Spectrum (ESI) m/z=367.1 [M+Na$^+$].

$^1$H NMR (400 MHz, DMSO-d6) δ 8.78 (d, J=8.7 Hz, 2H), 7.81 (d, J=8.9 Hz, 4H), 7.36-7.34 (m, 7H), 5.93 (d, J=5.5 Hz, 1H), 3.47 (s, 6H).

Step B

To a solution of bis(2-methoxynaphthalen-1-yl)methanol (3.0 g, 8.75 mmol) in DCM (30 mL) was added Dess-Martin Periodinane (7.5 g, 17.49 mmol) at 0° C. and the mixture was stirred for 1.5 h at 0° C. Upon completion, the reaction mixture was quenched with a 1:1 mixed solution of sat. NaHCO$_3$: 10% aq. Na$_2$S$_2$O$_5$. The mixture was stirred until both layers became clear. The layers were separated and the organic phase was washed with sat. NaHCO$_3$ (60 mL). The aqueous phase was extracted with DCM (60 mL×3). The organic extracts were combined, dried over Na$_2$SO$_4$, filtered and concentrated in vacuo. The crude bis(2-methoxynaphthalen-1-yl)methanone was purified by flash chromatography (EA/PE=1/10, v/v) to afford bis(2-methoxynaphthalen-1-yl)methanone(1.5 g, 50%) as a white solid.

Mass Spectrum (ESI) m/z=343.1 [M+H$^+$].

Step C

To a solution of bis(2-methoxynaphthalen-1-yl)methanone (1.5 g, 4.37 mmol) in DCM (50 mL) was added BBr$_3$ (4.4 mL, 1.0 M) at −78° C. The reaction mixture was stirred for 16 h at room temperature. Upon completion, the mixture was quenched with MeOH (30 mL) at room temperature and extracted with EtOAc (10 mL×3), dried over Na$_2$SO$_4$, filtered and concentrated in vacuo. The crude (2-hydroxynaphthalen-1-yl)(2-methoxynaphthalen-1-yl)methanone was purified by flash chromatography (EA/PE=1/10, v/v) to afford pure (2-hydroxynaphthalen-1-yl)(2-methoxynaphthalen-1-yl)methanone (0.6 g, 42%) as a yellow solid.

Mass Spectrum (ESI) m/z=329.0 [M+H$^+$].

Step D

To a solution of (2-hydroxynaphthalen-1-yl)(2-methoxynaphthalen-1-yl)methanone (100.0 mg, 0.31 mmol) and 1-(2-chloroethyl)pyrrolidine hydrochloride (53.0 mg, 0.31 mmol) in MeCN (3 mL) were added K$_2$CO$_3$ (124.0 mg, 0.93 mmol) and catalytic amount of NaI. The reaction mixture was stirred at room temperature overnight. After completion, the reaction mixture was diluted with water (3 mL) and extracted with EtOAc (4 mL×3). The combined organic layer was washed with brine and dried over Na$_2$SO$_4$, filtered and concentrated under vacuum. The crude was purified by prep-TLC to afford (2-methoxynaphthalen-1-yl)(2-(2-(pyrrolidin-1-yl)ethoxy)naphthalen-1-yl)methanone (130.0 mg, 98%) as a yellow solid.

Mass Spectrum (ESI) m/z=426.2 [M+H$^+$].

$^1$H NMR (400 MHz, DMSO-d6) δ 8.08 (d, J=9.1 Hz, 1H), 8.02 (s, 1H), 7.96 (d, J=8.0 Hz, 1H), 7.90-7.84 (m, 2H), 7.75 (d, J=8.5 Hz, 1H), 7.57-7.47 (m, 3H), 7.44-7.40 (m, 2H), 7.36 (t, J=7.5 Hz, 1H), 4.02 (t, J=5.8 Hz, 2H), 3.68 (s, 3H), 2.27 (s, 2H), 2.13 (s, 4H), 1.41 (s, 4H).

Step E

To a solution of (2-methoxynaphthalen-1-yl)(2-(2-(pyrrolidin-1-yl)ethoxy)naphthalen-1-yl)methanone (50.0 mg, 0.12 mmol) in DCM (1 mL) was added BBr$_3$ (0.3 mL, 1.0 M) at −78° C. The reaction mixture was stirred for 3 h at room temperature. Upon completion, the mixture was quenched with MeOH (2 mL) at room temperature and extracted with EtOAc (2 mL×3), dried over Na$_2$SO$_4$, filtered and concentrated in vacuo. The crude (2-hydroxynaphthalen-1-yl)(2-(2-(pyrrolidin-1-yl)ethoxy)naphthalen-1-yl)methanone was purified by prep-TLC to afford pure (2-hydroxynaphthalen-1-yl)(2-(2-(pyrrolidin-1-yl)ethoxy)naphthalen-1-yl)methanone (30.0 mg, 61%) as a yellow solid.

Mass Spectrum (ESI) m/z=412.5 [M+H$^+$].

$^1$H NMR (400 MHz, DMSO-d6) δ 11.09 (s, 1H), 8.18 (d, J=9.2 Hz, 1H), 8.03-7.99 (m, 1H), 7.97 (s, 1H), 7.78 (d, J=9.0 Hz, 2H), 7.63 (d, J=9.1 Hz, 1H), 7.58-7.51 (m, 2H), 7.49-7.43 (m, J=8.0, 6.7, 1.4 Hz, 2H), 7.39 (s, 1H), 7.30-7.24 (m, 1H), 4.23-4.15 (m, 2H), 2.16 (s, 4H), 1.32 (t, J=9.4 Hz, 4H), 1.24 (t, J=6.6 Hz, 2H).

Example 86: N-(2-(diethylamino)ethyl)-1-((2-methoxynaphthalen-1-yl)methyl)-2-naphthamide

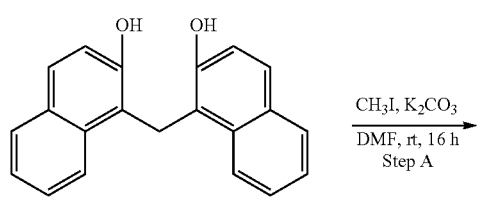

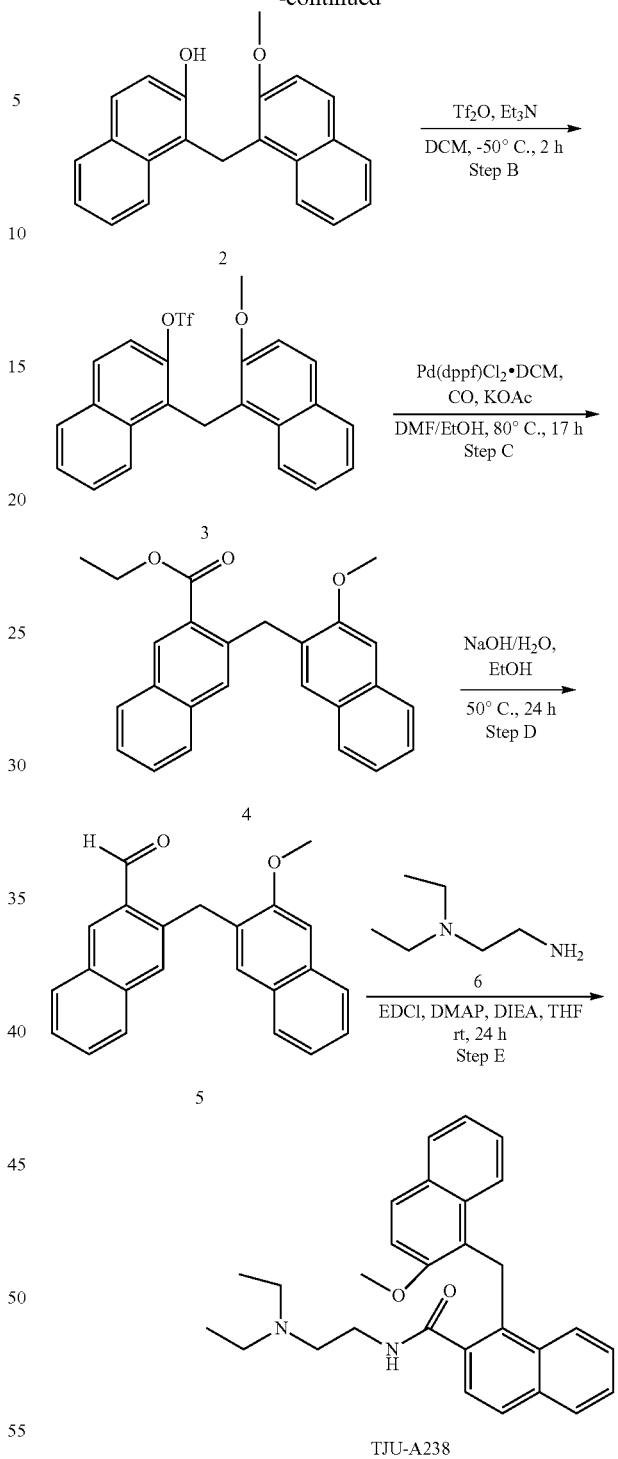

Step A

To a solution of 1,1'-methylenebis(naphthalen-2-ol) (2 g, 7 mmol) in anhydrous DMF (10 mL) were added K$_2$CO$_3$ (1.16 g, 8 mmol) and CH$_3$I (1.14 g, 8 mmol). The reaction mixture was stirred at room temperature under N$_2$ for 16 h. The reaction mixture was diluted with water (30 mL) and extracted with ethyl acetate (100 mL×3). The combined organic layer was washed with brine (30 mL×2), dried over anhydrous Na$_2$SO$_4$ and concentrated. The residue was purified by flash column chromatography on silica gel (PE/

EA=8/1, v/v) to afford 1-((2-methoxynaphthalen-1-yl)methyl)naphthalen-2-ol (1.18 g, 54%) as a white solid.

Mass Spectrum (ESI) m/z=337.1 (M+Na+).

¹H NMR (400 MHz, DMSO-d₆) δ 10.09 (s, 1H), 8.25 (d, J=8.3 Hz, 1H), 7.96 (d, J=8.5 Hz, 1H), 7.78-7.76 (m, 2H), 7.63-7.61 (m, 2H), 7.53-7.51 (m, 1H), 7.22-7.20 (m, 4H), 7.11 (t, J=7.1 Hz, 1H), 4.76 (s, 2H), 4.09 (s, 3H).

Step B

To a solution of 1-((2-methoxynaphthalen-1-yl)methyl)naphthalen-2-ol (1.1 g, 4 mmol) and Et₃N (1.67 mL, 12 mmol) in DCM (20 mL) was added trifluoromethanesulfonic anhydride (2.0 mL, 12 mmol) at −50° C. over a 30 min period. The reaction mixture was stirred at −50° C. for 2 h. Sat. NH₄Cl was added to quench the reaction and the mixture was extracted with DCM (50 mL×3). The organic phase was washed with 5% aq. HCl, sat. NaHCO₃ and brine, dried over Na₂SO₄ and concentrated. The residue was purified by silica gel column chromatography (PE/EA=10/1, v/v) to afford 1-((2-methoxynaphthalen-1-yl)methyl)naphthalen-2-yl trifluoromethanesulfonate (1.76 g, 95%) as a white solid.

Step C

To a solution of 1-((2-methoxynaphthalen-1-yl)methyl)naphthalen-2-yl trifluoromethanesulfonate (470 mg, 1.05 mmol), Pd(dppf)Cl₂·DCM (86 mg, 0.11 mmol) and KOAc (207 mg, 2.11 mmol) in EtOH/DMF (20/4 mL) was stirred for 17 h at 80° C. under CO atmosphere. The mixture was concentrated and purified by flash column (EA/PE=1/1, v/v) to afford ethyl 3-((3-methoxynaphthalen-2-yl)methyl)-2-naphthoate (370 mg, 94%) as an off-white solid.

Mass Spectrum (ESI) m/z=393.2 (M+Na+).

Step D

To a solution of ethyl 3-((3-methoxynaphthalen-2-yl)methyl)-2-naphthoate (370 mg, 1.0 mmol) in EtOH (9 mL) was added NaOH (160 mg, 4.0 mmol) in H₂O (3 mL). The mixture was stirred at 50° C. for 24 h. The mixture was concentrated and the residue was diluted with water, adjusted to pH=3 with 4 mol/L HCl. The precipitate was collected by filtration to give 3-((3-methoxynaphthalen-2-yl)methyl)-2-naphthoic acid (340 mg, 99%) as white solid.

Mass Spectrum (ESI) m/z=365.1 (M+H+).

Step E

To a solution of 3-((3-methoxynaphthalen-2-yl)methyl)-2-naphthoic acid (136.8 mg, 0.4 mmol), N1,N1-diethylethane-1,2-diamine (93.0 mg, 0.8 mmol), DMAP (89 mg, 0.48 mmol) and DIEA (103.4 mg, 0.8 mmol) was added EDCI (92 mg, 0.48 mmol) at room temperature. The mixture was stirred for 24 h at room temperature. The mixture was concentrated and purified by pre-HPLC to give N-(2-(diethylamino)ethyl)-1-((2-methoxynaphthalen-1-yl)methyl)-2-naphthamide (40.1 mg, 30%) as a white solid.

Mass Spectrum (ESI) m/z=441.3 (M+H+)

¹H NMR (400 MHz, DMSO-d6) δ 8.33 (t, J=5.6 Hz, 1H), 8.12-8.08 (m, 1H), 7.95 (d, J=8.6 Hz, 1H), 7.85-7.74 (m, 4H), 7.47 (dd, J=8.7 Hz, 5.9 Hz, 2H), 7.36 (t, J=7.5 Hz, 1H), 7.25-7.20 (m, 3H), 4.99 (s, 2H), 3.87 (s, 3H), 3.35-3.33 (m, 2H), 2.55 (s, 2H), 2.47 (d, J=7.2 Hz, 4H), 0.89-0.87 (m, J=7.1 Hz, 6H).

Example 87: 2-((1-((2-(ethoxymethoxy)naphthalen-1-yl)methyl)naphthalen-2-yl)oxy)ethan-1-amine (A244)

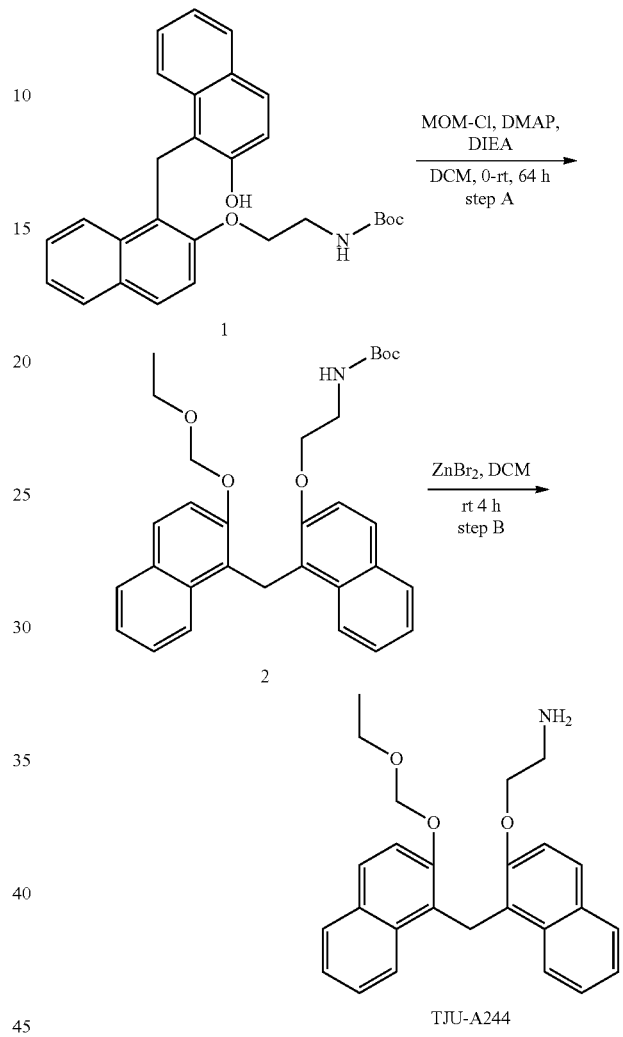

Step A

To a solution of tert-butyl (2-((1-((2-hydroxynaphthalen-1-yl)methyl)naphthalen-2-yl)oxy)ethyl)carbamate (300 mg, 0.68 mmol) in dichloromethane (9 mL) were added (chloromethoxy)ethane (129.2 mg, 1.36 mmol), diisopropyl ethylamine (263.2 mg, 2.04 mmol) and DMAP (41.48 mg, 0.34 mmol) at 0° C. under nitrogen. The reaction mixture was stirred at room temperature for 64 h. After completion, the mixture was quenched with water (30 mL) and extracted with ethyl acetate (30 mL×3). The combined organic layer was washed with brine (30 mL) and dried over anhydrous sodium sulfate and concentrated. The residue was purified by prep-TLC (EA/PE=5/1, v/v) to afford tert-butyl (2-((1-((2-(ethoxymethoxy)naphthalen-1-yl)methyl)naphthalen-2-yl)oxy)ethyl)carbamate (159 mg, 46%) as a yellow solid.

Mass Spectrum (ESI) m/z=524.2 (M+Na+).

Step B

To a solution of tert-butyl (2-((1-((2-(ethoxymethoxy)naphthalen-1-yl)methyl)naphthalen-2-yl)oxy)ethyl)carbamate (140 mg, 0.28 mmol) in dichloromethane (7 mL) was added zinc bromide (560 mg, 2.49 mmol). The mixture was stirred at room temperature for 4 h. After completion, the mixture was filtered and the filtrate was concentrated. The residue was purified by prep-HPLC (Chromatographic columns: Xbridge-C18 150×19*50 mm, 5 um; Mobile Phase: ACN-H$_2$O (0.05% NH$_3$); Gradient:60-70) to afford 2-((1-((2-(ethoxymethoxy)naphthalen-1-yl)methyl)naphthalen-2-yl)oxy)ethan-1-amine (27.30 mg, 24%) as a yellow solid.

Mass Spectrum (ESI) m/z=402.2 (M+H$^+$).

$^1$H NMR (400 MHz, DMSO-d6) δ 8.11 (d, J=12.0 Hz, 2H), 7.83-7.74 (m, 4H), 7.47 (dd, J=12.0 Hz, 8.0 Hz, 2H), 7.31-7.18 (m, 4H), 5.37 (s, 2H), 4.88 (s, 2H), 4.19 (t, J=4.0 Hz, 2H), 3.61 (q, J=8.0 Hz, 2H), 2.97 (d, J=4.0 Hz, 2H), 1.23 (s, 2H), 1.11 (t, J=8.0 Hz, 3H).

Example 88: 2-((1-((2-isopropoxynaphthalen-1-yl)methyl)naphthalen-2-yl)oxy)ethan-1-amine (A246)

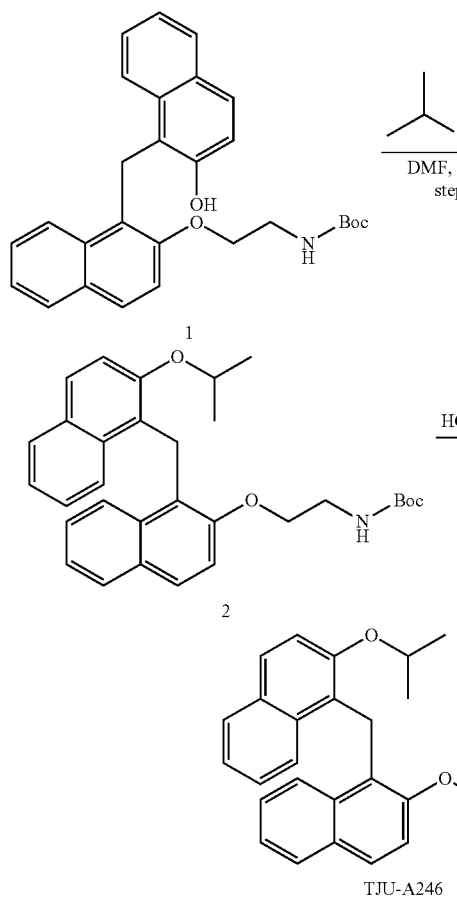

Step A

To a solution of tert-butyl (2-((1-((2-hydroxynaphthalen-1-yl)methyl)naphthalen-2-yl)oxy)ethyl)carbamate (200 mg, 0.45 mmol) in N,N-dimethylformamide (6 mL) at 0° C. were added potassium carbonate (93.2 mg, 0.68 mmol) and 2-iodopropane (76.5 mg, 0.45 mmol) under nitrogen, the mixture was stirred at room temperature for 16 h. After completion, the mixture was quenched with water (40 mL) and extracted with ethyl acetate (40 mL×3). The combined organic layer was washed with brine (40 mL) and dried over anhydrous sodium sulfate and concentrated. The residue was purified by prep-TLC (EA/PE=1/7, v/v) to afford tert-butyl (2-((1-((2-isopropoxynaphthalen-1-yl)methyl)naphthalen-2-yl)oxy)ethyl)carbamate (110.0 mg, 50%) as a yellow oil.

Mass Spectrum (ESI) m/z=508.2 (M+Na$^+$).

Step B

A solution of tert-butyl (2-((1-((2-isopropoxynaphthalen-1-yl)methyl)naphthalen-2-yl)oxy)ethyl)carbamate (100 mg, 0.21 mmol) in HCl/ethyl acetate (5 mL) was stirred at room temperature for 3 h. After completion, the mixture was concentrated to afford crude 2-((1-((2-isopropoxynaphthalen-1-yl)methyl)naphthalen-2-yl)oxy)ethan-1-amine (79.42 mg, 100%) as a white solid.

Mass Spectrum (ESI) m/z=386.3 (M+H$^+$).

$^1$H NMR (400 MHz, DMSO-d6) δ 8.24 (s, 2H), 8.12-8.01 (m, 2H), 7.84-7.73 (m, 4H), 7.51-7.43 (m, 2H), 7.34-7.20 (m, 4H), 4.89 (s, 2H), 4.86-4.80 (m, 1H), 4.35 (t, J=8.0 Hz, 2H), 3.17 (t, J=8.0 Hz, 2H), 1.23(d, J=4.0 Hz, 6H).

Example 89: 1-(2-((1-((2-(ethoxymethoxy)naphthalen-1-yl)methyl)naphthalen-2-yl)oxy)ethyl)pyrrolidine (A254)

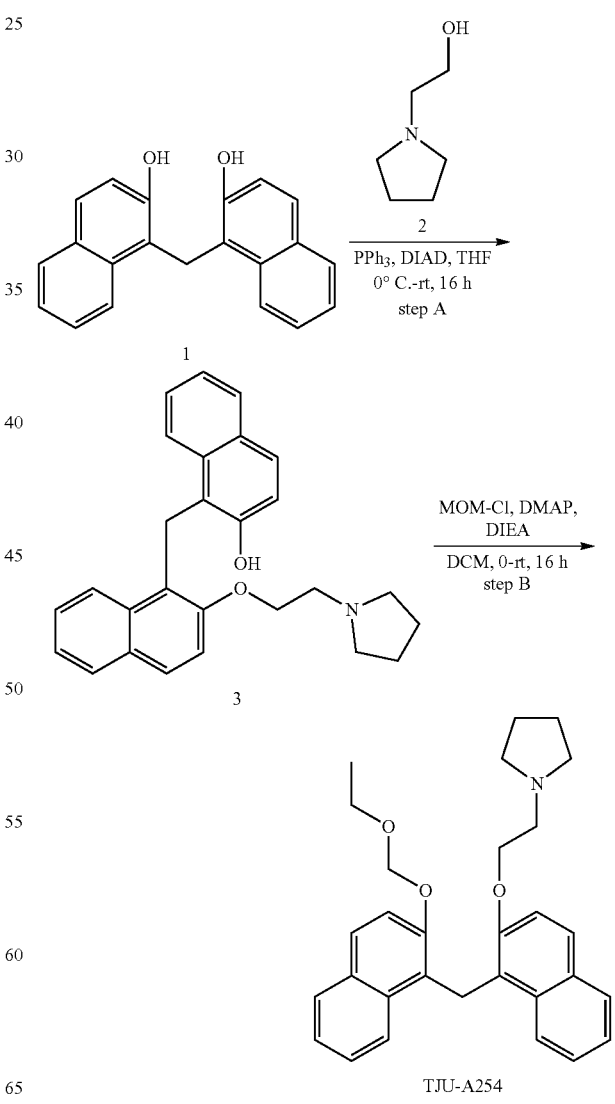

Step A

To a solution of 1,1'-methylenebis(naphthalen-2-ol) (6 g, 20.00 mmol) in tetrahydrofuran (80 mL) were added 2-(pyrrolidin-1-yl)ethan-1-ol (2.23 g, 20.00 mmol) and triphenyl phosphine (5.78 g, 22.00 mmol) and DIAD (4.44 g, 22.00 mmol) at 0° C. under nitrogen, the reaction mixture was stirred for 16 h at room temperature. After completion, the mixture was quenched with water (50 mL) and extracted with ethyl acetate (80 mL×3). The combined organic layer was washed with brine (80 mL), dried over anhydrous sodium sulfate and concentrated. The residue was purified by column chromatography (dichloromethane/methanol=20/1, v/v) to afford 1-((2-(2-(pyrrolidin-1-yl)ethoxy)naphthalen-1-yl)methyl)naphthalen-2-ol (3.55 g, 44%) as a yellow solid.

Mass Spectrum (ESI) m/z=398.2 (M+H$^+$).

Step B

To a solution of 1-((2-(2-(pyrrolidin-1-yl)ethoxy)naphthalen-1-yl)methyl)naphthalen-2-ol (100 mg, 0.25 mmol) in dichloromethane (6 mL) were added (chloromethoxy)ethane (48 mg, 0.50 mmol), diisopropyl ethylamine (97 mg, 0.75 mmol) and DMAP (15 mg, 0.12 mmol) at 0° C. under nitrogen. The reaction mixture was stirred at room temperature for 16 h. After completion, the mixture was quenched with water (20 mL) and extracted with dichloromethane (30 mL×3). The combined organic layer was washed with brine (20 mL) and dried over anhydrous sodium sulfate and concentrated. The residue was purified by prep-HPLC (Chromatographic columns: Kromasil-C18 100*21.2 mm 5 um; Mobile phase: ACN-H$_2$O (0.1% FA)) to afford 1-(2-((1-((2-(ethoxymethoxy)naphthalen-1-yl)methyl)naphthalen-2-yl)oxy)ethyl)pyrrolidine (114 mg, 99%) as a white solid.

Mass Spectrum (ESI) m/z=456.2 (M+H$^+$).

$^1$H NMR (400 MHz, DMSO-d6) δ 8.23 (d, J=8.0 Hz, 1H), 7.87 (dd, J=20.0 Hz, 8.0 Hz, 2H), 7.81-7.78 (m, 1H), 7.66 (dd, J=20.0 Hz, 8.0 Hz, 2H), 7.56 (d, J=12.0 Hz, 1H), 7.31-7.11 (m, 5H), 4.80 (d, J=4.0 Hz, 4H), 4.67 (t, J=4.0 Hz, 2H), 3.93-3.83 (m, 2H), 3.76 (q, J=8.0 Hz, 2H), 3.62 (d, J=4.0 Hz, 4H), 2.08 (d, J=5.0 Hz, 4H), 1.12 (t, J=7.0 Hz, 3H).

Example 90: 1-(2-((1-((2-ethoxynaphthalen-1-yl)methyl)naphthalen-2-yl)oxy)ethyl)pyrrolidine

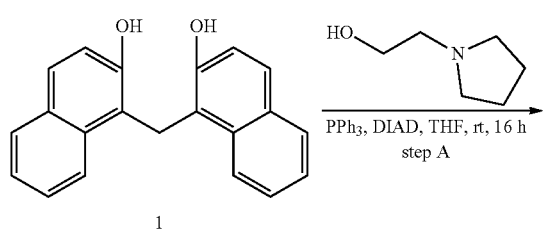

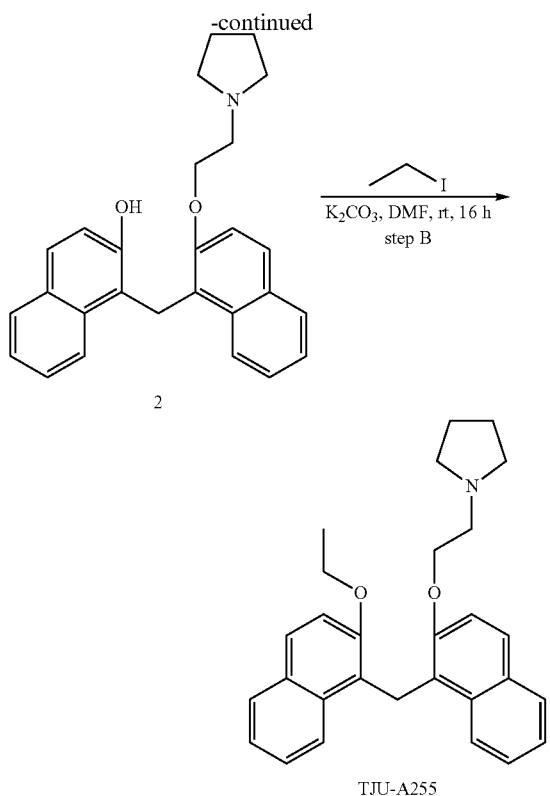

Step A

To a solution of 1,1'-methylenebis(naphthalen-2-ol) (6.0 g, 20.00 mmol) in THF (80 mL) were added 2-(pyrrolidin-1-yl)ethan-1-ol (2.2 g, 20.00 mmol), PPh$_3$ (5.8 g, 22.00 mmol) and DIAD (4.4 g, 22.00 mmol) at 0° C. under N$_2$. The mixture was stirred at room temperature for 16 h. The mixture was quenched with water (50 mL) and extracted with EtOAc (80 mL×3). The combined organic layer was washed with brine (80 mL) and dried over anhydrous Na$_2$SO$_4$ and concentrated. The residue was purified by column chromatography on silica gel (120 g) (DCM/MeOH=6/1,v/v) to afford the 1-((2-(2-(pyrrolidin-1-yl)ethoxy)naphthalen-1-yl)methyl)naphthalen-2-ol (3.6 g, 45%) as a yellow solid.

Mass Spectrum (ESI) m/z=398.2 (M+H$^+$).

Step B

To a solution of 1-((2-(2-(pyrrolidin-1-yl)ethoxy)naphthalen-1-yl)methyl)naphthalen-2-ol (100.0 mg, 0.25 mmol) in DMF (6 mL) were added K$_2$CO$_3$ (52.0 mg, 0.38 mmol) and iodoethane (39.0 mg, 0.25 mmol) at 0° C. under N$_2$. The mixture was stirred at room temperature for 16 h. The mixture was quenched with water (30 mL) and extracted with EtOAc (30 mL×3), the combined organic layer was washed with brine (40 mL) and dried over anhydrous Na$_2$SO$_4$ and concentrated. The residue was purified by prep-HPLC (Chromatographic columns: Kromasil-C18 100*21.2 mm 5 um; Mobile phase: ACN-H$_2$O (0.1% FA); Gradient: 40-50), fraction with MS signal of desired product was collected and concentrated to give 1-(2-((1-((2-ethoxynaphthalen-1-yl)methyl)naphthalen-2-yl)oxy)ethyl)pyrrolidine (20.0 mg, 19%) as a yellow solid.

Mass Spectrum (ESI) m/z=426.3 (M+H$^+$).

$^1$H NMR (400 MHz, DMSO-d6) δ 8.09 (dd, J=12.0, 8.0 Hz, 2H), 7.82-7.71 (m, 4H), 7.47 (dd, J=12.0, 8.0 Hz, 2H), 7.30-7.16 (m, 4H), 4.84 (s, 2H), 4.36-4.20 (m, 4H), 2.84-2.81 (m, 2H), 2.57 (s, 4H), 1.66 (s, 4H), 1.32 (t, J=8.0 Hz, 2H).

Example 91: 1-(2-((1-((2-isopropoxynaphthalen-1-yl)methyl)naphthalen-2-yl)oxy)ethyl)pyrrolidine (A256)

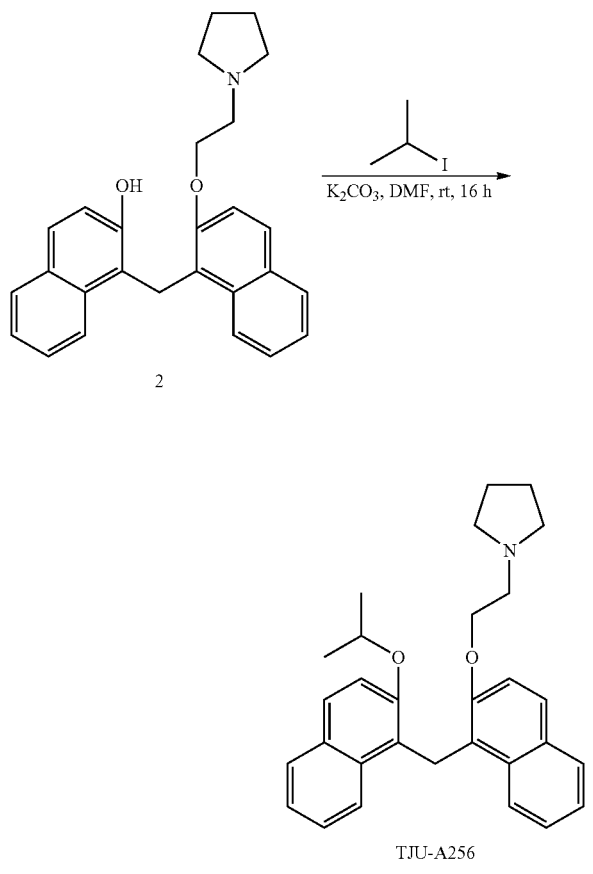

To a solution of 1-((2-(2-(pyrrolidin-1-yl)ethoxy)naphthalen-1-yl)methyl)naphthalen-2-ol (200.0 mg, 0.50 mmol) in DMF (8 mL) were added K₂CO₃ (104.0 mg, 0.75 mmol) and 2-iodopropane (85.0 mg, 0.50 mmol) at 0° C. under N₂. The mixture was stirred at rt for 16 h. Then the mixture was quenched with water (40 mL) and extracted with EtOAc (40 mL×3). The combined organic layer was washed with brine (40 mL) and dried over anhydrous Na₂SO₄ and concentrated. The residue was purified by prep-HPLC to give 1-(2-((1-((2-isopropoxynaphthalen-1-yl)methyl)naphthalen-2-yl)oxy)ethyl)pyrrolidine (14.3 mg, 6.5%) as a yellow solid.

Mass Spectrum (ESI) m/z=440.3 (M+H⁺).

¹H NMR (400 MHz, DMSO-d6) δ 8.15-8.05 (m, 2H), 7.76 (t, J=8.0 Hz, 4H), 7.46 (dd, J=16.0, 8.0 Hz, 2H), 7.30-7.17 (m, 4H), 4.88-4.76 (m, 3H), 4.27 (t, J=8.0 Hz, 2H), 2.79 (t, J=8.0 Hz, 2H), 2.55 (s, 4H), 1.78-1.58 (m, 4H), 1.22 (d, J=4.0 Hz, 6H),

Example 92: 4-(((1-((2-methoxynaphthalen-1-yl)methyl)naphthalen-2-yl)oxy)methyl)piperidine (A271) M

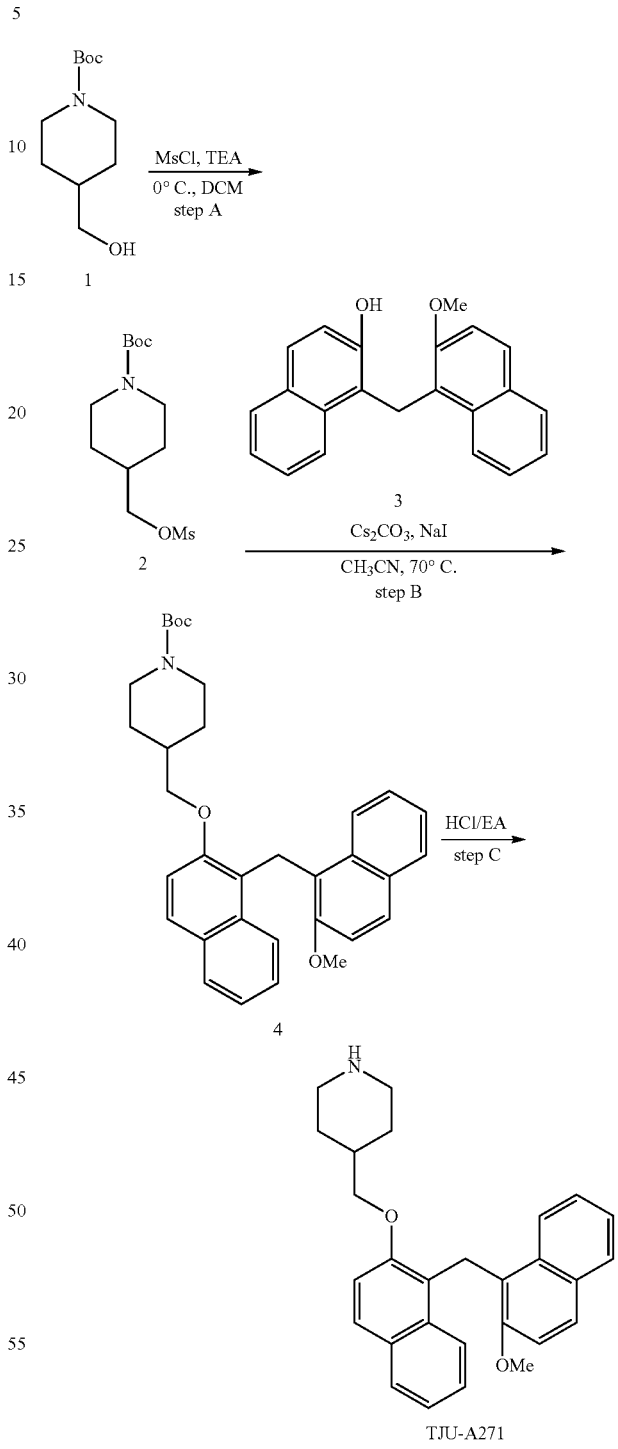

Step A

To a solution of tert-butyl 4-(hydroxymethyl)piperidine-1-carboxylate (4 g, 18.6 mmol) in dry dichloromethane(100 mL) were added MsCl (2.12 g, 18.6 mmol) and triethyl amine (2.25 g, 22.32 mmol) at 0° C., the reaction mixture was stirred at room temperature for 3 h. The reaction mixture was quenched with water and extracted with dichloromethane (50 mL×3). The combined organic layer was dried over sodium sulfate and concentrated to afford crude tert-butyl 4-(((methylsulfonyl)oxy)methyl)piperidine-1-carboxylate (5.73 g) which was used for the next step directly.

Step B

A mixture of 1-((2-methoxynaphthalen-1-yl)methyl)naphthalen-2-ol (200 mg, 0.64 mmol), tert-butyl 4-(((methylsulfonyl)oxy)methyl)piperidine-1-carboxylate (186.6 mg, 0.64 mmol), cesium carbonate (313 mg, 0.96 mmol) and sodium iodide (cat.) in acetonitrile (10 mL) was stirred at 70° C. for 17 h. After filtration, the filtrate was concentrated and the residue was purified by prep-TLC (EA/PE=2/1, v/v) to afford tert-butyl 4-(((1-((2-methoxynaphthalen-1-yl)methyl)naphthalen-2-yl)oxy)methyl)piperidine-1-carboxylate (250 mg) as a white solid.

Step C

Tert-butyl 4-(((1-((2-methoxynaphthalen-1-yl)methyl)naphthalen-2-yl)oxy)methyl)piperidine-1-carboxylate in 2N HCl/EA (3 mL) was stirred for 2 h at room temperature. The reaction mixture was concentrated to afford 4-(((1-((2-methoxynaphthalen-1-yl)methyl)naphthalen-2-yl)oxy)methyl)piperidine (25 mg).

Mass Spectrum (ESI) m/z=412.2 (M+H$^+$).

$^1$H NMR (400 MHz, DMSO-d6) δ 8.48 (s, 1H), 8.03 (dd, J=11.9 Hz, 8.4 Hz, 2H), 7.79 (d, J=8.8 Hz, 4H), 7.55-7.46 (m, 2H), 7.23 (dd, J=9.5 Hz, 7.5 Hz, 4H), 4.85 (s, 2H), 4.15 (d, J=5.6 Hz, 2H), 4.02 (s, 3H), 3.28 (d, J=12.7 Hz, 2H), 2.87 (dd, J=12.8 Hz, 10.2 Hz, 2H), 1.92 (d, J=12.6 Hz, 2H), 1.66-1.64 (m, 2H)

Example 4-(((1-((2-(ethoxymethoxy)naphthalen-1-yl)methyl)naphthalen-2-yl)oxy)methyl)piperidine (A279)

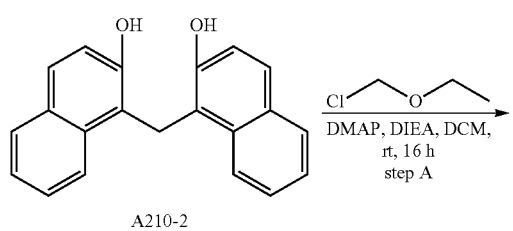

A210-2

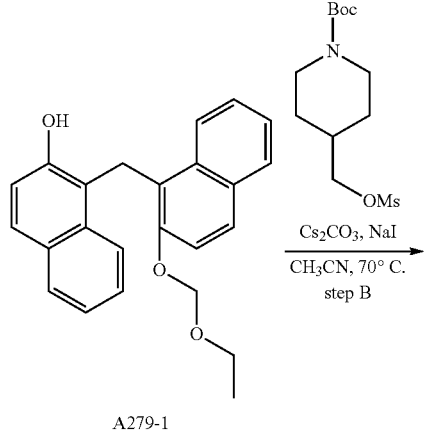

A279-1

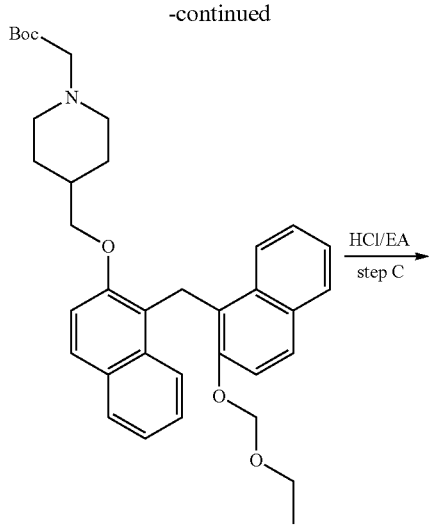

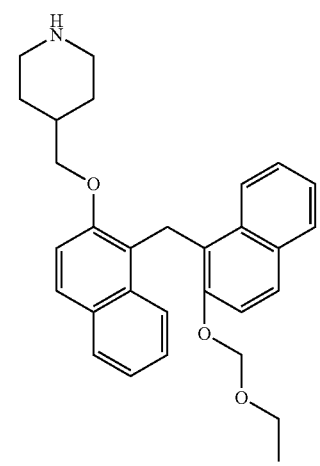

TJU-A279

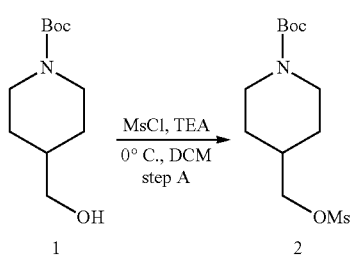

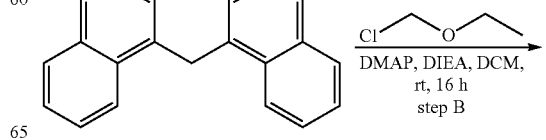

3

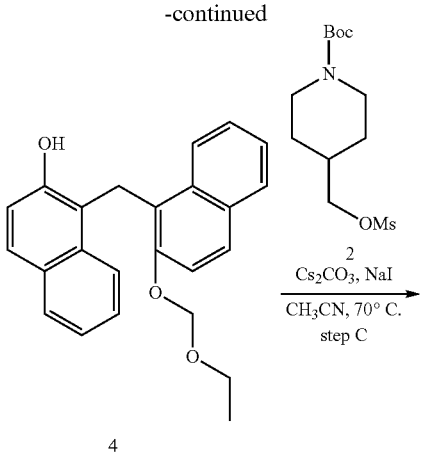

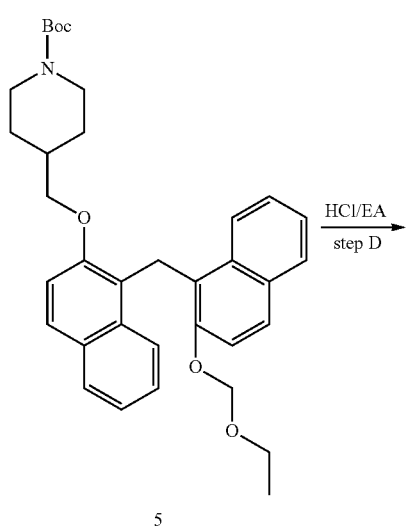

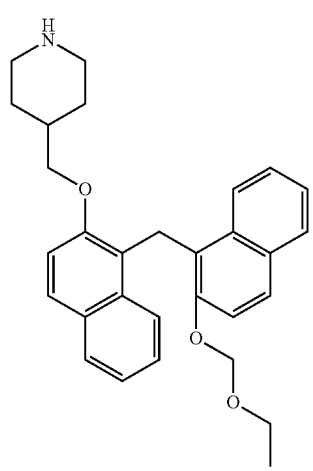

TJU-A279

Step A

To a solution of tert-butyl 4-(hydroxymethyl)piperidine-1-carboxylate (4 g, 18.6 mmol) in dry DCM (100 mL) were added MsCl (2.12 g, 18.6 mmol) and TEA (2.25 g, 22.32 mmol) at 0° C., the reaction mixture was stirred at room temperature for 3 h. The reaction mixture was quenched with water and extracted with DCM (50 mL×3). The combined organic layer was dried over $Na_2SO_4$ and concentrated to afford crude tert-butyl 4-(((methylsulfonyl)oxy)methyl)piperidine-1-carboxylate (5.73 g) which was used for the next step directly.

Step B

To a solution of 1,1'-methylenebis(naphthalen-2-ol) (204 mg, 0.68 mmol) in DCM (9 mL) were added (chloromethoxy)ethane (129.2 mg, 1.36 mmol), DIEA (263.2 mg, 2.04 mmol) and DMAP (41.48 mg, 0.34 mmol) at 0° C. under $N_2$. The reaction mixture was stirred at room temperature for 64 h. After completion, the mixture was quenched with water (30 mL) and extracted with EtOAc (30 mL×3). The combined organic layer was washed with brine (30 mL) and dried over anhydrous $Na_2SO_4$ and concentrated. to afford crude 1-((2-(ethoxymethoxy)naphthalen-1-yl)methyl)naphthalen-2-ol (220 mg) which was used for the next step directly.

Step C

A mixture of 1-((2-(ethoxymethoxy)naphthalen-1-yl)methyl)naphthalen-2-ol (229 mg, 0.64 mmol), tert-butyl 4-(((methylsulfonyl)oxy)methyl)piperidine-1-carboxylate (186.6 mg, 0.64 mmol), $Cs_2CO_3$ (313 mg, 0.96 mmol) and NaI (cat.) in $CH_3CN$ (20 mL) was stirred at 70° C. for 17 h. After filtration, the filtrate was concentrated and the residue was purified by prep-TLC (EA/PE=2/1, v/v) to afford tert-butyl 4-(((1-((2-(ethoxymethoxy)naphthalen-1-yl)methyl)naphthalen-2-yl)oxy)methyl)piperidine-1-carboxylate (200 mg, 71%) as a white solid.

Step D

A solution of tert-butyl 4-(((1-((2-(ethoxymethoxy)naphthalen-1-yl)methyl)naphthalen-2-yl)oxy)methyl)piperidine-1-carboxylate (116.6 mg, 0.21 mmol) in HCl/EtOAc (5 mL) was stirred at room temperature for 3 h. After completion, the mixture was concentrated to afford 4-(((1-((2-(ethoxymethoxy)naphthalen-1-yl)methyl)naphthalen-2-yl)oxy)methyl)piperidine (79.42 mg, 99%) as a white solid.

Mass Spectrum (ESI) m/z=456.3 (M+H$^+$).

$^1$H NMR (400 MHz, DMSO-d6) δ 8.06 (t, J=7.4 Hz, 2H), 7.77-7.74 (m, 4H), 7.50 (t, J=9.0 Hz, 2H), 7.25-7.24 (m, 4H), 5.41 (s, 2H), 4.86 (s, 2H), 4.13 (d, J=5.5 Hz, 2H), 3.67 (q, J=7.0 Hz, 2H), 3.26 (d, J=12.6 Hz, 2H), 2.84 (t, J=12.3 Hz, 2H), 1.88 (d, J=13.1 Hz, 2H), 1.58 (d, J=12.4 Hz, 2H), 1.22 (s, 1H), 1.14 (t, J=7.0 Hz, 3H).

Example 94: 2-(diethylamino)-N-(1-((2-methoxynaphthalen-1-yl)methyl)naphthalen-2-yl)acetamide (A284)

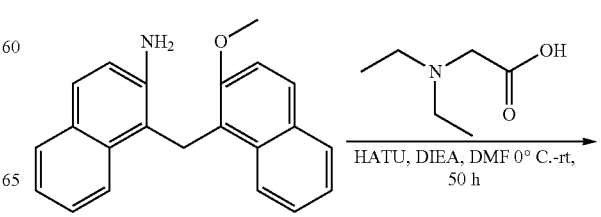

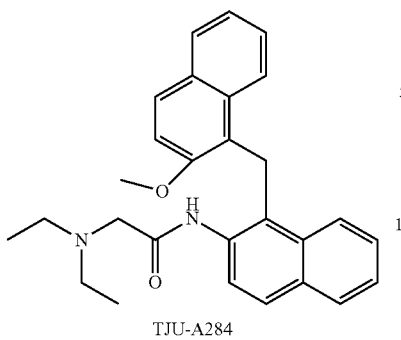

TJU-A284

HATU (365 mg, 0.96 mmol) was added to a solution of diethylglycine (105 mg, 0.80 mmol) in N,N-dimethylformamide (4 mL) at 0° C. and the mixture was stirred for 30 min, 1-((2-methoxynaphthalen-1-yl)methyl)naphthalen-2-amine (250 mg, 0.80 mmol) and diisopropyl ethylamine (516 mg, 4.0 mmol) were added and the mixture was stirred at room temperature for 50 h. After completion, the reaction mixture was quenched with water (30 mL) and extracted with ethyl acetate (40 mL×3). The combined organic layer was washed with brine (50 mL) and concentrated to afford a residue which was purified by prep-TLC (EA/PE=1/3, v/v) to get the crude product (190 mg, 55%) as a white solid, and 45 mg crude 2-(diethylamino)-N-(1-((2-methoxynaphthalen-1-yl)methyl)naphthalen-2-yl)acetamide was washed with ethyl acetate (4 mL) and filtered, the filter cake was collected and concentrated to get 2-(diethylamino)-N-(1-((2-methoxynaphthalen-1-yl)methyl)naphthalen-2-yl)acetamide (11.82 mg, 26%) as a white solid.

Mass Spectrum (ESI) m/z=427.3 (M+H$^+$).

$^1$H NMR (400 MHz, DMSO-d6) δ 10.00 (s, 1H), 8.27 (d, J=8.0 Hz, 1H), 7.94-7.70 (m, 6H), 7.51-7.45 (m, 1H), 7.41 (d, J=8.0 Hz, 1H), 7.36 (t, J=8.0 Hz, 1H), 7.29 (t, J=8.0 Hz, 1H), 7.14 (t, J=8.0 Hz, 1H), 4.71 (s, 2H), 3.73 (s, 3H), 3.21 (s, 2H), 2.59 (q, J=8.0 Hz, 4H), 0.96 (t, J=8.0 Hz, 6H).

Example 95: 1-((2-(2-(piperidin-4-yl)ethoxy)naphthalen-1-yl)methyl)naphthalen-2-ol (A286)

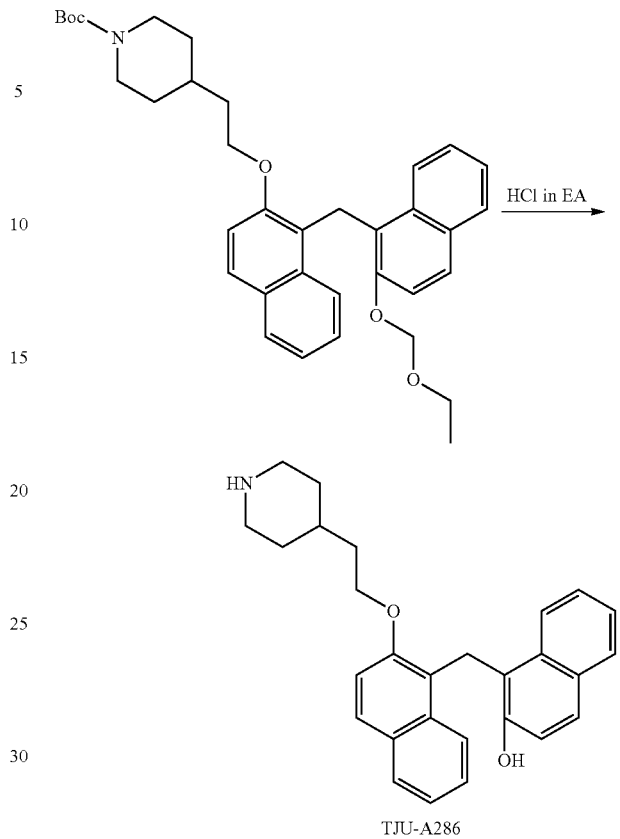

TJU-A286

1-((2-(2-(piperidin-4-yl)ethoxy)naphthalen-1-yl)methyl)naphthalen-2-ol (45.1 mg) was prepared as described for Example 93.

Mass Spectrum (ESI) m/z=412.1 (M+H$^+$).

$^1$H NMR (400 MHz, DMSO-d6) δ 10.11 (s, 1H), 8.46 (s, 2H), 8.21 (d, J=8.3 Hz, 1H), 7.93 (d, J=8.2 Hz, 1H), 7.73 (dd, J=15.5 Hz, 8.3 Hz, 2H), 7.61 (dd, J=20.3 Hz, 8.1 Hz, 2H), 7.47 (d, J=9.1 Hz, 1H), 7.31-7.05 (m, 5H), 4.74 (s, 2H), 4.30 (t, J=5.9 Hz, 2H), 3.20 (d, J=12.5 Hz, 2H), 2.74 (t, J=11.9 Hz, 2H), 1.96-1.71 (m, 5H), 1.37 (d, J=13.9 Hz, 2H).

Example 96: 2-((1-((2-(benzyloxy)naphthalen-1-yl)methyl)naphthalen-2-yl)oxy)-N,N-diethylethan-1-amine (A290)

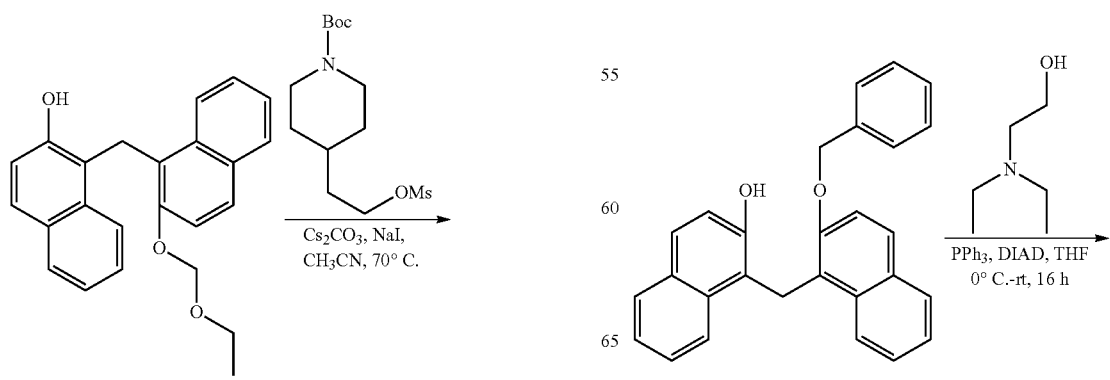

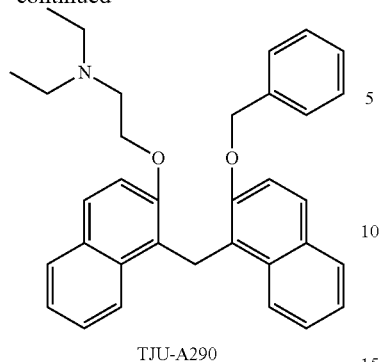

TJU-A290

2-((1-((2-(benzyloxy)naphthalen-1-yl)methyl)naphthalen-2-yl)oxy)-N,N-diethylethan-1-amine (46.2 mg) was prepared as described for Example 89.

Mass Spectrum (ESI) m/z=490.3 (M+H⁺).

¹H NMR (400 MHz, DMSO-d6) δ 8.24 (s, 0.5H), 8.11 (t, J=8.0 Hz, 2H), 7.83-7.73 (m, 4H), 7.58 (d, J=12.0 Hz, 1H), 7.48 (d, J=8.0 Hz, 3H), 7.41-7.28 (m, 3H), 7.27-7.17 (m, 4H), 5.37 (s, 2H), 4.88 (s, 2H), 4.22 (t, J=8.0 Hz, 2H), 2.79 (t, J=8.0 Hz, 2H), 2.57 (q, J=8.0 Hz, 4H), 0.95 (t, J=8.0 Hz, 6H).

Example 97: 1-(2-((1-((2-(benzyloxy)naphthalen-1-yl)methyl)naphthalen-2-yl)oxy)ethyl)pyrrolidine (A291)

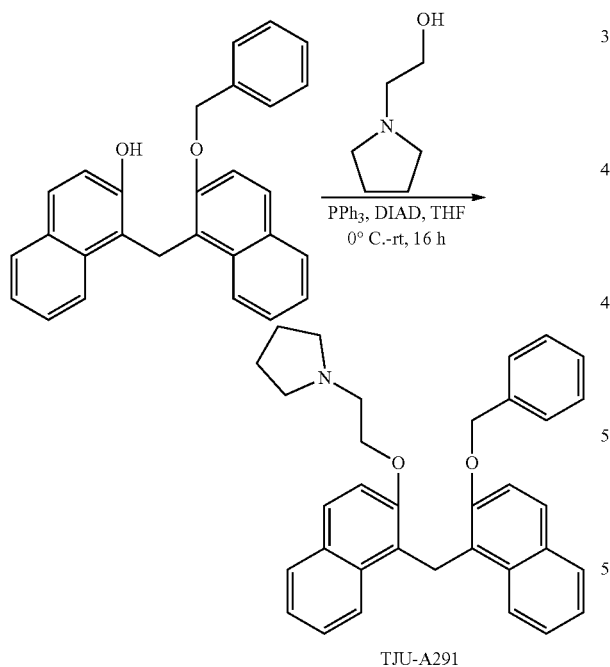

TJU-A291

4-(((1-((2-methoxynaphthalen-1-yl)methyl)naphthalen-2-yl)oxy)methyl)-1-methylpiperidine (45.1 mg) was prepared as described for Example 90.

Mass Spectrum (ESI) m/z=488.3 (M+H⁺).

¹H NMR (400 MHz, DMSO-d6) δ 8.28 (s, 0.2H), 8.16-8.04 (m, 2H), 7.82-7.72 (m, 4H), 7.58 (d, J=9.1 Hz, 1H), 7.50-7.43 (m, 3H), 7.42-7.28 (m, 3H), 7.28-7.17 (m, 4H), 5.37 (s, 2H), 4.87 (s, 2H), 4.28 (t, J=6.0 Hz, 2H), 2.81 (t, J=8.0 Hz, 2H), 2.58-2.52 (m, 4H), 1.74-1.53 (m, 4H).

Example 98: 1-(2-((1-((2-methoxynaphthalen-1-yl)methyl)naphthalen-2-yl)methoxy)ethyl)pyrrolidine (A296)

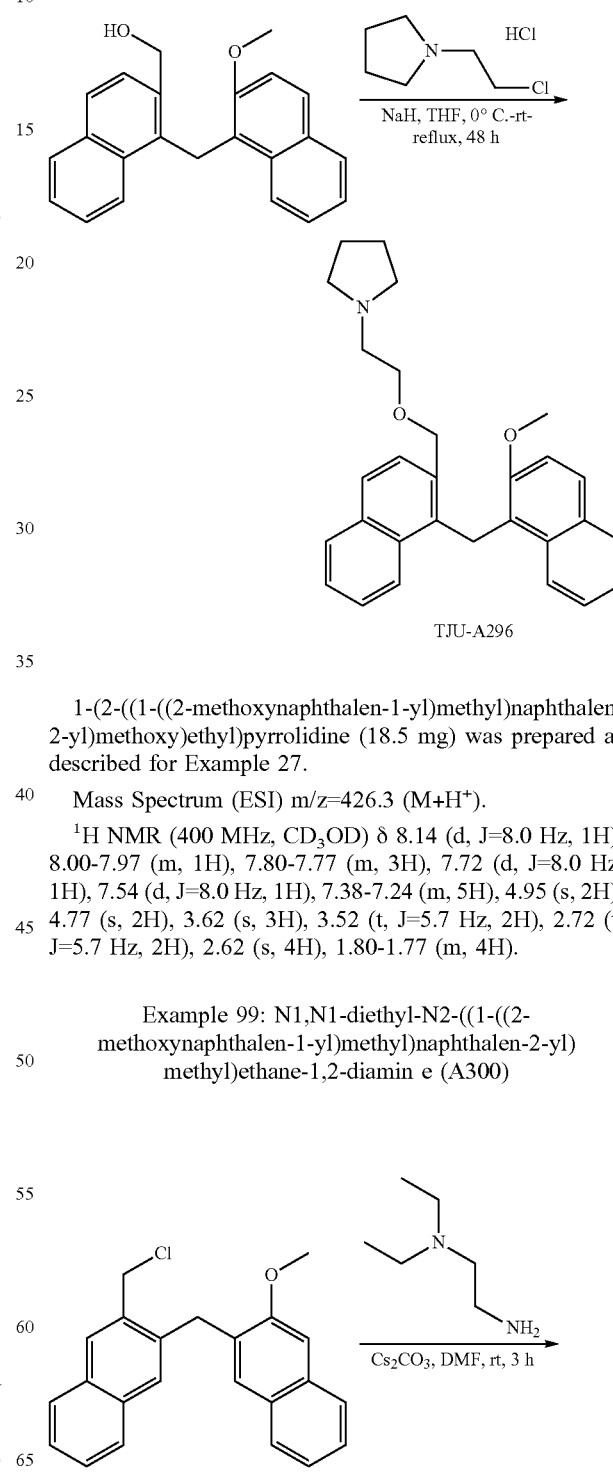

TJU-A296

1-(2-((1-((2-methoxynaphthalen-1-yl)methyl)naphthalen-2-yl)methoxy)ethyl)pyrrolidine (18.5 mg) was prepared as described for Example 27.

Mass Spectrum (ESI) m/z=426.3 (M+H⁺).

¹H NMR (400 MHz, CD₃OD) δ 8.14 (d, J=8.0 Hz, 1H), 8.00-7.97 (m, 1H), 7.80-7.77 (m, 3H), 7.72 (d, J=8.0 Hz, 1H), 7.54 (d, J=8.0 Hz, 1H), 7.38-7.24 (m, 5H), 4.95 (s, 2H), 4.77 (s, 2H), 3.62 (s, 3H), 3.52 (t, J=5.7 Hz, 2H), 2.72 (t, J=5.7 Hz, 2H), 2.62 (s, 4H), 1.80-1.77 (m, 4H).

Example 99: N1,N1-diethyl-N2-((1-((2-methoxynaphthalen-1-yl)methyl)naphthalen-2-yl)methyl)ethane-1,2-diamin e (A300)

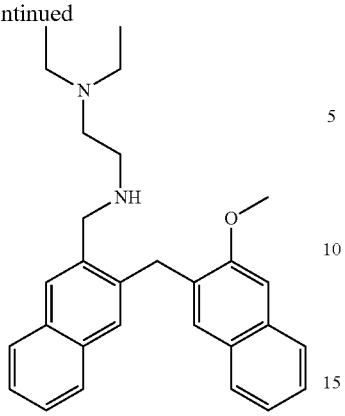

TJU-A300

N1,N1-diethyl-N2-((1-((2-methoxynaphthalen-1-yl)methyl)naphthalen-2-yl)methyl)ethane-1,2-diamin e (37.6 mg) was prepared as described for Example 93.

Mass Spectrum (ESI) m/z=427.2 (M+H⁺).

¹H NMR (400 MHz, DMSO-d6) δ 8.08 (d, J=8.6 Hz, 1H), 7.94-7.92 (m, 1H), 7.82 (t, J=8.5 Hz, 3H), 7.73 (d, J=8.4 Hz, 1H), 7.55 (d, J=8.4 Hz, 1H), 7.43 (d, J=9.0 Hz, 1H), 7.35 (s, 1H), 7.28-7.24 (m, 3H), 4.91 (s, 2H), 3.97 (s, 2H), 3.72 (s, 3H), 2.65-2.63 (m, 1H), 2.48 (s, 2H), 2.39-2.37 (m, 6H), 0.89 (t, J=7.1 Hz, 6H).

Example 100: 1-(2-((1-((2-(hexyloxy)naphthalen-1-yl)methyl)naphthalen-2-yl)oxy)ethyl)pyrrolidine (A257)

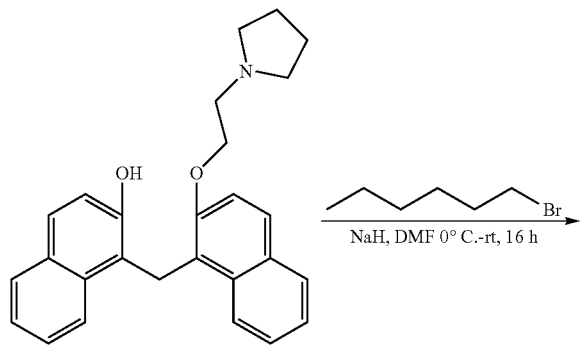

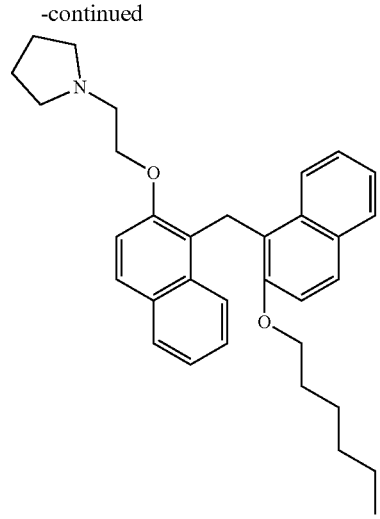

TJU-A257

1-(2-((1-((2-(hexyloxy)naphthalen-1-yl)methyl)naphthalen-2-yl)oxy)ethyl)pyrrolidine 189.6 mg) was prepared as described for Example 27.

Mass Spectrum (ESI) m/z=482.3 (M+H⁺).

¹H NMR (400 MHz, DMSO-d6) δ 8.09 (t, J=8.0 Hz, 2H), 7.82-7.72 (m, 4H), 7.48 (t, J=8.0 Hz, 2H), 7.28-7.18 (m, 4H), 4.85 (s, 2H), 4.30 (t, J=8.0 Hz, 2H), 4.21 (t, J=8.0 Hz, 2H), 2.81 (t, J=8.0 Hz, 2H), 2.57-2.54 (m, 4H), 1.78-1.69 (m, 2H), 1.69-1.62 (m, 4H), 1.50-1.40 (m, 2H), 1.35-1.21 (m, 4H), 0.84 (t, J=8.0 Hz, 3H).

Examples 101-166

The compounds in Table 1 were prepared in method that similar to Example 101-166 with different starting compound. The data for the compounds of Examples 101-166 are listed in Table 1.

TABLE 1

Compounds

| Example | Compd ID | Name | M.W. | LCMS | NMR |
|---|---|---|---|---|---|
| 101 | A137 | 1-({2-[2-(azetidin-1-yl)ethoxy]naphthalen-1-yl}methyl)naphthalen-2-ol; formic acid | 383.49 | 384.2 (M + 1) | ¹H NMR (400 MHz, DMSO-d6) δ 8.24 (d, J = 8.1 Hz, 1H), 8.21 (s, 1H), 7.98 (d, J = 8.2 Hz, 1H), 7.79-7.73 (m, 2H), 7.67-7.60 (m, 2H), 7.48 (d, J = 9.1 Hz, 1H), 7.28-7.10 (m, 5H), 4.78 (s, 2H), 4.24 (t, J = 5.5 Hz, 2H), 3.32 (t, J = 6.8 Hz, 4H), 2.89 (t, J = 5.5 Hz, 2H), 2.01-1.97 (m, 2H). |
| 102 | A139 | 1-[(2-{2-[bis(2-hydroxyethyl)amino]ethoxy}naphthalen-1-yl)methyl]naphthalen-2-ol | 431.53 | 432.2 (M + 1) | ¹H NMR (400 MHz, CDCl₃) δ 8.37 (d, J = 8.0 Hz, 1H), 8.16-8.06 (m, 1H), 7.82-7.74 (m, 3H), 7.66-7.52 (m, 2H), 7.38-7.29 (m, 3H), 7.11-6.96 (m, 2H), 4.84 (s, 2H), 4.39-4.28 (m, 2H), 3.79-3.67(m, 4H), 3.07 (t, J = 4.0 Hz, 2H), 2.85-2.72 (m, 4H). |

TABLE 1-continued

Compounds

| Example | Compd ID | Name | M.W. | LCMS | NMR |
|---|---|---|---|---|---|
| 103 | A142 | 8-[(2-hydroxynaphthalen-1-yl)methyl] quinolin-7-ol | 301.35 | [M + H]: 302.1 | $^1$H NMR (400 MHz, DMSO-d6) δ 8.89-8.88 (m, 1H), 8.83 (d, J = 8.0 Hz, 1H), 8.37 (d, J = 8.0 Hz, 1H), 7.80 (d, J = 8.0 Hz, 1H), 7.73 (d, J = 8.0 Hz, 1H), 7.66 (d, J = 12.0 Hz, 1H), 7. 45-7.39 (m, 3H), 7.25 (t, J = 8.0 Hz, 1H), 7.16 (d, J = 8.0 Hz, 1H), 4.68 (s, 2H). |
| 104 | A153 | 1-({2-[2-(diethylamino) ethoxy]naphthalen-1-yl}sulfonyl)naphthalen-2-ol | 449.57 | 450.2 (M + 1) | $^1$H NMR (400 MHz, CD$_3$OD) δ 8.91 (d, J = 8.0 Hz, 1H), 8.20 (d, J = 12.0 Hz, 1H), 7.98 (d, J = 8.2 Hz, 1H), 7.91 (d, J = 8.0 Hz, 1H), 7.81-7.74 (m, 2H), 7.59-7.54 (m, 2H), 7.48 (d, J = 8.0 Hz, 1H), 7.25-7.12 (m, 3H), 4.85-4.79 (m, 1H), 4.48-4.43 (m, 1H), 3.85-3.79 (m, 1H), 3.63-3.57 (m, 1H), 3.46-3.31 (m, 4H), 1.31-1.26 (m, 6H). |
| 105 | A154 | diethyl[2-({1-[(2-methoxynaphthalen-1-yl)sulfonyl]naphthalen-2-yl}oxy)ethyl]amine; formic acid | 463.59 | 464.2 (M + 1) | $^1$H NMR (400 MHz, CD$_3$OD) δ 9.31 (d, J = 8.0 Hz, 1H), 9.22 (d, J = 8.0 Hz, 2H), 8.43 (br, 1H), 8.09-8.06 (m, 2H), 7.97-7.91 (m, 2H), 7.74-7.70 (m, 1H), 7.64-7.59 (m, 1H), 7.54-7.45 (m, 3H), 7.34 (d, J = 9.0 Hz, 1H), 4.46-4.41 (m, 1H), 4.36-4.30 (m, 1H), 3.40 (s, 3H), 3.04 (t, J = 4.0 Hz, 2H), 2.97-2.80 (m, 4H), 1.04-0.96 (m, 6H). |
| 106 | A197 | 2-methoxy-N-methyl-N-(2-nitronaphthalen-1-yl)naphthalen-1-amine | 358.4 | 360.0 (M + 1) 382.1(M + 23) | $^1$H NMR (400 MHz, CDCl$_3$) δ 8.10 (d, J = 8.5 Hz, 1H), 7.90 (d, J = 8.8 Hz, 1H), 7.76 (m, 4H), 7.47-7.29 (m, 5H), 7.10 (m, 1H), 3.85 (s, 3H), 3.48 (s, 3H). |
| 107 | A210 | 1-({2-[2-(diethylamino) ethoxy] naphthalen-1-yl}methyl)naphthalen-2-amine | 398.55 | 399.2 (M + 1) | $^1$H NMR (400 MHz, DMSO-d6) δ 8.05 (d, J = 8.0 Hz, 1H), 7.98 (d, J = 8.0 Hz, 1H), 7.79-7.73 (m, 2H), 7.57 (d, J = 8.0 Hz, 1H), 7.51-7.45 (m, 2H), 7.22-7.13 (m, 3H), 7.02 (t, J = 8.0 Hz, 2H), 5.50 (s, 2H), 4.60 (s, 2H), 4.28 (t, J = 6.0 Hz, 2H), 2.88 (t, J = 5.7 Hz, 2H), 2.63-2.57 (m, 4H), 0.99 (t, J = 7.1 Hz, 6H). |
| 108 | A214 | N-[1-({2-[2-(diethylamino)ethoxy]naphthalen-1-yl}methyl)naphthalen-2-yl]methanesulfonamide | 476.64 | 477.2 (M + 1) | $^1$H NMR (400 MHz, CD$_3$OD) δ 8.27 (d, J = 8.2 Hz, 1H), 7.98 (s, 1H), 7.86-7.76 (m, 4H), 7.64 (d, J = 8.8 Hz, 1H), 7.39 (dd, J = 13.3, 7.9 Hz, 3H), 7.27 (dd, J = 6.3 Hz, 3.3 Hz, 2H), 5.04 (s, 2H), 4.25 (t, J = 5.7 Hz, 2H), 2.97 (s, 2H), 2.84 (d, J = 7.8 Hz, 4H), 2.36 (s, 3H), 1.15 (t, J = 7.2 Hz, 6H). |
| 109 | A215 | N-[1-({2-[2-(pyrrolidin-1-yl)ethoxy]naphthalen-1-yl}methyl)naphthalen-2-yl]methanesulfonamide | 474.62 | 475.1 (M + 1) | $^1$H NMR (400 MHz, CD$_3$OD) δ 8.19 (d, J = 8.5 Hz, 1H), 8.11 (d, J = 8.7 Hz, 1H), 7.83-7.75 (m, 4H), 7.63 (d, J = 8.8 Hz, 1H), 7.40-7.28 (m, 5H), 5.06 (s, 2H), 4.20 (t, J = 5.6 Hz, 2H), 2.92-2.84 (m, 6H), 2.47 (s, 3H), 1.94-1.91 (m, 4H). |
| 110 | A220 | 1-[(2-hydroxynaphthalen-1-yl)methyl]naphthalen-2-yl 2-(diethylamino)acetate | 413.52 | 414.2 (M + 1) | $^1$H NMR (400 MHz, CDCl$_3$) δ 8.19-8.17 (m, 1H), 7.99 (d, J = 8.0 Hz, 1H), 7.87-7.85 (m, 1H), 7.77 (d, J = 8.0 Hz, 2H), 7.64 (d, J = 8.0 Hz, 1H), 7.49-7.43 (m, 2H), 7.40-7.36 (m, 11H), 7.33-7.29 (m, 1H), 7.14 (d, J = 8.0 Hz, 1H), 7.07 (d, J = 8.0 Hz, 1H), 4.82 (s, 2H), 3.30 (s, 2H), 2.76-2.70 (m, 4H), 1.08 (t, J = 8.0 Hz, 6H). |
| 111 | A227 | 1-{2-[2-(diethylamino) ethoxy]naphthalene-1-carbonyl}naphthalen-2-ol | 413.52 | 414.2 (M + 1) | $^1$H NMR (400 MHz, CDCl$_3$) δ 8.05 (d, J = 8.0 Hz, 1H), 7.99 (d, J = 12.0 Hz, 1H), 7.93-7.91 (m, 1H), 7.80-7.77 (m, 1H), 7.72-7.69 (m, 1H), 7.52-7.45 (m, 2H), 7.30 (t, J = 8.0 Hz, 2H), 7.24-7.20 (m, 1H), 7.14 (d, J = 8.0 Hz, 1H), 7.00-6.95 (m, 1H), 2.09-2.62 (m, 6H), 1.25 (s, 2H), 1.13 (t, J = 7.0 Hz, 6H). |
| 112 | A233 | 2-(diethylamino)ethyl 1-[(2-methoxynaphthalen-1-yl)methyl]naphthalene-2-carboxylate | 441.57 | 442.3 (M + 1) | 1H NMR (400 MHz, CD$_3$OD) δ 8.22 (d, J = 8.0 Hz, 1H), 8.02 (d, J = 8.0 Hz, 1H), 7.84 (d, J = 8.0 Hz, 1H), 7.78-7.74 (m, 3H), 7.65 (d, J = 8.0 Hz, 1H), 7.47-7.43 (m, 1H), 7.37-7.25 (m, 4H), 5.21 (s, 2H), 4.11 (t, J = 8.0 Hz, 2H), 3.57 (s, 3H), 2.65 (t, J = 8.0 Hz, 2H), 2.57-2.52 (m, 4H), 1.00 (t, J = 8.0 Hz, 6H). |
| 113 | A235 | 1-(2-{[1-(2-methoxynaphthalene-1-carbonyl)naphthalen-2-yl]oxy}ethyl)pyrrolidine | 425.53 | 426.2 (M + 1) | 1H NMR (400 MHz, DMSO-d6) δ 8.08 (d, J = 9.1 Hz, 1H), 8.02 (s, 1H), 7.96 (d, J = 8.0 Hz, 1H), 7.90-7.84 (m, 2H), 7.75 (d, J = 8.5 Hz, 1H), 7.57-7.47 (m, 3H), 7.44-7.40 (m, 2H), 7.36 (t, J = 7.5 Hz, 1H), 4.02 (t, J = 5.8 Hz, 2H), 3.68 (s, 3H), 2.27 (s, 2H), 2.13 (s, 4H), 1.41 (s, 4H). |
| 114 | A239 | N-[2-(diethylamino)ethyl]-1-[(2-hydroxynaphthalen-1-yl)methyl]naphthalene-2-carboxamide; formic acid | 426.56 | 427.2 (M + 1) | $^1$H NMR (400 MHz, CDCl$_3$) δ 8.96 (s, 1H), 8.32 (d, J = 8.7 Hz, 1H), 7.85-7.72 (m, 4H),7.60 (d, J = 8.3 Hz, 3H), 7.41-7.32 (m, 2H), 7.12-7.06 (m, 1H), 7.02 (d, J = 8.8 Hz, 1H), 4.91 (s, 2H), 3.87 (d, J = 5.0 Hz, 2H), 3.24-3.18 (m, 2H), 3.07 (q, J = 7.2 Hz, 4H), 1.33 (t, J = 7.2 Hz, 6H). |
| 115 | A245 | 2-({1-[(2-ethoxynaphthalen-1-yl)methyl] naphthalen-2-yl}oxy)ethan-1-amine | 371.48 | 372.2 (M + 1) | $^1$H NMR (400 MHz, DMSO-d6) δ 8.18 (s, 2H), 8.05 (t, J = 8.0 Hz, 2H), 7.88-7.70 (m, 4H), 7.48 (t, J = 8.0 Hz, 2H), 7.37-7.17 (m, 4H), 4.91 (s, 2H), 4.37 (t, J = 4.0 Hz, 2H), 4.24 (q, J = 8.0 Hz, 2H), 3.21 (s, 2H), 1.31 (t, J = 7.0 Hz, 3H). |

TABLE 1-continued

Compounds

| Example | Compd ID | Name | M.W. | LCMS | NMR |
|---|---|---|---|---|---|
| 116 | A248 | 2-[(1-{[2-(2-methoxyethoxy)naphthalen-1-yl]methyl}naphthalen-2-yl)oxy]ethan-1-amine | 401.51 | 402.2 (M + 1) | $^1$H NMR (400 MHz, DMSO-d6) δ 8.23 (s, 2H), 8.10 (d, J = 8.0 Hz, 1H), 8.01 (d, J = 8.0 Hz, 1H), 7.79-7.77 (m, 4H), 7.49 (d, J = 8.0 Hz, 2H), 7.26-7.24 (m, 4H), 4.93 (s, 2H), 4.45-4.27 (m, 5H), 3.74-3.61 (m, 2H), 3.32 (s, 2H), 3.23 (s, 2H). |
| 117 | A259 | 1-({2-[(azetidin-3-yl)methoxy] naphthalen-1-yl} methyl)naphthalen-2-ol; bis(formic acid) | 369.46 | 370.2 (M + 1) | $^1$H NMR (400 MHz, DMSO-d6) δ 8.38 (s, 2H), 8.24 (d, J = 8.2 Hz, 1H), 7.92 (d, J = 8.5 Hz, 1H), 7.76 (dd, J = 16.1 Hz, 8.3 Hz, 2H), 7.62 (dd, J = 20.7 Hz, 8.3 Hz, 2H), 7.48 (d, J = 8.9 Hz, 1H), 7.30-7.04 (m, 5H), 4.77 (s, 2H), 4.40 (d, J = 5.4 Hz, 2H), 3.81-3.85 (m, 5H). |
| 118 | A260 | 1-({2-[(1-methylazetidin-3-yl)methoxy]naphthalen-1-yl}methyl)naphthalen-2-ol; formic acid | 383.49 | 384.1 (M + 1) | $^1$H NMR (400 MHz, DMSO-d6) δ 8.26 (s, 0.5H), 8.24 (s, 1H), 7.96 (d, J = 8.0 Hz, 1H), 7.83-7.72 (m, 2H), 7.64 (dd, J = 20.0 Hz, 8.0 Hz, 2H), 7.49 (d, J = 8.0 Hz, 1H), 7.32-7.07 (m, 5H), 4.78 (s, 2H), 4.40 (d, J = 4.0 Hz, 2H), 3.65 (t, J = 8.0 Hz, 2H), 3.50-3.42 (m, 2H), 3.08-2.97 (m, 1H), 2.42 (s, 3H). |
| 119 | A263 | 1-({2-[(piperidin-4-yl)methoxy]naphthalen-1-yl}methyl)naphthalen-2-ol hydrochloride | 397.52 | 398.1 (M + 1) | $^1$H NMR (400 MHz, DMSO-d6) δ 10.15 (s, 1H), 8.51 (s, 2H), 8.21 (d, J = 8.2 Hz, 1H), 7.93 (d, J = 8.4 Hz, 1H), 7.75 (dd, J = 17.2, 8.2 Hz, 2H), 7.62 (dd, J = 18.2, 8.1 Hz, 2H), 7.49 (d, J = 9.1 Hz, 1H), 7.31-7.06 (m, 5H), 4.78 (s, 2H), 4.19 (d, J = 5.4 Hz, 2H), 3.28 (s, 2H), 2.88 (m, 2H), 2.14 (m, 1H), 1.99 (d, J = 12.6 Hz, 2H), 1.69 (m, 2H). |
| 120 | A264 | 1-({2-[(1-methylpiperidin-4-yl)methoxy]naphthalen-1-yl}methyl)naphthalen-2-ol | 411.55 | 412.2 (M + 1) | $^1$H NMR (400 MHz, DMSO-d6) δ 10.22 (s, 1H), 8.25 (d, J = 8.0 Hz, 1H), 7.94 (d, J = 8.0 Hz, 1H), 7.84-7.56 (m, 4H), 7.50 (d, J = 8.0 Hz, 1H), 7.37-7.06 (m, 5H), 4.80 (s, 2H), 4.19 (s, 2H), 3.42 (d, J = 8.0 Hz, 2H), 3.05-2.89 (m, 2H), 2.78-2.63 (m, 3H), 2.21-1.97 (m, 3H), 1.88-1.72 (m, 2H). |
| 121 | A267 | 3-[({1-[(2-methoxynaphthalen-1-yl)methyl]naphthalen-2-yl}oxy)methyl] azetidine; formic acid | 383.49 | 384.2 (M + 1) | $^1$H NMR (400 MHz, DMSO-d6) δ 8.38 (s, 2H), 8.05 (t, J = 8.0 Hz, 2H), 7.79 (dd, J = 16.3, 8.3 Hz, 4H), 7.49 (t, J = 8.2 Hz, 2H), 7.26-7.24 (m, 4H), 4.83 (s, 2H), 4.37 (d, J = 5.6 Hz, 3H), 3.98 (s, 2H), 3.85 (s, 2H), 3.74 (s, 2H), 2.00 (dd, J = 14.6, 7.0 Hz, 1H). |
| 122 | A272 | 4-[({1-[(2-methoxynaphthalen-1-yl)methyl]naphthalen-2-yl}oxy)methyl]-1-methylpiperidine; formic acid | 425.57 | 426.3 (M + 1) | $^1$H NMR (400 MHz, DMSO-d6) δ 8.34 (s, 1H), 8.04 (d, J = 5.5 Hz, 2H), 7.86-7.67 (m, 4H), 7.49 (dd, J = 14.2, 9.1 Hz, 2H), 7.33-7.13 (m, 4H), 4.82 (d, J = 3.1 Hz, 2H), 4.21-4.07 (m, 2H), 4.01 (d, J = 5.4 Hz, 3H), 3.47 (s, 3H), 2.14 (s, 2H), 1.95 (s, 1H), 1.80 (m, 4H), 1.49-1.35 (m, 2H). |
| 123 | A276 | 3-{[(1-{[2-(ethoxymethoxy)naphthalen-1-yl]methyl}naphthalen-2-yl)oxy]methyl}-1-methylazetidine; formic acid | 441.57 | 442.2 (M + 1) | $^1$H NMR (400 MHz, DMSO-d6) δ 8.31 (s, 1H), 8.09 (dd, J = 8.0 Hz, 4.0 Hz, 2H), 7.83-7.73 (m, 4H), 7.48 (t, J = 8.0 Hz, 2H), 7.34-7.19 (m, 4H), 5.37 (s, 2H), 4.85 (s, 2H), 4.31 (d, J = 8.0 Hz, 2H), 3.65-3.61 (m, 2H), 3.38 (t, J = 8.0 Hz, 2H), 3.15 (t J = 8.0 Hz, 2H), 2.87-2.73 (m, 1H), 2.26 (s, 3H), 1.11 (t, J = 8.0 Hz, 3H). |
| 124 | A278 | 3-{[(1-{[2-(ethoxymethoxy)naphthalen-1-yl]methyl}naphthalen-2-yl)oxy]methyl}-1-methylpyrrolidine | 455.60 | 456.3 (M + 1) | $^1$H NMR (400 MHz, DMSO-d6) δ 8.09 (t, J = 8.0 Hz, 2H), 7.78 (dd, J = 12.0, 8.0 Hz, 4H), 7.49 (t, J = 8.0 Hz, 2H), 7.39-7.14 (m, 4H), 5.38 (s, 2H), 4.85 (s, 2H), 4.11 (t, J = 8.0 Hz, 2H), 3.64 (q, J = 8.0 Hz, 2H), 2.65-2.56 (m, 2H), 2.24 (s, 3H), 2.04-1.89 (m, 2H), 1.66-1.38 (m, 3H), 1.12 (t, J = 8.0 Hz, 3H). |
| 125 | A280 | 4-{[(1-{[2-(ethoxymethoxy)naphthalen-1-yl]methyl}naphthalen-2-yl)oxy]methyl}-1-methylpiperidine | 469.63 | 470.2 (M + 1) | $^1$H NMR (400 MHz, DMSO-d6) δ 8.24 (s, 0.5H), 8.13-8.08 (m, 2H), 7.86-7.73 (m, 4H), 7.49 (dd, J = 12.0 Hz, 8.0 Hz, 2H), 7.36-7.18 (m, 4H), 5.40 (s, 2H), 4.86 (s, 2H), 4.07 (d, J = 4.0 Hz, 2H), 3.66 (q, J = 4.0 Hz, 2H), 2.86 (d, J = 8.0 Hz, 2H), 2.23 (s, 3H), 2.02 (t, J = 12.0 Hz, 2H), 1.75 (d, J = 8.0 Hz, 3H), 1.43 (m, 2H), 1.13 (t, J = 8.0 Hz, 3H). |
| 126 | A287 | 4-{2-[(1-{[2-(ethoxymethoxy)naphthalen-1-yl]methyl}naphthalen-2-yl)oxy]ethyl}piperidine; formic acid | 469.63 | 470.3 (M + 1) | $^1$H NMR (400 MHz, DMSO-d6) δ 8.30 (s, 0.4H), 8.09 (t, J = 8.0 Hz, 2H), 7.82-7.73 (m, 4H), 7.49 (t, J = 8.0 Hz, 2H), 7.30-7.20 (m, 4H), 5.36 (s, 2H), 4.84 (s, 2H), 4.21 (t, J = 8.0 Hz, 2H), 3.61 (q, J = 8.0 Hz, 2H), 3.17 (d, J = 12.0 Hz, 2H), 2.68 (t, J = 12.0 Hz, 2H), 1.80 (d, J = 16.0 Hz, 2H), 1.65 (t, J = 8.0 Hz, 3H), 1.27 (dd, J = 24.0 Hz, 2H), 1.11 (t J = 8.0 Hz, 3H). |
| 127 | A291 | 1-{2-[(1-{[2-(benzyloxy)naphthalen-1-yl]methyl}naphthalen-2-yl)oxy]ethyl}pyrrolidine; formic acid | 487.64 | 488.3 (M + 1) | $^1$H NMR (400 MHz, DMSO-d6) δ 8.28 (s, 0.2H), 8.16-8.04 (m, 2H), 7.82-7.72 (m, 4H), 7.58 (d, J = 9.1 Hz, 1H), 7.50-7.43 (m, 3H), 7.42-7.28 (m, 3H), 7.28-7.17 (m, 4H), 5.37 (s, 2H), 4.87 (s, 2H), 4.28 (t, J = 6.0 Hz, 2H), 2.81 (t, J = 8.0 Hz, 2H), 2.58-2.52 (m, 4H), 1.74-1.53 (m, 4H). |

TABLE 1-continued

Compounds

| Example | Compd ID | Name | M.W. | LCMS | NMR |
|---|---|---|---|---|---|
| 128 | A294 | 1-({2-[2-(azetidin-3-yl)ethoxy]naphthalen-1-yl}methyl)naphthalen-2-ol; formic acid | 383.49 | 384.2 (M + 1) | 1H NMR (400 MHz, DMSO-d6) δ 8.45 (s, 1H), 8.24 (d, J = 8.0 Hz, 1H), 7.90 (d, J = 8.0 Hz, 1H), 7.81-7.70 (m, 2H), 7.63 (m, 2H), 7.47 (d, J = 12.0 Hz, 1H), 7.36-7.04 (m, 5H), 4.74 (s, 2H), 4.26 (t, J = 4.0 Hz, 2H), 3.95-3.85 (m, 2H), 3.74-3.65 (m, 2H), 3.05 (s, 2H), 2.22-2.08 (m, 2H). |
| 129 | A295 | diethyl[2-({1-[(2-methoxynaphthalen-1-yl)methyl]naphthalen-2-yl}methoxy)ethyl]amine | 427.59 | 428.2 (M + 1) | ¹H NMR (400 MHz, DMSO-d6) δ 8.21 (s, 0.25H), 8.07 (d, J = 8.6 Hz, 1H), 7.96-7.93 (m, 1H), 7.85-7.81 (m, 3H), 7.77 (d, J = 8.5 Hz, 1H), 7.57 (d, J = 8.5 Hz, 1H), 7.43 (d, J = 9.1 Hz, 1H), 7.36 (d, J = 7.1 Hz, 1H), 7.28-7.26 (m, 3H), 4.87 (s, 2H), 4.76 (s, 2H), 3.72 (s, 3H), 3.48 (t, J = 6.1 Hz, 2H), 2.60 (t, J = 6.1 Hz, 2H), 2.49-2.47 (m, 4H), 0.92 (t, J = 7.1 Hz, 6H). |
| 130 | A297 | diethyl(2-{[1-(2-methoxynaphthalene-1-carbonyl)naphthalen-2-yl]oxy}ethyl)amine | 427.54 | 428.2 (M + 1) | ¹H NMR (400 MHz, DMSO-d6) δ 8.09 (d, J = 9.0 Hz, 1H), 8.05 (s, 1H), 7.97 (d, J = 8.0 Hz, 1H), 7.88 (dd, J = 14.1 Hz, 8.3 Hz, 2H), 7.75 (d, J = 7.1 Hz, 1H), 7.51 (m, 3H), 7.44 (d, J = 6.8 Hz, 2H), 7.37 (d, J = 7.2 Hz, 1H), 3.96 (s, 2H), 3.68 (s, 3H), 3.30 (s, 2H), 2.19 (s, 4H), 0.69 (s, 6H). |
| 131 | A298 | diethyl[2-({1-[(naphthalen-1-yl)methyl]naphthalen-2-yl}oxy)ethyl]amine | 383.54 | 384.3 (M + 1) | 1H NMR (400 MHz, CDCl₃) δ 8.39 (d, J = 8.0 Hz, 1H), 7.95-7.83 (m, 3H), 7.73-7.61 (m, 3H), 7.57-7.52 (m, 1H), 7.40-7.30 (m, 3H), 7.17-7.12 (m, 1H), 6.63 (d, J = 7.2 Hz, 1H), 4.90 (s, 2H), 4.21 (s, 2H), 2.78 (s, 2H), 2.48 (s, 4H), 0.87 (t, J = 7.2 Hz, 6H). |
| 132 | A299 | 1-[2-({1-[(naphthalen-1-yl)methyl]naphthalen-2-yl}oxy)ethyl]pyrrolidine | 381.52 | 382.3 (M + 1) | 1H NMR (400 MHz, CDCl₃) δ 8.39 (d, J = 8.4 Hz, 1H), 7.87 (ddd, J = 7.7, 6.7, 5.2 Hz, 3H), 7.75-7.70 (m, 1H), 7.68-7.61 (m, 2H), 7.58-7.53 (m, 1H), 7.40-7.32 (m, 3H), 7.18-7.13 (m, 1H), 6.62 (dd, J = 7.2, 0.9 Hz, 1H), 4.91 (s, 2H), 4.28 (q, J = 5.6 Hz, 2H), 2.84 (s, 2H), 2.47 (s, 4H), 1.60-1.52 (m, 4H). |
| 133 | A301 | 3-{2-[(1-{[2-(ethoxymethoxy)naphthalen-1-yl]methyl}naphthalen-2-yl)oxy]ethyl}azetidine hydrogen hydride | 441.57 | 442.2 (M + 1) | 1H NMR (400 MHz, DMSO-d6) δ 8.42 (s, 2H), 8.06 (t, J = 8.0 Hz, 2H), 7.82-7.74 (m, 4H), 7.48 (dd, J = 16.0 Hz, 8.0 Hz, 2H), 7.34-7.18 (m, 4H), 5.40 (s, 2H), 4.82 (s, 2H), 4.19 (s, 2H), 3.82 (s, 3H), 3.69-3.62 (m, 3H), 2.09-1.96 (m, 2H), 1.27-1.20 (m, 2H), 1.13 (t, J = 8.0 Hz, 3H). |
| 134 | A302 | 1-{2-({[2-(diethylamino)ethyl]amino}methyl)naphthalen-1-yl]methyl}naphthalen-2-ol | 412.58 | 413.2 (M + 1) | 1H NMR (400 MHz, DMSO-d6) δ 8.23 (s, 1H), 7.99 (t, J = 8.0 Hz, 2H), 7.83 (d, J = 8.0 Hz, 1H), 7.79-7.72 (m, 2H), 7.63 (d, J = 8.0 Hz, 1H), 7.54 (d, J = 8.0 Hz, 1H), 7.37-7.28 (m, 2H), 7.24-7.15 (m, 2H), 7.06 (d, J = 8.0 Hz, 1H), 4.93-4.77 (m, 3H), 4.18 (s, 2H), 2.74-2.65 (m, 2H), 2.65-2.58 (m, 2H), 2.57-2.53 (m, 4H), 0.95 (t, J = 8.0 Hz, 6H). |
| 135 | A303 | ({1-[(2-methoxynaphthalen-1-yl)methyl]naphthalen-2-yl}methyl)[2-(pyrrolidin-1-yl)ethyl]amine | 424.59 | 425.2 (M + 1) | ¹H NMR (400 MHz, CD₃OD) δ 8.22 (d, J = 8.6 Hz, 1H), 8.00-7.96 (m, 1H), 7.84-7.77 (m, 4H), 7.72 (d, J = 8.4 Hz, 1H), 7.46-7.27 (m, 6H), 4.99 (s, 2H), 3.94 (s, 2H), 3.59 (s, 3H), 2.54-2.47 (m, 2H), 2.45-2.36 (m, 6H), 1.71-1.68 (m, 4H). |
| 136 | A304 | formic acid; {2-[(1-{[2-(benzyloxy)naphthalen-1-yl]methyl}naphthalen-2-yl)methoxy]ethyl}diethylamine | 502.70 | 504.3 (M + 1) | ¹H NMR (400 MHz, CD₃OD) δ 8.53 (br, 1H), 8.14 (d, J = 8.6 Hz, 1H), 8.06 (d, J = 8.3 Hz, 1H), 7.82-7.72 (m, 4H), 7.43-7.21 (m, 9H), 7.07-7.05 (m, 2H), 4.99 (s, 2H), 4.92 (s, 2H), 4.67 (s, 2H), 3.46 (t, J = 5.3 Hz, 2H), 2.96-2.87 (m, 6H), 1.10 (t, J = 7.3 Hz, 6H). |
| 137 | A305 | 1-[2-{[2-(diethylamino)ethoxy]methyl}naphthalen-1-yl)methyl]naphthalen-2-ol | 413.56 | 414.2 (M + 1) | 1H NMR (400 MHz, CD₃OD) δ 8.33 (d, J = 8.6 Hz, 1H), 7.85-7.80 (m, 1H), 7.75 (d, J = 8.4 Hz, 1H), 7.70-7.62 (m, 3H), 7.50 (d, J = 8.4 Hz, 1H), 7.44-7.33 (m, 2H), 7.16-7.04 (m, 3H), 4.97 (s, 2H), 4.88 (s, 2H), 3.59-3.56 (m, 2H), 3.15-3.13 (m, 2H), 3.10-3.04 (m, 4H), 1.18 (t, J = 7.3 Hz, 6H). |
| 138 | A306 | 1-{2-[(1-{[2-(benzyloxy)naphthalen-1-yl]methyl}naphthalen-2-yl)methoxy]ethyl}pyrrolidine | 501.67 | 502.3 (M + 1) | 1H NMR (400 MHz, CD₃OD) δ 8.55 (s, 0.25H), 8.12-8.06 (m, 2H), 7.80-7.70 (m, 4H), 7.44 (d, J = 8.5 Hz, 1H), 7.37-7.18 (m, 8H), 7.08-7.05 (m, 2H), 4.98 (s, 2H), 4.92 (s, 2H), 4.65 (s, 2H), 3.46 (t, J = 5.7 Hz, 2H), 2.75-2.66 (m, 6H), 1.79-1.76 (m, 6H). |
| 139 | A308 | [(1-{[2-(benzyloxy)naphthalen-1-yl]methyl}naphthalen-2-yl)methyl][2-(diethylamino)ethyl]amine | 502.70 | 503.3 (M + 1) | ¹H NMR (400 MHz, CD₃OD) δ 8.20 (d, J = 8.6 Hz, 1H), 8.06-8.02 (m, 1H), 7.82-7.71 (m, 4H), 7.38-7.23 (m, 9H), 7.09-7.06 (m, 2H), 5.00 (s, 2H), 4.94 (s, 2H), 3.86 (s, 2H), 2.48-2.38 (m, 8H), 0.94 (t, J = 7.2 Hz, 6H). |
| 140 | A309 | diethyl[2-({1-[(2-methoxynaphthalen-1-yl)(phenyl)methyl]naphthalen-2-yl}oxy)ethyl]amine; formic acid | 489.66 | 490.2 (M + 1) | 1H NMR (400 MHz, DMSO-d6) δ 8.18 (s, 0.25H), 7.92-7.89 (m, 3H), 7.80 (d, J = 8.2 Hz, 1H), 7.51-7.48 (m, 2H), 7.39-7.31 (m, 5H), 7.24-7.20 (m, 3H), 7.15 (s, 1H), 7.02 (d, J = 7.4 Hz, 2H), 6.76 (s, 1H), 3.93-3.76 (m, 5H), 2.35 (dd, J = 13.4 Hz, 6.4 Hz, 4H), 2.25 (s, 2H), 0.79 (t, J = 7.0 Hz, 6H). |

TABLE 1-continued

Compounds

| Example | Compd ID | Name | M.W. | LCMS | NMR |
|---|---|---|---|---|---|
| 141 | A310 | [(1-{[2-(benzyloxy)naphthalen-1-yl]methyl}naphthalen-2-yl)methyl][2-(pyrrolidin-1-yl)ethyl]amine | 500.69 | 501.3 (M + 1) | 1H NMR (400 MHz, CD$_3$OD) δ 8.18 (d, J = 8.6 Hz, 1H), 8.07 (d, J = 8.3 Hz, 1H), 7.83-7.72 (m, 4H), 7.39-7.22 (m, 9H), 7.07-7.04 (m, 2H), 5.01 (s, 2H), 4.92 (s, 2H), 3.90 (s, 2H), 2.56-2.49 (m, 8H), 1.74-1.71 (m, 4H). |
| 142 | A311 | 1-{2-({[2-(pyrrolidin-1-yl)ethyl]amino}methyl)naphthalen-1-yl]methyl}naphthalen-2-ol; formic acid | 410.56 | 411.2 (M + 1) | 1H NMR (400 MHz, CD$_3$OD) δ 8.53 (s, 1H), 8.22 (d, J = 8.7 Hz, 1H), 7.91-7.82 (m, 2H), 7.80-7.72 (m, 2H), 7.66 (d, J = 8.8 Hz, 1H), 7.48 (d, J = 8.4 Hz, 1H), 7.41 (t, J = 8.0 Hz, 1H), 7.33-7.29 (m, 1H), 7.27-7.19 (m, 2H), 7.08 (d, J = 8.8 Hz, 1H), 5.00 (s, 2H), 4.28 (s, 2H), 2.87-2.80 (m, 8H), 1.79-1.73 (m, 4H). |
| 143 | A313 | [2-({1-[(3,4-dimethoxyphenyl)methyl]naphthalen-2-yl}oxy)ethyl]diethylamine | 393.53 | 394.2 (M + 1) | 1H NMR (400 MHz, CDCl$_3$) δ 7.89 (d, J = 8.5 Hz, 1H), 7.81 (d, J = 8.6 Hz, 2H), 7.42 (t, J = 7.6 Hz, 1H), 7.34 (t, J = 7.8 Hz, 2H), 6.76 (s, 1H), 6.68 (d, J = 8.2 Hz, 1H), 6.55 (d, J = 8.1 Hz, 1H), 4.47-4.33 (m, 4H), 3.78 (d, J = 9.3 Hz, 6H), 3.13 (t, J = 5.2 Hz, 2H), 2.85-2.82 (m, 4H), 1.13 (t, J = 7.1 Hz, 6H). |
| 144 | A314 | 1-[2-({1-[(3,4-dimethoxyphenyl)methyl]naphthalen-2-yl}oxy)ethyl]pyrrolidine | 391.51 | 392.2 (M + 1) | 1H NMR (400 MHz, CDCl$_3$) δ 7.90 (d, J = 8.5 Hz, 1H), 7.80 (d, J = 8.8 Hz, 2H), 7.42 (t, J = 7.6 Hz, 1H), 7.33-7.31 (m, 2H), 6.77 (s, 1H), 6.68 (d, J = 8.2 Hz, 1H), 6.56 (d, J = 8.1 Hz, 1H), 4.43 (s, 2H), 4.37 (d, J = 5.1 Hz, 2H), 3.78 (d, J = 7.4 Hz, 6H), 3.13 (s, 2H), 2.84 (s, 4H), 1.83 (s, 4H) |
| 145 | A315 | N-[2-({1-[(2-ethoxynaphthalen-1-yl)methyl]naphthalen-2-yl}oxy)ethyl]acetamide | 413.52 | 436.1 (M + 23) | 1H NMR (400 MHz, DMSO-d6) δ 8.18-8.03 (m, 3H), 7.81-7.68 (m, 4H), 7.46 (d, J = 8.0 Hz, 2H), 7.32-7.11 (m, 4H), 4.86 (s, 2H), 4.36-4.14 (m, 4H), 3.47 (dd, J = 12.0 Hz, 4.0 Hz, 2H), 1.74 (s,3H), 1.36 (t, J = 8.0 Hz, 3H) |
| 146 | A316 | N-{2-[(1-{[2-(hexyloxy)naphthalen-1-yl]methyl}naphthalen-2-yl)oxy]ethyl}acetamide | 469.63 | 492.2 (M + 23) | 1H NMR (400 MHz, DMSO-d6) δ 8.16-7.99 (m, 3H), 7.79-7.70 (m, 4H), 7.47 (dd, J = 8.0 Hz, 4.0 Hz, 2H), 7.33-7.12 (m, 4H), 4.87 (s, 2H), 4.23 (t, J = 8.0 Hz, 4H), 3.48 (dd, J = 12.0 Hz, 4.0 Hz, 2H), 1.86-1.69 (m, 5H), 1.56-1.41 (m, 2H), 1.39-1.18 (m, 4H), 0.84 (t, J = 8.0 Hz, 3H). |
| 147 | A317 | N-{2-[(1-{[2-(2-methoxyethoxy)naphthalen-1-yl]methyl}naphthalen-2-yl)oxy]ethyl}acetamide | 443.54 | 444.1 (M + 1) | 1H NMR (400 MHz, DMSO-d6) δ 8.19-7.94 (m, 3H), 7.89-7.59 (m, 4H), 7.45 (t, J = 8.0 Hz, 2H), 7.19 (s, 4H), 4.85 (s, 2H), 4.33 (s, 4H), 4.21 (s, 2H), 3.69 (s, 2H), 3.46 (d, J = 4.0 Hz, 2H), 3.31 (s, 3H), 1.72 (s, 3H). |
| 148 | A318 | 1-(2-{[1-(3,4-dimethoxybenzoyl)naphthalen-2-yl]oxy}ethyl)pyrrolidine | 405.49 | 406.2 (M + 1) | 1H NMR (400 MHz, CDCl$_3$) δ 7.86 (d, J = 9.0 Hz, 1H), 7.76 (d, J = 7.5 Hz, 1H), 7.62 (s, 1H), 7.46 (d, J = 8.0 Hz, 1H), 7.35-7.28 (m, 2H), 7.19 (s, 1H), 7.11 (d, J = 8.3 Hz, 1H), 6.67 (d, J = 8.4 Hz, 1H), 4.15 (t, J = 5.6 Hz, 2H), 3.88 (S, 3H), 3.83 (S, 3H), 2.66 (t, J = 5.6 Hz, 2H), 2.36 (s, 4H), 1.60 (s, 4H). |
| 149 | A319 | (2-{[1-(3,4-dimethoxybenzoyl)naphthalen-2-yl]oxy}ethyl)diethylamine | 407.51 | 408.3 (M + 1) | 1H NMR (400 MHz, CDCl$_3$) δ 8.44 (s, 1H), 7.87 (d, J = 8.9 Hz, 1H), 7.77 (d, J = 4.9 Hz, 1H), 7.59 (s, 1H), 7.40 (d, J = 4.9 Hz, 1H), 7.30 (d, J = 7.7 Hz, 2H), 7.09 (d, J = 8.0 Hz, 1H), 6.69 (d, J = 8.2 Hz, 1H), 4.35 (s, 2H), 3.87 (s, 3H), 3.83 (s, 3H), 3.03 (s, 2H), 2.74 (d, J = 6.9 Hz, 4H), 0.97 (t, J = 6.7 Hz, 6H). |
| 150 | A320 | 4-{[(1-{[2-(ethoxymethoxy)naphthalen-1-yl]sulfanyl}naphthalen-2-yl)oxy]methyl}piperidine | 473.63 | 474.1 (M + 1) | 1H NMR (400 MHz, DMSO-d6) δ 8.66-8.62 (m, 2H), 8.33 (s, 1H), 7.91-7.85 (m, 3H), 7.55-7.49 (m, 2H), 7.42-7.33 (m, 4H), 4.98 (s, 2H), 3.75 (d, J = 8.0 Hz, 2H), 3.02-2.94 (m, 4H), 2.41-2.33 (m, 3H), 1.34 (d, J = 12 Hz, 2H), 1.07-0.97 (m, 2H), 0.81 (t, J = 8.0 Hz, 3H). |
| 151 | A321 | 2-[(1-{[2-(ethoxymethoxy)naphthalen-1-yl]sulfanyl}naphthalen-2-yl)oxy]ethan-1-amine | 419.54 | 420.2 (M + 1) | 1H NMR (400 MHz, DMSO-d6) δ 8.64 (d, J = 12.0 Hz, 2H), 7.88 (dd, J = 12.0 Hz, 8.0 Hz, 4H), 7.54-7.49 (m, 2H), 7.42-7.33 (m, 4H), 5.02 (s, 2H), 3.90 (t, J = 8.0 Hz, 2H), 2.98 (q, J = 8.0 Hz, 2H), 2.32 (s, 2H), 0.80 (t, J = 8.0 Hz, 3H). |
| 152 | A323 | 1-(4-{[(1-{[2-(ethoxymethoxy)naphthalen-1-yl]methyl}naphthalen-2-yl)oxy]methyl}piperidin-1-yl)ethan-1-one | 497.64 | 520.2 (M + 23) | 1H NMR (400 MHz, DMSO-d6) δ 8.08 (d, J = 8.0 Hz, 2H), 7.82-7.69 (m, 4H), 7.50-7.42 (m, 2H), 7.23 (m, 4H), 5.35 (s, 2H), 4.83 (s, 2H), 4.34 (d, J = 12.0 Hz, 1H), 4.04 (d, J = 8.0 Hz, 2H), 3.78 (d, J = 12.0 Hz, 1H), 3.61 (q, J = 8.0 Hz, 2H), 2.96 (t, J = 12.0 Hz, 1H), 2.43 (s, 2H), 1.94 (s, 3H), 1.72 (m, 2H), 1.34-1.15 (m, 2H), 1.10 (t, J = 8.0 Hz, 3H) |
| 153 | A324 | 4-{[(1-{[2-(2-methoxyethoxy)naphthalen-1-yl]methyl}naphthalen-2-yl)oxy]methyl}piperidine hydrochloride | 455.60 | 456.3 (M + 1) | 1H NMR (400 MHz, DMSO-d6) δ 8.48 (s, 1H), 8.04 (dd, J = 12.0 Hz, 8.0 Hz, 2H), 7.85-7.65 (m, 4H), 7.48 (dd, J = 8.0 Hz, 4.0 Hz, 2H), 7.21-7.19 (m, 4H), 4.85 (s, 2H), 4.39-4.28 (m, 2H), 4.14 (d, J = 4.0 Hz, 2H), 3.74-3.63 (m, 2H), 3.31-3.29 (s, 3H), 3.26 (d, J = 16.0 Hz, 1H), 2.85 (t, J = 12.0 Hz, 2H), 2.08 (s, 1H), 1.91 (d, J = 12.0 Hz, 2H), 1.70-1.56 (m, 2H). |

TABLE 1-continued

Compounds

| Example | Compd ID | Name | M.W. | LCMS | NMR |
|---|---|---|---|---|---|
| 154 | A326 | 3-({1-[(2-methoxynaphthalen-1-yl)methyl]naphthalen-2-yl}oxy)cyclobutan-1-amine; formic acid | 383.49 | 384.3 (M + 1) | 1H NMR (400 MHz, CD$_3$OD) δ 8.24 (d, J = 8.6 Hz, 1H), 8.08 (d, J = 9.2 Hz, 1H), 7.84-7.63 (m, 4H), 7.41-7.19 (m, 5H), 7.04 (d, J = 9.0 Hz, 1H), 4.58-4.55 (m, 2H), 3.84 (m, 3H), 3.42(s, 1H), 2.94-2.83 (m, 1H), 2.48-2.15 (m, 4H). |
| 155 | A328 | N-{2-[(1-{[2-(ethoxymethoxy)naphthalen-1-yl]methyl}naphthalen-2-yl)oxy]ethyl}acetamide | 443.54 | 466.2 (M + 23) | 1H NMR (400 MHz, DMSO-d6) δ 8.09 (t, J = 6.4 Hz, 3H), 7.82-7.71 (m, 4H), 7.48 (dd, J = 16.0 Hz, 8.0 Hz, 2H), 7.31-7.17 (m, 4H), 5.42 (s, 2H), 4.88 (s, 2H), 4.21 (t, J = 5.6 Hz, 2H), 3.66 (q, J = 8.0 Hz, 2H), 3.45 (dd, J = 8.0 Hz, 4.0Hz, 2H), 1.74 (s, 3H), 1.14 (t, J = 8.0 Hz, 3H). |
| 156 | A329 | 1-{[2-(2-aminoethoxy)naphthalen-1-yl]methyl}naphthalen-2-ol hydrochloride | 343.43 | 344.1 (M + 1) | 1H NMR (400 MHz, DMSO-d6) δ 10.12 (s, 1H), 8.43-8.19 (m, 3H), 7.90 (d, J = 8.0 Hz, 1H), 7.84-7.73 (m, 2H), 7.66 (d, J = 8.0 Hz, 1H), 7.61 (d, J = 8.0 Hz, 1H), 7.50 (d, J = 8.0 Hz, 1H), 7.34-7.19 (m, 4H), 7.12 (t, J = 8.0 Hz, 1H), 4.85 (s, 2H), 4.46 (t, J = 4.0 Hz, 2H), 3.31 (t, J = 4.0 Hz, 2H). |
| 157 | A330 | 1-{[2-(2-aminophenoxy)naphthalen-1-yl]methyl}naphthalen-2-ol | 391.47 | 392.0 (M + 1) | 1H NMR (400 MHz, DMSO-d6) δ 10.14 (s, 1H), 8.29-8.27 (m, 1H), 8.19 (d, J = 8.5 Hz, 1H), 7.79-7.73 (m, 2H), 7.69 (d, J = 8.0 Hz, 1H), 7.63 (d, J = 8.9 Hz, 1H), 7.33-7.21 (m, 4H), 7.16 (t, J = 7.4 Hz, 1H), 7.07 (d, J = 9.0 Hz, 1H), 6.92 (t, J = 7.3 Hz, 1H), 6.86 (d, J = 6.6 Hz, 1H), 6.72 (d, J = 7.8 Hz, 1H), 6.59 (t, J = 6.9 Hz, 1H), 4.98 (s, 2H), 4.82 (s, 2H). |
| 158 | A331 | 2-({1-[(2-methoxynaphthalen-1-yl)methyl]naphthalen-2-yl}oxy)aniline | 405.50 | 406.1 (M + 1) | 1H NMR (400 MHz, DMSO-d6) δ 8.20 (d, J = 8.5 Hz, 1H), 8.14 (d, J = 8.0 Hz, 1H), 7.88-7.71 (m, 4H), 7.48 (d, J = 9.1 Hz, 1H), 7.42-7.29 (m, 3H), 7.29-7.20 (m, 1H), 7.02 (d, J = 9.0 Hz, 1H), 6.93-6.79 (m, 2H), 6.61-6.47 (m, 2H), 4.87 (d, J = 10.4 Hz, 3H), 3.94 (s, 2H). |
| 159 | A334 | 1-{[2-(2-aminoethoxy)naphthalen-1-yl]sulfanyl}naphthalen-2-ol | 361.46 | 362.1 (M + 1) | 1H NMR (400 MHz, DMSO-d6) δ 8.72 (d, J = 8.0 Hz, 1H), 8.52 (br, 2H), 8.28 (d, J = 8.0 Hz, 1H), 7.93-7.88 (m, 2H), 7.78 (d, J = 8.0 Hz, 1H), 7.58-7.54 (m, 1H), 7.44-7.39 (m, 2H), 7.37-7.33 (m, 1H), 7.26-7.20 (m, 2H), 4.14 (t, J = 5.4 Hz, 2H), 2.91 (t, J = 5.4 Hz, 2H). |
| 160 | A335 | 1-({2-[(piperidin-4-yl)methoxy]naphthalen-1-yl}sulfanyl)naphthalen-2-ol | 415.55 | 416.1 (M + 1) | 1H NMR (400 MHz, CDCl$_3$) δ 8.81 (d, J = 8.0 Hz, 1H), 8.44 (s, 1H), 8.26 (d, J = 8.0 Hz, 1H), 7.72 (s, 2H), 7.63 (s, 2H), 7.56-7.52 (m, 1H), 7.37-7.33 (m,1H), 7.31-7.27 (m, 1H), 7.22-7.19 (m, 1H), 7.11-7.04 (m, 2H), 3.78 (d, J = 6.0 Hz, 2H), 3.28 (d, J = 6.0 Hz, 2H), 2.73-2.67 (m, 2H), 1.83 (s, 1H), 1.67 (d, J = 6.0 Hz, 2H), 1.51-1.42 (m, 2H). |
| 161 | A337 | 2-({1-[(2-methoxynaphthalen-1-yl)methyl]naphthalen-2-yl}oxy)ethan-1-amine | 357.45 | 358.2 (M + 1) | 1H NMR (400 MHz, DMSO-d6) δ 8.19 (s, 2H), 8.03-8.00 (m, 2H), 7.83-7.74 (m, 4H), 7.51-7.47 (m, 2H), 7.32-7.19 (m, 4H), 4.89 (s, 2H), 4.38 (t, J = 4.0 Hz, 2H), 3.97 (s, 3H), 3.23 (t, J = 4.0 Hz, 2H). |
| 162 | A340 | 1-({2-[2-(ethylamino)ethoxy]naphthalen-1-yl}methyl)naphthalen-2-ol hydrochloride | 371.48 | 372.1 (M + 1) | 1H NMR (400 MHz, DMSO-d6) δ 10.12 (s, 1H), 9.06 (s, 2H), 8.24 (d, J = 8.0 Hz, 1H), 7.89 (d, J = 8.0 Hz, 1H), 7.84-7.73 (m, 2H), 7.67 (d, J = 8.0 Hz, 1H), 7.62 (d, J = 8.0 Hz, 1H), 7.52 (d, J = 12.0 Hz, 1H), 7.32-7.18 (m, 4H), 7.12 (t, J = 8.0 Hz, 1H), 4.85 (s, 2H), 4.52 (t, J = 4.0 Hz, 2H), 3.41 (s, 2H), 3.09 (s, 2H), 1.23 (t, J = 8.0 Hz, 3H). |
| 163 | A341 | {2-[(1-{[2-(ethoxymethoxy)naphthalen-1-yl]methyl}naphthalen-2-yl)oxy]ethyl}(ethyl)amine | 429.56 | 430.2 (M + 1) | 1H NMR (400 MHz, DMSO-d6) δ 8.09 (t, J = 8.0 Hz, 2H), 7.83-7.74 (m, 4H), 7.48 (dd, J = 8.8 Hz, 7.2 Hz, 2H), 7.34-7.18 (m, 4H), 5.35 (s, 2H), 4.89 (s, 2H), 4.29 (t, J = 5.2 Hz, 2H), 3.58 (q, J = 6.8 Hz, 2H), 3.06 (t, J = 5.2 Hz, 2H), 2.81 (dd, J = 14.4 Hz, 7.2 Hz, 2H), 1.09 (q, J = 7.2 Hz, 6H). |
| 164 | A344 | 4-({1-[(2-methoxynaphthalen-1-yl)methyl]naphthalen-2-yl}oxy)aniline; formic acid | 405.50 | 428.2 (M + 23) | 1H NMR (400 MHz, DMSO-d6) δ 8.29 (s, 1H), 8.20 (d, J = 8.5 Hz, 1H), 8.13 (d, J = 8.3 Hz, 1H), 7.83-7.67 (m, 4H), 7.49 (d, J = 9.0 Hz, 1H), 7.29-7.21 (m, 4H), 7.06 (d, J = 9.0 Hz, 1H), 6.72 (d, J = 8.7 Hz, 2H), 6.59 (d, J = 8.7 Hz, 2H), 4.87 (s, 2H), 3.99 (s, 3H). |
| 165 | A004 | 1-[(2-hydroxynaphthalen-1-yl)sulfanyl]naphthalen-2-ol | 318.1 | 341.1 (M + 23) | 1H NMR (400 MHz, DMSO-d6) δ 10.19 (s, 2H), 8.54-8.52 (d, J = 8Hz,2H), 7.75-7.73(d, J = 8Hz,2H), 7.42-7.38(m, 2H), 7.27-7.23(m, 2H), 7.19-7.17(d, J = 8Hz,2H) |
| 166 | A051 | (1-{[2-(hydroxymethyl)naphthalen-1-yl]methyl}naphthalen-2-yl)methanol | 328.4 | 351.1 (M + 23) | 1H NMR (400 MHz, DMSO-d6) δ 8.00 (d, J = 8 Hz, 2H), 7.87 (d, J8 Hz, 2H), 7.83 (d, J8 Hz, 2H), 7.67 (d, J8 Hz, 2H), 7.37 (t, J = 4 Hz, 2H), 7.28-7.24 (m, 2H), 5.24 (t, J = 4 Hz, 2H), 4.97 (s, 2H), 4.56 (d, J = 4 Hz, 4H) |

Biological Test Example 1: Ion Channel Activity Measurement 1.1 Cell Preparation
hERG channel cell line:
  HEK293 cell line expressing the human ERG (ether-a-go-go related gene) potassium channel (Potassium voltage-gated channel subfamily H member 2). cDNA strictly similar to GenBank accession number: NM_000238
CaV1.2 Channel Cell Line:
  CHO cell line stably expressing human calcium channel, voltage-dependent, L type,
  CACNA1C: cDNA strictly similar to GenBank accession number: NM_000719
  CACNB2: cDNA strictly similar to GenBank accession number: NM_000724
  CACNA2D1: cDNA strictly similar to GenBank accession number: NM_000722
Iks Channel Cell Line:
  CHO cell line stably expressing Iks potassium voltage-gated channel subfamily Q member 1(KCNQ1) and potassium voltage-gated channel subfamily E regulatory subunit 1 (KCNE1), cDNA strictly similar to GenBank accession number: NM_000218 and NM_000219

Cells expressing channels were cultured in medium supplemented with 20% FBS in HAM'S F12 culture dish. Cells grew in a humidified incubator at 37° C. under 5% carbon dioxide. To passage cells, remove poor medium and rinse the cells once with PBS 1X. Then add 1 ml of 0.25%-Trypsin-EDTA solution. Place plate on a 37° C. warming incubator 5 min. As soon as cells are detached, add 5 ml of 37° C. complete medium. Draw cell suspension into a sterile pipet and homogenize cells gently to dissociate cells aggregates. Amplify or maintain the cells by seeding 2.5*105 cells in a 6 cm dish (final volume: 5 ml). To maintain electrophysiological performances, cell density must not exceed 80%. On the day before patch clamp experiment, 3*103 cells were seeded on coverslips in the 24-well plate and incubated at 37° C. in 5% carbon dioxide.

1.2 Solution:
For hERG recording:
  Extracellular solution: 140 mM NaCl, 3.5 mM KCl, 1 mM $MgCl_2 \cdot 6H_2O$, 2 mM $CaCl_2$, 10 mM D-glucose, 10 mM HEPES, 1.25 mM $NaH_2PO_4$ pH=7.4 with NaOH.
  Internal pipette solution: 20 mM KCl, 115 mM K-Aspartic, 1 mM $MgCl_2 \cdot 6H_2O$, 5 mM EGTA, 10 mM HEPES, 2 mM $Na_2$-ATP pH=7.2 with KOH.
For Cav1.2 Recording:
  Bath solution: 140 mM TEA-Cl, 2 mM $MgCl_2 \cdot 6H_2O$, 10 mM $CaCl_2$, 10 mM HEPES, 5 mM D-glucose, pH=7.4 with TEA-OH. Pipette solution: 120 mM CsCl, 1 mM $MgCl_2 \cdot 6H_2O$, 10 mM HEPES, 10 mM EGTA, 0.3 mM $Na_2$-GTP, 4 mM Mg-ATP, pH=7.2 with CsOH.

For IKs Recording:
  Extracellular solution (mM): 140 NaCl, 2.5 KCl, 1 $MgCl_2$, 2 $CaCl_2$, 5 Glucose, 10 HEPES, pH=7.4 with NaOH.
  Pipette solution (mM): 120 K-aspartic, 10 HEPES, 5 $MgCl_2$, 5 EGTA, 4 $Na_2$-ATP 0.3 $Na_2$-GTP, 14 mM Phosphocreatine disodium salt, 20 u/mL Creatine phosphor kinse pH 7.2 with KOH All the pipette solutions were aliquoted in 1 mL tube after prepared and stored at −20° C. The new pipette solutions were used in the experiment every day. All the pipette solutions were used up to one month. The old pipette solutions exceeding one month were discard.

1.3 Electrophysiological Measurement
  Glass pipette (BF150-86-10, Sutter Instruments) was made by puller (P97, Sutter Instruments). The glass pipette was manipulated using Micro-manipulator (Carm-C-S, MCI Instruments) under the microscope (AE31EF-INV, Motic). After touching the cell, a slight suction was applied to achieve high seal (GΩ). Fast capacitance (in pF) compensation was made after high seal was achieved; after achieving high seal, the membrane was broken, Cell capacitance (in pF) compensation was made from whole-cell capacitance compensation after the whole cell mode was achieved. No leak subtraction was made.

Cell was incubated with the test article for 5 minutes, or until the current reached a steady-state level. Multiple concentrations of test article were tested. The test articles were applied gradually from low to high concentration. The test and control solutions were flown into a recording chamber mounted on the stage of an inverted microscope via a gravity-fed solution delivery system. During the experiment, solutions were withdrawn from the recording chamber by vacuum aspiration. Each concentration was tested at multiple times. Each cell acted as its own control. All tests were performed at room temperature (23-25° C.).

hERG current was recorded under a holding potential at −80 mV and then depolarized to 30 mV for 2.5 seconds to activate the hERG channel. The peak tail currents were induced by a repolarizing pulse to −50 mV for 4 seconds. This voltage-clamp pulse protocol was performed continuously during the experiment. An interpulse interval of 10 seconds allowed recovery from inactivation. An interpulse of −50 mV test for 0.5 second before 30 mV depolarized step was included for leak current correction Cav1.2 current was recorded under a holding potential at −80 mV and then depolarized to +10 mV for 0.3 seconds. This protocol was repeated at 20 s intervals to observe the effect of test articles on the peak of Cav1.2 current.

$I_{Ks}$ current was measured using a pulse protocol consisting of −80 mV holding potential increment up to +60 mV over a period of 5 seconds. And then quickly repolarizedat −40 mV and maintained for 4 seconds.

1.4 Results
  The results of Biological test Example are shown in Table 2.

TABLE 2

| | | | Ion-channel inhibition data | | | | | |
|---|---|---|---|---|---|---|---|---|
| Compound ID | Compound name | Example No. | Iks 1 μM | Iks 10 μM | Cav1.2 1 μM | CaV 1.2 10 μM | hERG 1 μM | hERG 10 μM |
| A001 | 1,1'-methylenebis(naphthalen-2-ol) | 01 | B | A | D | A | D | A |
| A003 | 1,1'-(methylazanediyl)bis(naphthalen-2-ol) | 02 | C | B | D | C | C | A |
| A005 | 1,1'-sulfonylbis(naphthalen-2-ol) | 03 | C | C | ND | ND | ND | ND |
| A006 | 1,1'-sulfinylbis(naphthalen-2-ol) | 04 | D | C | D | D | D | D |
| A040 | bis(2-methoxynaphthalen-1-yl)methanol | 05 | D | C | ND | ND | ND | ND |
| A007 | bis(2-hydroxynaphthalen-1-yl)methanone | 06 | ND | ND | D | B | D | C |
| A012 | 1,1'-(ethane-1,1-diyl)bis (naphthalen-2-ol) | 07 | ND | ND | D | A | D | C |

TABLE 2-continued

Ion-channel inhibition data

| Compound ID | Compound name | Example No. | Iks 1 μM | Iks 10 μM | Cav1.2 1 μM | CaV 1.2 10 μM | hERG 1 μM | hERG 10 μM |
|---|---|---|---|---|---|---|---|---|
| A014 | 1-((2-methoxynaphthalen-1-yl)methyl)naphthalen-2-ol | 08 | D | D | D | B | D | A |
| A015 | bis(2-methoxynaphthalen-1-yl)methane | 09 | D | D | ND | ND | | |
| A016 | 2,2'-methylenediphenol | 10 | D | D | ND | ND | | |
| A017 | 2,2'-methylenebis(3,4-dimethylphenol) | 11 | ND | ND | D | C | D | C |
| A021 | 1-((2-aminonaphthalen-1-yl)methyl)naphthalen-2-ol | 12 | ND | ND | D | D | D | D |
| A022 | 1,1'-methylenebis(naphthalen-2-amine) | 13 | ND | ND | D | B | D | B |
| A022-2 | 4-((2-aminonaphthalen-1-yl)methyl)naphthalen-2-amine | 14 | ND | ND | D | C | D | A |
| A024-3 | N-(3-((2-(methylsulfonamido)naphthalen-1-yl)methyl)naphthalen-2-yl)methanesulfonamide | 15 | ND | ND | D | C | | |
| A024 | N,N'-(methylenebis(naphthalene-1,2-diyl))dimethanesulfonamide | 16 | ND | ND | D | D | | |
| A024-2 | N-(1-((3-(methylsulfonamido)naphthalen-1-yl)methyl)naphthalen-2-yl)methanesulfonamide | 17 | ND | ND | D | C | D | B |
| A025 | N-(1-((2-hydroxynaphthalen-1-yl)methyl)naphthalen-2-yl)methanesulfonamide | 18 | ND | ND | D | C | D | C |
| A026 | N-(1-((2-hydroxynaphthalen-1-yl)methyl)naphthalen-2-yl)benzenesulfonamide | 19 | A | A | D | A | D | C |
| A027 | 4-((2-hydroxynaphthalen-1-yl)methyl)isoquinolin-3-ol | 20 | ND | ND | D | C | D | D |
| A031 | 1-((2-hydroxynaphthalen-1-yl)methyl)-3-methylnaphthalen-2-ol | 21 | D | B | D | C | D | B |
| A032 | 1,1'-methylenebis(3-methylnaphthalen-2-ol) | 22 | ND | ND | D | D | D | D |
| A034 | 2,2''-methylenebis(([1,1'-biphenyl]-3-ol)) | 23 | ND | ND | D | B | D | D |
| A035 | 2,2'-methylenebis(3-methylnaphthalen-1-ol) | 24 | ND | ND | D | A | D | B |
| A044 | 2-hydroxy-N-(2-hydroxynaphthalen-1-yl)-1-naphthamide | 28 | ND | ND | D | D | D | C |
| A046 | 1,1'-methylenebis(3-chloronaphthalen-2-ol) | 29 | ND | ND | D | D | D | D |
| A047 | 1,1'-methylenebis(3-(2-hydroxypropan-2-yl)naphthalen-2-ol) | 30 | ND | ND | D | B | D | ND |
| A049 | 1,1'-methylenebis(3-fluoronaphthalen-2-ol) | 31 | ND | ND | D | B | D | B |
| A050 | 1,1'-methylenebis(3-methoxynaphthalen-2-ol) | 32 | ND | ND | D | D | D | D |
| A052 | 1-(naphthalen-1-ylmethyl)naphthalen-2-ol | 33 | C | ND | D | A | D | A |
| A056 | 1-((2-hydroxynaphthalen-1-yl)methyl)-1H-benzo[d]108yrrolidi-2-ol | 35 | ND | ND | D | C | D | D |
| A057 | 1-((2-hydroxynaphthalen-1-yl)methyl)indolin-2-one | 36 | ND | ND | D | D | D | D |
| A059 | 1-((2-hydroxynaphthalen-1-yl)methyl)-4-phenyl-1H-pyrazol-5-ol | 37 | ND | ND | D | D | D | D |
| A075 | N,N-bis(2-hydroxynaphthalen-1-yl)acetamide | 38 | ND | ND | D | D | D | D |
| A076 | 8-(ethoxymethoxy)-3,4-dihydronaphthalen-1(2H)-one | 39 | ND | ND | D | C | D | B |
| A077 | 1',2',3',4'-tetrahydro-[1,1'-binaphthalene]-2,8'-diol | 40 | ND | ND | D | D | D | B |
| A077-2 | 1',2',3',4',5,6,7,8-octahydro-[1,1'-binaphthalene]-2,8'-diol | 41 | ND | ND | D | D | D | B |
| A078 | 1-(4-hydroxy-1H-inden-3-yl)naphthalen-2-ol | 42 | ND | ND | D | D | D | D |
| A079 | 1-(7-hydroxy-2,3-dihydro-1H-inden-1-yl)naphthalen-2-ol | 43 | ND | ND | D | B | D | A |
| A080 | bis(2-(((4-methoxybenzyl)oxy)methyl)naphthalen-1-yl)methanol | 44 | ND | ND | D | C | D | D |
| A081 | 1,1'-methylenebis(3-isopropylnaphthalen-2-ol) | 45 | ND | ND | D | C | D | B |
| A093 | 1-((2-(2-(diethylamino)ethoxy)naphthalen-1-yl)methyl)naphthalen-2-ol formate | 46 | D | A | C | A | A | A |
| A098 | 1-((2-(2-(diethylamino)ethoxy)naphthalen-1-yl)methyl)-3-methylnaphthalen-2-ol | 47 | ND | ND | D | D | C | A |
| A100 | 1,1'-methylenebis(2-naphthoic acid) | 48 | ND | ND | D | D | D | D |
| A101 | 1,1'-methylenebis(2-naphthamide) | 49 | ND | ND | D | D | D | B |
| A102 | 1-((2-(2-(diethylamino)ethoxy)-3-isopropylnaphthalen-1-yl)methyl)-3-isopropylnaphthalen-2-ol hydrochloride salt | 50 | ND | ND | D | A | B | A |
| A103 | 2,2'-((methylenebis(naphthalene-1,2-diyl))bis(oxy))bis(N,N-diethylethan-1-amine) formic acid | 51 | ND | ND | D | D | ND | ND |
| A107 | 1,1'-methylenebis(2-naphthoic acid) | 52 | ND | ND | D | D | D | D |
| A106 | 1-((2-hydroxynaphthalen-1-yl)methyl)-2-naphthoic acid | 53 | ND | ND | D | D | D | D |
| A108 | 1-((2-(2-(diethylamino)ethoxy)-3-methylnaphthalen-1-yl)methyl)-3-methylnaphthalen-2-ol | 54 | ND | ND | D | C | D | D |

TABLE 2-continued

Ion-channel inhibition data

| Compound ID | Compound name | Example No. | Iks 1 μM | Iks 10 μM | Cav1.2 1 μM | CaV 1.2 10 μM | hERG 1 μM | hERG 10 μM |
|---|---|---|---|---|---|---|---|---|
| A109 | 8-((2-hydroxynaphthalen-1-yl)methyl)isoquinolin-7-ol | 55 | ND | ND | C | B | D | A |
| A111-I-1 | 2-(2-(diethylamino)ethoxy)-N-(2-methoxynaphthalen-1-yl)naphthalen-1-amine | 56 | D | A | D | ND | A | A |
| A111-I-2 | 2-(2-(diethylamino)ethoxy)-N-(2-methoxynaphthalen-1-yl)-N-methylnaphthalen-1-amine 2,2,2-trifluoroacetate | 57 | ND | ND | D | C | B | A |
| A114 | 6-hydroxy-5-((2-hydroxynaphthalen-1-yl)methyl)-2-naphthoic acid | 58 | ND | ND | D | D | D | B |
| A117 | 2,2'-methylenebis(3-(108yrrolid-3-yl)phenol) | 59 | ND | ND | D | C | D | D |
| A117-I-1 | 2-(2-methoxy-6-(108yrrolid-3-yl)benzyl)-3-(108yrrolid-3-yl)phenol | 60 | ND | ND | D | D | D | C |
| A118-I-1 | 2-(2-methoxy-6-(109yrrolid-4-yl)benzyl)-3-(109yrrolid-4-yl)phenol | 62 | ND | ND | D | D | D | C |
| A122 | 6-hydroxy-5-((2-hydroxynaphthalen-1-yl)methyl)-2-naphthamide | 63 | ND | ND | D | A | C | A |
| A123 | 5,5'-methylenebis(6-hydroxy-2-naphthamide) | 64 | ND | ND | D | D | D | C |
| A125 | 5-((6-carboxy-2-(2-(diethylamino)ethoxy)naphthalen-1-yl)methyl)-6-hydroxy-2-naphthoic acid | 65 | ND | ND | D | A | D | ND |
| A127 | 5,5'-methylenebis(6-(2-(diethylamino)ethoxy)-2-naphthoic acid) | 66 | ND | ND | ND | ND | ND | ND |
| A129 | 1-((2-(109yrrolidine-1-yl)ethoxy)naphthalen-1-yl)methyl)naphthalen-2-ol | 67 | C | A | C | A | A | ND |
| A129-2 | 1-(2-((1-((2-methoxynaphthalen-1-yl)methyl)naphthalen-2-yl)oxy)ethyl)-1-methylpyrrolidin-1-ium formate | 68 | ND | ND | C | A | C | ND |
| A130 | 1-((2-(2-morpholinoethoxy)naphthalen-1-yl)methyl)naphthalen-2-ol | 69 | ND | ND | C | A | D | A |
| A130-2 | 4-(2-((1-((2-methoxynaphthalen-1-yl)methyl)naphthalen-2-yl)oxy)ethyl)-4-methylmorpholin-4-ium formate | 70 | D | C | B | A | A | ND |
| A134 | 1-((2-(2-(dimethylamino)ethoxy)naphthalen-1-yl)methyl)naphthalen-2-ol | 71 | C | A | D | A | A | A |
| A135 | 1-((2-(3-(diethylamino)propoxy)naphthalen-1-yl)methyl)naphthalen-2-ol | 72 | D | A | C | A | A | A |
| A138 | 1-((2-(2-(piperidin-1-yl)ethoxy)naphthalen-1-yl)methyl)naphthalen-2-ol | 73 | ND | ND | D | A | A | ND |
| A139-2 | 2-((1-((2-methoxynaphthalen-1-yl)methyl)naphthalen-2-yl)oxy)ethan-1-ol | 74 | ND | ND | D | A | A | A |
| A141 | 8-((2-hydroxynaphthalen-1-yl)methyl)-1,2,3,4-tetrahydroisoquinolin-7-ol | 75 | ND | ND | D | D | D | C |
| A141-I-1 | 8-((2-hydroxy-5,6,7,8-tetrahydronaphthalen-1-yl)methyl)-1,2,3,4-tetrahydroisoquinolin-7-ol | 76 | ND | ND | D | D | D | D |
| A151 | 1-((2-(2-(diethylamino)ethoxy)naphthalen-1-yl)thio)naphthalen-2-ol | 77 | C | A | D | A | A | A |
| A152 | N,N-diethyl-2-((1-((2-methoxynaphthalen-1-yl)thio)naphthalen-2-yl)oxy)ethan-1-amine | 78 | D | B | D | A | A | ND |
| A168 | 1-((6-(2-(diethylamino)ethoxy)quinoxalin-5-yl)methyl)naphthalen-2-ol | 79 | ND | ND | D | D | D | D |
| A191 | diethyl(2-((1-((2-methoxynaphthalen-1-yl)thio)naphthalen-2-yl)oxy)ethyl)(methyl)-l4-azane, | 80 | D | ND | C | A | A | A |
| A194 | 1-((2-(diethylamino)ethyl)(3,4-dimethoxyphenyl)amino)naphthalen-2-ol | 81 | ND | ND | C | B | D | C |
| A195 | 2,2'-((2-((1-((2-methoxynaphthalen-1-yl)methyl)naphthalen-2-yl)oxy)ethyl)azanediyl)bis(ethan-1-ol) | 82 | ND | ND | D | A | A | A |
| A196 | 2-methoxy-N-(2-nitronaphthalen-1-yl)naphthalen-1-amine | 83 | ND | ND | D | D | D | D |
| A232 | 1-((2-methoxynaphthalen-1-yl)methyl)naphthalen-2-yl diethylglycinate | 84 | ND | ND | D | A | B | A |
| A234 | (2-hydroxynaphthalen-1-yl)(2-(2-(109yrrolidine-1-yl)ethoxy)naphthalen-1-yl)methanone | 85 | ND | ND | D | A | A | A |
| A238 | N-(2-(diethylamino)ethyl)-1-((2-methoxynaphthalen-1-yl)methyl)-2-naphthamide | 86 | ND | ND | C | A | A | A |
| A244 | 2-((1-((2-(ethoxymethoxy)naphthalen-1-yl)methyl)naphthalen-2-yl)oxy)ethan-1-amine | 87 | ND | ND | D | C | A | A |
| A246 | 2-((1-((2-isopropoxynaphthalen-1-yl)methyl)naphthalen-2-yl)oxy)ethan-1-amine | 88 | ND | ND | ND | ND | C | ND |
| A254 | 1-(2-((1-((2-(ethoxymethoxy)naphthalen-1-yl)methyl)naphthalen-2-yl)oxy)ethyl)pyrrolidine | 89 | ND | ND | D | B | D | A |
| A255 | 1-(2-((1-((2-(ethoxynaphthalen-1-yl)methyl)naphthalen-2-yl)oxy)ethyl)pyrrolidine | 90 | ND | ND | D | A | A | A |
| A256 | 1-(2-((1-((2-isopropoxynaphthalen-1-yl)methyl)naphthalen-2-yl)oxy)ethyl)pyrrolidine | 91 | ND | ND | D | A | B | A |

TABLE 2-continued

Ion-channel inhibition data

| Compound ID | Compound name | Example No. | Iks 1 μM | Iks 10 μM | Cav1.2 1 μM | CaV 1.2 10 μM | hERG 1 μM | hERG 10 μM |
|---|---|---|---|---|---|---|---|---|
| A271 | 4-(((1-((2-methoxynaphthalen-1-yl)methyl)naphthalen-2-yl)oxy)methyl)piperidine | 92 | ND | ND | B | ND | A | A |
| A279 | 4-(((1-((2-(ethoxymethoxy)naphthalen-1-yl)methyl)naphthalen-2-yl)oxy)methyl)piperidine | 93 | ND | ND | D | A | A | A |
| A284 | 2-(diethylamino)-N-(1-((2-methoxynaphthalen-1-yl)methyl)naphthalen-2-yl)acetamide | 94 | ND | ND | D | D | C | ND |
| A286 | 1-({2-[2-(piperidin-4-yl)ethoxy]naphthalen-1-yl}methyl)naphthalen-2-ol hydrochloride | 95 | ND | ND | D | A | A | ND |
| A290 | {2-[(1-{[2-(benzyloxy)naphthalen-1-yl]methyl}naphthalen-2-yl)oxy]ethyl}diethylamine | 96 | ND | ND | c | B | A | A |
| A291 | 1-{2-[(1-{[2-(benzyloxy)naphthalen-1-yl]methyl}naphthalen-2-yl)oxy]ethyl}pyrrolidine; formic acid | 97 | ND | ND | D | ND | A | ND |
| A296 | 1-[2-({1-[(2-methoxynaphthalen-1-yl)methyl]naphthalen-2-yl}methoxy)ethyl]pyrrolidine | 98 | ND | ND | D | A | A | ND |
| A300 | [2-(diethylamino)ethyl]({1-[(2-methoxynaphthalen-1-yl)methyl]naphthalen-2-yl}methyl)amine | 99 | ND | ND | D | A | A | ND |
| A257 | 1-{2-[(1-{[2-(hexyloxy)naphthalen-1-yl]methyl}naphthalen-2-yl)oxy]ethyl}pyrrolidine | 100 | ND | ND | ND | ND | ND | ND |
| A258 | 1-{2-[(1-{[2-(2-methoxyethoxy)naphthalen-1-yl]methyl}naphthalen-2-yl)oxy]ethyl}pyrrolidine | 25 | ND | ND | D | A | A | A |
| A262 | 1-({2-[(1-methylpyrrolidin-3-yl)methoxy]naphthalen-1-yl}methyl)naphthalen-2-ol; formic acid | 26 | ND | ND | D | A | A | A |
| A247 | 2-[(1-{[2-(hexyloxy)naphthalen-1-yl]methyl}naphthalen-2-yl)oxy]ethan-1-amine | 27 | ND | ND | D | ND | D | ND |

Definition: A = 75-100%; B = = 50-75%; C = 25-50%; D = <25%

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

What is claimed:

1. A compound or a pharmaceutically acceptable salt, a solvate, or a stereoisomer thereof,
wherein
the compound is a compound of formula (IIh);

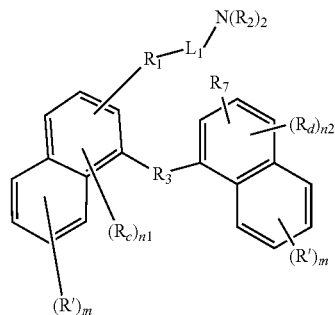

wherein
$R_1$ is —O—, or —S—;
$R_3$ is selected from the group consisting of: —O—, —S—, —N($R_a$)—, and —C($R_b$)$_2$—; wherein $R_a$ is selected from the group consisting of H, and C1-C4 alkyl, and $R_b$ is each independently selected from the group consisting of H and C1-C6 alkyl;
$L_1$ is substituted or unsubstituted C3-C8 cycloalkyl or unsubstituted C1-C6 alkylene group;
$R_7$ is selected from the group consisting of: H, —OH, halogen, $R_f$—, $R_f$—O—, $R_f$—S—, $R_f$—C(O)O—, $R_f$—S(O)$_2$—, $R_f$—S(O)—, $R_f$—C(O)—, NHR$_f$, NH(SO$_2$)R$_f$, and —R$_{1a}$-L$_{1a}$-R$_{da}$, wherein $R_f$ is selected from the group consisting of: H, substituted or unsubstituted C1-C6 alkyl, substituted or unsubstituted C3-C6 cycloalkyl; $R_{1a}$ is —O—, or —S—; $L_{1a}$ is unsubstituted C1-C6 alkylene group, or substituted or unsubstituted C3-C8 cycloalkyl;
each $R_2$ is independently selected from the group consisting of: H, and substituted or unsubstituted C1-C6 alkyl; or two $R_2$ and the nitrogen atom to which they are attached form a substituted or unsubstituted 4 to 10 membered heterocyclic group, and the heterocyclyl contains 1 or 2 N atoms and 0, 1, or 2 O or S heteroatoms;
$R_c$, $R_d$ and $R_{da}$ are each independently selected from the group consisting of —OH, nitro, cyano, sulfonyl, R", —N(R")$_2$—, R"—O—, R"—S—, R"—S(O)$_2$—, R"—S(O)—, R"—C(O), R"—C(O)O—, and R"—OC(O)—;
n1 and n2 are each independently 0, 1, or 2;
each of m is independently 0, 1, 2 or 3; and
unless otherwise specified, the term "substituted" refers to one or more hydrogens in the group is replaced with an R' group;
each R' is independently selected from the group consisting of D, halogen, —OH, nitro, cyano, sulfonyl, R", —N(R"), R"—O—, R"—S—, R"—S(O)$_2$—, R"—S(O)—, R"—C(O), R"—C(O)O—, R"—OC(O)—, and oxo (O=); or when two R' attached to the same carbon atom, the two R' and the carbon atom to which they are attached form substituted or unsubstituted C3-C8 cycloalkyl, substituted or unsubstituted C6-C10 aryl, substituted or unsubstituted 4 to 7 membered heterocyclic group or 5 to 7-membered heteroaryl;

R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, -C1-C4 alkylene-C3-C6 cycloalkyl, -C1-C4 alkylene-C6-C10 aryl, -C1-C4 alkylene-(4 to 7-membered heterocycloalkyl), and -C1-C4 alkylene-(5 to 7-membered heteroaryl); and in R", the alkyl, alkenyl, alkynyl, cycloalkyl, aryl, heterocycloalkyl or heteroaryl, as a whole group or a partial group, is optionally substituted by a substituent selected from the group consisting of: halogen, C1-C4 alkyl, C1-C4 alkoxy, C1-C4 haloalkyl, —OH, nitro, cyano, sulfonyl, and amino;

or the compound is selected from the following table:

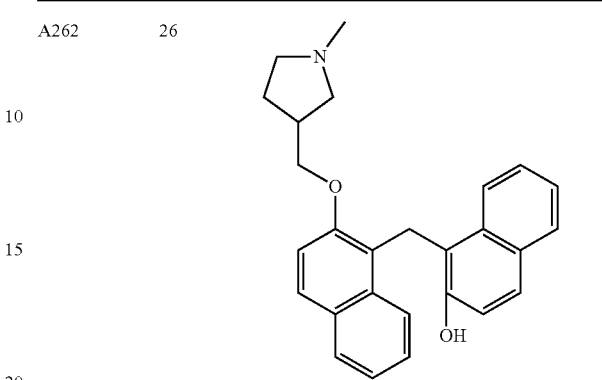

| Compd ID | Example No. | Structure |
|---|---|---|
| A286 | 95 | 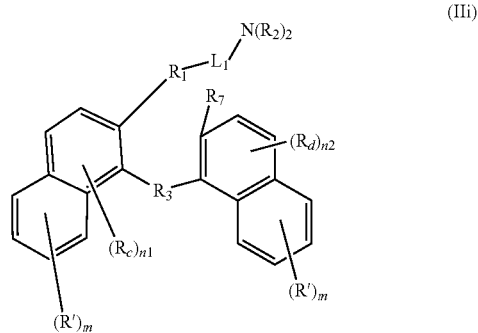<br>TJU-A286 |
| A191 | 80 | 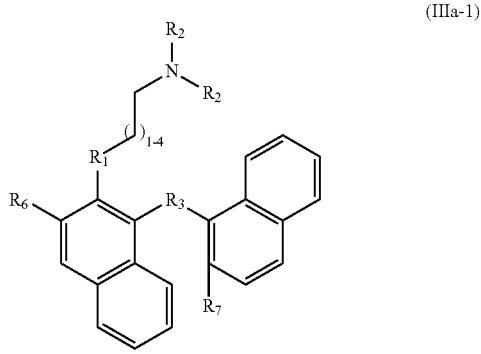<br>TJU-A191 |

2. The compound of claim 1, or the pharmaceutically acceptable salt, the solvate, or the stereoisomer thereof, wherein the compound of formula (IIh) is a compound of formula (IIi)

(IIi)

wherein, $R_1$, $R_2$, $R_3$, $R_7$, $R_c$, $R_d$, $L_1$, R', n1, n2, and m are as defined in claim 1.

3. The compound of claim 1, or the pharmaceutically acceptable salt, the solvate, or a stereoisomer thereof, wherein the compound of formula (IIh) is a compound of formula (IIIa):

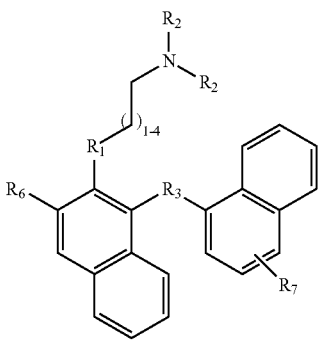

(IIIa)

wherein, $R_1$ is O, or S;

$R_2$ is substituted or unsubstituted C1-C3 alkyl;

$R_3$ is —N($R_a$)—, —CH$_2$—, or —S—; wherein $R_a$ is selected from the group consisting of H, and C1-C4 alkyl;

$R_7$ is selected from the group consisting of: H, F, Cl, Br, —OH, NHR$_f$, NH(SO$_2$)R$_f$, R$_f$—, R$_f$—O—, R$_f$—C(O)O—, R$_f$—S(O)$_2$—, R$_f$—S(O)—, R$_f$—C(O)—, and —R$_{1a}$—L$_{1a}$-R$_{da}$; wherein R$_f$ is selected from the group consisting of: H, substituted or unsubstituted C1-C6 alkyl, substituted or unsubstituted C3-C6 cycloalkyl; R$_{1a}$ and L$_{1a}$ are as defined in claim 1; and $R_6$ is H.

4. The compound of claim 3, or the pharmaceutically acceptable salt, the solvate, or the stereoisomer thereof, wherein the compound of formula (IIIa) is a compound of formula (IIIa-1):

(IIIa-1)

wherein, $R_1$, $R_2$, $R_3$, $R_6$, and $R_7$ are as defined in claim 3.

5. A compound selected from the following table:
| Compd ID | Example No. | Structure |
|---|---|---|
| A093 | 46 | 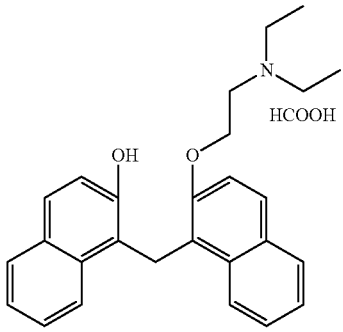 TJU-A093 |
| A098 | 47 | 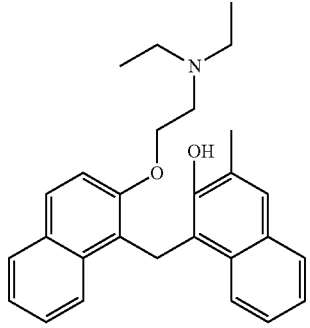 TJU-A098 |
| A102 | 50 | 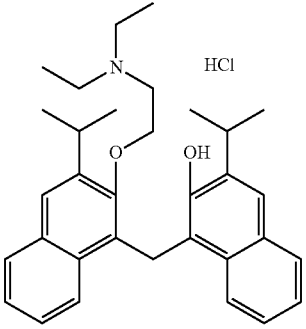 TJU-A102 |
| A108 | 54 | 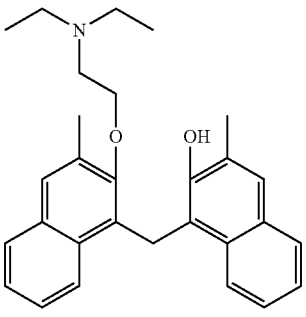 TJU-A108 |
-continued
| Compd ID | Example No. | Structure |
|---|---|---|
| A111-I-1 | 56 | 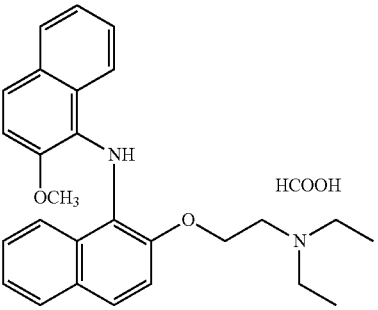 [SMILES: CCN(CC)CCOc1ccc2ccccc2c1Nc1c(OC)ccc2ccccc12 ; "HCOOH"] TJU-A111-I-1 |
| A111-I-2 | 57 | 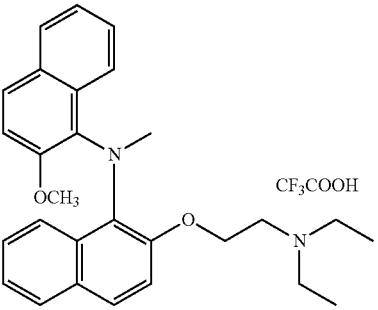 [SMILES: CCN(CC)CCOc1ccc2ccccc2c1N(C)c1c(OC)ccc2ccccc12 ; "CF3COOH"] TJU-A111-I-2 |
| A125 | 65 | 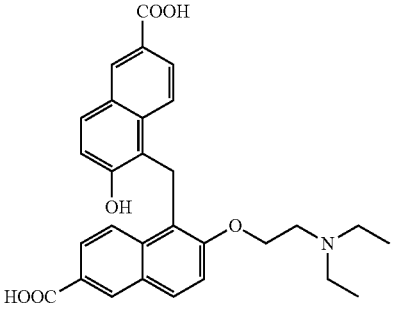 [SMILES: CCN(CC)CCOc1ccc2cc(C(=O)O)ccc2c1Cc1c(O)ccc2cc(C(=O)O)ccc12] TJU-A125 |
| A129 | 67 | 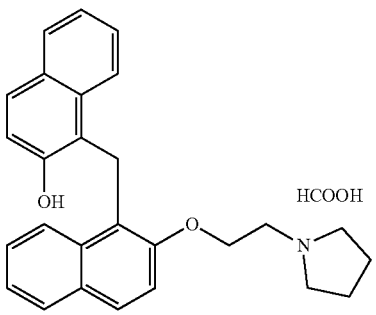 [SMILES: Oc1ccc2ccccc2c1Cc1c(OCCN2CCCC2)ccc2ccccc12 ; "HCOOH"] TJU-A129 |

| Compd ID | Example No. | Structure |
|---|---|---|
| A129-2 | 68 | 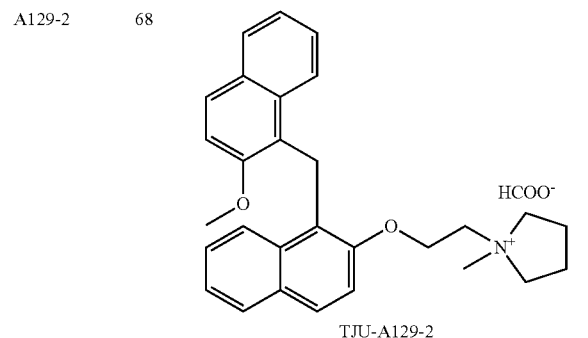<br>TJU-A129-2 |
| A130 | 69 | 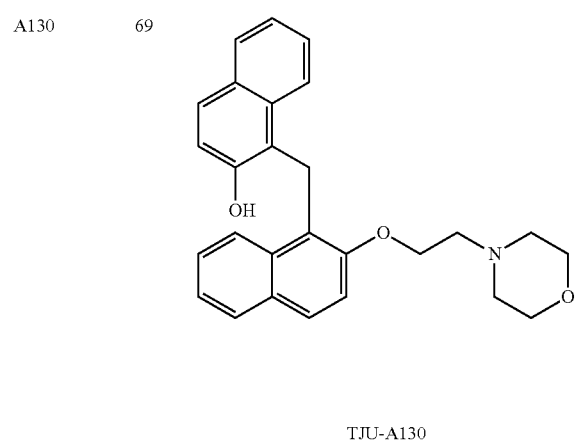<br>TJU-A130 |
| A130-2 | 70 | 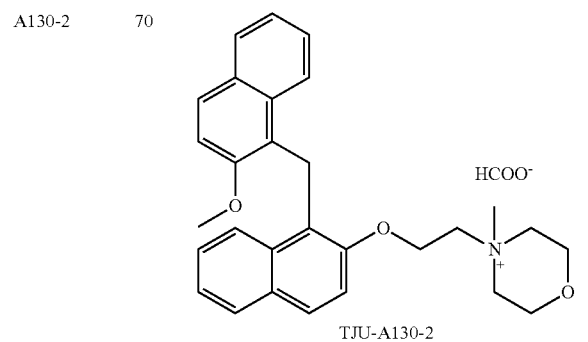<br>TJU-A130-2 |
| A134 | 71 | 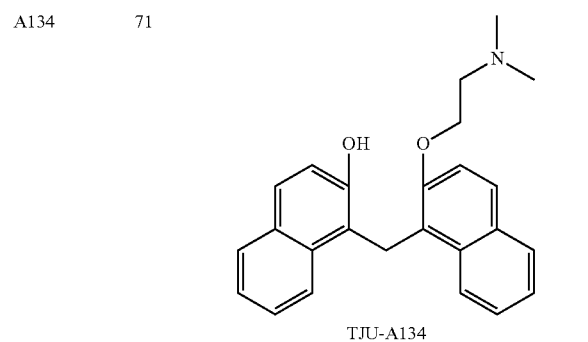<br>TJU-A134 |
| A135 | 72 | 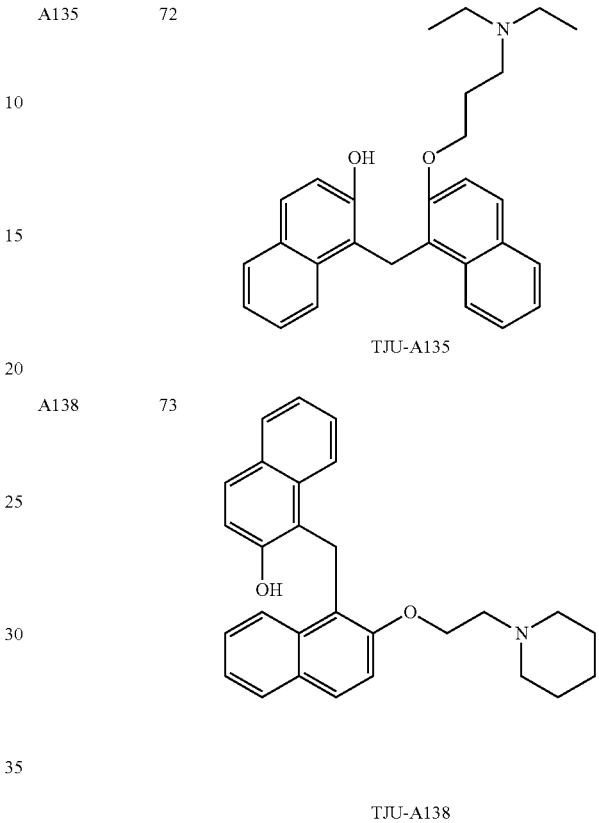<br>TJU-A135 |
| A138 | 73 | TJU-A138 |
| A139-2 | 74 | 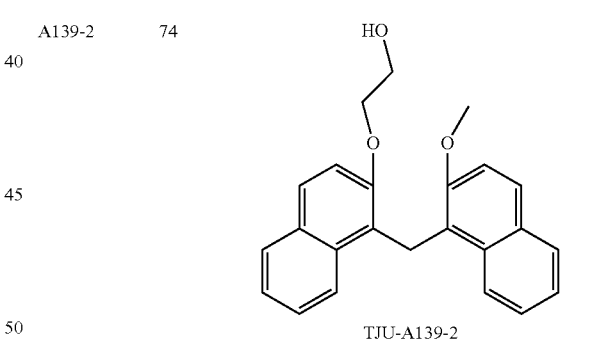<br>TJU-A139-2 |
| A151 | 77 | 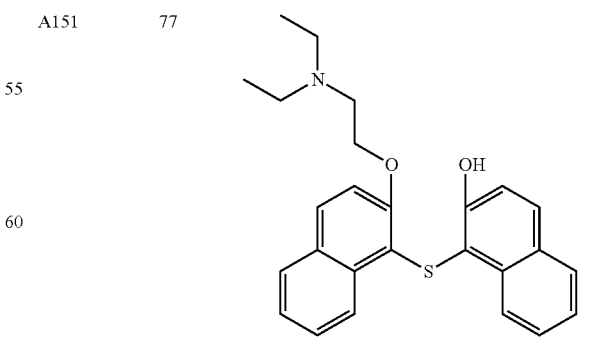<br>TJU-A151 |

-continued
| Compd ID | Example No. | Structure |
|---|---|---|
| A152 | 78 | 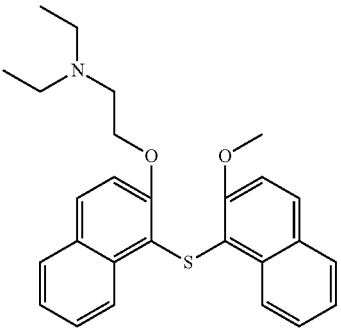 [SMILES: CCN(CC)CCOc1ccc2ccccc2c1Sc1c(OC)ccc2ccccc12]<br>TJU-A152 |
| A191 | 80 | 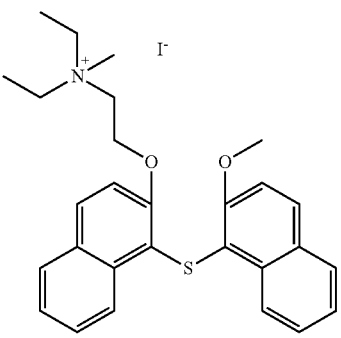<br>TJU-A191 |
| A195 | 82 | 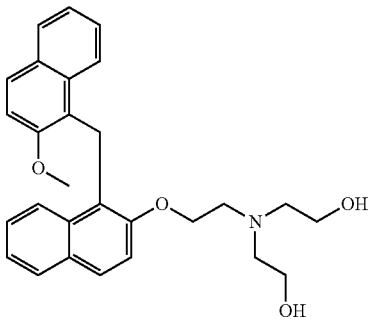 [SMILES: COc1ccc2ccccc2c1Cc1c(OCCN(CCO)CCO)ccc2ccccc12]<br>TJU-A195 |
| A244 | 87 | 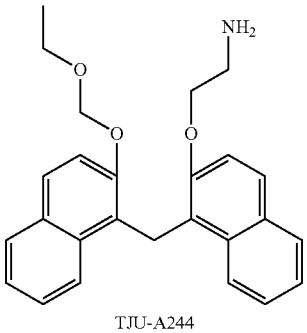<br>TJU-A244 |
-continued
| Compd ID | Example No. | Structure |
|---|---|---|
| A246 | 88 | 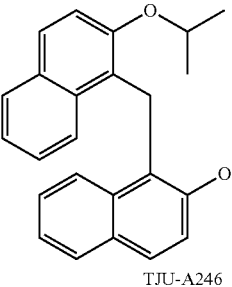<br>TJU-A246 |
| A254 | 89 | 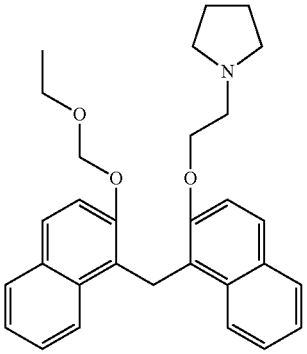<br>TJU-A254 |
| A255 | 90 | 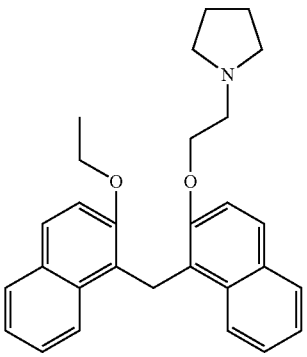 [SMILES: CCOc1ccc2ccccc2c1Cc1c(OCCN2CCCC2)ccc2ccccc12]<br>TJU-A255 |
| A256 | 91 | 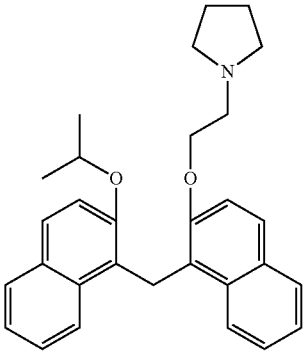 [SMILES: CC(C)Oc1ccc2ccccc2c1Cc1c(OCCN2CCCC2)ccc2ccccc12]<br>TJU-A256 |

-continued
| Compd ID | Example No. | Structure |
|---|---|---|
| A257 | 100 | 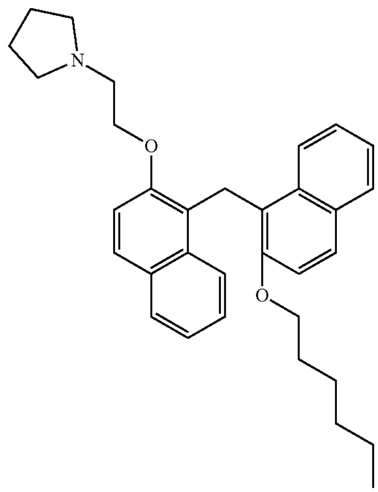 [SMILES: CCCCCCOc1ccc2ccccc2c1Cc1c(OCCN2CCCC2)ccc2ccccc12] |
| A258 | 25 | 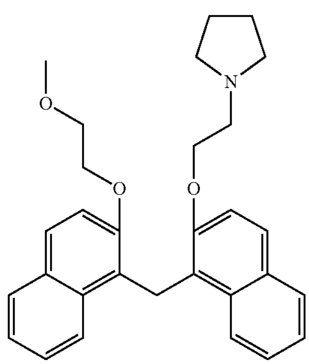 [SMILES: COCCOc1ccc2ccccc2c1Cc1c(OCCN2CCCC2)ccc2ccccc12] |
| A262 | 26 | 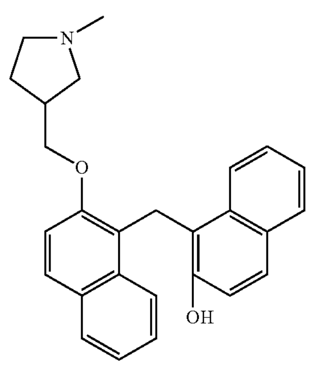 [SMILES: CN1CCC(COc2ccc3ccccc3c2Cc2c(O)ccc3ccccc23)C1] |
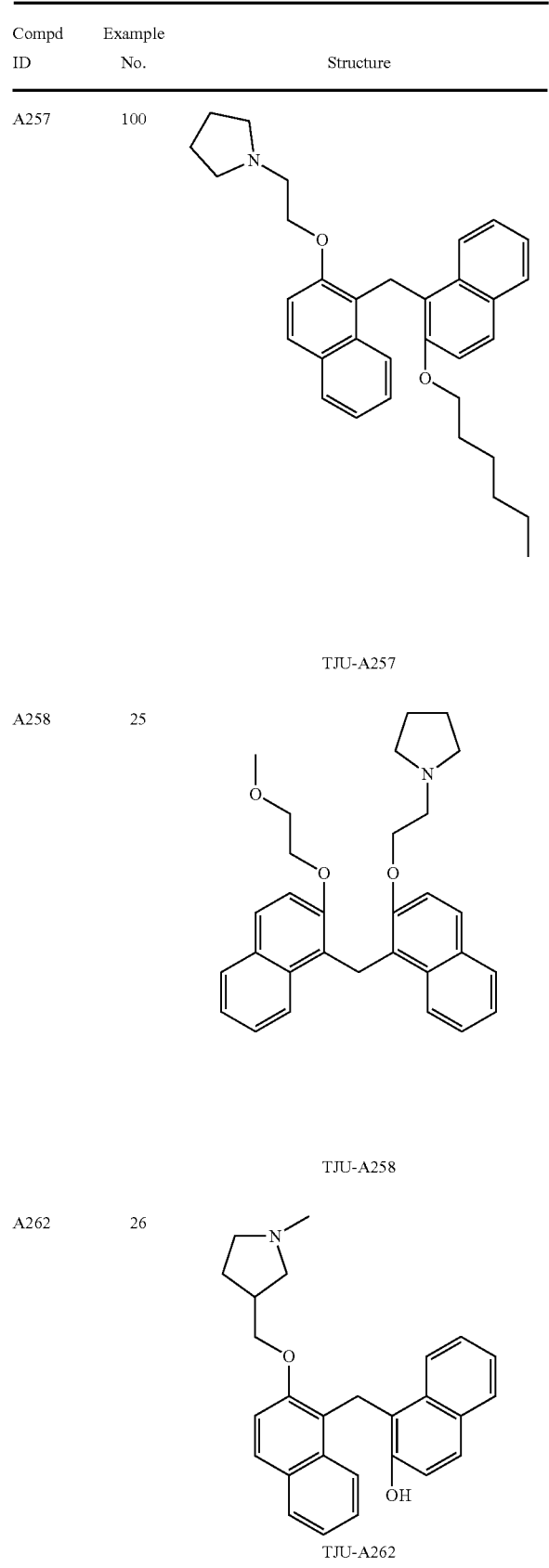
-continued
| Compd ID | Example No. | Structure |
|---|---|---|
| A271 | 92 | 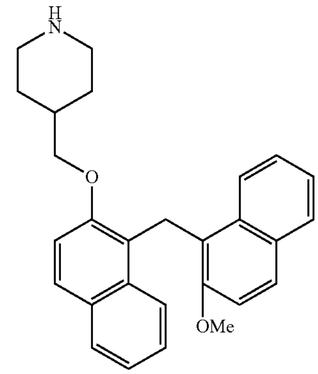 [SMILES: COc1ccc2ccccc2c1Cc1c(OCC2CCNCC2)ccc2ccccc12] |
| A279 | 93 | 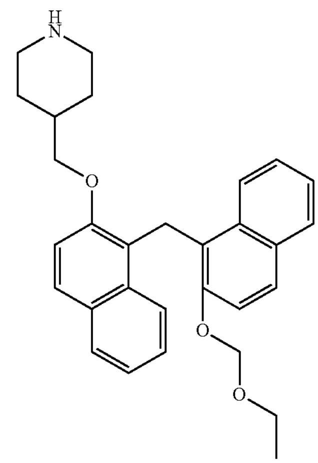 [SMILES: CCOCOc1ccc2ccccc2c1Cc1c(OCC2CCNCC2)ccc2ccccc12] |
| A286 | 95 | 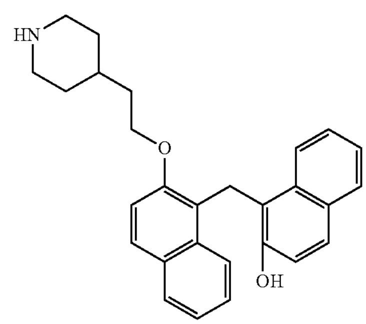 [SMILES: Oc1ccc2ccccc2c1Cc1c(OCCC2CCNCC2)ccc2ccccc12] |
| A290 | 96 | 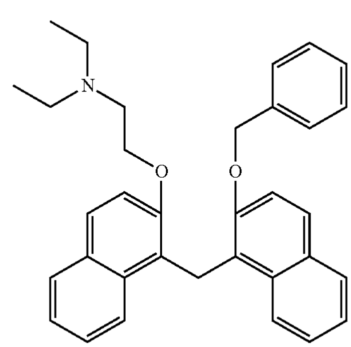 [SMILES: CCN(CC)CCOc1ccc2ccccc2c1Cc1c(OCc2ccccc2)ccc2ccccc12] |
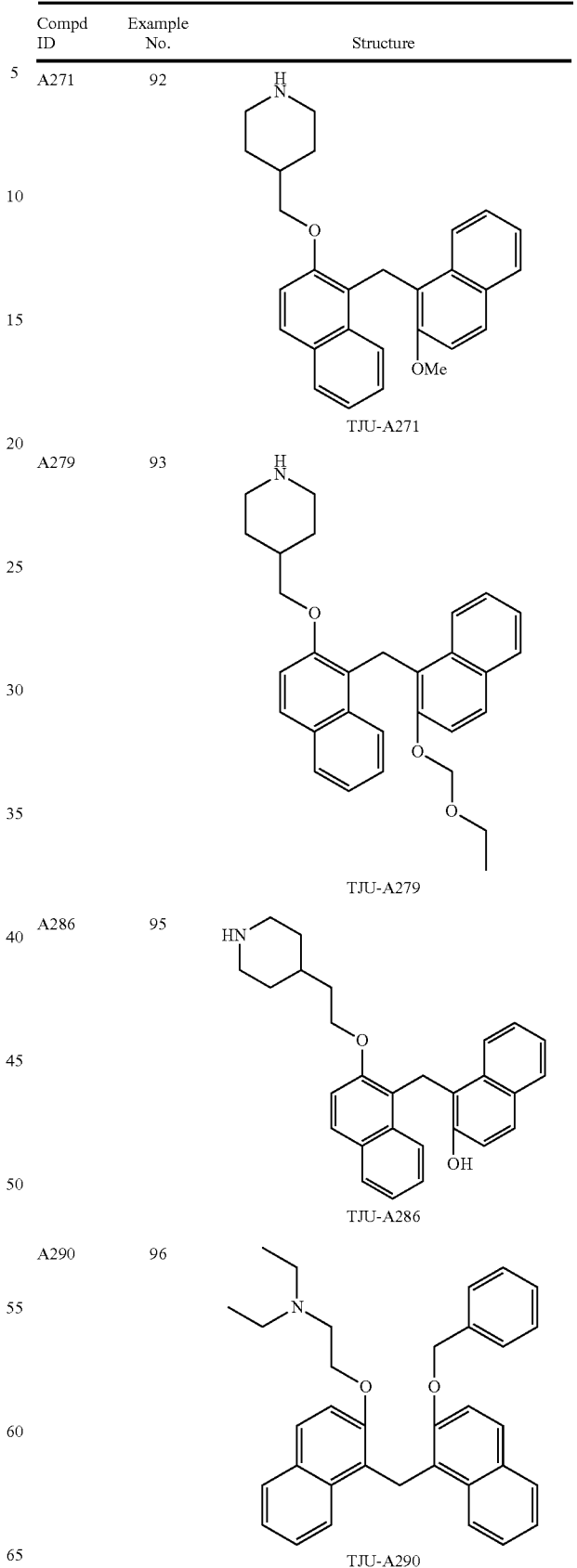

| Compd ID | Example No. | Structure |
|---|---|---|
| A291 | 97 | 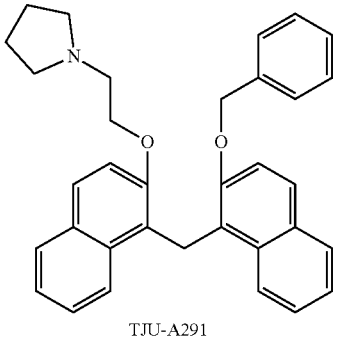<br>TJU-A291 |
| A296 | 98 | 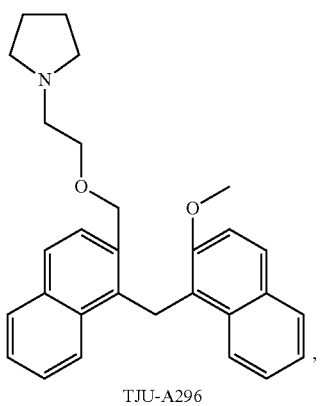<br>TJU-A296 |

6. A pharmaceutical composition comprising the compound of claim 1, or the pharmaceutically acceptable salt, the solvate, or the stereoisomer thereof, and a pharmaceutically acceptable carrier.

7. A method for promoting growth of cardiomyocytes in vitro, which comprises a step of:
culturing cardiomyocyte in the presence of the compound of claim 1, or the pharmaceutically acceptable salt, the solvate, or the stereoisomer thereof.

8. A method for inhibiting ion channel in vitro, which comprises a step of:
contacting cardiomyocyte with the compound of claim 1, or the pharmaceutically acceptable salt, the solvate, or the stereoisomer thereof, thereby inhibiting ion channel.

9. A method for treating or preventing an ion channel related disease, which comprises a step of: administering the compound according to claim 1 or the pharmaceutically acceptable salt, the solvate, or the stereoisomer thereof to a subject in need thereof.

10. The method of claim 4, wherein
the ion channel related disease is selected from the group consisting of cardiovascular disease, Parkinsons, and seizures, or a combination thereof; or
the ion channel related disease is selected from the group consisting of arterial arrhythmia (AF), and ventricular arrhythmia (VF) disease, or a combination thereof.

11. The compound of claim 1, or the pharmaceutically acceptable salt, the solvate, or the stereoisomer thereof, wherein $R_1$ is —O—.

12. The compound of claim 1, or the pharmaceutically acceptable salt, the solvate, or the stereoisomer thereof, wherein $L_1$ is unsubstituted C1-C6 alkylene group.

13. The compound of claim 1, or the pharmaceutically acceptable salt, the solvate, or the stereoisomer thereof, wherein $R_3$ is selected from the group consisting of —S—, —N($R_a$)—, and —$CH_2$—, and $R_a$ is selected from the group consisting of H and methyl.

14. The compound of claim 1, or the pharmaceutically acceptable salt, the solvate, or the stereoisomer thereof, wherein each $R_2$ is independently selected from the group consisting of H and substituted or unsubstituted C1-C6 alkyl; or two $R_2$ and the nitrogen atom to which they are attached form a substituted or unsubstituted 4 to 10 membered heterocyclic group, and the heterocyclyl contains 1 N atom and 0 or 1 O atom.

15. The compound of claim 1, or the pharmaceutically acceptable salt, the solvate, or the stereoisomer thereof, wherein $R_7$ is selected from the group consisting of H, $R_f$—O—, $R_f$—S—, and —$R_{1a}$—$L_{1a}$-$R_{da}$; wherein $R_f$ is selected from the group consisting of H, substituted or unsubstituted C1-C6 alkyl, and substituted or unsubstituted C3-C6 cycloalkyl; $R_{1a}$ is —O— or —S— and $L_{1a}$ is C1-C6 alkylene group; and $R_{da}$ is R"—O— or R"—S—.

16. The compound of claim 15, or the pharmaceutically acceptable salt, the solvate, or the stereoisomer thereof, wherein $R_7$ is selected from the group consisting of $R_f$—O—, and —$R_{1a}$—$L_{1a}$-$R_{da}$; wherein $R_f$ is selected from the group consisting of H, substituted or unsubstituted C1-C6 alkyl; $R_{1a}$ is —O— and $L_{1a}$ is C1-C6 alkylene group; and $R_{da}$ is R"—O—.

17. The compound of claim 1, or the pharmaceutically acceptable salt, the solvate, or the stereoisomer thereof, wherein each R' is independently selected from the group consisting of D and R"; wherein R" is each independently selected from the group consisting of H and C1-C6 alkyl.

18. The compound of claim 1, or the pharmaceutically acceptable salt, the solvate, or the stereoisomer thereof, wherein the compound or the pharmaceutically acceptable salt, the solvate, or the stereoisomer thereof is used as ion channel antagonist or blocker.

\* \* \* \* \*